(12) United States Patent
Abreu

(10) Patent No.: US 10,238,847 B2
(45) Date of Patent: Mar. 26, 2019

(54) DEVICES AND METHODS FOR TRANSDERMAL DRUG DELIVERY

(71) Applicant: GEELUX HOLDINGS, LTD., Tortola (VG)

(72) Inventor: Marcio Marc Abreu, Bridgeport, CT (US)

(73) Assignee: Geelux Holdings, Ltd., Tortola (VG)

( * ) Notice: Subject to any disclaimer, the term of this patent is extended or adjusted under 35 U.S.C. 154(b) by 714 days.

(21) Appl. No.: 14/603,353

(22) Filed: Jan. 22, 2015

(65) Prior Publication Data
US 2015/0202417 A1    Jul. 23, 2015

Related U.S. Application Data

(60) Provisional application No. 61/930,262, filed on Jan. 22, 2014.

(51) Int. Cl.
*A61M 37/00*    (2006.01)
*A61F 7/00*    (2006.01)
(Continued)

(52) U.S. Cl.
CPC .............. *A61M 35/00* (2013.01); *A61B 5/01* (2013.01); *A61F 2007/0003* (2013.01); *A61F 2007/0052* (2013.01); *A61F 2007/0075* (2013.01); *A61F 2007/026* (2013.01); *A61F 2007/0261* (2013.01); *A61M 2205/3368* (2013.01); *A61M 2210/0618* (2013.01)

(58) Field of Classification Search
CPC .... A61K 9/7007; A61K 9/7023; A61K 9/703; A61K 9/7038; A61K 9/7084; A61K 9/7092; A61F 2007/0002; A61F 2007/0003; A61F 2007/0004; A61F 2007/0005; A61F 2007/0006; A61F 2007/0007; A61F 2007/0008; A61F 2007/0052; A61F 2007/0075; A61F 2007/026; A61F 2007/0261; A61F 7/007; A61M 2205/3368; A61M 2210/06; A61M 2210/0606; A61M 2210/0618; A61M 35/00; A61M 37/00
See application file for complete search history.

(56) References Cited

U.S. PATENT DOCUMENTS 3,463,885 A    8/1969   Upton
3,531,642 A    9/1970   Barnes et al.
(Continued)

FOREIGN PATENT DOCUMENTS

CN    2398565 Y    9/2000
CN    2446955 Y    9/2001
(Continued)

OTHER PUBLICATIONS

International Search Report; PCTUS2015/010873; dated Apr. 10, 2015.
(Continued)

*Primary Examiner* — Adam Marcetich
(74) *Attorney, Agent, or Firm* — Studebaker & Brackett PC

(57) ABSTRACT

Provided are devices for therapeutic interaction with an Abreu brain thermal tunnel (ABTT) terminus. Such devices are configured to provide one or more drugs to an ABTT terminus, and may provide heat to or remove heat from the ABTT terminus while providing the one or more drugs.

8 Claims, 80 Drawing Sheets

US 10,238,847 B2

Page 2

(51) Int. Cl.
*A61F 7/02* (2006.01)
*A61M 35/00* (2006.01)
*A61B 5/01* (2006.01)

(56) References Cited

U.S. PATENT DOCUMENTS

| | | |
|---|---|---|
| 3,545,260 A | 12/1970 | Lichtenstein et al. |
| 3,585,849 A | 6/1971 | Grolman |
| 3,626,757 A | 12/1971 | Benzinger |
| 3,724,263 A | 4/1973 | Rose et al. |
| 3,769,961 A | 11/1973 | Fatt et al. |
| 3,897,272 A | 7/1975 | Medlar |
| 3,897,790 A | 8/1975 | Magilton et al. |
| 3,963,019 A | 6/1976 | Quandt |
| 4,186,184 A | 1/1980 | Zaffaroni |
| 4,231,052 A | 10/1980 | Day et al. |
| 4,297,685 A | 10/1981 | Brainard, II |
| 4,305,399 A | 12/1981 | Beale |
| 4,312,358 A | 1/1982 | Barney |
| 4,321,261 A | 3/1982 | Ellis et al. |
| 4,330,299 A | 5/1982 | Cerami |
| 4,331,161 A | 8/1982 | Patel |
| 4,344,315 A | 8/1982 | Moxon et al. |
| 4,344,438 A | 8/1982 | Schultz |
| 4,386,831 A | 6/1983 | Grounauer |
| 4,444,990 A | 4/1984 | Viillar |
| 4,485,820 A | 12/1984 | Flower |
| 4,488,558 A | 12/1984 | Simbruner et al. |
| 4,595,020 A | 6/1986 | Palti |
| 4,597,392 A | 7/1986 | Opitz et al. |
| 4,628,938 A | 12/1986 | Lee |
| 4,629,424 A | 12/1986 | Lauks et al. |
| 4,771,792 A | 9/1988 | Seale |
| 4,784,149 A | 11/1988 | Berman et al. |
| 4,830,014 A | 5/1989 | Goodman et al. |
| 4,846,196 A | 7/1989 | Wiksell et al. |
| 4,860,755 A | 8/1989 | Erath |
| 4,922,913 A | 5/1990 | Waters, Jr. et al. |
| 4,944,303 A | 7/1990 | Katsuragi |
| 4,947,849 A | 8/1990 | Takahashi et al. |
| 4,951,671 A | 8/1990 | Coan |
| 4,979,831 A | 12/1990 | Schertz et al. |
| 5,005,577 A | 4/1991 | Frenkel |
| 5,046,482 A | 9/1991 | Everest |
| 5,062,432 A | 11/1991 | James et al. |
| 5,076,274 A | 12/1991 | Matsumoto |
| 5,109,852 A | 5/1992 | Kaye et al. |
| 5,115,815 A | 5/1992 | Hansen |
| 5,148,807 A | 9/1992 | Hsu |
| 5,165,409 A | 11/1992 | Coan |
| 5,179,953 A | 1/1993 | Kursar |
| 5,183,044 A | 2/1993 | Nishio et al. |
| 5,190,039 A | 3/1993 | Takeuchi et al. |
| 5,209,231 A | 5/1993 | Cote et al. |
| 5,217,015 A | 6/1993 | Kaye et al. |
| 5,222,495 A | 6/1993 | Clarke et al. |
| 5,222,809 A | 6/1993 | Ehrenkranz |
| 5,246,867 A | 9/1993 | Lakowicz et al. |
| 5,251,627 A | 10/1993 | Morris |
| 5,255,979 A | 10/1993 | Ferrari |
| 5,295,495 A | 3/1994 | Maddess |
| 5,297,554 A | 3/1994 | Glynn et al. |
| 5,341,805 A | 8/1994 | Stavridi et al. |
| 5,342,283 A | 8/1994 | Good |
| 5,342,789 A | 8/1994 | Chick et al. |
| 5,352,411 A | 10/1994 | Khuri |
| 5,356,780 A | 10/1994 | Robinson et al. |
| 5,375,595 A | 12/1994 | Sinha et al. |
| 5,383,452 A | 1/1995 | Buchert |
| 5,433,197 A | 7/1995 | Stark |
| 5,435,307 A | 7/1995 | Friauf et al. |
| 5,441,476 A | 8/1995 | Kitado et al. |
| 5,503,770 A | 4/1996 | James et al. |
| 5,522,662 A | 6/1996 | Shiokawa |
| 5,636,635 A | 6/1997 | Massie et al. |
| 5,653,239 A | 8/1997 | Pompei et al. |
| 5,662,624 A * | 9/1997 | Sundstrom ............ A61F 7/007 602/2 |
| 5,664,578 A | 9/1997 | Boczan |
| 5,673,692 A | 10/1997 | Schulze et al. |
| 5,711,915 A | 1/1998 | Siegmund et al. |
| 5,796,341 A | 8/1998 | Stratiotis |
| 5,813,982 A | 9/1998 | Baratta |
| 5,817,008 A | 10/1998 | Rafert et al. |
| 5,820,557 A | 10/1998 | Hattori et al. |
| 5,830,139 A | 11/1998 | Abreu |
| 5,833,633 A | 11/1998 | Sarvazyan |
| 5,854,078 A | 12/1998 | Asher et al. |
| 5,860,934 A | 1/1999 | Sarvazyan |
| 5,862,803 A | 1/1999 | Besson et al. |
| 5,898,004 A | 4/1999 | Asher et al. |
| 5,984,880 A | 11/1999 | Lander et al. |
| 5,994,701 A | 11/1999 | Tsuchimoto et al. |
| 6,011,984 A | 1/2000 | Van Antwerp et al. |
| 6,028,323 A | 2/2000 | Liu |
| 6,040,194 A | 3/2000 | Chick et al. |
| 6,042,266 A | 3/2000 | Cheslock et al. |
| 6,047,203 A | 4/2000 | Sackner et al. |
| 6,072,180 A | 6/2000 | Kramer et al. |
| 6,120,460 A | 9/2000 | Abreu |
| 6,123,668 A | 9/2000 | Abreu |
| 6,126,595 A | 10/2000 | Amano et al. |
| 6,135,968 A | 10/2000 | Brounstein |
| 6,152,875 A | 11/2000 | Hakamata |
| 6,178,346 B1 | 1/2001 | Amundson et al. |
| 6,181,957 B1 | 1/2001 | Lambert et al. |
| 6,187,599 B1 | 2/2001 | Asher et al. |
| 6,196,714 B1 | 3/2001 | Bellifemine et al. |
| 6,197,534 B1 | 3/2001 | Lakowicz et al. |
| 6,197,928 B1 | 3/2001 | Tsien et al. |
| 6,203,193 B1 | 3/2001 | Egawa |
| 6,213,943 B1 | 4/2001 | Abreu |
| 6,245,347 B1 * | 6/2001 | Zhang ................ A61K 9/0009 424/402 |
| 6,256,522 B1 | 7/2001 | Schultz |
| 6,290,658 B1 | 9/2001 | Kolich |
| 6,292,685 B1 | 9/2001 | Pompei |
| 6,300,871 B1 | 10/2001 | Irwin et al. |
| 6,312,393 B1 | 11/2001 | Abreu |
| 6,319,540 B1 | 11/2001 | Van Antwerp et al. |
| 6,385,473 B1 | 5/2002 | Haines et al. |
| 6,385,474 B1 | 5/2002 | Rather et al. |
| 6,423,001 B1 | 7/2002 | Abreu |
| 6,432,050 B1 | 8/2002 | Porat et al. |
| 6,465,709 B1 * | 10/2002 | Sun .................... A61F 7/034 602/41 |
| 6,470,893 B1 | 10/2002 | Boesen |
| 6,529,617 B1 | 3/2003 | Prokoski |
| 6,536,945 B2 | 3/2003 | Rolston |
| 6,542,081 B2 | 4/2003 | Torch |
| 6,543,933 B2 | 4/2003 | Stergiopoulos et al. |
| 6,544,193 B2 | 4/2003 | Abreu |
| 6,681,127 B2 | 1/2004 | March |
| 6,731,976 B2 | 5/2004 | Penn et al. |
| 6,789,901 B1 | 9/2004 | Kormos |
| 6,791,087 B1 | 9/2004 | Okumura |
| 6,846,106 B1 | 1/2005 | Chen et al. |
| 7,187,960 B2 | 3/2007 | Abreu |
| 7,340,293 B2 | 3/2008 | McQuilkin |
| 7,346,386 B2 | 3/2008 | Pompei |
| 7,515,054 B2 | 4/2009 | Torch |
| 7,597,668 B2 | 10/2009 | Yarden |
| 7,621,877 B2 | 11/2009 | Schnall |
| 7,689,437 B1 | 3/2010 | Teller et al. |
| 7,756,559 B2 | 7/2010 | Abreu |
| 7,787,938 B2 | 8/2010 | Pompei |
| 7,837,623 B2 | 11/2010 | Aubry et al. |
| 8,103,071 B2 | 1/2012 | Schnell et al. |
| 8,172,459 B2 | 5/2012 | Abreu |
| 8,328,420 B2 | 12/2012 | Abreu |
| 8,500,271 B2 | 8/2013 | Howell et al. |
| 8,527,022 B1 | 9/2013 | Lash et al. |
| 8,721,562 B2 | 5/2014 | Abreu |
| 8,834,020 B2 | 9/2014 | Abreu |

(56) References Cited

U.S. PATENT DOCUMENTS

| | | | |
|---|---|---|---|
| 8,849,379 | B2 | 9/2014 | Abreu |
| 9,007,220 | B2 | 4/2015 | Johns et al. |
| 9,327,105 | B2* | 5/2016 | Ramdas ............ A61M 37/0092 |
| 2001/0028309 | A1 | 10/2001 | Torch |
| 2002/0004063 | A1* | 1/2002 | Zhang ................ A61K 9/0034 424/443 |
| 2002/0026119 | A1 | 2/2002 | Pompei |
| 2002/0035340 | A1 | 3/2002 | Fraden et al. |
| 2002/0049374 | A1 | 4/2002 | Abreu |
| 2002/0049389 | A1 | 4/2002 | Abreu |
| 2002/0068080 | A1 | 6/2002 | Lerner |
| 2002/0068876 | A1 | 6/2002 | Pompei et al. |
| 2002/0111657 | A1 | 8/2002 | Dae et al. |
| 2002/0119186 | A1* | 8/2002 | Zhang ................ A61K 9/0009 424/449 |
| 2002/0126731 | A1 | 9/2002 | Stergiopoulos et al. |
| 2003/0055473 | A1 | 3/2003 | Ramsden et al. |
| 2003/0060863 | A1 | 3/2003 | Dobak, III |
| 2003/0067958 | A1 | 4/2003 | Jang |
| 2003/0108223 | A1 | 6/2003 | Prokoski |
| 2003/0111605 | A1 | 6/2003 | Sato et al. |
| 2003/0179094 | A1 | 9/2003 | Abreu |
| 2003/0210146 | A1 | 11/2003 | Tseng |
| 2003/0212340 | A1 | 11/2003 | Lussier et al. |
| 2004/0039298 | A1 | 2/2004 | Abreu |
| 2004/0043062 | A1* | 3/2004 | Sun ...................... A61K 36/484 424/449 |
| 2004/0059212 | A1 | 3/2004 | Abreu |
| 2004/0076316 | A1 | 4/2004 | Fauci |
| 2004/0082862 | A1 | 4/2004 | Chance |
| 2004/0125996 | A1 | 7/2004 | Eddowes et al. |
| 2004/0152991 | A1 | 8/2004 | Pompei |
| 2004/0154550 | A1 | 8/2004 | McQuilkin |
| 2004/0170216 | A1 | 9/2004 | Russak et al. |
| 2004/0210159 | A1 | 10/2004 | Kibar |
| 2004/0242976 | A1* | 12/2004 | Abreu .................. A61B 5/0008 600/315 |
| 2004/0246548 | A1 | 12/2004 | Papuchon et al. |
| 2004/0265353 | A1* | 12/2004 | Zhang ................ A61K 9/0009 424/423 |
| 2005/0096574 | A1* | 5/2005 | Wibaux ................ H05B 3/342 602/2 |
| 2005/0250996 | A1 | 11/2005 | Shirai et al. |
| 2006/0105029 | A1* | 5/2006 | Zhang .................. A61K 9/703 424/448 |
| 2006/0122473 | A1 | 6/2006 | Kill et al. |
| 2006/0135911 | A1 | 6/2006 | Mittur |
| 2006/0210616 | A1* | 9/2006 | Linder ...................... A61F 9/04 424/449 |
| 2006/0215728 | A1 | 9/2006 | Jang |
| 2006/0264726 | A1 | 11/2006 | Manheimer et al. |
| 2006/0265029 | A1* | 11/2006 | Huang .................... A61N 5/06 607/88 |
| 2007/0055171 | A1 | 3/2007 | Fraden |
| 2007/0219434 | A1 | 9/2007 | Abreu |
| 2008/0043809 | A1 | 2/2008 | Herbert |
| 2008/0086072 | A1 | 4/2008 | Bonutti et al. |
| 2008/0200830 | A1 | 8/2008 | Pompei |
| 2008/0214949 | A1 | 9/2008 | Stivoric et al. |
| 2008/0262329 | A1 | 10/2008 | Say et al. |
| 2008/0269570 | A1* | 10/2008 | Leung ................ A61B 5/14539 600/300 |
| 2009/0005745 | A1* | 1/2009 | Zhang .................... A61F 7/034 604/291 |
| 2009/0105605 | A1 | 4/2009 | Abreu |
| 2009/0157056 | A1 | 6/2009 | Ferren et al. |
| 2009/0234382 | A1* | 9/2009 | Dillon .................. A61K 8/0208 606/204.35 |
| 2010/0018542 | A1* | 1/2010 | Konrad .................. A45D 40/30 132/200 |
| 2010/0022909 | A1 | 1/2010 | Padiy |
| 2010/0113894 | A1 | 5/2010 | Padiy |
| 2010/0204765 | A1 | 8/2010 | Hall et al. |
| 2011/0024626 | A1 | 2/2011 | O'Donnell et al. |
| 2011/0040161 | A1 | 2/2011 | Abreu |
| 2011/0077546 | A1 | 3/2011 | Fabian |
| 2011/0086913 | A1* | 4/2011 | Zhang .................... A61F 7/034 514/535 |
| 2011/0092822 | A1 | 4/2011 | Pompei |
| 2012/0031405 | A1 | 2/2012 | Geist et al. |
| 2012/0136285 | A1 | 5/2012 | Korb et al. |
| 2013/0109674 | A1* | 5/2013 | Leighton .............. A61K 9/0014 514/217 |
| 2013/0124039 | A1 | 5/2013 | Abreu |
| 2013/0215928 | A1 | 8/2013 | Bellifemine |
| 2013/0247928 | A1* | 9/2013 | Valucci .................. A45D 44/00 132/200 |
| 2013/0292571 | A1 | 11/2013 | Mukherjee et al. |
| 2013/0298931 | A1* | 11/2013 | Samain ................ A45D 44/22 132/200 |
| 2014/0206947 | A1* | 7/2014 | Isserow .................. A61F 7/034 600/301 |

FOREIGN PATENT DOCUMENTS

| | | |
|---|---|---|
| CN | 1328432 A | 12/2001 |
| DE | 4433104 C1 | 5/1996 |
| EP | 0236028 A2 | 9/1987 |
| EP | 0411121 A1 | 2/1991 |
| EP | 2 120 681 B1 | 7/2011 |
| EP | 1 951 110 B1 | 10/2012 |
| JP | S61-48369 A | 3/1986 |
| JP | H10-075934 A | 3/1998 |
| JP | H10-239158 A | 9/1998 |
| JP | H11-164826 A | 6/1999 |
| JP | 2001-500394 A | 1/2001 |
| JP | 2001/031151 A | 2/2001 |
| JP | 2002-525132 A | 8/2002 |
| JP | 3885024 B2 | 2/2007 |
| WO | 93/01745 A1 | 2/1993 |
| WO | 97/19188 A1 | 5/1997 |
| WO | 98/22820 A1 | 5/1998 |
| WO | 99/51142 A2 | 10/1999 |
| WO | 00/10007 A2 | 2/2000 |
| WO | 00/13580 A1 | 3/2000 |
| WO | 00/16051 A1 | 3/2000 |
| WO | 00/16099 A1 | 3/2000 |
| WO | 00/18237 A1 | 4/2000 |
| WO | 00/64492 A1 | 11/2000 |
| WO | 02/03855 A1 | 1/2002 |
| WO | 02/28271 A2 | 4/2002 |
| WO | 02/067688 A1 | 9/2002 |
| WO | 2005/015163 A2 | 2/2005 |
| WO | 2010-042738 A2 | 4/2010 |

OTHER PUBLICATIONS

The International Search Report dated Jun. 12, 2015, which corresponds to International Patent Application No. PCT/US15/10938 and is related to U.S. Appl. No. 14/603,353.

International Preliminary Report on Patentability; PCT/US2015/010938 dated Jul. 12, 2016; and is related to U.S. Appl. No. 14/603,353.

An Examiner's First Report; issued by the Australian Government, IP Australia on Apr. 21, 2009, which corresponds to Australian Patent Application No. 2006306422.

An Examiner's Report No. 2; issued by the Australian Government, IP Australia on Nov. 10, 2010, which corresponds to Australian Patent Application No. 2006306422.

English translation of an Office Action; issued by the Korean Intellectual Property Office dated Jun. 21, 2013, which corresponds to Korean Patent Application No. 10-2008-7012335.

English translation of an Office Action; issued by the Japanese Patent Office dated Nov. 17, 2011, which corresponds to Japanese Patent Application No. 2008-537828.

English translation of a Second Office Action; issued by the Japanese Patent Office dated Nov. 13, 2012, which corresponds to Japanese Patent Application No. 2008-537828.

English translation of a Third Office Action; issued by the Japanese Patent Office dated Nov. 26, 2013, which corresponds to Japanese Patent Application No. 2008-537828.

(56) References Cited

OTHER PUBLICATIONS

Overton, Staci. "Brain Temperature Tunnel Discovered." Medical Breakthroughs Reported by Ivanhoe, Jun. 2, 2003.
International Search Report; PCT/US2014/060199; dated Jan. 8, 2015.
International Search Report; PCT/US2014/060201; dated Mar. 3, 2015.
Dittmar, A. et al., A Non Invasive Wearable Sensor for the Measurement of Brain Temperature. Proceedings of the 28th IEEE EMBS Annual International Conference. Aug. 30-Sep. 3, 2006. pp. 900-902, New York City, USA.
An Office Action and Examination Search Report issued by the Canadian Intellectual Property Office dated Mar. 26, 2015, which corresponds to Canadian Patent Application No. 2,627,278.
RCA Technical Notes, Contact Lens Tonometer by Robert E. Morey, RCA TN No. 602, dated Dec. 1964, 2 pages.
Ophthal. Physiol. Opt., 1989, vol. 9, April, Research Note, Multiple Applications of the NCT: An Assessment of Instrument's Effect on IOP by G.E. Russell and J.P.G. Bergmanson, pp. 212-214.
Arch Ophthalmol—vol. 97, Mar. 1979, The Pneumatonograph—A Laboratory Study, by Robert A. Moses, M.D. and Walter J. Grodzki Jr., D.D.S., pp. 547-552.
IEEE Transactions on bio-Medical Engineering, vol. BME-14, No. 2, Apr. 1967, Miniature Passive Pressure Transensor for Implanting in the Eye, by C.C. Collins, pp. 74-83.
Trans. Amer. Acad. of O. & O., Jan.-Feb. 1957, Tonometer Calibration, An Attempt to Remove Discrepancies Found in the 1954 Calibration Scale for Schiotz Tonometers by Jonas S. Friedenwald, M.D., pp. 108-123.
Investigative Ophthalmology, Feb. 1962, The Relationship Between Pressure and Volume Changes in Living and Dead Rabbit Eyes, by John E. Eisenlohr and Maurice E. Langham, pp. 63-77.
Investigative Ophthalmology, Sep. 1971, vol. 10, No. 9, Theory and Calibration of the Schiotz Tonometer VII. Experimental Results of Tonometric Measurements: Scale Reading Versus Indentation Volume, by Robert A. Moses and Walter J. Grodzki, pp. 716-723.
The British Journal of Ophthalmology, Jun. 1920, Communications-Tonometry, by HJ. Schiötz, pp. 249-261.
American Journal of Opthalmology, vol. 20, No. 10, Oct. 1937, Contribution to the Theory and Practice of Tonometry by Jonas S. Friedenwald, M.D., pp. 985-1024.
Ophthalmologica vol. 150, No. 5, (1965), Rheology of the Human Sclera, Unifying Formulation of Ocular Rigidity, by W.K. McEwen and Roger St. Helen, pp. 321-346.
A.M.A Archives of Ophthalmology, vol. 57, Apr. 1957, Tonometer Calibration, by Earle H. McBain, M.D., pp. 520-531.
The Photonics Dictionary, 1996 Book 4, 42nd Edition, pp. D-24, D153.
Manual of Skin Diseases, Fifth Edition, Gordon C. Sauer, MD., 1985, pp. 204, 373.
FM-2 Fluorotron™ Master Ocular Fluorophotometer, 1994 OcuMetrics, Inc.
Textbook of Biochemistry With Clinical Correlations, Second Edition, Thomas M. Devlin, Ph.D., 1986, pp. 118, 139.
Physical Optics, Third Revised Edition, Robert W. Wood, 1961, pp. 650-651.
An Examiner's First Report; issued by the Australian Government, IP Australia on Dec. 18, 2008, which corresponds to Australian Patent Application No. 2004263812.
An Examiner's First Report; issued by the Australian Government, IP Australia on Mar. 10, 2010, which corresponds to Australian Patent Application No. 2009212808.
An Examiner's First Report; issued by the Australian Government, IP Australia on Feb. 19, 2010, which corresponds to Australian Patent Application No. 2009212861.
An Examiner's First Report; issued by the Australian Government, IP Australia on Nov. 4, 2013, which corresponds to Australian Patent Application No. 2012247045.

An Office Action issued by the Canadian Intellectual Property Office dated May 3, 2012, which corresponds to Canadian Patent Application No. 2,517,869.
English translation of a First Office Action and Search Report; issued by the State Intellectual Property Office of the People's Republic of China dated Jul. 21, 2014, which corresponds to Chinese Patent Application No. 201310097177.3.
English translation of a First Office Action and Search Report; issued by the State Intellectual Property Office of the People's Republic of China dated Jul. 22, 2014, which corresponds to Chinese Patent Application No. 201310097142.X.
A supplementary European Search Report; issued by the European Patent Office dated Oct. 17, 2008, which corresponds to European Patent Application No. 04785841.0-1265.
A "Communication pursuant to Article 94(3) EPC," issued by the European Patent Office dated Jan. 27, 2009, which corresponds to European Patent Application No. 04785841.0-1265.
A "Communication pursuant to Article 94(3) EPC," issued by the European Patent Office dated Sep. 12, 2013, which corresponds to European Patent Application No. 04785841.0-1657.
English Translation of Relevant Portion of Office Action; issued by the State of Israel Department of Justice, Patent Office dated Jul. 3, 2013, which corresponds to Israeli Patent Application No. 1704896.
English translation of Notification of Reasons for Refusal; issued by the Japanese Patent Office dated Jun. 11, 2009, which corresponds to Japanese Patent Application No. 2006-508817.
English translation of Notification of Reasons for Refusal; issued by the Japanese Patent Office dated Jan. 12, 2010, which corresponds to Japanese Patent Application No. 2006-508817.
A Summarized English Translation of Office Action; issued by the Instituto Mexicano de la Propiedad Industrial dated Jul. 4, 2008, which corresponds to Mexican National Phase Patent Application No. PA/a/2005/009159.
An Office Action; issued by the Instituto Mexicano de la Propiedad Industrial dated Sep. 25, 2009, which corresponds to Mexican National Phase Patent Application No. PA/a/2005/009159.
International Search Report & Written Opinion; PCT/US2004/005496; dated May 6, 2005.
English translation of an Office Action; issued by the Japanese Patent Office dated Jan. 22, 2009, which corresponds to Japanese Patent Application No. 2004-515642.
English translation of an Office Action; issued by the National Institute of Industrial Property dated Jul. 1, 2013, which corresponds to Brazilian Patent Application PI0309578-9.
English translation of the "First Office Action," and "Search Report," issued by the State Intellectual Property Office of the People's Republic of China dated Jun. 4, 2014, which corresponds to Chinese Application No. 201210361917.5.
A "Communication pursuant to Article 94(3) EPC," issued by the European Patent Office dated Jan. 27, 2009, which corresponds to European Patent Application No. 03 754 363.4-1265.
A second "Communication pursuant to Article 94(3) EPC," issued by the European Patent Office dated Sep. 13, 2013, which corresponds to European Patent Application No. 03 754 363.4-1657.
A third "Communication pursuant to Article 94(3) EPC," issued by the European Patent Office dated Mar. 4, 2014, which corresponds to European Patent Application No. 03 754 363.4-1657.
A fourth "Communication pursuant to Article 94(3) EPC," issued by the European Patent Office dated Sep. 24, 2014, which corresponds to European Patent Application No. 03 754 363.4-1657.
English translation of an Office Action; issued by the State of Israel Department of Justice, Patent Office dated Nov. 26, 2008, which corresponds to Israeli Patent Application No. 164685.
English translation of an Office Action; issued by the Korean Intellectual Property Office dated Dec. 26, 2011, which corresponds to Korean Patent Application No. 10-2010-7018173.
International Search Report; PCT/US03/12382; dated May 13, 2005.
International Search Report; PCT/US2006/041238; dated Aug. 31, 2007.
An Office Action issued by the Canadian Intellectual Property Office dated Aug. 2, 2011, which corresponds to Canadian Patent Application No. 2,627,278.

(56) References Cited

OTHER PUBLICATIONS

A Second Office Action issued by the Canadian Intellectual Property Office dated Mar. 14, 2012, which corresponds to Canadian Patent Application No. 2,627,278.
A "Communication pursuant to Particle 94(3) EPC," issued by the European Patent Office dated May 13, 2011, which corresponds to European Patent Application No. 06 826 452.2-2319.
English translation of an Office Action; issued by the State of Israel Department of Justice, Patent Office dated Jun. 23, 2011, which corresponds to Israeli Patent Application No. 191039.
An Examiner's First Report; issued by the Australian Government, IP Australia dated Jan. 13, 2012, which corresponds to Australian Patent Application No. 2011202015.
Patent Examination Report No. 1; issued by the Australian Government, IP Australia dated Dec. 13, 2013, which corresponds to Australian Patent Application No. 2012203667.
International Search Report; PCT/US2015/012546 dated Jul. 14, 2015; 4pp.
Written Opinion; PCT/US2015/012546 dated Feb. 26, 2016; 7pp.

\* cited by examiner

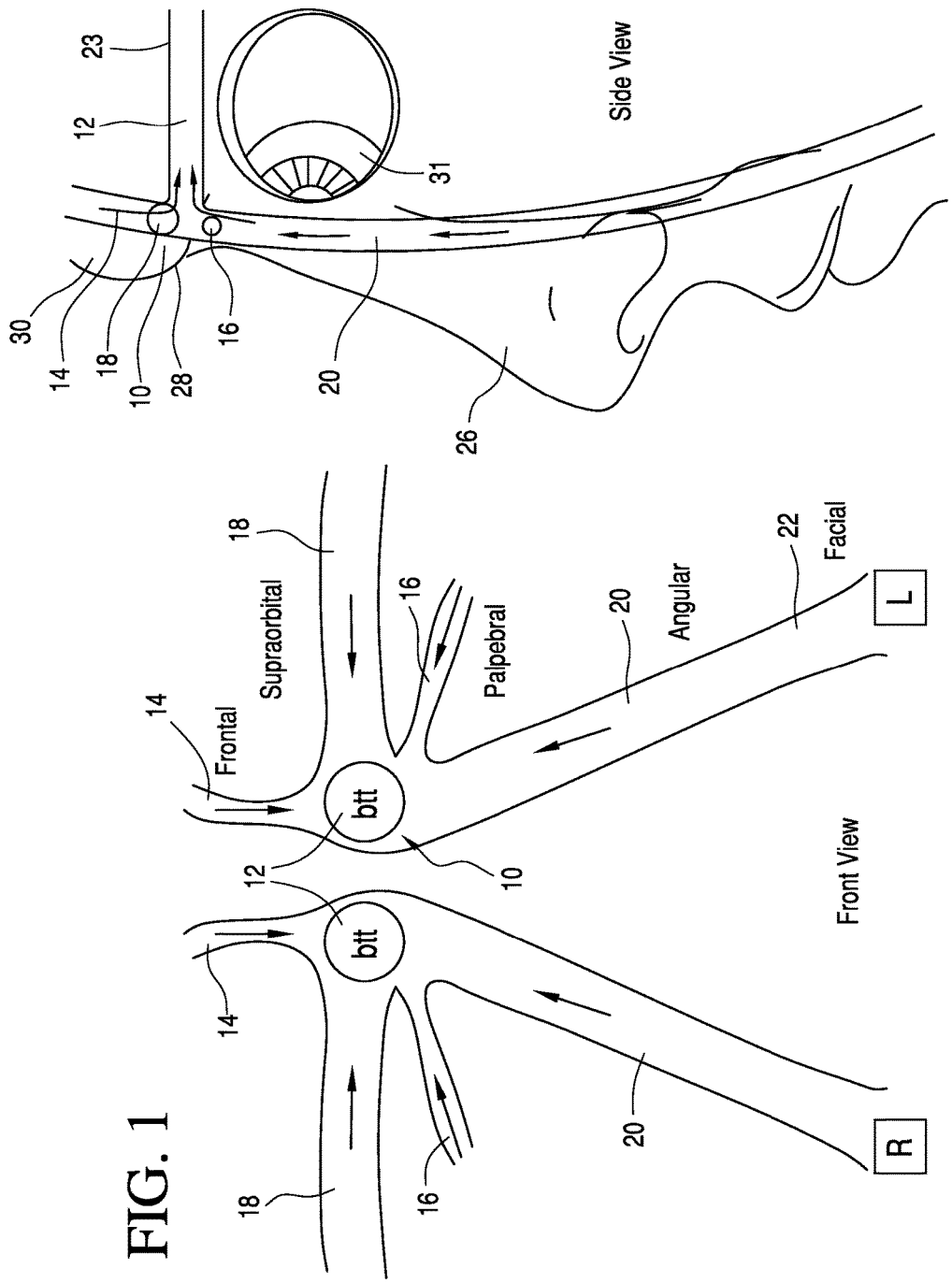

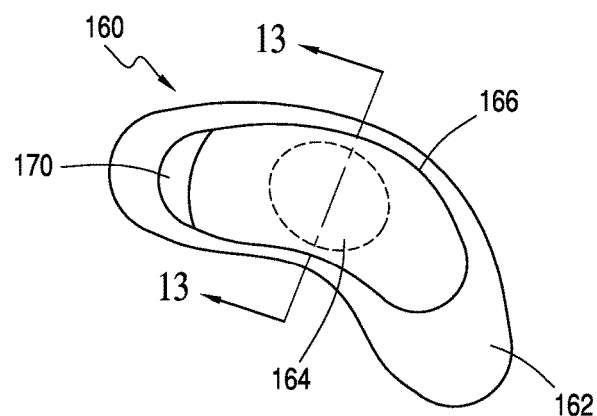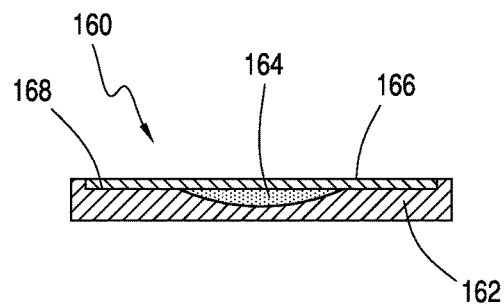
FIG. 12
FIG. 13
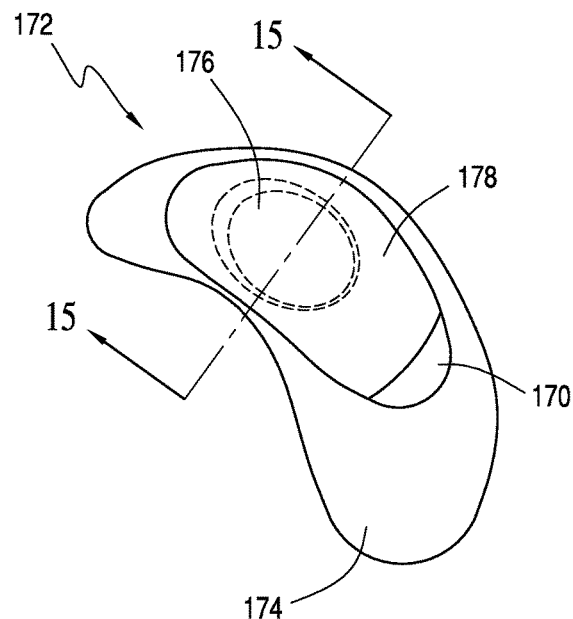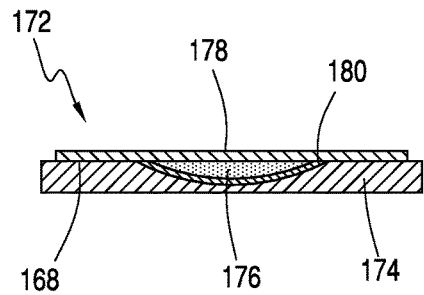
FIG. 14
FIG. 15

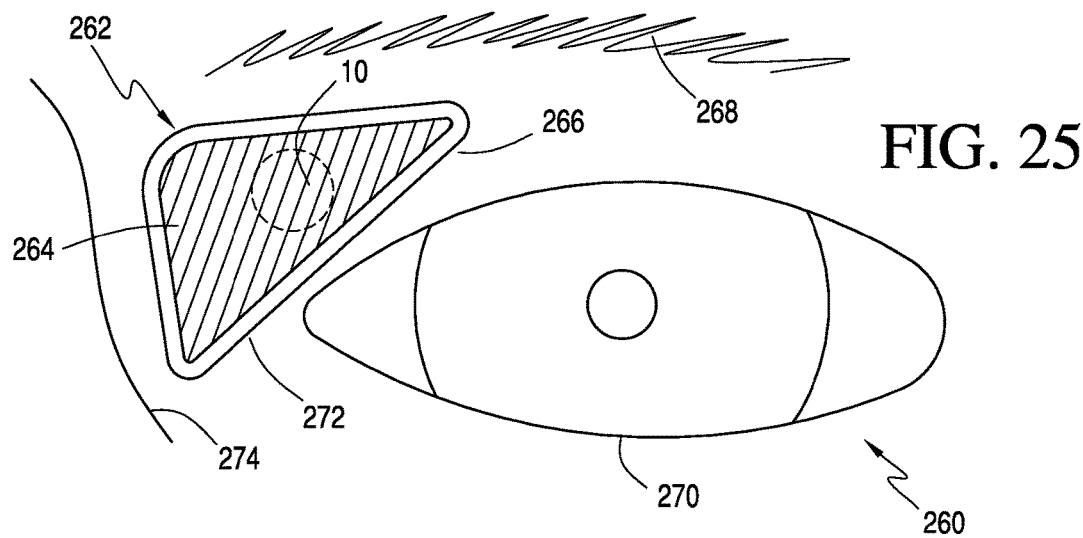
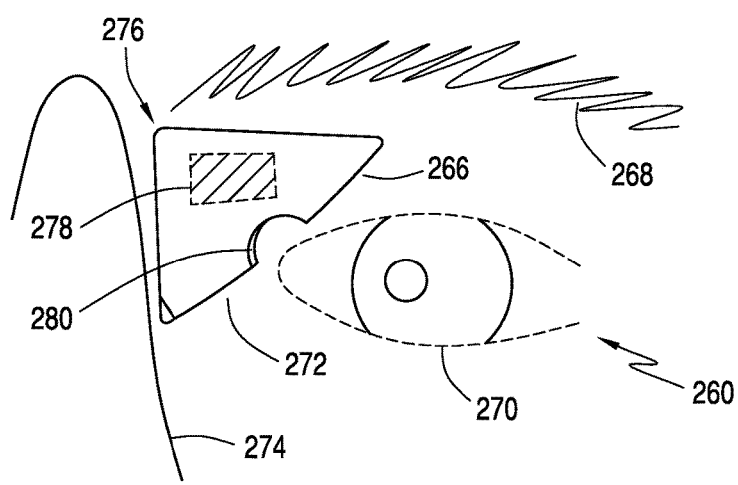
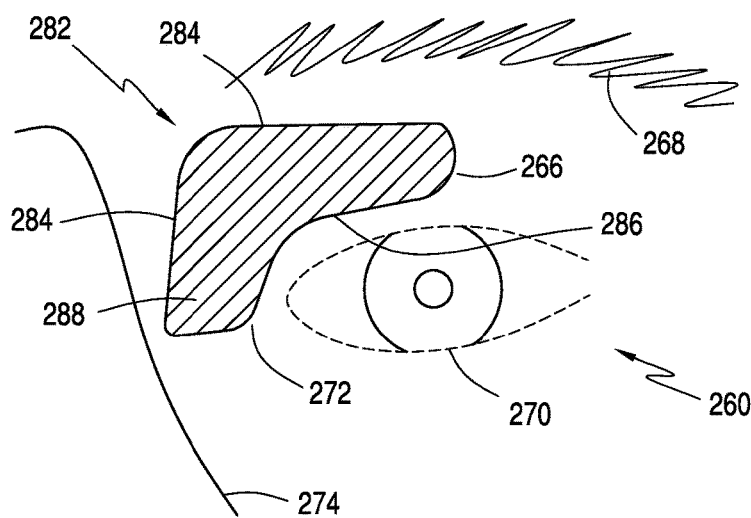

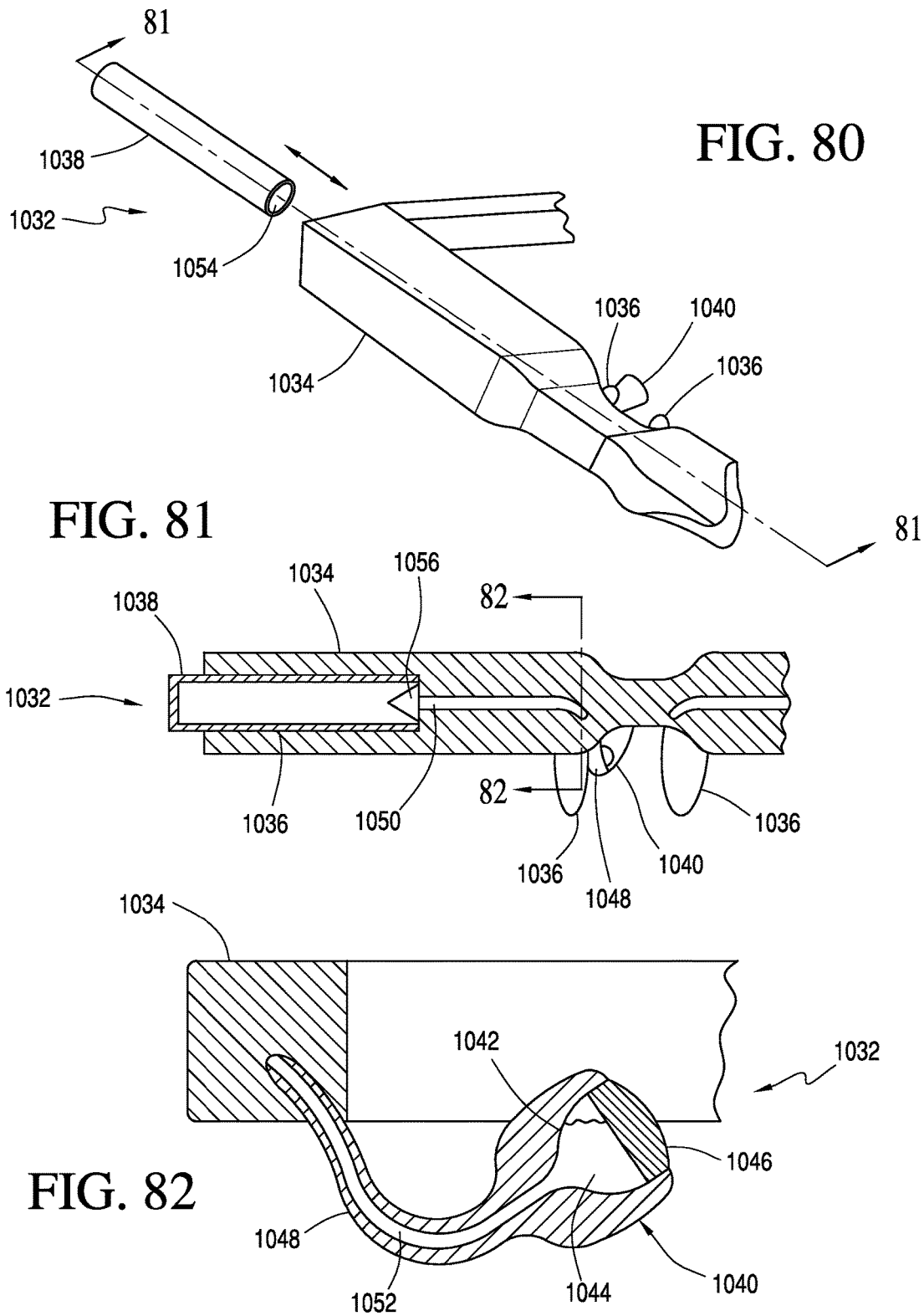

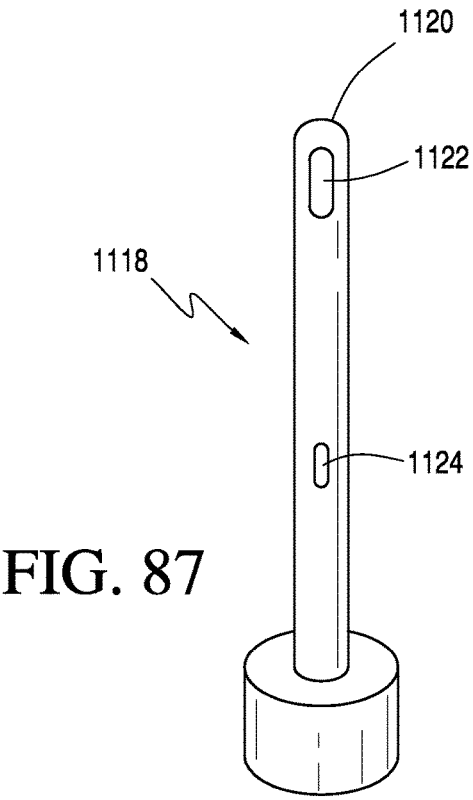
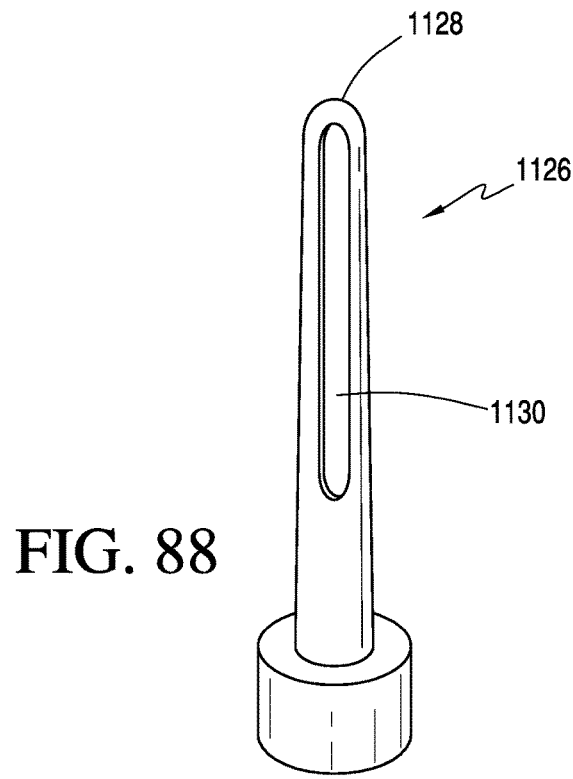
FIG. 87     FIG. 88
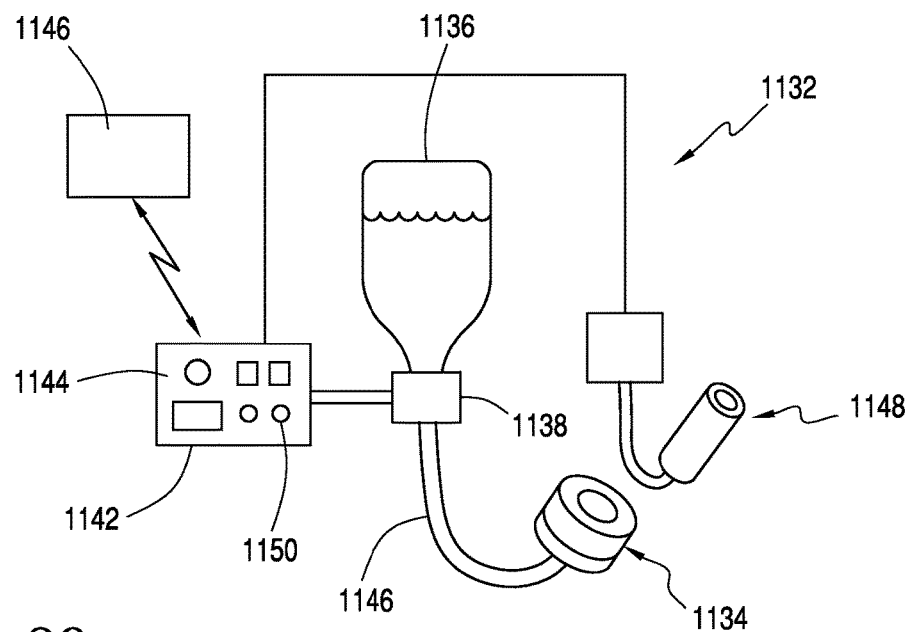
FIG. 89

DEVICES AND METHODS FOR TRANSDERMAL DRUG DELIVERY

CROSS-REFERENCE TO RELATED APPLICATIONS

This application claims the benefit of priority to U.S. Provisional Patent Application No. 61/930,262, filed on Jan. 22, 2014, which is hereby incorporated by reference in their entirety.

TECHNICAL FIELD

This disclosure relates to medical devices configured to monitor biological parameters non-invasively and to provide therapeutic applications of drugs at the skin on, over, or adjacent to an Abreu brain thermal tunnel (ABTT) terminus.

BACKGROUND

Drugs are administered by several routes, including subcutaneously, orally, intramuscular, intravenously, and transdermally. Each of these approaches includes drawbacks when considering the effectiveness and side effects of the drug. With the blood-brain barrier serving to keep unwanted substances out of the brain, current methods of administering anesthesia and certain other drugs require that a very large dose of the compound be injected into the blood stream so that the drug is received by the brain. As the drug travels throughout the body, the drug may be absorbed by parts of the body not intended to intended to be exposed to the drug, sometimes resulting in severe and adverse side effects.

Oral ingestion wastes drugs because of the passage of the drugs through the digestive system, in addition to the drugs being subject to first-pass metabolism where there is a reduced effectiveness caused by liver enzymes. In addition, these compounds may take a long time to produce the desired effect when administered orally.

Injection allows therapeutic agents to bypass the effects of metabolism, but injections are painful and carry the risk of infection, besides producing large amounts of hazardous waste, e.g., used needles contaminated with body fluid.

In addition to the drawbacks described elsewhere herein, conventional methods administer drugs in locations that are remote from the brain, where portions of the pharmacological effects are realized in the body, though the desired effect is in the brain.

In order to remove dependence on needles and invasive administration, a method of transdermally introducing chemical compounds into the bloodstream via intact skin is known. Transdermal administration delivers drugs or other chemicals through the skin to local tissue, and then into the systemic circulatory system without cutting or penetration of the skin. Using transdermal methods rather than injections reduces pain, biohazardous waste, and risk of infection. Currently, transdermal delivery systems have been proposed or developed for a variety of drugs or therapeutic agents to treat many conditions and diseases.

While transdermal delivery of drugs presents many potential benefits and wide applications, its development is limited due to the biological nature of the skin, which presents a barrier to penetration because the low permeability of the skin limits the application of transdermal delivery. The transdermal flux of a drug depends on the diffusion coefficient of the drug; the thickness of the epidermis and dermis; and the condition of the skin at the application site; and the concentration gradient across the skin.

Passive transdermal delivery methods comprise the use of patches that contain a drug, and often a permeation enhancer. The structure of transdermal delivery patches generally comprises an outer layer, a middle layer that contains the drug, and a liner and/or a release liner that protects the adhesive layer, which is removed prior to use.

As briefly described above, transdermal delivery of active agents is generally executed in an area of the body that is remote from the brain or active control center that is affected by the drug being introduced into the body such as, for example, the arm, buttock, back, or leg. All of the areas currently used for transdermal delivery have a great deal of adipose tissue, i.e., fat, which serves as a significant barrier to transdermal delivery of therapeutic agents. These sites present limitations to the transdermal delivery methods, as a high dosage must be used to ensure that an effective dose reaches the control center designed to be treated by the drug. Excess drugs and active agents circulating throughout the body may be absorbed by organs and tissues not intended to be treated, thus resulting in an increased risk for damaging side effects. For this reason especially, transdermal delivery is extremely limited or impossible for use with potent drugs.

SUMMARY

This disclosure provides a series of interfaces. The interface may comprise a layer facing the ABTT skin that includes an adhesive having pores, holes and the like. Adjacent to this adhesive layer is a medication-containing layer or alternatively a reservoir housing medication. In an exemplary embodiment, the present disclosure includes an interface having a reservoir housing an absorbent material such as a sponge, a pad, a gel, and the like, said absorbent material being soaked with a solution of a medication, said absorbent material preferably being compressible. It is understood that the reservoir may include liquid, solution, cream, paste, and the like, or a combination thereof. In another embodiment, the aforementioned medication is applied through a membrane-like surface. It is also understood that the interface does not need to have an adhesive layer facing the skin and is positioned against the skin without adhesive by means of a mechanism applying pressure. Medication referred herein includes any chemical compound.

In an exemplary embodiment, the interface contacts the skin of the ABTT and may include additional adjacent areas, wherein medication is administered through a layer in contact with said skin of the ABTT. In another exemplary embodiment, the interface contacts the skin overlying the veins associated with the ABTT and may include adjacent areas, as disclosed herein, wherein medication is administered through a layer in contact with said skin. In another exemplary embodiment, the interface contacts a combination of the skin of the ABTT and the skin overlying the veins associated with the ABTT and may include adjacent areas. In exemplary embodiments, the adjacent areas range from greater than zero to 35 mm from the center of the ABTT.

The dimensions of the interface in contact with the skin prevent unwanted thermal stimulation of the skin and also prevent delivery of medication away from the target areas, namely the ABTT skin and/or skin overlying the veins associated with the ABTT. By isolating the area, the effect of the medication is increased and side effects are decreased or eliminated.

In one exemplary embodiment, the interface may comprise a multi-layer structure, including an outer layer that can function as a water repellent. In one exemplary embodiment, the interface may include an adjustable arm, said adjustable arm being preferably connected to a frame, including but not limited to a frame of eyeglasses, goggles, eye mask, head-gear, neck-gear, and the like. It should be understood that the arm may be connected by a support structure having an adhesive surface, said adhesive functioning as an anchoring means, not as a drug delivery means. The arm is constructed of suitably flexible materials, so as to be able to bend and be positioned against the ABTT skin.

In one exemplary embodiment, the interface can have any shape, including, but not limited to, oval, rectangular, square, oblong, and the like. In another exemplary embodiment, the interface can further include a releasable liner.

In one exemplary embodiment, the interface is constructed with at least one outer impermeable layer such as polyethylene, polyester, and the like.

In one exemplary embodiment, the adhesive surface includes medical grade adhesive, pressure sensitive adhesive, and the like.

In one exemplary embodiment of the interface, the medication is preferably contained in a mid-portion bordered by an outer cover or layer.

In one exemplary embodiment, the support device may include a flexible circuit and thermoelectric devices preferably spaced from each other.

The interface includes a surface that is permeable to allow diffusion of the medication.

By having an interface that relies on pressure mechanisms, the present disclosure provides embodiments that eliminate the drawbacks and limitations of using adhesives, such as discomfort, skin maceration, residues on the skin after removal and the like.

Advantages and features of the embodiments of this disclosure will become more apparent from the following detailed description of exemplary embodiments when viewed in conjunction with the accompanying drawings.

BRIEF DESCRIPTION OF THE DRAWINGS

FIG. 1 is a simplified view of the ABTT and facial veins associated with the ABTT.

FIG. 2A is a simplified partial cross-sectional view through a human skull in a vertical direction, showing the Abreu brain thermal tunnel and certain other facial features.

FIG. 12 is a plan view of a yet further transdermal delivery device in accordance with an exemplary embodiment of the present disclosure.

FIG. 13 is a cross-sectional view of the transdermal delivery device of FIG. 12 along the lines 13-13.

FIG. 14 is a plan view of another transdermal delivery device in accordance with an exemplary embodiment of the present disclosure.

FIG. 15 is a cross-sectional view of the transdermal delivery device of FIG. 14 along the lines 15-15.

FIG. 25 is a view of a patient or subject's face with a transdermal delivery device in accordance with an exemplary embodiment of the present disclosure positioned thereon.

FIG. 26 is a view of a patient or subject's face with another transdermal delivery device in accordance with an exemplary embodiment of the present disclosure positioned thereon.

FIG. 27 is a view of a patient or subject's face with yet another transdermal delivery device in accordance with an exemplary embodiment of the present disclosure positioned thereon.

FIG. 80 is a perspective view of a portion of a frame configured to include a removable reservoir, in accordance with an exemplary embodiment of the present disclosure.

FIG. 81 is a cross-sectional view of the frame of FIG. 80 along the lines 81-81, with the removable reservoir installed in the frame.

FIG. 82 is a cross-sectional view of the frame of FIGS. 80 and 81, along the lines 82-82.

FIG. 87 is a perspective view of a puncture or penetrating device of FIG. 86, in accordance with an exemplary embodiment of the present disclosure.

FIG. 88 is a perspective view of a puncture or penetrating device of FIG. 86, in accordance with an exemplary embodiment of the present disclosure.

FIG. 89 is a view of a transdermal delivery system in accordance with an exemplary embodiment of the present disclosure.

FIG. 121 is a view of a transdermal delivery device positioned on a head of a subject or patient in accordance with an exemplary embodiment of the present disclosure.

FIG. 122 is a view of the transdermal delivery device of FIG. 121.

FIG. 123 is a perspective view of an iontophoretic system in accordance with an exemplary embodiment of the present disclosure.

FIG. 124 is a view of a portion of the iontophoretic system of FIG. 123.

FIG. 125 is a cross-sectional view of the iontophoretic system of FIGS. 123 and 124.

FIG. 126 is a view of an arm of iontophoretic system in accordance with an alternative embodiment of the present disclosure.

FIG. 127 is a view of a portion of an iontophoretic system in accordance with an exemplary embodiment of the present disclosure.

FIG. 128 is a view of another iontophoretic system in accordance with an exemplary embodiment of the present disclosure.

FIG. 129 is a view of yet another iontophoretic system in accordance with an exemplary embodiment of the present disclosure.

DETAILED DESCRIPTION

Figure 2B:
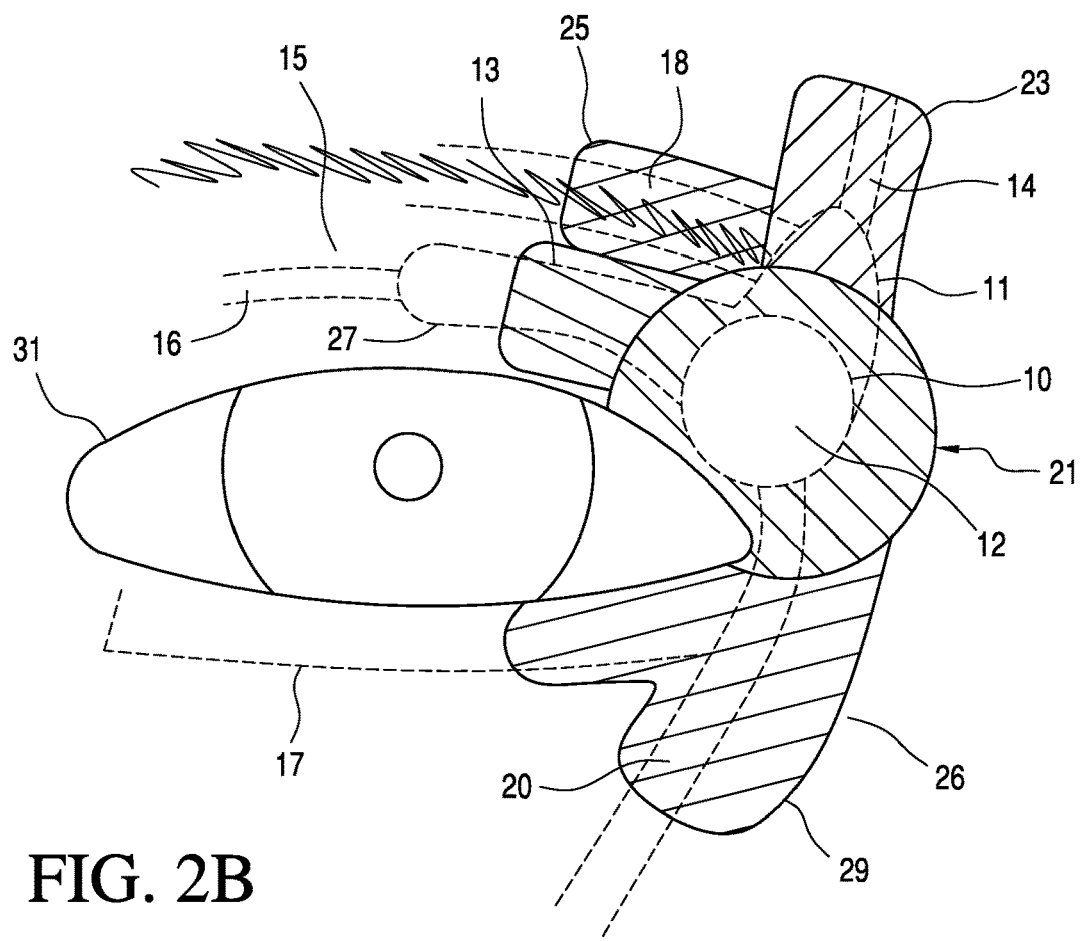
FIG. 2B is a simplified view of the ABTT area and veins associated with the ABTT area.

The present disclosure arises from the discovery that an Abreu brain thermal tunnel or ABTT provides the first known structure for brain-surface thermodynamic communication and thermal connection directly with the center of the brain. Anatomically and physiologically speaking, and as shown in FIGS. 1-3, ABTT 12 includes a continuous, direct, and undisturbed connection between a brain core 24 at the control center of the brain and the skin of ABTT terminus 10. The skin of ABTT terminus 10 is unique in that it is the thinnest skin with the fewest layers, a fat layer is absent, and has the high thermal conductivity of any skin on the human body.

The physical and physiological events at one end of the tunnel are reproduced at the opposite end. ABTT 12 enables the direct transfer of inputs to ABTT 12 to brain core 24 without significant bathers, as described in co-pending U.S. patent application Ser. No. 14/512,421, filed on Oct. 11, 2014, incorporated by reference herein in its entirety. Accordingly, the present disclosure describes apparatus, systems, devices, mechanisms, and methods that use ABTT terminus 10 and ABTT 12 to delivery compounds, chemicals, medications, biologics, such as vaccines and genes, and drugs to the brain core.

Anatomy shows the convergence of four veins at ABTT target area 10: frontal 14, superior palpebral 16, supraorbital 18, and angular 20. As angular vein 20 extends further from ABTT 12, it transitions into facial vein 22. Having converged, the blood from these veins flows toward brain core 24 from ABTT target area 10 between an eye 31 and the eyebrow into the center of the brain, which is the temperature center present in the hypothalamus or thermal storage area of the body present in the cavernous sinus. From the thermal storage area, blood is distributed throughout the brain tissue and the body, and may be used to effectively and efficiently treat and/or prevent medical conditions by the transmission of medications, chemicals, and compounds to the brain.

Figure 3:
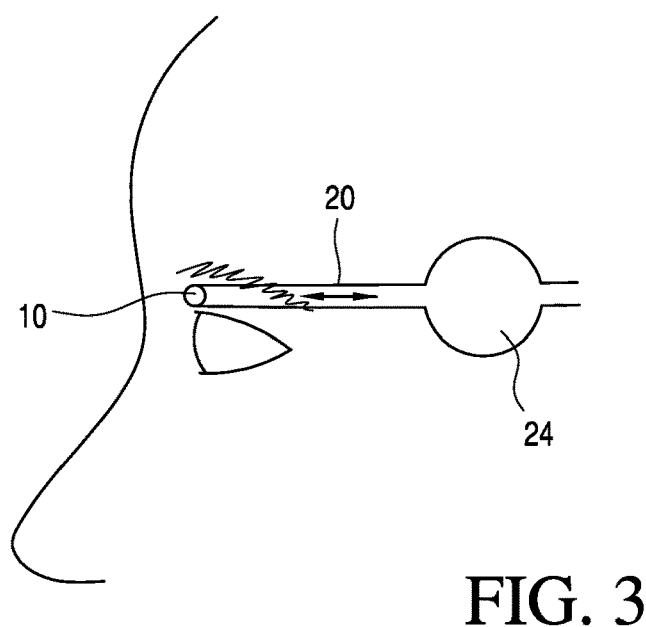
FIG. 3 is a stylized representation of the flow of blood into a brain core.

FIGS. 1, 2A, and 2B show the approximate location of these veins in relation to other facial features. Angular/facial vein 20/22 runs up alongside nose 26, superior palpebral vein 16 runs along eyebrow 28, and frontal vein 14 and supraorbital vein 18 run through forehead 30. Delivery of medication to these veins, and particularly ABTT terminus 10, provides a path between the skin and brain core 24 with the least barrier or resistance to drug transport identified in the human body. For the purposes of disclosure, terminology referring to relevant facial areas or veins herein will be described as one or more of the above-referenced veins and ABTT target area 10.

As described herein, veins 14, 16, 18, 20, and 22 converge in the superomedial orbit in the region of the upper eyelid and adjacent to the bridge of the nose, and flow directly, without inhibition, to the center of the brain. The skin in this area, as shown in pending application by the Applicant, is the thinnest skin in the body and free of fat, providing thereby the area most permeable to administering drugs, and by being in direct communication with the brain, the most direct path for drug delivery to the brain. These vessels lack valves, which are typically an important barrier to flow and direct transmission of pharmacologically agents. Without valves, these blood vessels truly provide a direct, uninhibited passage for transporting therapeutic agents directly to the hypothalamic region of the brain. Moreover, ABTT 12 includes a superior ophthalmic vein (SOV) 23, which connects the skin surface to the brain and corresponds to the central portion of the tunnel (ABTT 12), is valveless and has bidirectional blood flow. The SOV lies directly underneath the skin of the superomedial orbit, between eye 31 and eyebrow, and is a direct conduit from surface to the brain to the hypothalamus. The hypothalamic region of the brain is the link between the central nervous system and the endocrine system and, as such, acts as the center of control for many basic bodily functions such as, for example, hunger, thirst, body temperature, fatigue, blood pressure, immune responses, circadian cycles, hormone production and secretion, and many others.

As shown in, for example, FIG. 2B, the facial end of ABTT 12, herein referred to as a target area, or terminus 10 on the skin on, over, or adjacent to ABTT 12, measures about 11 mm in diameter measured from the medial corner of eye 31 at the medial canthal tendon and extends superiorly for about an additional 6 or 7 mm in an ABTT superior projection 11, and then extends into an upper eyelid 15 in a horn-like projection 13 for another 22 mm. ABTT terminus 10 is absent fat, and ABTT superior project 11 and horn-like project 13 are absent fat in areas near to ABTT terminus 10, with a fat layer present in areas a spaced distance away from ABTT terminus 10. It should be understood that the dashed lines in FIG. 2B represent features under the skin, and facial features are shown for approximate reference.

ABTT target area 10, as described herein, provides a direct link to the control center of the brain, since the skin of ABTT target area 10 is free from adipose tissue and other barriers. Because the blood vessels carrying blood into the brain are superficial and lie just under the top layer of thin skin, ABTT target area or terminus 10 is the ideal location for transdermal delivery to occur. In fact, the direct flow to the brain may allow doses of drugs and other chemical compounds delivered transdermally to be reduced drastically. These lower doses may, in turn, reduce the side-effects involved with many drugs, decrease waiting time before the effects of a drug are noticed, increase effectiveness of certain drugs, and remove the necessity for invasive and painful use of needles. Also, transdermal delivery of many drugs may no longer need to be carried out remotely. Since drugs can reach the hypothalamus and brain directly, the apparatus and method of the present disclosure may be used for treatment of numerous diseases and conditions that are regulated by the center of the brain such as, by way of illustration, but not of limitation, Alzheimer's disease, Parkinson's disease, thyroid conditions, seizures, pain, and hunger. Examples of drugs that may be administered using this method are contraceptives, anesthesia, antibiotics, narcotics, any hormonal associated drugs, cancer agents, and any drug to treat any condition or disease.

The present disclosure concerns a device, apparatus, or mechanism and method for transdermally delivering drugs and other chemical compounds or therapeutic agents through the skin of ABTT target area 10.

In one example of an application of the present disclosure, as carried out in a research setting, a patch designed to transdermally deliver melatonin (MEL] through the skin of ABTT target area 10 was shown to provide an intended therapeutic effect. Oral introduction of MEL is suggested to elevate plasma MEL and reduce waking after sleep onset by promoting sleep in the latter part of an 8-hour sleep opportunity. MEL has been shown to improve daytime sleep, but the hormone's short elimination half-life limits its use as a hypnotic in shift workers and individuals with jet lag or other sleep problems. As a solution to this problem, MEL was applied transdermally on the skin of ABTT target area 10 using a patch that contained, in a solvent formulation, water, propylene glycol, lauric acid, and hydroxypropylcellulose, and also comprised a non-rate-limiting membrane designed to have active contact with an area 1.0 cm$^2$. Experiments show that ABTT terminus 10 and the dose were best suited to produce the intended plasma profile for clinical effect. It should be understood that any type of membrane or porous material can be used in accordance with the principles of the present disclosure.

In the present disclosure, the terms therapeutic agent, medication, compound, and drug are used to describe any compound, molecule, solution, element or other chemical intended to be intentionally presented into the body to provide an intended benefit. Most often, the present disclosure is intended for use in conjunction with drugs prescribed by a doctor or the like and intended to treat a certain condition such as, for example, pain or a disease. However, it should be understood that the present disclosure is not limited to the examples herein or for use with common drugs or to treat specific diseases. For example, although it may not be preferred, the present disclosure may be used in conjunction with any chemical compound to include even drugs such as cocaine, cannabis, lysergic acid, amphetamines, and the like. It should also be understood that homeopathic drugs, and drugs that are used in minimal concentrations or amounts, are also within the scope of the present invention. It should also be understood that any naturally occurring substance, such as, by way of illustration, any vegetables, including garlic, caffeine, and the like, as well as any type of vitamins, energizing compounds, nutritional compounds, food compounds, and the like, are within the scope of the invention. Although any chemical compound or any drug can be administered according to the principles of the present invention, examples of drugs that may be delivered by devices according to this disclosure include, but are not limited to, prochlorperzine edisylate, ferrous sulfate, aminocaproic acid, mecamylamine hydrochloride, procainamide hydrochloride, amphetamine sulfate, methamphetamine hydrochloride, benzamphetamine hydrochloride, isoproterenol sulfate, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methyiphenidate hydrochloride, theophylline cholinate, cephalexin hydrochloride, diphenidol, meclizine hydrochloride, prochiorperazine maleate, phenoxybenz amine, thiethylperzine maleate, anisindone, diphenadione erythrityl tetranitrate, digoxin, isofluorphate, acetazolamide, methazolamide, bendroflumethiazide, chloropromaide, tolazamide, chlormadinone acetate, phenaglycodol, allopurinol, aluminum aspirin, methotrexate, acetyl sulfisoxazole, erythromycin, hydrocortisone, hydrocorticosterone acetate, cortisone acetate, dexamethasone and its derivatives such as betamethasone, triamcinolone, methyltestosterone, 17-.beta.-Estradiol, ethinyl estradiol, ethinyl estradiol 3-methyl ether, prednisolone, 17-.alpha.-hydroxyprogesterone acetate, 19-nor-progesterone, norgestrel, norethindrone, norethisterone, norethiederone, progesterone, norgesterone, norethynodrel, aspirin, indomethacin, naproxen, fenoprofen, sulindac, indoprofen, nitroglycerin, isosorbide dinitrate, propranolol, timolol, atenolol, alprenolol, cimetidine, clonidine, imipra mine, levodopa, chlorpromazine, methyldopa, dihydroxyphenylalanine, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, capropril, mandol, quanbenz, hydrochiorothiazide, ranitidine, flubiprofen, fenufen, fluprofen, tolmetin, aicofenac, mefenamic, flufenamic, difiuinal, nimodipinefnitrendipine, nisoldipine, nicardipine, felodipine, lidoflazine, tiapamil, gallopamil, amlodipine, mioflazine, lisinoipril, enalapril, enalaprilat, captopril, ramiprii, famotidine, nizatidine, sucralfate, etintidine, tetratolol, minoxidil, chiordiazepoxide, diazepam, amitriptyline, and imipramine. Further examples are proteins and peptides that include, but are not limited to, insulin, colchicine, glucagon, thyroid-stimulating hormone, parathyroid and pituitary hormones, calcitonin, rennin, prolactin, corticotrophin, thyrotropic hormone, follicle-stimulating hormone, chorionic gonadotropin, gonadotropin-releasing hormone, bovine somatotropin, porcine somatotropin, oxytocin, vasopressln, GRF, somatostatin, lypressin, pancreozymin, luteinizing hormone, LHRH, LHRH agonists and antagonists, leuprolide, interferons (including alpha, beta, delta, and gamma), interleukins, growth hormones such as human growth hormone, bovine growth hormone and porcine growth hormone, fertility inhibitors such as the prostaglandins, fertility promoters, growth factors, coagulation factors, human pancreas hormone-releasing factor, analogs and derivatives of these compounds, and pharmaceutically acceptable salts of these compounds, or their analogs or derivatives.

Some exemplary embodiments of the present disclosure are intended for the transdermal delivery of drugs, therapeutic agents, or other chemical compounds into the body through ABTT target area 10 using the teachings of the exemplary embodiments of the present disclosure.

In an exemplary embodiment, a passive type apparatus of the present disclosure in an exemplary embodiment includes a housing containing a drug or other compound that has a protective backing and is adapted to be secured to ABTT target area 10, which in an exemplary embodiment may be accomplished by using an adhesive material, such as a patch delivery method described in detail herein. The patch may be configured for one-time use to deliver a single dose of medication or it may comprise a liner that is adapted to release a specific amount of compound over an extended period of time, or to release several doses of medication over a further prolonged period of time. In alternate embodiments, the passive apparatus may also employ the use of any permeation enhancers or other topical passive permeation methods as described in detail herein. The patch can also be reusable and used for certain period of time and then removed. In this embodiment, a new adhesive surface may be used to secure the patch to the skin. The chemical compound can also be replaced once the original compound has been delivered to the skin in its entirety.

As described herein, the present disclosure describes apparatus, devices, mechanisms, systems, and methods of delivering compounds, chemicals, and drugs to the brain core. For the sake of simplicity, all substances deliverable to the brain core are described herein as "drugs." Generally, devices for delivering drugs through ABTT terminus 10 can be categorized as passive devices, which operate by the presence of the drug on the skin of ABTT terminus 10 and/or associated veins 14, 16, 18, 20 and 22, or active devices, which include one or more features to control drug delivery to ABTT terminus 10 and/or associated veins 14, 16, 18, 20 and 22, or to control drug flow through ABTT terminus 10 and/or associated veins 14, 16, 18, 20 and 22. Generally, the configurations and dimensions shown for passive transdermal devices can be applied to active transdermal devices, and vice versa, when an active or passive embodiment can be configured with such configurations and dimensions, unless otherwise specified.

Passive transdermal delivery devices are configured to deliver precise amounts of drugs to ABTT terminus 10 and/or the skin over associated veins 14, 16, 18, 20, and 22, for permeation through the skin at ABTT terminus 10 and/or associated veins 14, 16, 18, 20, and 22, and subsequent transmission through ABTT 12 to brain core 24. While the various embodiments of transdermal delivery devices disclosed herein bear similarity to conventional passive transdermal patches, a plurality of differences exist, as will be understood by a person of ordinary skill in that art reading and applying the teachings of the present disclosure.

Many aspects of the disclosure are described in terms of sequences of actions to be performed by elements of a computer system or other hardware capable of executing programmed instructions, for example, a general purpose computer, special purpose computer, workstation, or other programmable data processing apparatus. It will be recognized that in each of the embodiments including active or electronic elements, the various actions could be performed by specialized circuits (e.g., discrete logic gates interconnected to perform a specialized function), by program instructions (software), such as logical blocks, program modules etc. being executed by one or more processors (e.g., one or more microprocessors, a central processing unit (CPU), and/or application specific integrated circuit), or by a combination of both. For example, embodiments can be implemented in hardware, software, firmware, middleware, microcode, or any combination thereof. The instructions can be program code or code segments that perform necessary tasks and can be stored in a non-transitory, machine-readable medium such as a storage medium or other storage(s). A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents.

The non-transitory machine-readable medium can additionally be considered to be embodied within any tangible form of computer readable carrier, such as solid-state memory, magnetic disk, and optical disk containing an appropriate set of computer instructions, such as program modules, and data structures that would cause a processor to carry out the techniques described herein. A computer-readable medium may include the following: an electrical connection having one or more wires, magnetic disk storage, magnetic cassettes, magnetic tape or other magnetic storage devices, a portable computer diskette, a random access memory (RAM), a read-only memory (ROM), an erasable programmable read-only memory (e.g., EPROM, EEPROM, or Flash memory), or any other tangible medium capable of storing information.

It should be noted that the systems of the present disclosure are illustrated and discussed herein as having various modules and units which perform particular functions. It should be understood that these modules and units are merely schematically illustrated based on their function for clarity purposes, and do not necessarily represent specific hardware or software. In this regard, these modules, units and other components may be hardware and/or software implemented to substantially perform their particular functions explained herein. The various functions of the different components can be combined or segregated as hardware and/or software modules in any manner, and can be useful separately or in combination. Input/output or I/O devices or user interfaces including but not limited to keyboards, displays, pointing devices, and the like can be coupled to the system either directly or through intervening I/O controllers. Thus, the various aspects of the disclosure may be embodied in many different forms, and all such forms are contemplated to be within the scope of the disclosure.

Figure 4:
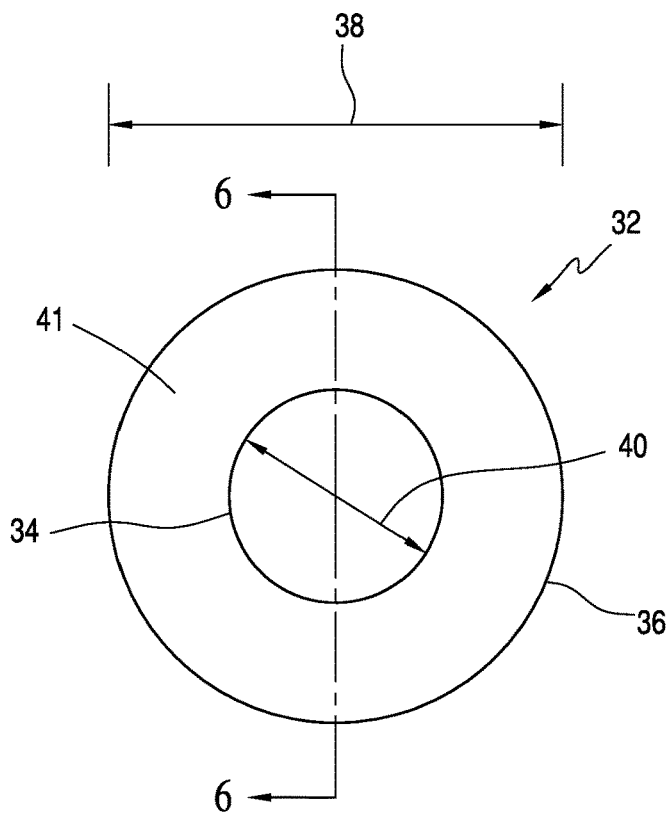
FIG. 4 is a plan view of a passive transdermal delivery device in accordance with an exemplary embodiment of the present disclosure.
Figure 5:
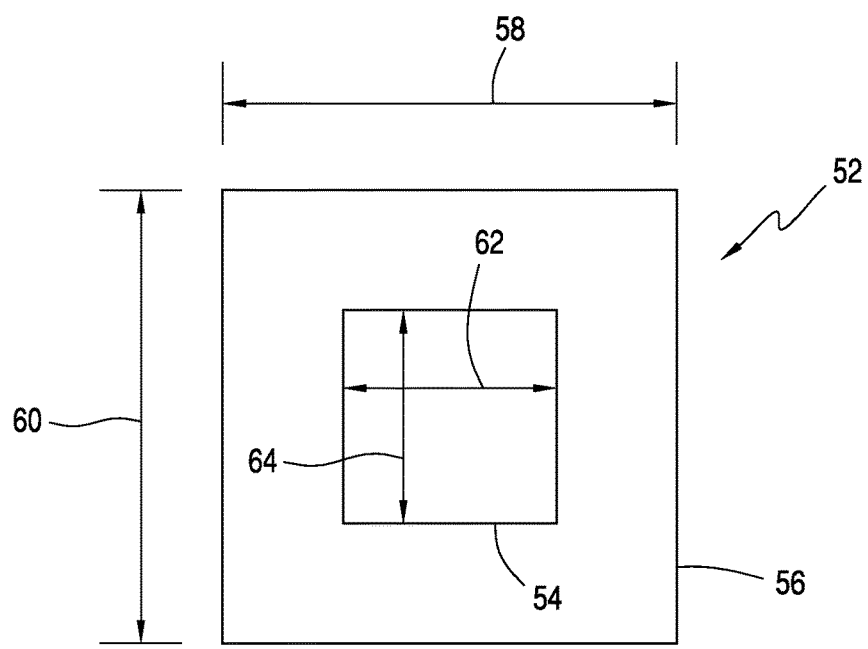
FIG. 5 is a plan view of another passive transdermal delivery device in accordance with an exemplary embodiment of the present disclosure.
Figure 6:
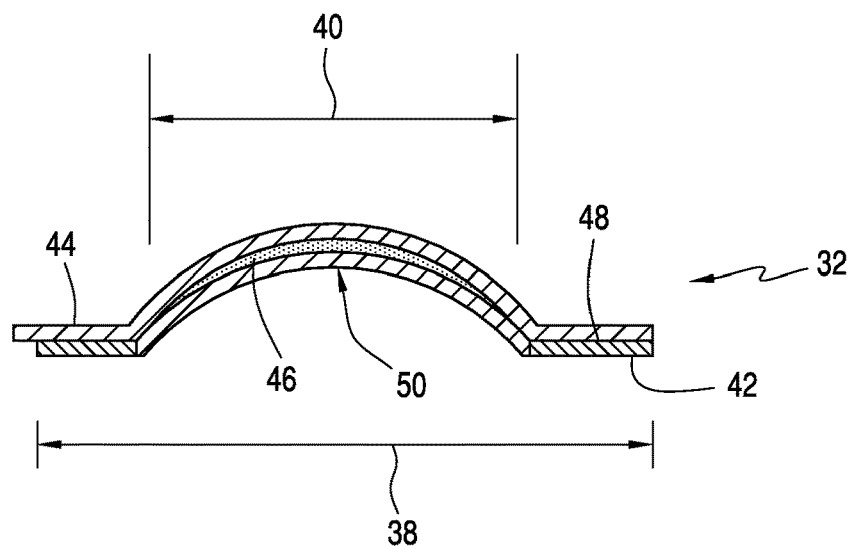
FIG. 6 is a cross-sectional view of the passive transdermal delivery device of FIG. 4 along the lines 6-6.

Basic passive transdermal delivery devices are shown in FIGS. 4-6. A first configuration of a passive transdermal delivery device in accordance with an exemplary embodiment of the present disclosure is shown in FIGS. 4 and 6, indicated generally at 32. In the embodiment of FIG. 4, passive device 32 includes a first portion 34, which may also be described as a drug container or reservoir, and a second portion 36, which may also be described as a border or edge.

Device 32 is configured to include dimensions that are optimized for interfacing with ABTT terminus 10. In an exemplary embodiment, device 32 is configured with a device diameter 38 of less than or equal to about 25 mm. In this exemplary embodiment, drug container 34 includes a diameter 40 of less than or equal to 15 mm. However, in another exemplary embodiment, drug container diameter 40 can also be less than or equal to 10 mm, and in yet another exemplary embodiment, drug container diameter 40 can be less than or equal to 7.5 mm. In yet another exemplary embodiment, device diameter 38 can be less than or equal to 30 mm, and drug container diameter 40 can be less than or equal to 20 mm, less than or equal to 15 mm, less than or equal to 10 mm, or less than or equal to 7.5 mm. In a further exemplary embodiment, device diameter 38 can be less than or equal to 20 mm, and drug container diameter 40 can be less than or equal to 10 mm, or less than or equal to 7.5 mm. In yet a further exemplary embodiment, device diameter 38 can be less than or equal to 10 mm, and drug container diameter 40 can be less than or equal to 2.5 mm. The area outside drug containing area 34 is referred as an edge or border 41, and the dimension of edge or border 41 is associated with the strength of the adhesive. Therefore, an edge with a strong adhesive can be made very small, such as including a width that is equal to or less than 1 mm, for example, and in this embodiment drug containing area 34 can have a diameter (or largest dimension) in a range from 1 mm to 40 mm. It should be noted that the whole surface area (identified as diameter 38) can be covered by an adhesive surface, with the drug disposed behind this surface, and in this embodiment the whole area contains drug and there is not a separate edge with adhesive.

Dimensions of the surface containing drug of the embodiments of the present disclosure can be made smaller as compared to traditional patches or devices because less drug is necessary since ABTT terminus 10 area has the highest permeation rate of the body and there is a direct communication with the blood vessels and direct path to the brain.

The larger diameter 40 of drug container 34 becomes, the easier it is to assure drug placement on ABTT terminus 10. However, the larger diameter 40 becomes, the more uncontrolled delivery of drugs becomes. Accordingly, smaller diameters 40 are preferred for controlled, efficient delivery of drugs located in drug container 34 to ABTT terminus 10. However, a minimum diameter 40 is preferred because the diameter of ABTT terminus 10 is approximately 3 mm to 11 mm, used to define the diameter, and as will be seen, beyond ABTT terminus 10 a layer of fat under the skin reduces the flow rate of drugs into ABTT 12.

The larger diameter 38 of device 32 becomes, the easier it is to handle and place device 32. However, diameter 38 is practically determined by an adjacent eye of a patient or subject, since ABTT terminus 10 is very near to the eye, and most patients or subjects object to the placement of objects on or over the eye. Accordingly, a smaller diameter 38 is preferred for patient comfort, but the smaller diameter 38 becomes, the more difficult it is to handle and place device 32.

FIG. 6 shows an exemplary cross section of device 32 of FIG. 4. Device 32 includes at least a backing or support layer 42 on which is positioned, either directly or indirectly, a protective layer 44. A drug 46 is positioned directly between protective layer 44 and backing layer 42. Protective layer 44 and backing layer 42 may be configured to be impermeable to drug 46, or additional layers may be provided in device 32 to protect protective layer 44 and backing layer 42 from drug 46, or to control flow of drug 46 out of device 32. In an exemplary embodiment, an adhesive layer 48 is also positioned between protective layer 44 and backing layer 42. Adhesive layer 48 is configured to secure device 32 to a patient or subject's skin to permit drug 46 to be directly in contact with the patient or subject's skin to permit the permeation of the skin by drug 46. In an exemplary embodiment, drug 46 is infused into adhesive layer 48, and removal of protective layer 44 exposes adhesive layer 48 and drug 46 such that an exemplary device 32 is configured to be secured to a patient or subject's skin across the entirety of device 32 by adhesive layer 48.

Figure 7:
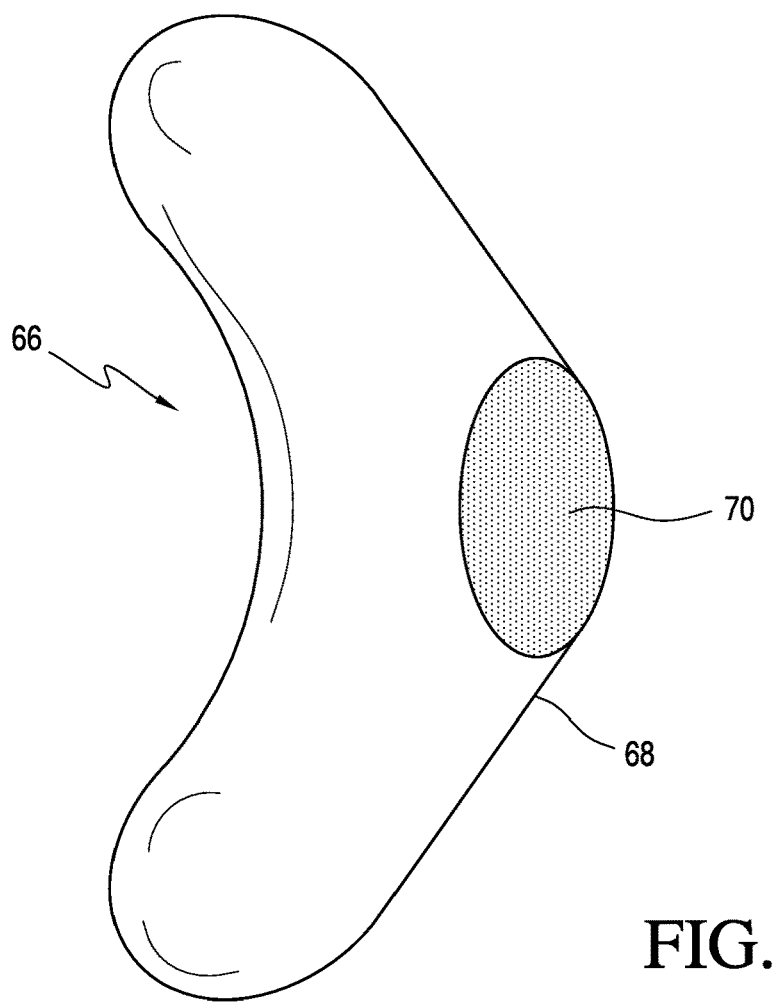
FIG. 7 is a perspective view of yet another passive transdermal delivery device in accordance with an exemplary embodiment of the present disclosure.

In the exemplary embodiment of FIG. 7, device 32 is configured to include a convex curvature 50. Curvature 50 is configured to be an approximate match to the unique curvature of the face at ABTT terminus 10. It should also be understood that each of the disclosed embodiments can or does include a similar curvature to match the area on and adjacent to ABTT terminus 10. It should also be understood that a flat patch or device, including a conventional flat patch or flat bandage are within the scope of the invention. A flat patch or flat device includes flexible areas, or can be flexible in its entirety so as to conform to the geometry and shape of the ABTT terminus 10.

FIG. 5 is a view of another passive transdermal delivery device in accordance with an exemplary embodiment of the present disclosure, indicated generally at 52. Device 52 is configured to be approximately square in a plan view. Similar to device 32, device 52 includes a first portion 54, which may also be described as a drug container or reservoir, and a second portion 56, which may also be described as a border or edge.

Similar to device 32, device 52 is configured to include dimensions that are optimized for interfacing with ABTT terminus 10. In an exemplary embodiment, device 52 is configured with a device width 58 and a device length 60, each of which is less than or equal to about 35 mm. In this exemplary embodiment, drug container 54 includes a container width 62 and a container length 64, each of which is less than or equal to 25 mm. However, in another exemplary embodiment, container width 62 and a container length 64 can each also be less than or equal to 10 mm, and in yet another exemplary embodiment, container width 62 and container length 64 can each be less than or equal to 7.5 mm. In yet another exemplary embodiment, device width 58 and device length 60 can each be less than or equal to 30 mm, and container width 62 and container length 64 can each be less than or equal to 20 mm, less than or equal to 15 mm, less than or equal to 10 mm, or less than or equal to 7.5 mm. In a further exemplary embodiment, device width 58 and device length 60 can each be less than or equal to 20 mm, and container width 62 and container length 64 can each be less than or equal to 10 mm, or less than or equal to 7.5 mm. In yet a further exemplary embodiment, device width 58 and device length 60 can each be less than or equal to 10 mm, and container width 62 and container length 64 can each be less than or equal to 2.5 mm. The area outside the drug containing area is referred as edge or border 56, and the dimension of edge 56 is associated with the strength of the adhesive. Therefore, an edge with a strong adhesive can be made very small, such as equal to or less than 1 mm for example, and in this embodiment, the drug container 54 can have a container width 62 or a container length 64 measuring in a range from 1 mm to 40 mm. It should be noted that the whole surface area, identified by device width 58 and device length 60, can be covered by an adhesive surface, with the drug disposed behind this surface, and in this embodiment the whole area contains drug and there is not a separate edge with adhesive.

The larger container width 62 and container length 64 of drug container 54 become, the easier it is to assure drug placement on ABTT terminus 10. However, the larger container width 62 and container length 64 become, the more uncontrolled delivery of drugs becomes. Accordingly, smaller container widths 62 and container lengths 64 are preferred for controlled, efficient delivery of drugs located in drug container 54 to ABTT terminus 10.

The larger device width 58 and device length 60 of device 52 become, the easier it is to handle and place device 52. However, device width 58 and device length 60 are practically determined by an adjacent eye of a patient or subject, since ABTT terminus 10 is very near to the eye, and most patients or subjects object to the placement of objects on or over the eye. Accordingly, a smaller device width 58 and device length 60 are preferred for patient comfort, but the smaller device width 58 and device length 60 become, the more difficult it is to handle and place device 52.

As described herein, it should be understood that skin without fat is present under ABTT terminus 10, extending about 22 mm along the upper eyelid, and 6 to 7 mm along a line perpendicular to the eyelid, as shown in FIG. 2B, terminating at the superior edge of the eyebrow. A lower eyelid skin surface 17 with a minimal amount of fat is located along the edge of the lower eyelid, and extends about 10 mm from the edge of the lower eyelid, and is also a preferred area for administering drugs transdermally. While this area includes some fat, and does not include a vein, the numerous capillaries in this area feed veins that flow into ABTT 12, such as angular vein 20.

FIG. 7 shows another passive transdermal delivery device in accordance with an exemplary embodiment of the present disclosure, indicated generally at 66. Device 66 is configured to include a shape that is adapted to fit to the curved anatomy of ABTT terminus that may be described by many terms, including kidney, bean, banana, boomerang, comma, curvilinear, and arc. As with the configuration of FIGS. 4 and 6, a portion 68 of device 66 that is configured to interface with ABTT terminus 10 is configured with a convex curvilinear shape, on which is positioned a drug patch or reservoir 70, shown exposed in FIG. 7.

Figure 8:
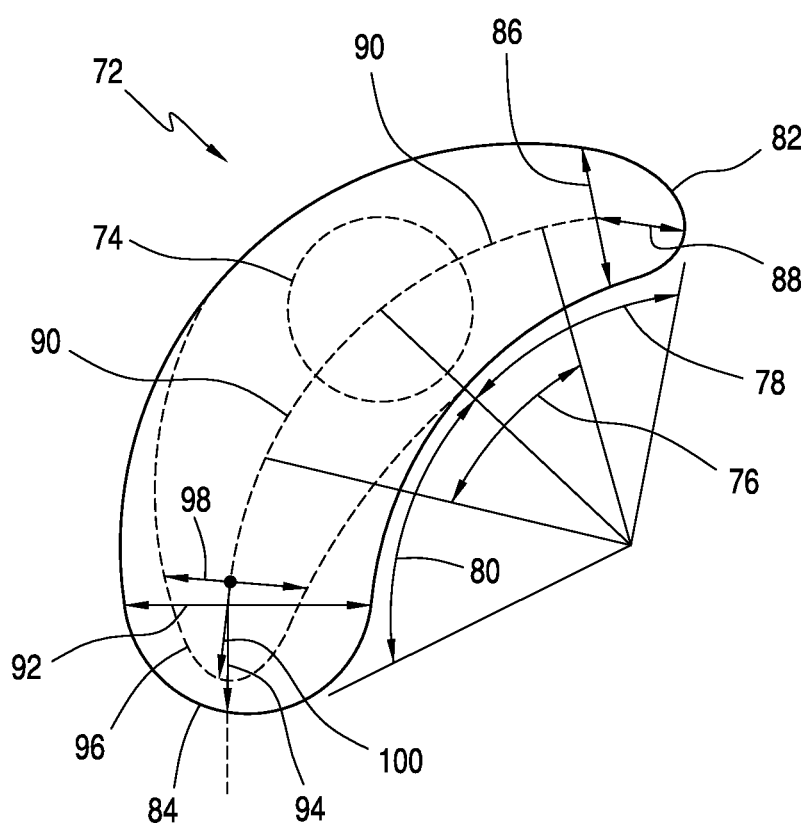
FIG. 8 is a plan view of a general configuration of passive transdermal delivery devices in accordance with an exemplary embodiment of the present disclosure.

FIG. 8 is a view of a general configuration of a transdermal delivery device in accordance with an exemplary embodiment of the present disclosure, indicated generally at 72. Device 72 includes a first, drug container portion 74 is positioned along device 72. Device 72 includes a shape similar to device 66 shown in FIG. 7. In an exemplary embodiment, device 72 extends in an arc 76 of about 60 degrees, centered on drug container portion 74. However, in another exemplary embodiment, device 72 extends in a first arc 78 of at least 50 degrees from a center of drug container portion 74, and a second arc 80 of at least 50 degrees from a center of drug container portion 74. Device 72 further includes a first end 82, which is configured to be positioned in a region between a patient's eye and eyebrow, and a second end 84, which is configured to be positioned in a region between a patient's eye and a patient's nose. In an exemplary embodiment, first end 82 includes a first transverse width 86 positioned a first longitudinal length 88 from first end 82 along a centerline 90 of device 72, and first transverse width 86 is 15 mm±8 mm, and first longitudinal length 88 is 7.5 mm±5 mm. Also in an exemplary embodiment, second end 84 includes a second transverse width 92 positioned a second longitudinal length 94 from second end 84 along centerline 90, and second transverse width 92 is greater than or equal to first transverse width 86 and second longitudinal length 94 is approximately equal to first longitudinal length 94. The effect of these dimensions is that first end 82 is smaller in width than second end 84, giving device 72 a shape similar to an elongated and curved tear drop.

In another exemplary embodiment, device 72 can include a second end 96, shown in dashed lines in FIG. 8, and a third transverse width 98 positioned a third longitudinal distance 100 from second end 96 along centerline 90, wherein third transverse width 98 is approximately equal to first transverse width 86 and third longitudinal distance 100 is approximately equal to first longitudinal length 88. The effect of this configuration is that device 72 attains a shape more similar to a boomerang than a teardrop.

One challenge with transdermal delivery devices is assuring sufficient adherence to the skin on and adjacent to ABTT terminus 10. One solution is to provide sufficient area for adhesive on a device, such as device 72, to adhere to a patient's skin. The exemplary configuration of device 72 includes an elongated shape that extends along centerline 90 for at least twice the diameter of drug container portion 74, in addition to the diameter of drug container portion 74, for a total length along centerline 90 of at least three times the diameter of drug container portion. It should also be understood that a strong adhesive allows decreasing the dimensions of the area surrounding the drug area, as described herein.

One way to define an inner and outer dimension of a transdermal delivery device is by using two circles.

Figure 9:
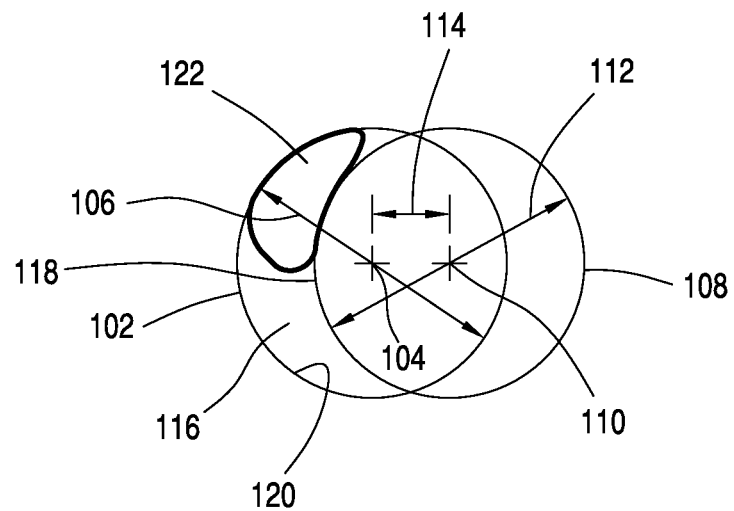
FIG. 9 is a view of two overlapping circles used to define the limits of a transdermal delivery device in accordance with an exemplary embodiment of the present disclosure.

In an exemplary embodiment shown in FIG. 9, a first circle 102 including a first center or origin 104 and a first diameter 106 is overlapped by a second circle 108 including a second center or origin 110 and a second diameter 112. In an exemplary embodiment, first diameter 106 is greater than or equal to second diameter 112, with first diameter 106 being in a range 15 mm to 50 mm, and second diameter 112 being in a range 8 mm to 50 mm. Second center or origin 110 is offset from first center or origin 104 by an offset distance 114 that is determined by first diameter 106 and second diameter 112, which determines a gap or width 116 between an exterior 118 of second circle 108 and an interior 120 of first circle 102. The choices of first diameter 106, second diameter 112, and offset distance 114, along with a design position 122 for a transdermal delivery device, is determined at least partially by a desired width of a drug container or reservoir. In an exemplary embodiment, gap or width 116 will be configured to provide a drug container or reservoir width of at least 3 mm. In yet another exemplary embodiment, second diameter 112 is approximately one half first diameter 106. It should be understood that the dimensions of the drug container or reservoir can have any dimension that fits between the eye and eyebrow and that includes the ABTT terminus 10 or any of the veins 14, 16, 18, 20, and 22.

Figure 10:
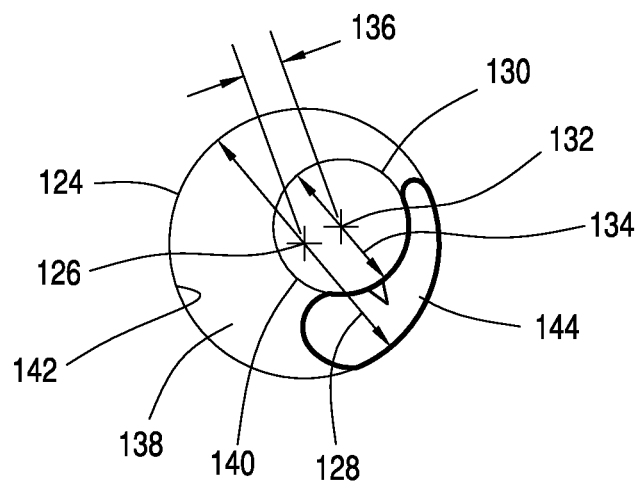
FIG. 10 is a view of two non-overlapping circles used to define the limits of a transdermal delivery device in accordance with an exemplary embodiment of the present disclosure.

In another exemplary embodiment shown in FIG. 10, a second circle 130 including a second center or origin 132 and a second diameter 134 is positioned within a first circle 124 including a first center or origin 126 and a first diameter 128. In an exemplary embodiment, first diameter 128 is greater than or equal to second diameter 134, with first diameter 128 being in a range 10 mm to 60 mm, and second diameter 134 being in a range 5 mm to 50 mm. Second center or origin 132 is offset from first center or origin 126 by an offset distance 136 that is determined by first diameter 128 and second diameter 134, which determines a gap or width 138 between an exterior 140 of second circle 130 and an interior 142 of first circle 124. The choices of first diameter 128, second diameter 134, and offset distance 136, along with a design position 144 for a transdermal delivery device, is determined at least partially by a desired width of a drug container or reservoir. In an exemplary embodiment, gap or width 138 will be configured to provide a drug container or reservoir width of at least 3 mm. In yet another exemplary embodiment, second diameter 134 is approximately one half first diameter 128. A tear drop shape as previously described is included in this embodiment. Preferably, the whole surface of the tear drop and boomerang embodiments of FIGS. 8-10 contain drug, and in these embodiments, the drug surface includes an adhesive.

Figure 11:
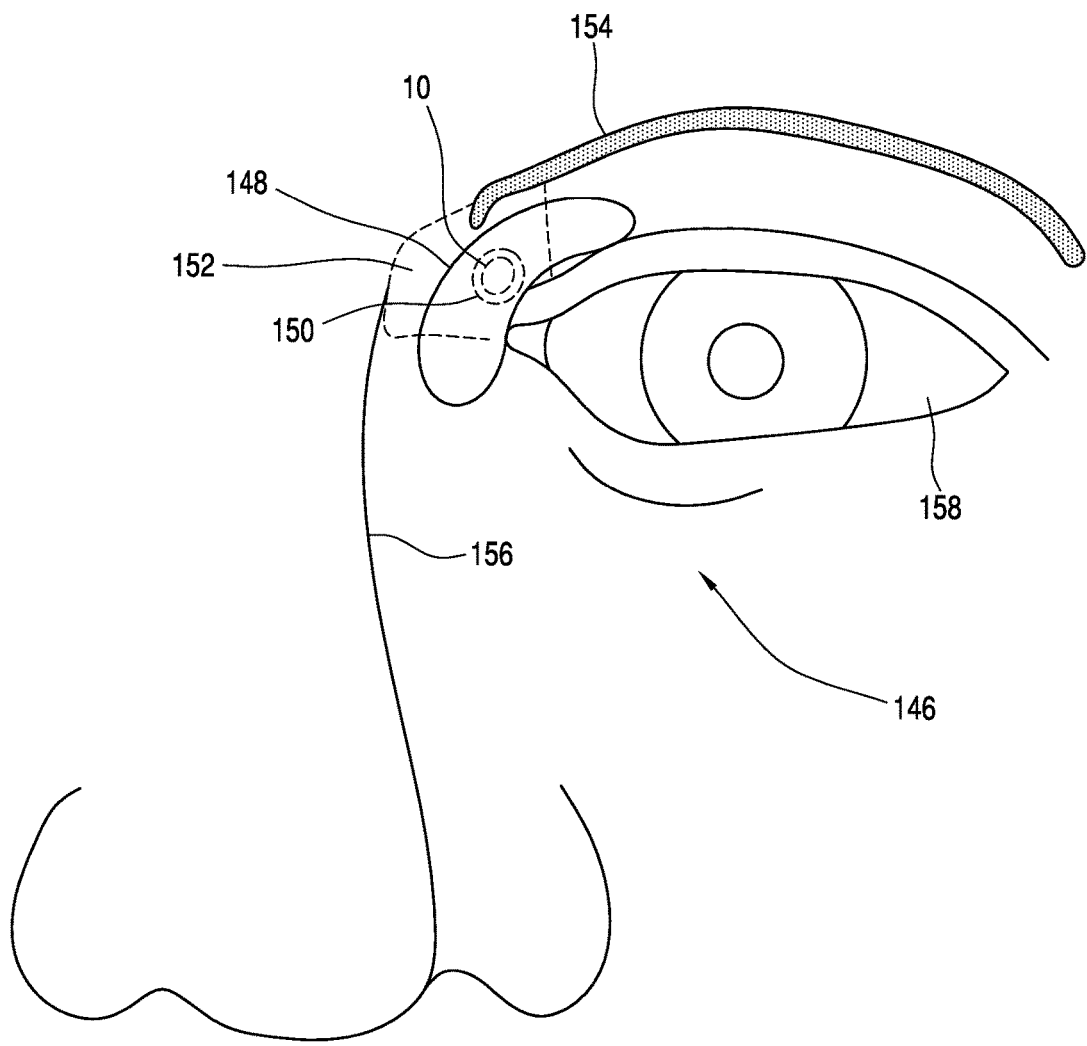
FIG. 11 is a view of a further transdermal delivery device in accordance with an exemplary embodiment of the present disclosure positioned on a subject or patient's face.

FIG. 11 is a view of a patient or subject's face 146 on which is positioned a passive transdermal delivery device 148 configured in accordance with an exemplary embodiment of the present disclosure. Transdermal drug delivery device 148 includes a drug delivery region 150 that can be larger than ABTT terminus 10, but preferably needs to be in a region 152 bounded by eyebrow 154, nose 156, and eye 158, where ABTT terminus 10 is located. Drug delivery region or portion 150, though shown in phantom lines in FIG. 11 as a circular shape, can be other shapes, such as kidney, polygonal, etc., as long as region 150 substantially overlaps ABTT terminus 10. In the context of this disclosure, substantially overlaps is preferably an overlap of ABTT terminus 10 by drug delivery region 150 of at least 80%, though an overlap as low as 50% can still provide a therapeutically effective dose in some situations. The goal in every case should be a 100% overlap of ABTT terminus 10 by drug delivery region 150.

It should be understood that the drug delivery area does not need to be exactly overlying ABTT terminus 10, but can be located adjacent to ABTT terminus 10, since drug entering the skin in the region adjacent to ABTT terminus 10 will be carried towards ABTT terminus 10. The adjacent areas vary with the location on the face. As shown in FIG. 2B, a first adjacent area 21 extends over a diameter of about 35 mm centered on ABTT terminus 10, excluding eye 31. A second adjacent area 23 extends superiorly about 25 mm from first adjacent area 21 along front vein 14. A third adjacent area 25 extends transversely or laterally about 25 mm from second adjacent area 23 along supraorbital vein 18. A fourth adjacent area 27 extends transversely or laterally about 30 mm from first adjacent area 21. A fifth adjacent area 29 extends about 30 mm along angular vein 20 from first adjacent area 21 and about 25 mm along lower eyelid skin surface 17 from first adjacent area 21. It should be understood that while application of transdermal delivery devices applied in the aforementioned adjacent areas provide drug delivery to veins or capillaries that flow into ABTT 12, the further these areas are from ABTT terminus 10, the less effective drug application becomes. Accordingly, the smallest possible distance from ABTT terminus 10 is preferred for drug delivery. Thus, while first adjacent area 21 can be 35 mm in diameter, a smaller diameter centered on ABTT terminus 10 is preferred, such as a diameter of about 30 mm, 25 mm, 20 mm, or less.

FIGS. 12 and 13 are views of a passive transdermal delivery device in accordance with an exemplary embodiment of the present disclosure, indicated generally at 160. Device 160 includes a device support 162 that serves to provide structure and support for the various elements of device 160. Device 160 further includes a drug container or reservoir 164 positioned on device support 162 in a location that locates drug container 164 over ABTT terminus 10 when device 160 is placed as shown, for example, in FIG. 11. Drug container 164 is covered prior to use by a removable or peelable layer 166, which may also be described as a release liner, which protects drug container 164 and protects people coming into contact with device 160 from the drug in drug container 164. Removable layer 166 is adhered to device 160 by an adhesive layer 168 positioned between device support 162 and removable layer 166. Removable layer 166 can be configured to include a tab 170 that is without or absent adhesive to enable a user to grasp a portion of removable layer 166 more easily to separate removable layer 166 from device 160. Once removable layer 166 is separated from device 160, the drug located in drug container 164 is exposed and ready for application to ABTT terminus 10 for transdermal delivery through ABTT terminus 10 to ABTT 12.

While drug container 164 is shown as a bubble or unified structure, it should be understood that a deliverable drug may also be infused or available in adhesive layer 168. Further, in the exemplary embodiment of FIG. 13, the drug located in drug container 164 may be activated by a separate chemical once removable layer 166 is separated from device 160. For example, alcohol, water, a liquid permeability enhancer, or another activation compound may be applied to the drug in drug container 164 prior to placement of device 160 on a patient or subject.

FIGS. 14 and 15 are views of another passive transdermal delivery device in accordance with an exemplary embodiment of the present disclosure, indicated generally at 172. Device 172 includes features that may be similar to device 160, including a support 174 that can be similar to device support 162, a drug container or reservoir 176 positioned on device support 174 in a location that locates drug container 176 over ABTT terminus 10 when device 172 is placed as shown, for example, in FIG. 11. Drug container 176 is covered prior to use by a removable or peelable layer 178 that protects drug container 176 and protects people coming into contact with device 172 from the drug in drug container 176. Removable layer 178 is adhered to device 172 by an adhesive layer 168 positioned between device support 174 and removable layer 178. Removable layer 178 can be configured to include a tab 170 that is without or absent adhesive to enable a user to grasp a portion of removable layer 178 more easily to separate removable layer 178 from device 172. Once removable layer 178 is separated from device 172, the drug located in drug container 176 is exposed and ready for application to ABTT terminus 10 for transdermal delivery through ABTT terminus 10 to ABTT 12.

Device 172 includes an absorbent layer 180 positioned between device support 174 and drug container 176. The drug located in drug container 176 may be activated by a separate chemical once removable layer 178 is separated from device 172. For example, alcohol, water, a liquid permeability enhancer, or another activation compound may be applied to the drug in drug container 164 prior to placement of device 160 on a patient or subject. However, absorbent layer 180 is configured to absorb the separate chemical and then to activate the drug by enhancing permeation, such as, for example, by adding ethanol, including by liquefying the drug, or infusing the drug with a liquid to improve permeability with skin. In the embodiment of FIG. 15, the drug may go through a phase change or soften from a portion of the drug that is away from the skin of a patient, which provides a mechanism to control the initial rate of drug flow into a patient that is different from the embodiment of FIG. 13.

Figure 17:
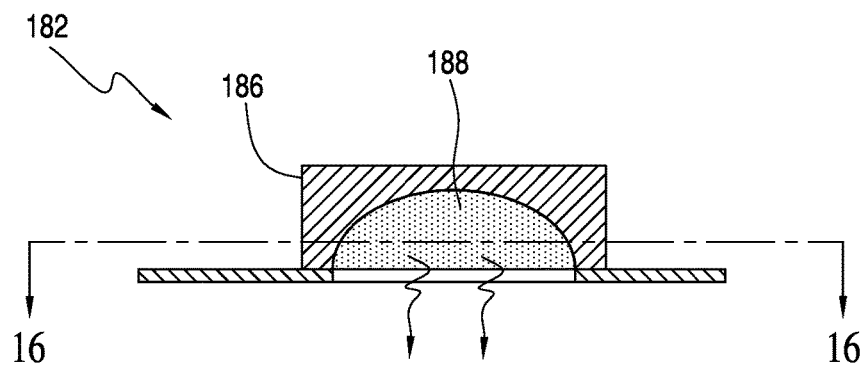
FIG. 17 is a cross-sectional view of the transdermal delivery device of FIG. 16 along the lines 17-17, as though the device in FIG. 16 were whole.
Figure 16:
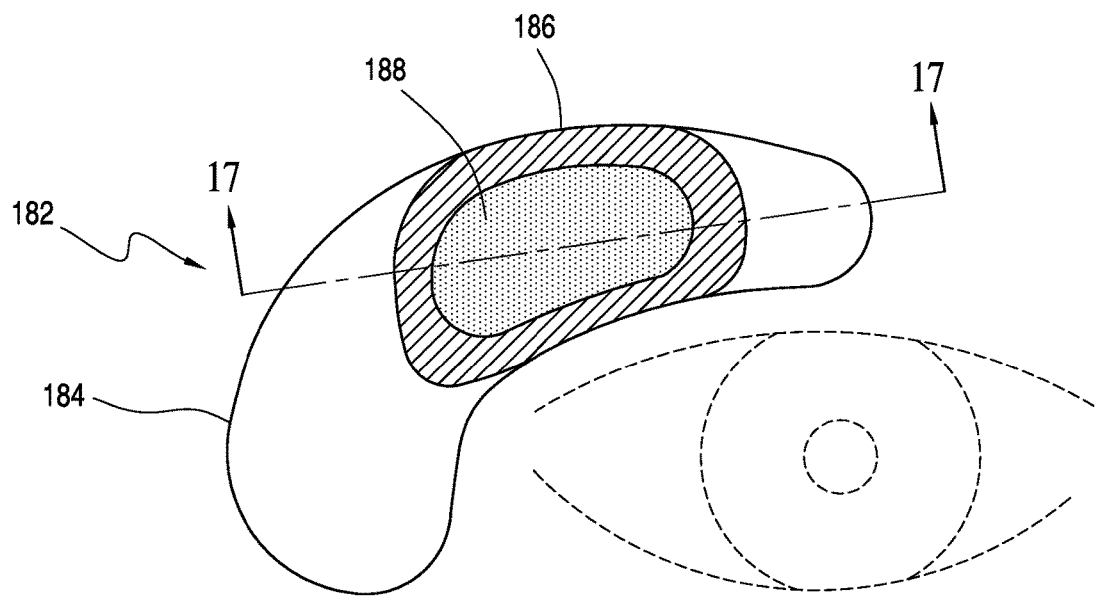
FIG. 16 is a cross-sectional view of a transdermal delivery device in accordance with an exemplary embodiment of the present disclosure, along the lines 16-16 in FIG. 17, as though the device in FIG. 17 were whole.

FIGS. 16 and 17 are views of a passive transdermal delivery device in accordance with an exemplary embodiment of the present disclosure, indicated generally at 182. Device 182 includes a support 184 on which is located a drug container or reservoir 186. When a removable or peelable layer (not shown in this embodiment) is separated from device 182, a drug 188 is accessible from an exterior of device 182 and is able to flow through ABTT terminus 10 when device 182 is positioned such that drug container 186 is positioned on, over, or adjacent to ABTT terminus 10.

Figure 18:
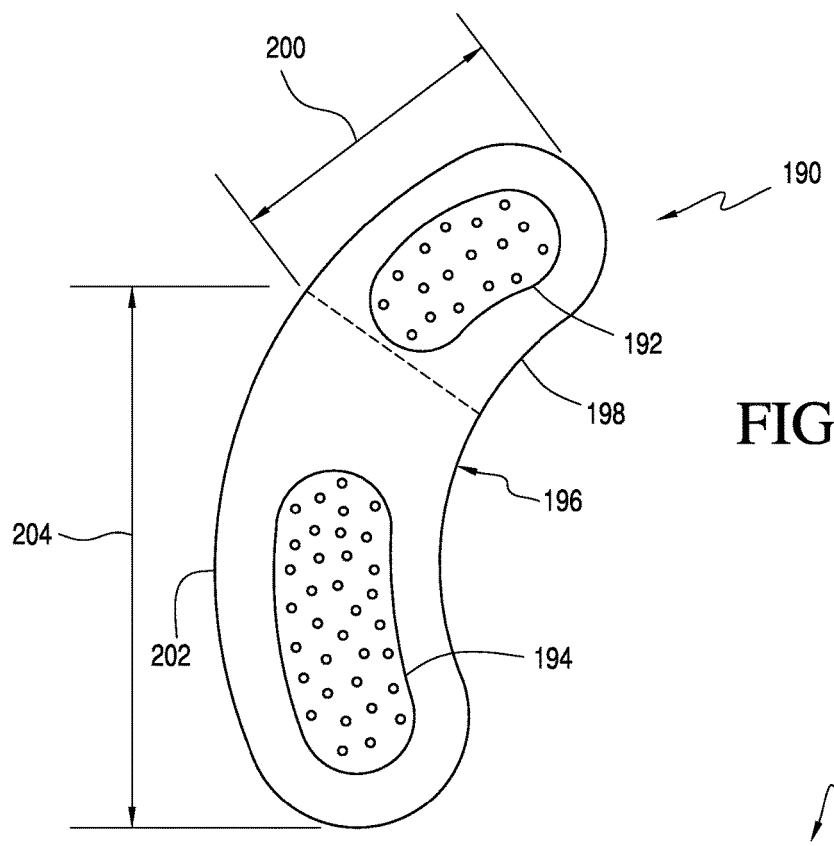
FIG. 18 is a plan view of a transdermal delivery device configured to include two drug containers, in accordance with an exemplary embodiment of the present disclosure.

FIG. 18 is a view of another passive transdermal delivery device in accordance with an exemplary embodiment of the present disclosure, indicated generally at 190. Device 190 includes a first drug container or reservoir 192 and a second drug container or reservoir 194 positioned on a support 196. First drug container 192 is positioned on a first portion 198 of device support 196, and when device 190 is positioned on a patient or subject's face, first drug container 192 is configured to be positioned at least on ABTT terminus 10, and can extend to cover a portion of superior palpebral vein 16. In an exemplary embodiment, a first portion length 200 of first portion 198 is equal to or less than 30 mm. In another exemplary embodiment, first portion length 200 is equal to or less than 20 mm. In a further exemplary embodiment, first portion length 200 is equal to or less than 15 mm. In yet another exemplary embodiment, first portion length 200 is equal to or less than 5 mm. Second drug container 194 is positioned on a second portion 202 of device support 196, and when device 190 is positioned on a patient or subject's face, second drug container 194 is configured to be positioned to extend along a portion of angular vein 20. In an exemplary embodiment, second portion length 204 is greater than or equal to 5 mm. In another exemplary embodiment, second portion length 204 is greater than or equal to 15 mm. In yet another exemplary embodiment, second portion length 204 is greater than or equal to 25 mm. In a further exemplary embodiment, second portion length 204 is greater than or equal to 40 mm. Device 190 also includes a removable or peelable portion that has been removed to better show certain features of FIG. 18. While drug delivery to ABTT terminus 10 is preferred due to the lack of fat under ABTT terminus 10, in some situations the amount of drug needed is such that more transdermal drug flow is required than ABTT terminus 10 alone can provide. In such situations, including any device of the present disclosure that overlies de area of any of the veins 14, 16, 18, 20, and 22 may augment the effect and the amount of drug delivered to the brain via ABTT 12.

Figure 19:
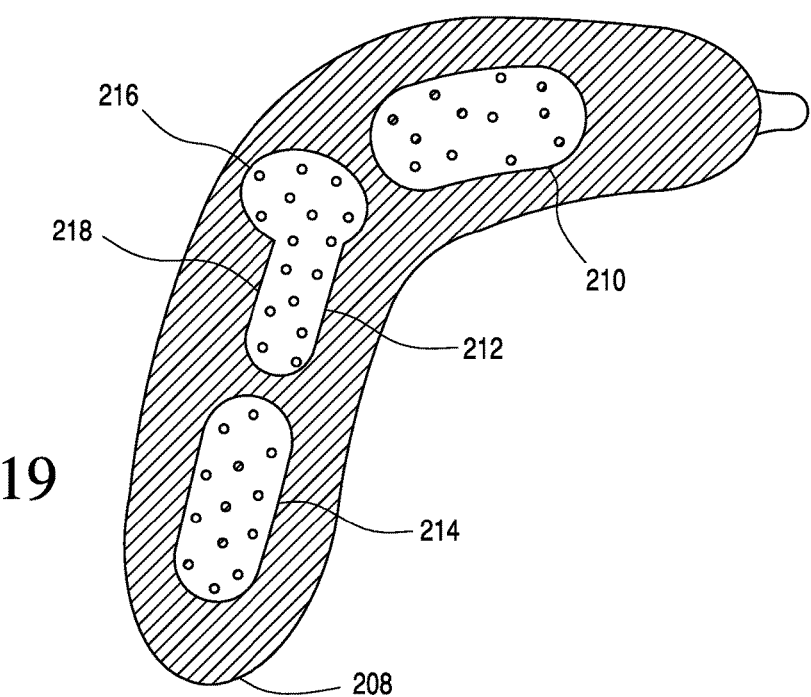
FIG. 19 is a plan view of a transdermal delivery device configured to include three drug containers, in accordance with an exemplary embodiment of the present disclosure.

FIG. 19 is a view of a passive transdermal delivery device in accordance with an exemplary embodiment of the present disclosure, indicated generally at 206. Device 206 includes a support 208, and support 208 includes a first drug container or reservoir 210, a second drug container or reservoir 212, and a third drug container or reservoir 214, positioned thereon. Second drug container 212 includes an ABTT interface portion 216 and an angular vein interface portion 218. When device 206 is positioned on a subject or patient's face such that ABTT interface portion 216 is located on the subject or patient's ABTT terminus 10, angular vein interface portion 218 extends along the subject or patient's angular vein 20. First drug container 210 is positioned on device support 208 such that first drug container 210 is located on, over, or adjacent to at least a portion of superior palpebral vein 16 when device 206 is positioned on a patient or subject's face in an orientation such as that shown in FIG. 11. Third drug container 214 is positioned on device support 208 such that third drug container 214 is located on, over, or adjacent to at least a portion of angular vein 20 when device 206 is positioned on a patient or subject's face in an orientation such as that shown in FIG. 11.

Figure 20:
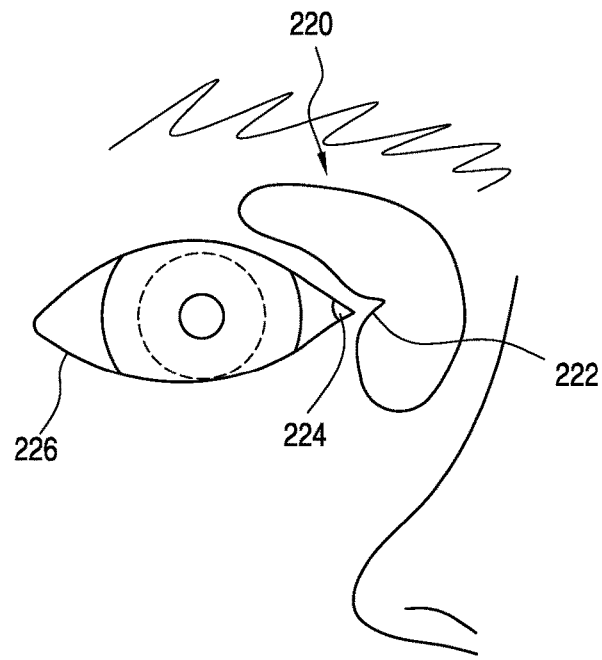
FIG. 20 is a plan view of a transdermal delivery device, in accordance with an exemplary embodiment of the present disclosure.

FIG. 20 is a view of a transdermal delivery device in accordance with an exemplary embodiment of the present disclosure, indicated generally at 220. The transdermal delivery devices disclosed herein can be a challenge to properly place for some individuals, and for those inexperienced in positioning devices on ABTT terminus 10, given its size and location. To assist in placement of the various devices disclosed herein, a notch or indicator 222 may be located to align device 220 with a facial feature, such as a corner 224 of an eye 226.

Figure 21:
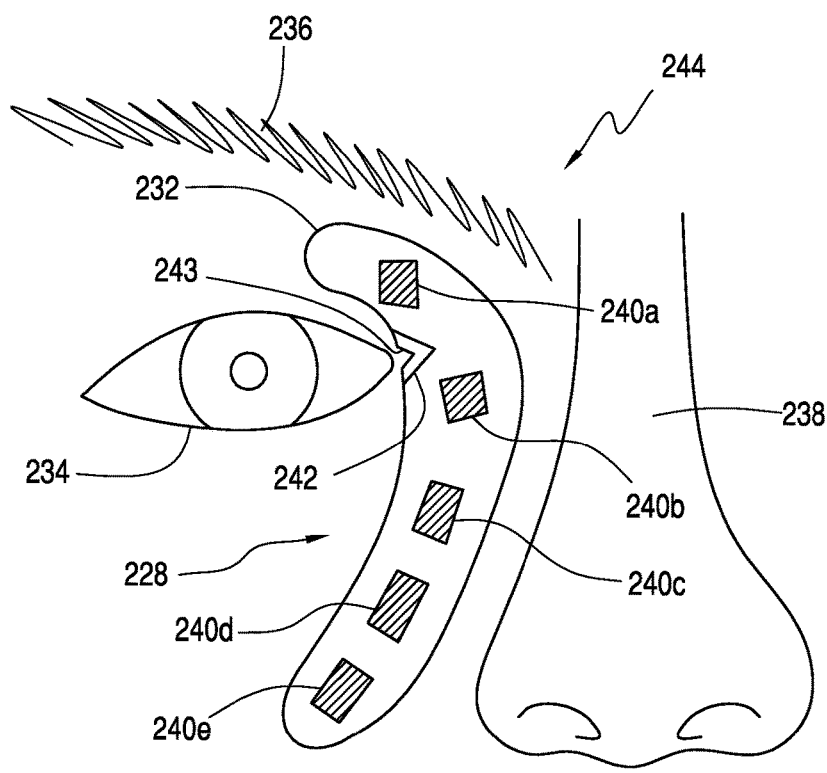
FIG. 21 is a plan view of a transdermal delivery device positioned on a face of a subject or patient, in accordance with an exemplary embodiment of the present disclosure.

FIG. 21 is a view of another passive transdermal delivery device in accordance with an exemplary embodiment of the present disclosure, indicated generally at 228. Device 228 includes a support 230 that extends from a region 232 between an eye 234 and an eyebrow 236, over ABTT terminus 10, and then alongside a nose 238. Positioned on device support 230 is a plurality of drug containers or reservoirs 240a-e that may be configured as round, elliptical, or elongated, as shown herein, or may be square or rectangular, as shown in FIG. 21. Device 228 can also include an alignment aid, such as an indicator 242 or notch 243. In the exemplary embodiment of FIG. 21, drug container 240a configured to be positioned on, over, or adjacent ABTT terminus 10 when device 228 is properly positioned on a patient or subject's face 244. Drug containers 240b-e are configured to be positioned on, over, or adjacent angular vein 20 when device 228 is properly positioned on face 244, to augment the flow of drugs into ABTT 12. Alternatively, a thermoelectric device can be included with each drug container 240a-e, making device 228 an active device.

Figure 22:
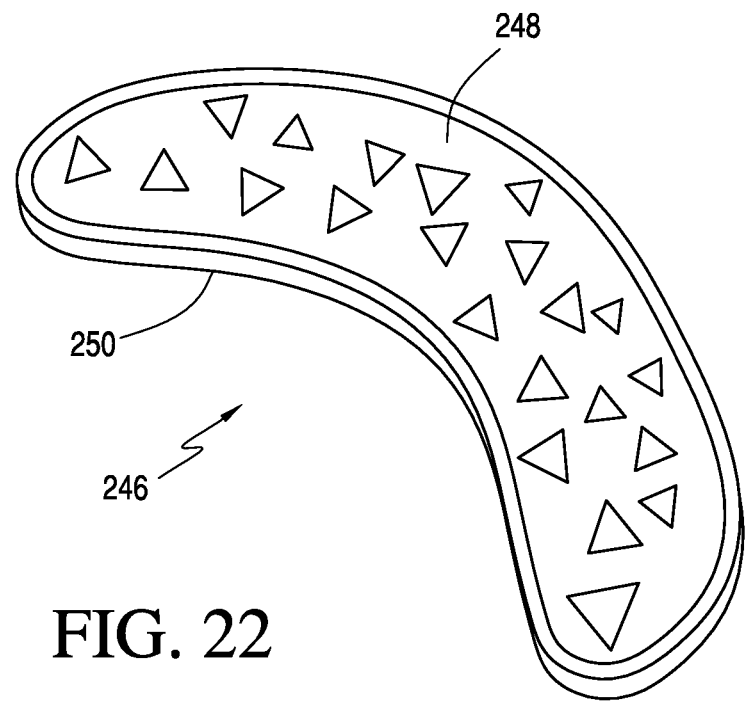
FIG. 22 is a perspective view of a transdermal delivery device in accordance with an exemplary embodiment of the present disclosure.
Figure 23:
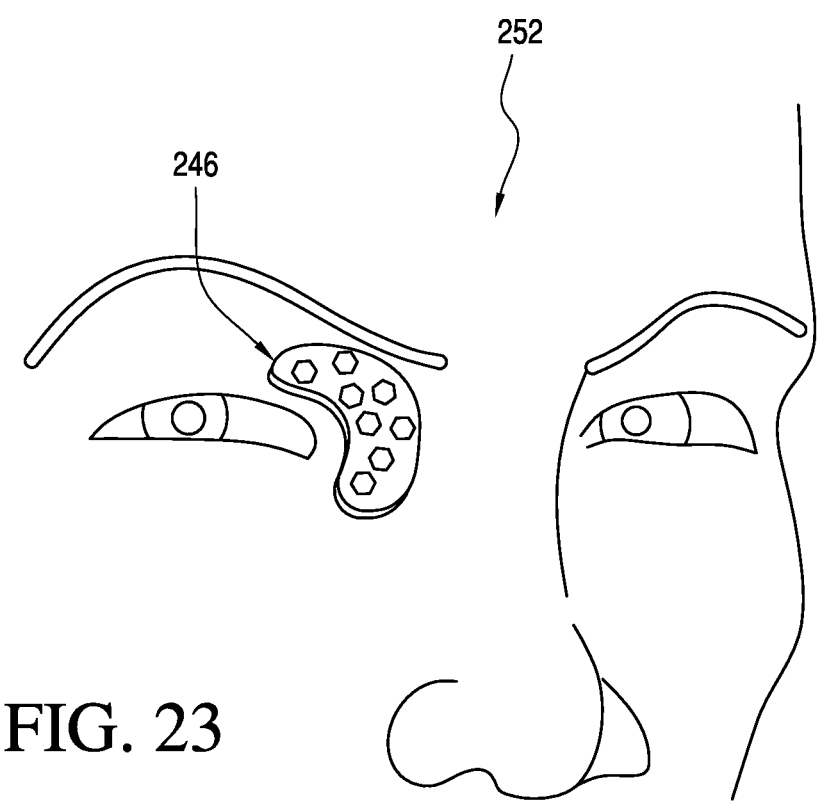
FIG. 23 is a view of a patient or subject's face with the transdermal delivery device of FIG. 22 positioned on the patient or subject's ABTT terminus.

FIG. 22 is a perspective view of a passive transdermal delivery device in accordance with an exemplary embodiment of the present disclosure, indicated generally at 246. Device 246 includes a first, drug delivery side 248, and a second, support side 250. Device 246 further includes a removable or peelable portion that has been removed to show drug delivery side 248. In the embodiment of FIG. 22, drugs are configured to extend over most or all of first, drug delivery side 248. The configuration of device 246 increases the likelihood of placement of device 246 over ABTT terminus 10, though some drugs may permeate areas of a patient or subject's face that are less effective than ABTT terminus 10. FIG. 23 is a view of device 246 positioned on a patient or subject face 252.

Figure 24:
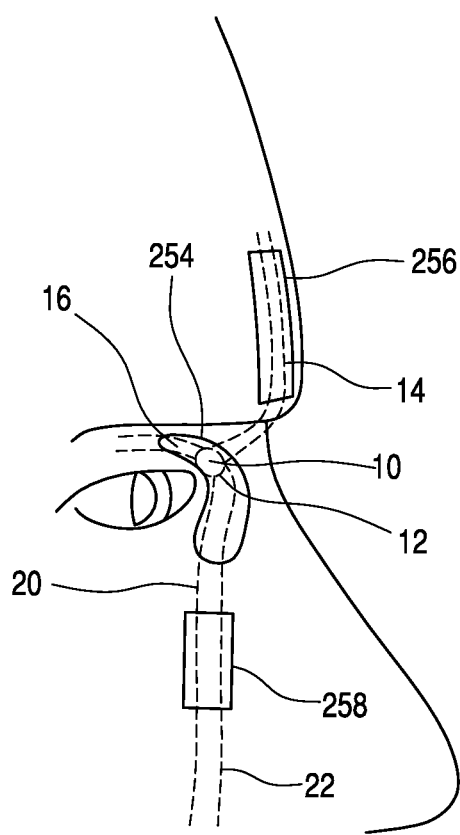
FIG. 24 is a side view of a patient or subject's face with a plurality of transdermal delivery devices positioned thereon, in accordance with an exemplary embodiment of the present disclosure.

FIG. 24 is a side view of a patient's face on which are positioned a plurality of passive transdermal delivery devices in accordance with an exemplary embodiment of the present disclosure. A first transdermal delivery device 254, which may be similar or identical to any of the transdermal delivery devices configured to be positioned on ABTT terminus 10, shown in phantom lines in FIG. 24, and compatible with the other transdermal delivery devices associated with this embodiment, is configured to be positioned to deliver drugs to ABTT terminus 10, at least a portion of superior palpebral vein 16, shown in phantom lines in FIG. 24, and at least a portion of angular vein 20, also shown in phantom lines in FIG. 24. A second transdermal delivery device 256 is positioned on the skin along and over at least a portion of frontal vein 14 and/or supraorbital vein 18, shown in phantom lines in FIG. 24. A third transdermal delivery device 258 is positioned along and over at least a portion of angular vein 20. As has been described herein, frontal vein 14, superior palpebral vein 16, and angular vein 20 all feed into ABTT 12, shown in phantom in FIG. 24, and then into the core of the human brain. While ABTT terminus 10 provides a unique location for transdermal delivery of drugs given the lack of fat, and the minimal thickness of the skin in this location, the amount of drugs needed may be such that transdermal delivery to ABTT terminus 10 only is insufficient for a therapeutically effective dosage, in the event that a large amount of drugs need to be administered or when there is a need for extended period for drug release. Accordingly, additional drugs can be delivered to ABTT 12 by way of veins 14, 16, 18, and 20/22, all of which make use of the direct connection of these veins to ABTT 12 and the core of the brain. In these embodiments, the drug delivery device may lie adjacent to the nose when overlying angular vein 20, below the nose when overlying facial vein 22, between the eyebrow and on the forehead when overlying the frontal vein 14, along the inferior edge of the eyebrow, in the region of the upper eyelid, when overlying the superior palpebral vein 16, and along the superior edge of the eyebrow on the forehead region when overlying the supraorbital vein 18. The additional drug delivery devices provide an increased quantity of drugs, and because the permeation rate is lower through the skin over veins 14, 16, 18, and 20/22, the drugs in devices in those locations provide drugs for a longer period.

FIG. 25 is a view of a patient or subject's face 260 with a passive transdermal delivery device in accordance with an exemplary embodiment of the present disclosure positioned thereon, indicated generally at 262. Device 262 is configured as a triangular shape, and is configured to include a drug delivery region or portion 264 that extends over substantially the entire surface of device 262. In the context of this embodiment, substantially is at least 90% of the surface of device 262. Though an arc, banana, bean, etc., shape, such as that shown in FIG. 23, provides a relatively good match with the unique geometry of the face around ABTT terminus 10, other shapes can also provide an acceptable match with this geometry, such as a triangle. The triangular shape of device 262 is configured to extend into a first region 266 between an eyebrow 268 and an eye 270, and into a second region 272 between a nose 274 and eye 270.

FIG. 26 is a view of face 260 with another passive transdermal delivery device in accordance with an exemplary embodiment of the present disclosure positioned thereon, indicated generally at 276. Device 276 is triangular, similar to device 262, and is positioned generally in the same location as device 262. However, device 276 is configured to include a drug delivery container, reservoir, or region 278 that is configured to be positioned on, over, or adjacent to ABTT terminus 10 when device 276 is properly positioned on face 260. Additionally, drug delivery container 278 is sized and dimensioned to be the approximate size of ABTT terminus 10. Device 276 is further configured to include a notch or indicator 280 to assist with the positioning of device 276.

FIG. 27 is a view of face 260 with yet another passive transdermal delivery device in accordance with an exemplary embodiment of the present disclosure positioned thereon, indicated generally at 282. Device 282 is configured with a triangular portion 284 on the portions of device 282 that extend along eyebrow 268 and nose 274, and an arced portion 286 on the portions of device 282 that extend along eye 270. Thus, exemplary transdermal delivery devices may combine the geometry of more than one embodiment disclosed herein effectively to take advantage of the various disclosed embodiments. Device 282 further includes a drug container, reservoir, or delivery portion 288 that extends over substantially an entire side of device 282 that interfaces with the skin of face 260 in an area around ABTT terminus 10.

Figure 28:
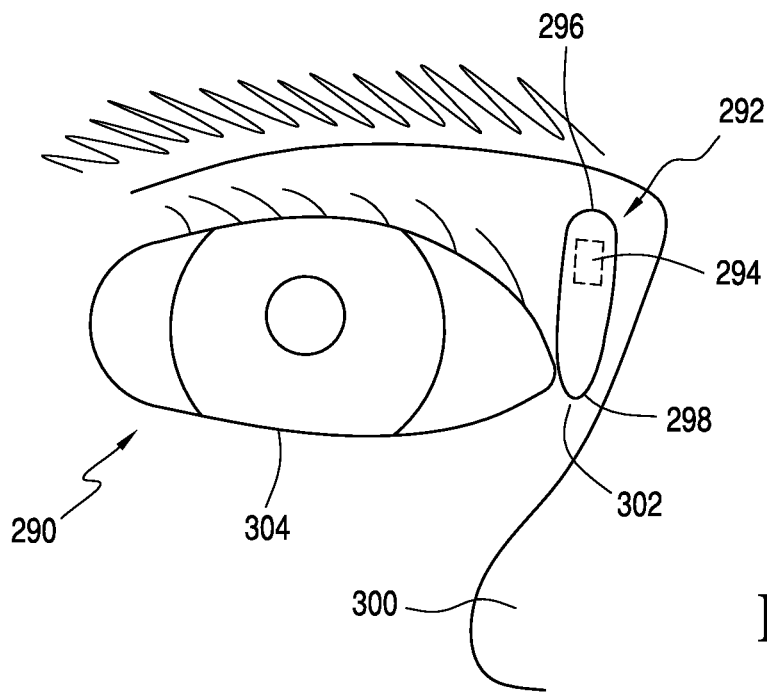
FIG. 28 is a view of a patient or subject's face with a further transdermal delivery device in accordance with an exemplary embodiment of the present disclosure positioned thereon.

FIG. 28 is a view of a patient or subject's face 290 with a further passive transdermal delivery device in accordance with an exemplary embodiment of the present disclosure positioned thereon, indicated generally at 292. Device 292 includes a drug container or reservoir 294 configured to be positioned on ABTT terminus 10. Device 292 includes a shape that can be described as elongated or elliptical, with drug container 294 positioned closer to a first end 296 of device 292 than a second end 298 of device 292. Device 292 extends downwardly on face 290 alongside a nose 300 in a region 302 between nose 300 and an eye 304.

Figure 29:
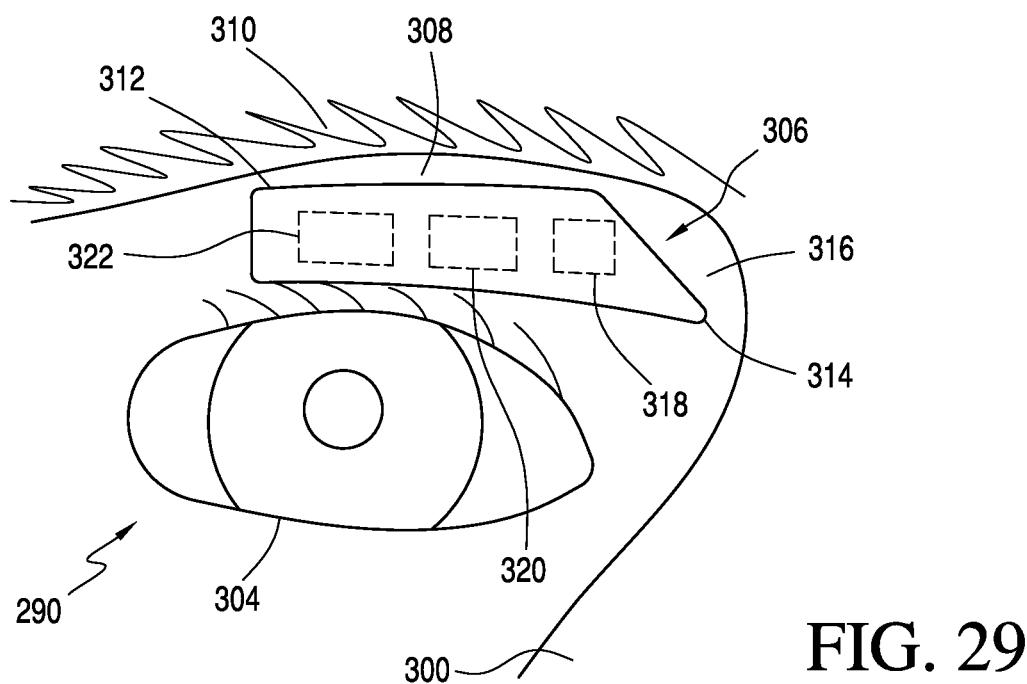
FIG. 29 is a view of a patient or subject's face with a still further transdermal delivery device in accordance with an exemplary embodiment of the present disclosure positioned thereon.

FIG. 29 is a view of face 290 with a still further transdermal delivery device in accordance with an exemplary embodiment of the present disclosure positioned thereon, indicated generally at 306. Device 306 is configured to extend along a region 308 located between eye 304 and an eyebrow 310. Device 306 includes a first portion 312 that is approximately rectangular in shape and a second portion 314 that includes a triangular shape configured to extend into a corner region 316 bounded by eyebrow 310, nose 300, and eye 304. Device 306 includes a first drug container 318, a second drug container 320, and a third drug container 322, all of which are shown with hidden lines, extending along the longitudinal length of device 306. First drug container 318 is configured to be positioned on ABTT terminus 10. Second drug container 320 and third drug container 322 are configured to be positioned on a portion of superior palpebral vein 16 when device 306 is located on face 290. Device 306 may include a single removable or peelable portion, or it may include a plurality of removable portions, with at least one portion associated with at least one drug container. The benefit of such a configuration is that it permits significant variation in drug doses to be applied to the face for delivery into ABTT 12.

Figure 30:
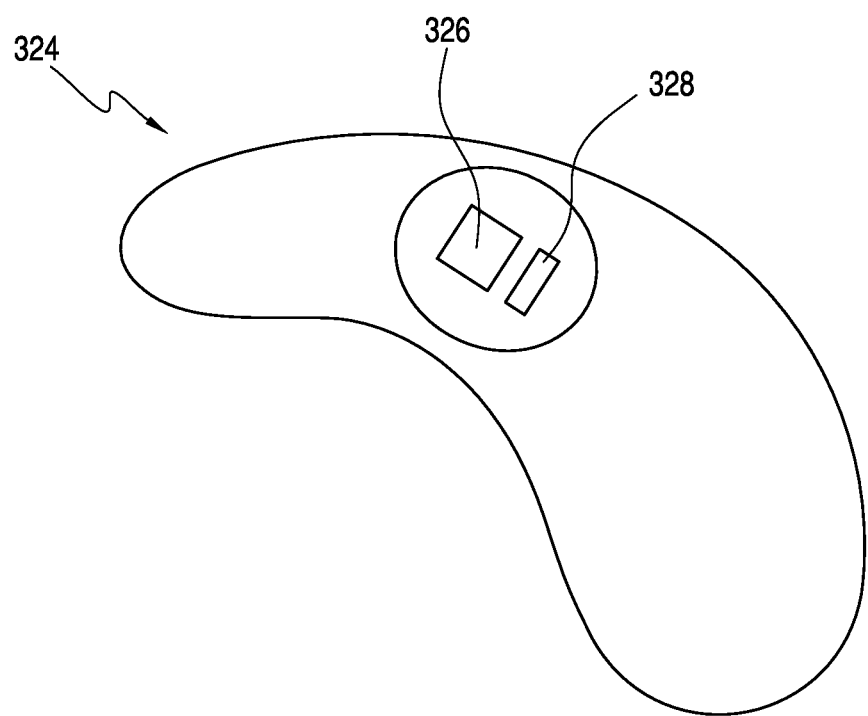
FIG. 30 is a view of a passive transdermal delivery device configured to simultaneously delivery two different drugs, in accordance with an exemplary embodiment of the present disclosure.

FIG. 30 is a plan view of a passive transdermal delivery device configured to simultaneously delivery two different drugs, in accordance with an exemplary embodiment of the present disclosure, indicated generally at 324. Device 324 is configured with a first drug delivery container 326 and a second drug delivery container 328, both of which are configured to be positioned over ABTT terminus 10 at the same time. When a removable strip (not shown) is separate from device 324, the drugs in first container 326 and second container 328 are available to be positioned in contact with the skin of a patient or subject. First container 326 and second container 328 can be identical in size with a different skin permeability, effectively modifying the ratio of drugs delivered to a patient or subject's ABTT 12. First container 326 and second container 328 can be configured to have different cross-sectional areas, as shown in FIG. 30, with approximately the same skin permeability, which then delivers two different quantities of the drugs in first container 326 and second container 328 through the skin of a patient into ABTT 12. It should be understood that by selecting a combination of cross-sectional areas and skin permeability, an infinite number of ratios of drug delivery can be configured for delivery through the skin of ABTT terminus 10. A configuration such as that of device 324 is beneficial for delivery of at least two drugs simultaneously, which is desirable for certain medical conditions. It should be understood that one container may have a permeation enhancer and a second container may have a drug, the permeation enhancer being released first by virtue of permeability of a membrane holding the permeation enhancer, followed by the drug release.

Figure 31:
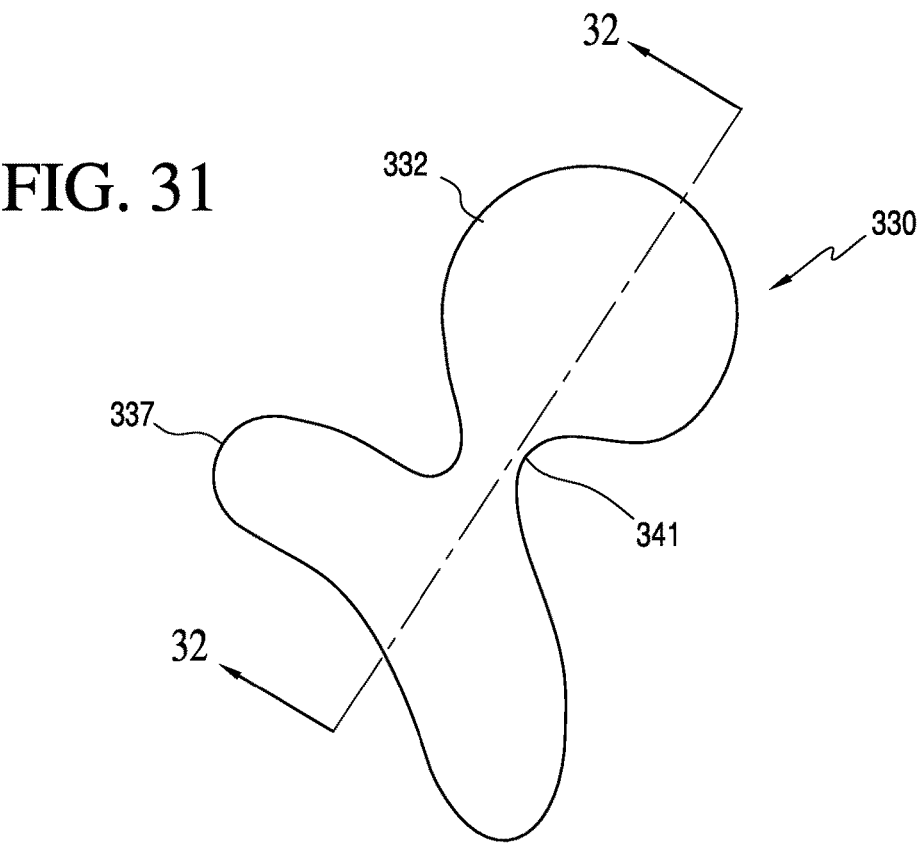
FIG. 31 is a plan view of a further passive transdermal delivery device, in accordance with an exemplary embodiment of the present disclosure.
Figure 32:
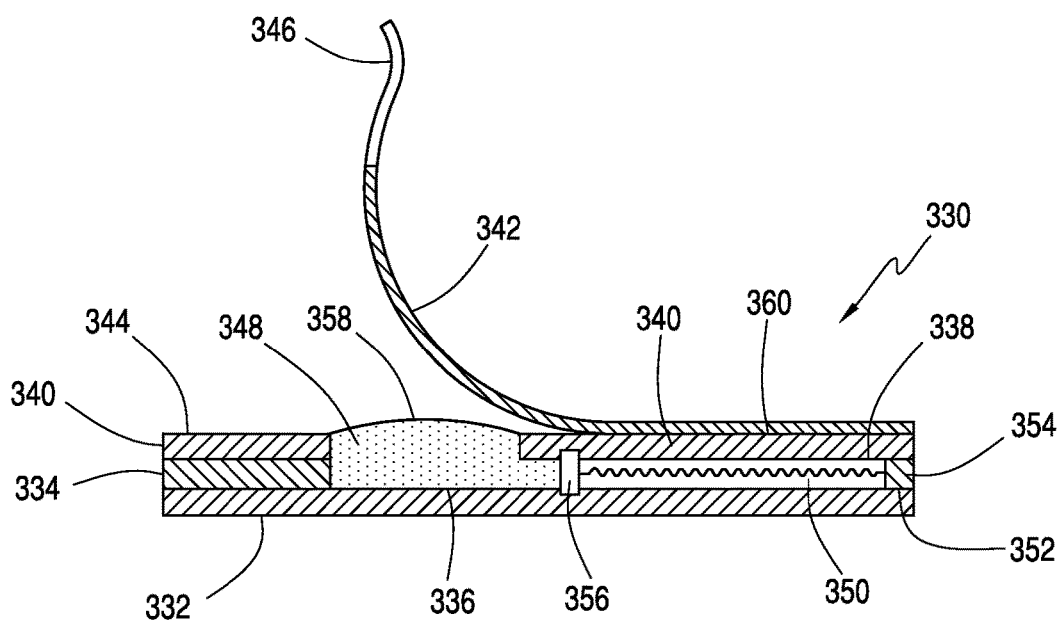
FIG. 32 is a cross-sectional view of the passive transdermal delivery device of FIG. 31 along the lines 32-32.
Figure 33:
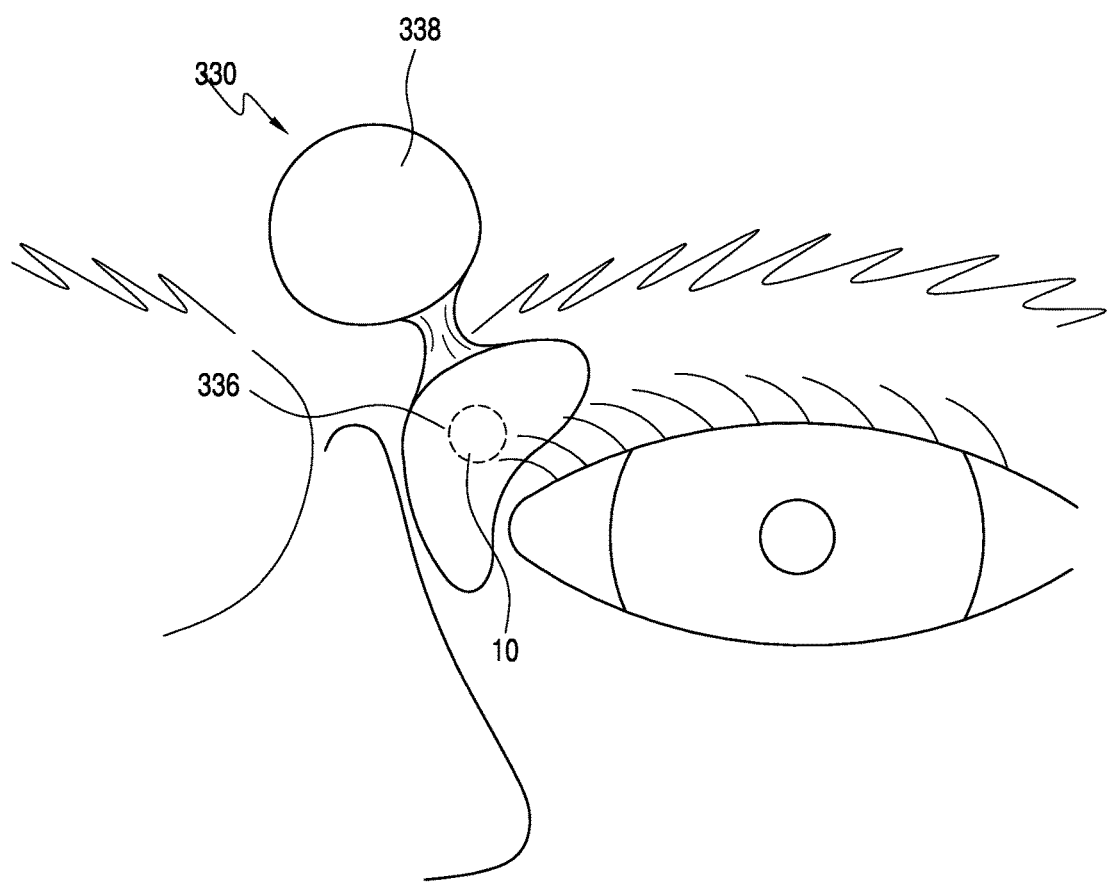
FIG. 33 is a view of a patient or subject with the passive transdermal delivery device of FIGS. 31 and 32 positioned thereon.

FIGS. 31-33 are views of a passive transdermal delivery device with extended drug delivery capability in accordance with an exemplary embodiment of the present disclosure, indicated generally at 330. Device 330 includes a support 332 on which is positioned a spacer layer 334 that is configured with cutouts to define a first volume 336, located in a first portion 337, and a second volume 338 located in a second portion 339. First portion 337 is connected to second portion 339 by connection portion 341. A cover layer 340 is positioned over spacer layer 334 and is configured to cover second volume 338 while leaving first volume 336 open. A removable or peelable layer 342 is configured to cover and protect first volume 336, along with an adhesive layer 344 positioned between removable layer 342 and cover layer 340. Removable layer 342 may include a tab 346 that extends beyond device 330 to enable grasping of removable layer 342 to remove layer 342. An absorbent material 348 is positioned in first volume 336 that readily absorbs a drug for transdermal delivery. A drug 350 is located in second volume 338, which serves as a feeder reservoir to absorbent material 348 in first volume 336. Drug 350 may be inserted or enter through an opening 352 formed in spacer layer 334, and opening 352 can then be closed by a plug 354. Device 330 can be configured to include a flow control membrane 356 positioned between feeder reservoir 338 and absorbent material 348. Flow control membrane 356 moderates the rate of flow from feeder reservoir 338 to absorbent material 348. Absorbent material 348 can be configured to include a protruding portion 358 that extends beyond an outer plane 360 of adhesive layer 344. Protruding portion 358 assures contact with the skin of ABTT terminus 10 when removable layer 342 is separated from device 330.

Device 330 is configured to provide an extended duration of drug delivery to ABTT terminus 10. Such extended duration is provided by feeder reservoir 338, and the rate of delivery to absorbent material 348, which can be moderated or modified by flow control membrane 356. The flow from feeder reservoir 338 to absorbent material 348 is possible because feeder reservoir 338 is configured to be positioned at a location on a patient higher than absorbent material 348, such as a forehead of a patient, as shown in FIG. 33. Reservoir 338 feeds liquid drug 350, by gravity, into first volume 336 positioned over ABTT terminus 10, where drug 350 permeates absorbent material 348 until drug 350 reaches ABTT terminus 10.

Figure 34:
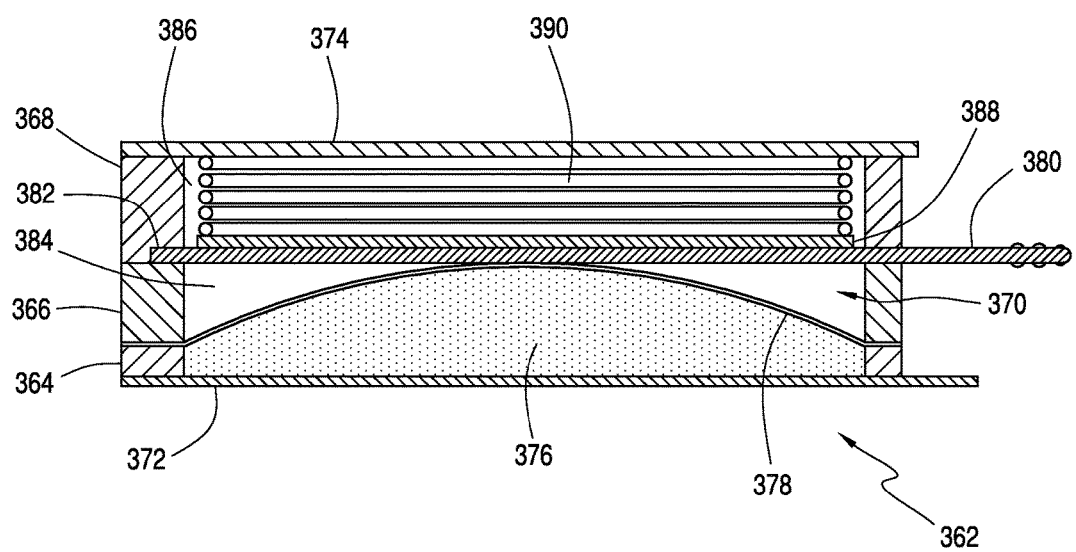
FIG. 34 is a cross-sectional view of a passive transdermal delivery device that includes an enhanced drug delivery feature, in accordance with an exemplary embodiment of the present disclosure.

While most of the drug delivery devices described to this point are considered passive delivery devices, even a passive delivery device can be configured to include enhanced delivery features. One such passive transdermal delivery device is shown in FIG. 34 and indicated generally at 362. Device 362 includes a first layer 364, an adjacent second layer 366, and another adjacent third layer 368, which define an internal volume 370. Internal volume 370 is enclosed by a removable layer 372 at one end, and a cover layer 374 at a second end opposite the first end.

An absorbent material 376 containing a skin-permeable drug is positioned adjacent to removable layer 372 and is exposed when removable layer 372 is separated from device 362. A flexible, impermeable membrane 378 separates absorbent material 376 from the portion of internal volume 370 that is adjacent the second end of internal volume 370. Flexible, impermeable membrane 378 is attached to at least one of first layer 364 and second layer 366 or is captured between first layer 364 and second layer 366, which can then be secured to each other by an adhesive or other fastening apparatus. A slide plate 380 is positioned in a slot 382 formed in at least one layer, or formed between, for example, second layer 366 and third layer 368, which then divides internal volume 370 into a lower volume 384, which is configured to contain absorbent material 376, and an upper volume 386.

A spring 390 and a pressure plate 388 are positioned in upper volume 386, exerting force on slide plate 380. When slide plate 380 is pulled from device 362, the force of spring 390 causes pressure plate 388 to move toward flexible impermeable membrane 378, placing pressure on membrane 378 and, consequently, absorbent material 376. The pressure placed on absorbent material 376 forces the drug in absorbent material 376 to move outwardly, toward the skin of ABTT terminus 10 when device 362 is properly positioned to locate absorbent material 376 on, over, or adjacent the skin of ABTT terminus 10. It should be understood that other fastening apparatuses, devices, or mechanisms can be used to position device 362 on the skin of ABTT terminus 10, such as an annular structure, a structure connected to a frame, and the like, which positions and presses absorbent material 376 against the skin, and in those embodiments there is no need for an adhesive surface area.

Figure 35:
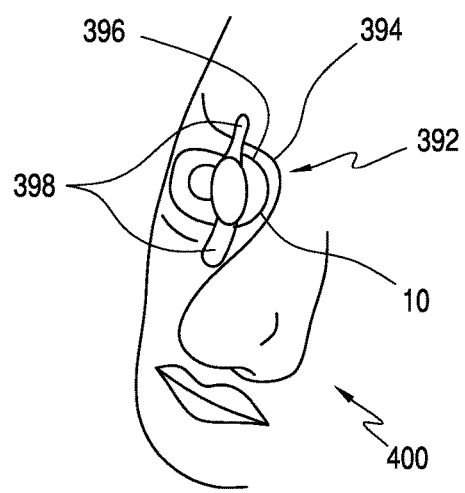
FIG. 35 is a view of a subject or patient's face with a passive transdermal delivery device in accordance with an exemplary embodiment of the present disclosure fixed thereto.
Figure 36:
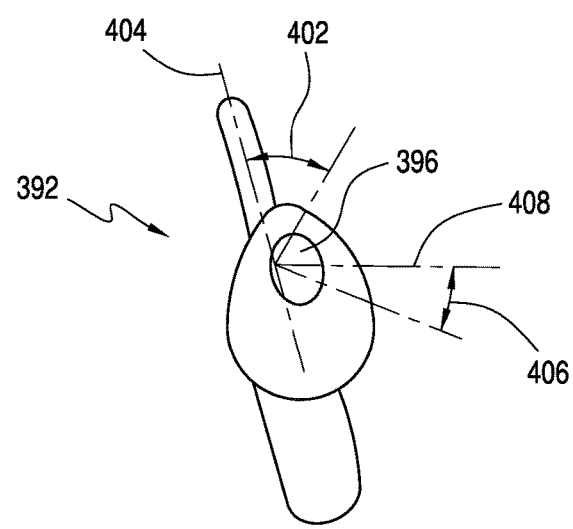
FIG. 36 is a view of the transdermal delivery device of FIG. 35.

FIGS. 35 and 36 are views of another passive transdermal delivery device in accordance with an exemplary embodiment of the present disclosure, indicated generally at 392. Device 392 is configured to include a shape that matches the recess of a human eye socket 394. A drug container or reservoir 396 is oriented such that when device 392 is positioned in eye socket 394, drug container 396 is in contact with ABTT terminus 10. Device 392 can be secured by a plurality of adhesive strips 398 positioned on device 392 and configured to be secured to the skin of a face 400. In an exemplary embodiment, drug container 396 is oriented at a first angle 402 extending from a vertically extending axis 404, and at a second angle 406 extending from a horizontally extending axis 408 that is approximately perpendicular to face 400. In an exemplary embodiment, first angle 402 is in the range of 20 to 75 degrees, and second angle 406 is in the range of 10 to 50 degrees. Adhesive tabs may have dissimilar dimensions, to secure device 392 to the skin, based on the amount of space, which is more limited in the upper portion in contrast to the nose and cheek area.

Figure 37:
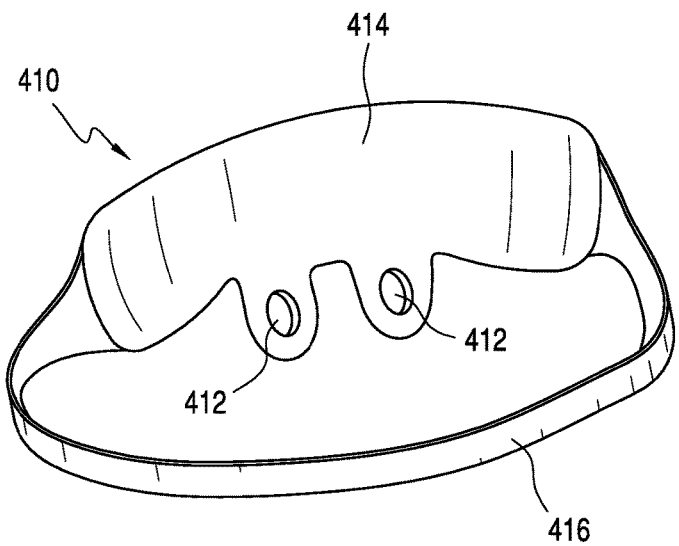
FIG. 37 is a view of a device support for the transdermal delivery device of FIG. 36.

FIG. 37 is a view of a support device for transdermal delivery device 392, indicated generally at 410. Support device 410 is configured to position at least one device 392 on a patient by positioning device 392 in a socket 412. Each socket 412 is configured in a flexible plate 414 that provides sufficient rigidity to maintain drug container 396 of device 392 in contact with ABTT terminus 10. A stretchable or adjustable strap 416 is configured to secure flexible plate 414 on a patient's forehead, also providing the force needed to maintain drug container 396 in contact with ABTT terminus 10.

Figure 38:
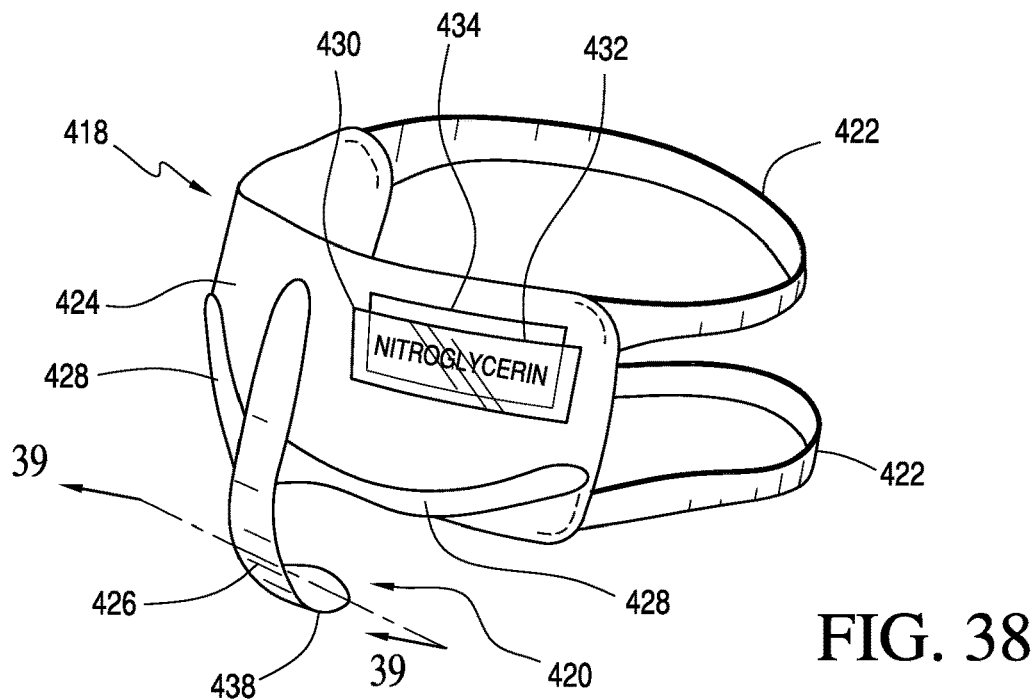
FIG. 38 is a view of another transdermal delivery device and support device in accordance with an exemplary embodiment of the present disclosure.
Figure 39:
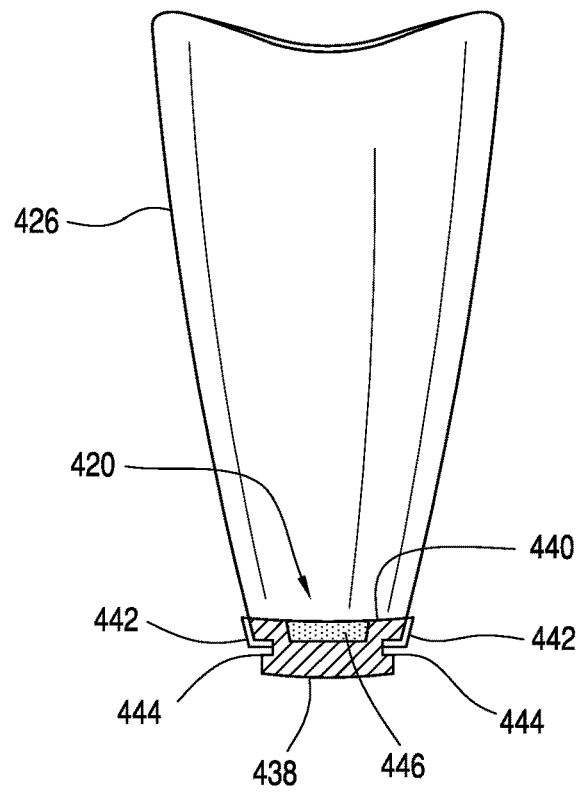
FIG. 39 is a view of the transdermal delivery device of FIG. 38 along the lines 39-39.

FIGS. 38 and 39 are views of a support apparatus and passive transdermal delivery device in accordance with an exemplary embodiment of the present disclosure, indicated at 418 and 420, respectively. Support apparatus 410 includes one or more straps 422 for securing support apparatus 410 to a subject or patient's head. Straps 422 can be configured to be flexible or adjustable. Support apparatus 410 further includes a flexible plate 424 configured to support a vertically-extending support arm 426. One or more angled braces 428 can connect vertically-extending support arm 426 to plate 424 to provide rigidity to support arm 426. Flexible plate 424 is configured to include a pocket 430 formed by a clear sheet 432. A sheet 434 including a label for a drug being applied by delivery device 420 can be inserted into pocket 430 for view by an external observer, such as a doctor, nurse, paramedic, technician, and the like. Support arm 426 includes an angled support pad 438 containing a pocket 440. Transdermal delivery device 420 includes a securing mechanism 442 provided on device 420 to attach device 420 to a mating feature 444 in angled support pad 438. Once device 420 is secured to support apparatus 418, a removable layer can be separated from support apparatus 418 to expose a drug container or reservoir 446, after which support apparatus 418 can be secured to a head such that drug container 446 is positioned against ABTT terminus 10.

Figure 40:
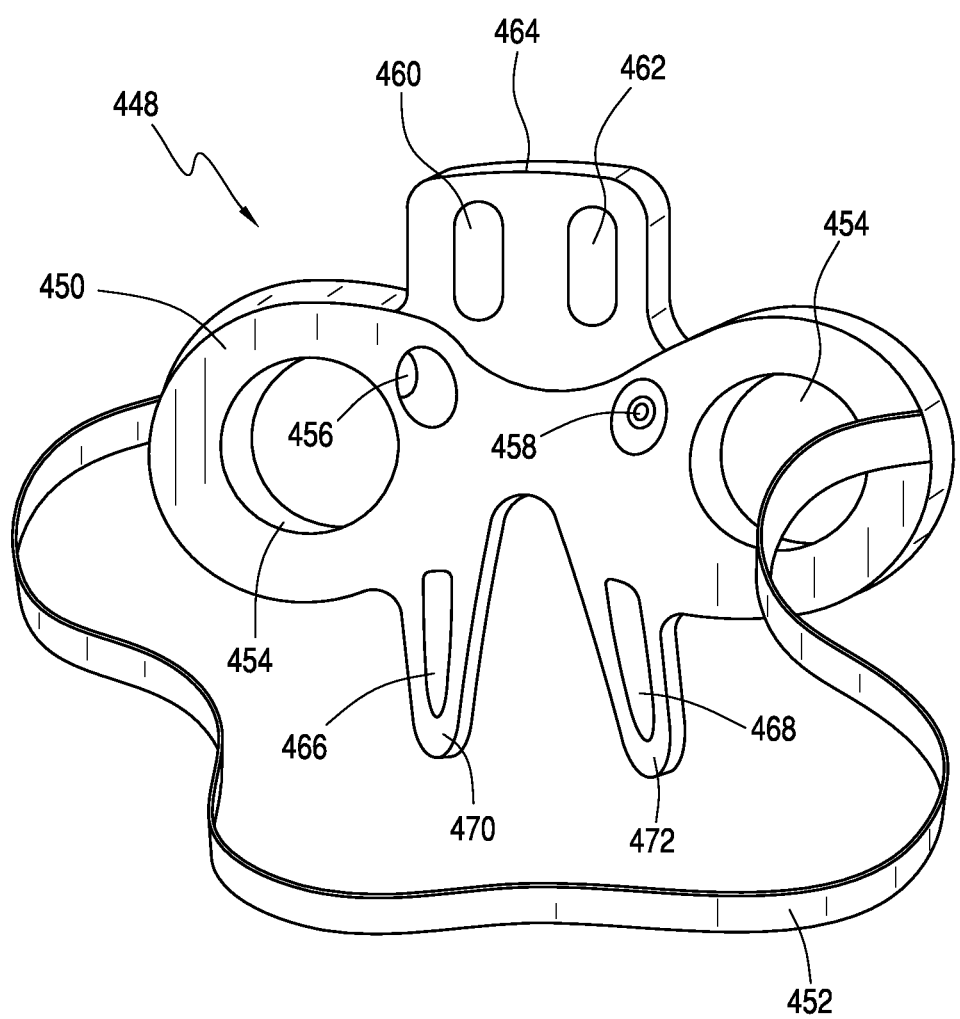
FIG. 40 is a view of a passive transdermal delivery device in accordance with an exemplary embodiment of the present disclosure.

FIG. 40 is a view of another passive transdermal delivery device in accordance with an exemplary embodiment of the present disclosure, indicated generally at 448. Device 448 includes a support 450 and a strap 452 configured to secure device support 450 to a patient or subject's head. Support 450 is further configured to include a plurality of openings 454 that permits the patient or subject to see while wearing device support 450. Device support 450 includes a first drug container 456 and a second drug container 458 configured to be oriented similar to the embodiment of FIGS. 35-37 to position first drug container 456 and second drug container 458 in contact with a patient or subject's ABTT terminuses 10. Device support 450 further includes a third drug container 460 and a fourth drug container 462 positioned on an extension plate 464 to extend vertically above first drug container 456 and second drug container 458. Third drug container 460 and fourth drug container 462 are positioned to be in contact with at least a portion of frontal veins 14 or supraorbital veins 18. Device support 450 yet further includes a fifth drug container 466 and a sixth drug container 468 positioned on a first angular extension 470 and a second angular extension 472, respectively. Fifth drug container 466 and sixth drug container 468 are configured to contact at least a portion of angular veins 20 and may extend to contact at least a portion of facial veins 22 in the cheek.

Figure 41:
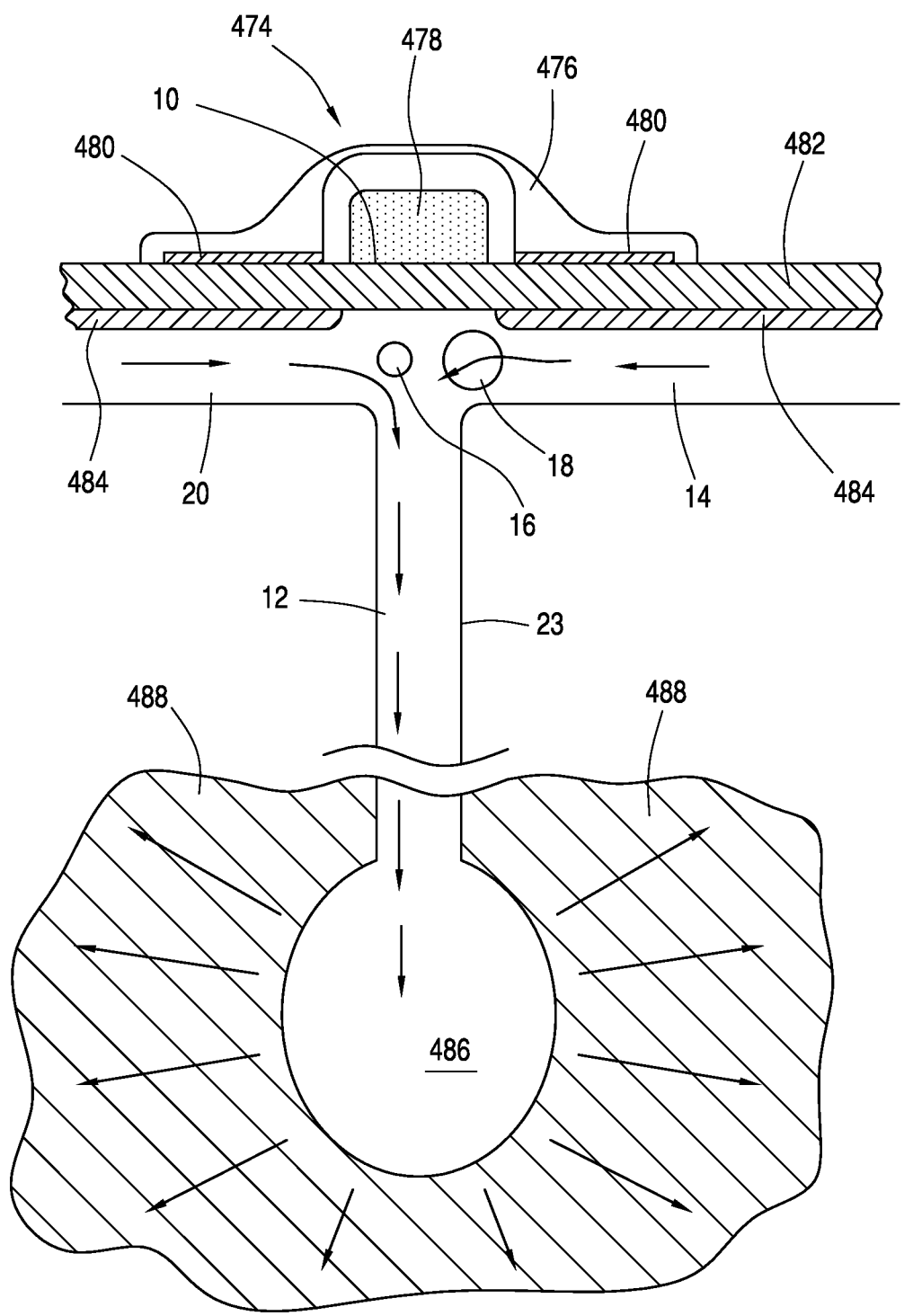
FIG. 41 is a view of a passive transdermal delivery device in accordance with an exemplary embodiment of the present disclosure, positioned on an ABTT terminus.

FIG. 41 is a view of another passive transdermal delivery device in accordance with an exemplary embodiment of the present disclosure, indicated generally at 474. Transdermal delivery device 474 is shown positioned on ABTT terminus 10. Device 474 includes a support 476 and a drug container or reservoir 478. Device 474 further includes an adhesive layer 480 that is configured to generate heat when a removable layer is separated from device 474. The benefit of heat generation in device 474 is that heat improves the permeability of skin 482 to the drug in drug container 478. FIG. 41 also shows the lack of fat and the thinnest skin in the body at ABTT terminus 10, and fat with thick skin 484 located in areas outside ABTT terminus 10. As has been explained herein, drugs that flow through the skin of ABTT terminus 10 flow into ABTT 10, and then into cavernous sinus 486. From cavernous sinus 486, drugs flow directly into the surrounding tissues of a brain 488, without the complexities of flowing through the digestive system and the circulatory system, including the liver and the kidneys. Accordingly, drugs that flow directly into ABTT 12 from all sources, especially ABTT terminus 10 and veins 14, 16, 18, 20, and 22, provide a greater effect on brain tissues than any other application of drugs to the human body, and consequently, fewer amounts of drugs and/or lower drug concentration than what is used in conventional patches, as described herein, need to be applied at these locations to be effective.

Figure 42:
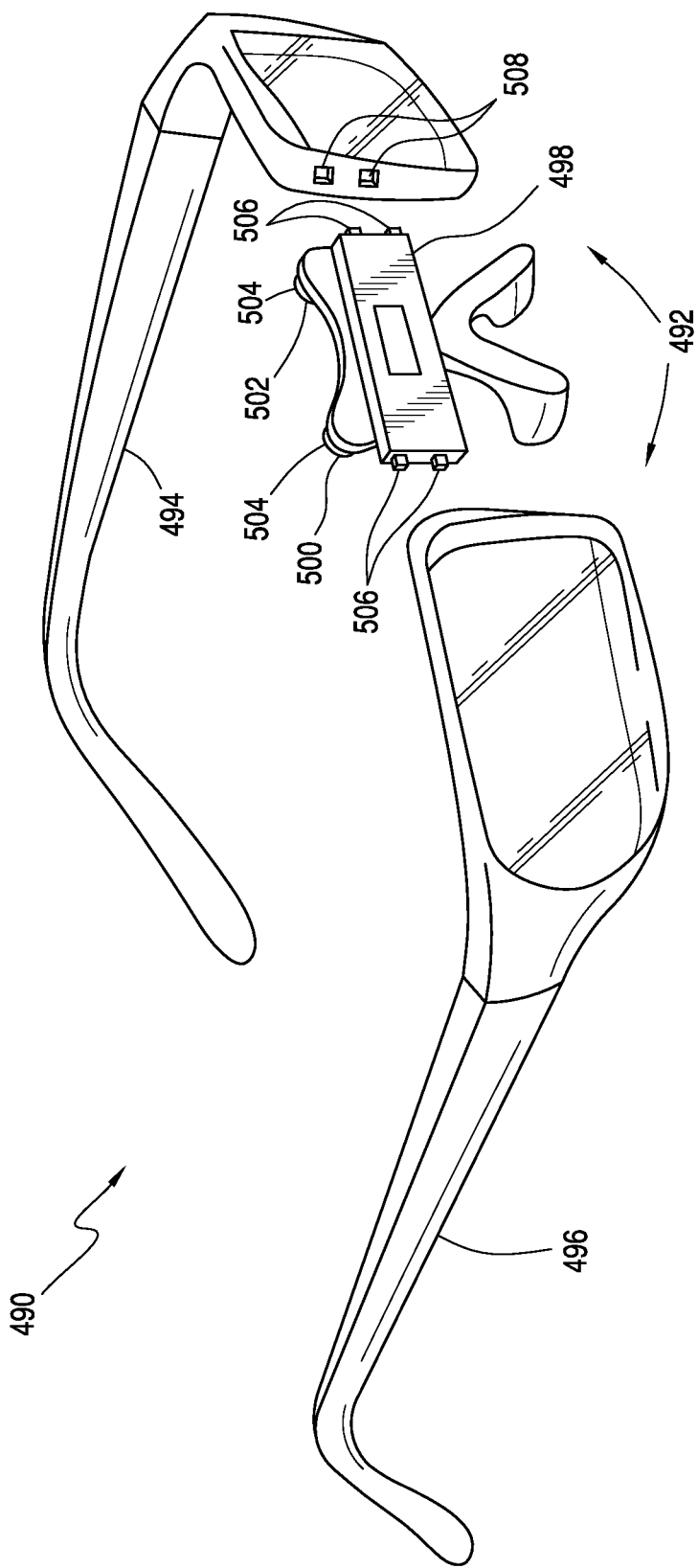
FIG. 42 is a view of a passive transdermal delivery device in accordance with an exemplary embodiment of the present disclosure incorporated in an eyeglass frame.

FIG. 42 shows yet another passive transdermal delivery device in accordance with an exemplary embodiment of the present disclosure, indicated generally at 490. Device 490 includes a pair of glasses 492 with a first or left side frame 494, and a second or right side frame 496, which are configured to connect to each other by way of a removable and exchangeable nose piece 498. Removable nose piece 498 is configured to include projections 500 and 502 in the right and left side respectively. Each project 500 and 502 includes a drug container 504 configured to be positioned at angles similar to the angles described for the embodiment of FIG. 36, thus configured to be in a location that places each drug container 504 in contact with ABTT terminus 10. Removable nose piece 498 is configured to connect left frame 494 to right frame 496, and to support left frame 494 and right frame 496 as an assembly, pair of glasses 492. Removable nose piece 498 further includes at least one attachment or fastening feature 506 on each side of removable nose piece 498 configured to mate with complementary attachment or fastening features 508 located in left frame 494 and right frame 496.

Figure 43:
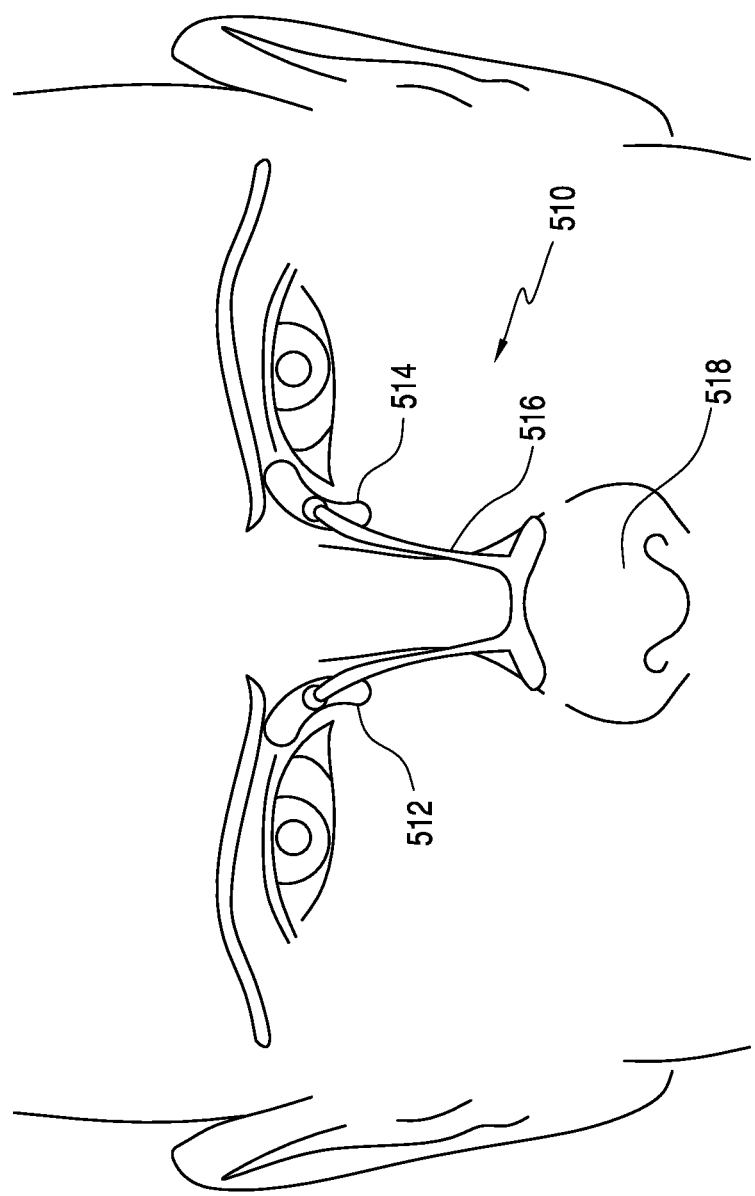
FIG. 43 is a view of a passive transdermal delivery device in accordance with an exemplary embodiment of the present disclosure configured as a nose clip.

FIG. 43 is a view of a passive transdermal delivery device in accordance with an exemplary embodiment of the present disclosure, indicated at 510. Device 510 includes a first drug container or reservoir (not shown) positioned on a first pad 512 and a second drug container or reservoir (not shown) positioned on a second pad 514, with each drug container configured to be positioned over a respective ABTT terminus 10 when device 510 is properly positioned on a face. Each pad 512 and 514 can be configured similar to, for example, the embodiments of FIGS. 12, 16, and 18. Device 510 further includes a nose clip 516 configured to be supported on a nose 518. The frictional contact of nose clip 516 with nose 518 provides sufficient support for device 510 to maintain contact between first pad 512 and second pad 514 with a respective ABTT terminus 10.

Figure 44:
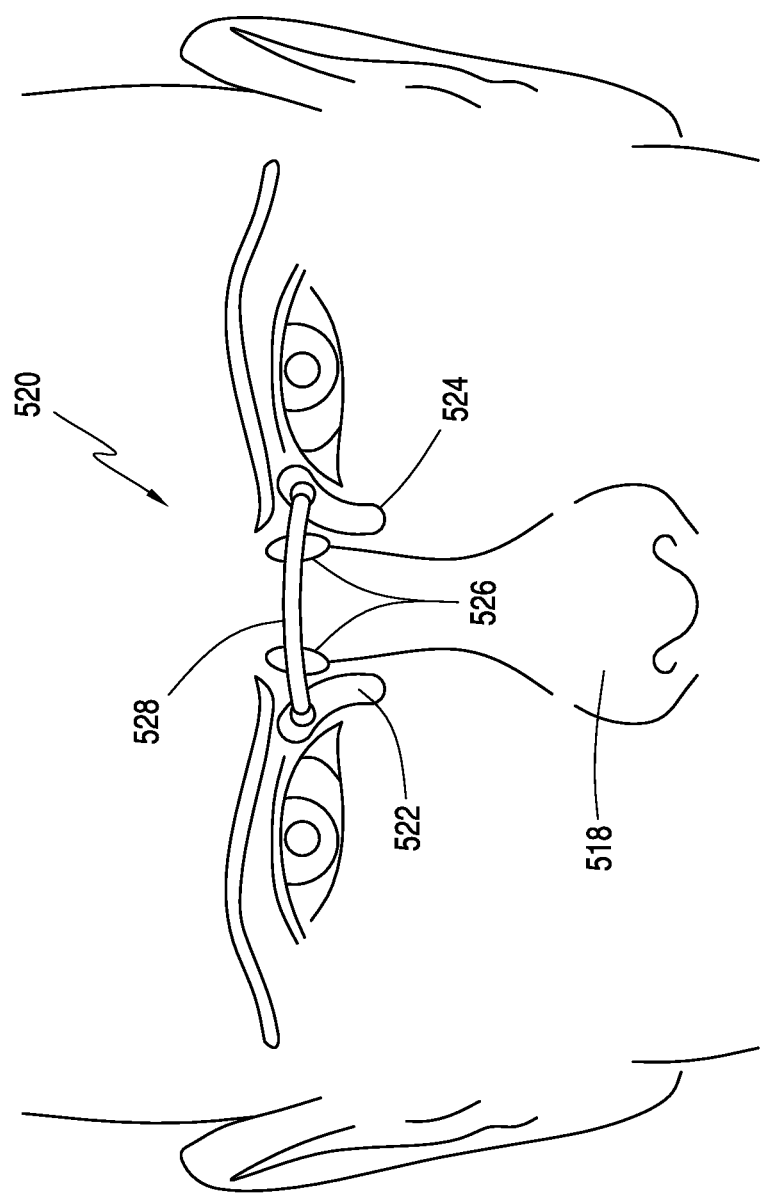
FIG. 44 is a view of another passive transdermal delivery device configured as a nose clip in accordance with an exemplary embodiment of the present disclosure.

FIG. 44 is a view of another passive transdermal delivery device in accordance with an exemplary embodiment of the present disclosure, indicated generally at 520. Device 520 includes a first drug container or reservoir (not shown) positioned on a first pad 522 and a second drug container or reservoir (not shown) positioned on a second pad 524, with each drug container configured to be positioned over a respective ABTT terminus 10 when device 520 is properly positioned on a face. Each pad 522 and 524 can be configured similar to, for example, the embodiments of FIGS. 12, 16, and 18. Device 520 further includes a pair of nose pads 526 configured to be supported on nose 518. The frictional contact of nose pads 526 with nose 518 provides sufficient support for device 520 to maintain contact between first pad 512 and second pad 514 with a respective ABTT terminus 10. First pad 522, second pad 524, and nose pads 526 are positioned on a frame support 528, such that the grip of nose pads 526 is configured to support first pad 522 and second pad 524. It should be understood that a clip-like mechanism and spring-like mechanisms can be present to further secure device 520 to the nose.

Figure 46:
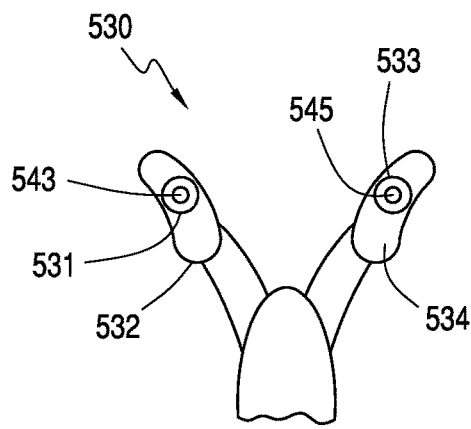
FIG. 46 is a view or a portion of the transdermal delivery device of FIG. 45.
Figure 45:
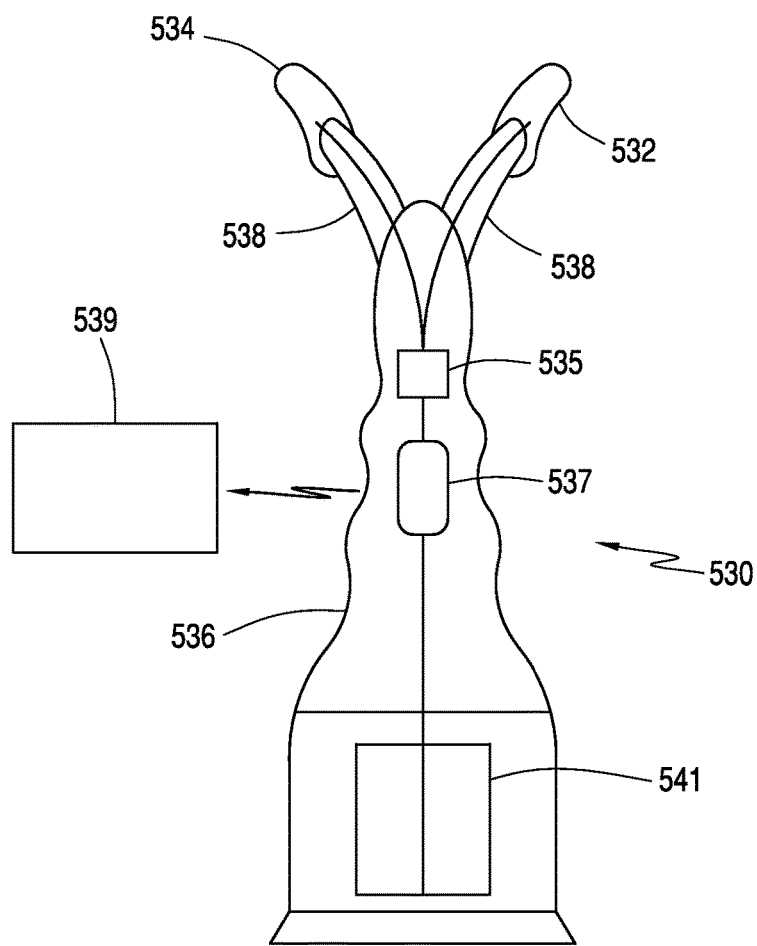
FIG. 45 is a view of a handheld passive transdermal delivery device in accordance with an exemplary embodiment of the present disclosure.

FIGS. 45 and 46 are views of a transdermal delivery device in accordance with an exemplary embodiment of the present disclosure, indicated generally at 530. Device 530 includes a first drug container 531 positioned on a first pad 532 and a second drug container 533 positioned on a second pad 534. Device 530 also includes a first thermoelectric device 543 positioned in a central portion of first drug container 531 and a second thermoelectric device 545 positioned in a central portion of second drug container 533. Thus, first drug container 531 and second drug container 533 are configured as annuluses, each with a center opening in which is positioned a thermoelectric device. Device 530 is configured with a handle 536, and a pair of flexible arms 538 configured to support first pad 532 and second pad 534. Handle 536 is configured to be held by a subject or patient, or may be held by another person. In an exemplary embodiment, handle 536 is of a material sufficient rigid to secure first pad 532 and second pad 534 against at least one ABTT terminus 10. Device 530 further includes a controller 535 for operating device 530, a transmitter 537 for communicating with a remote electronic device 539, such as a cell phone, and a power supply 541, all of which are located in handle 536.

Figure 47:
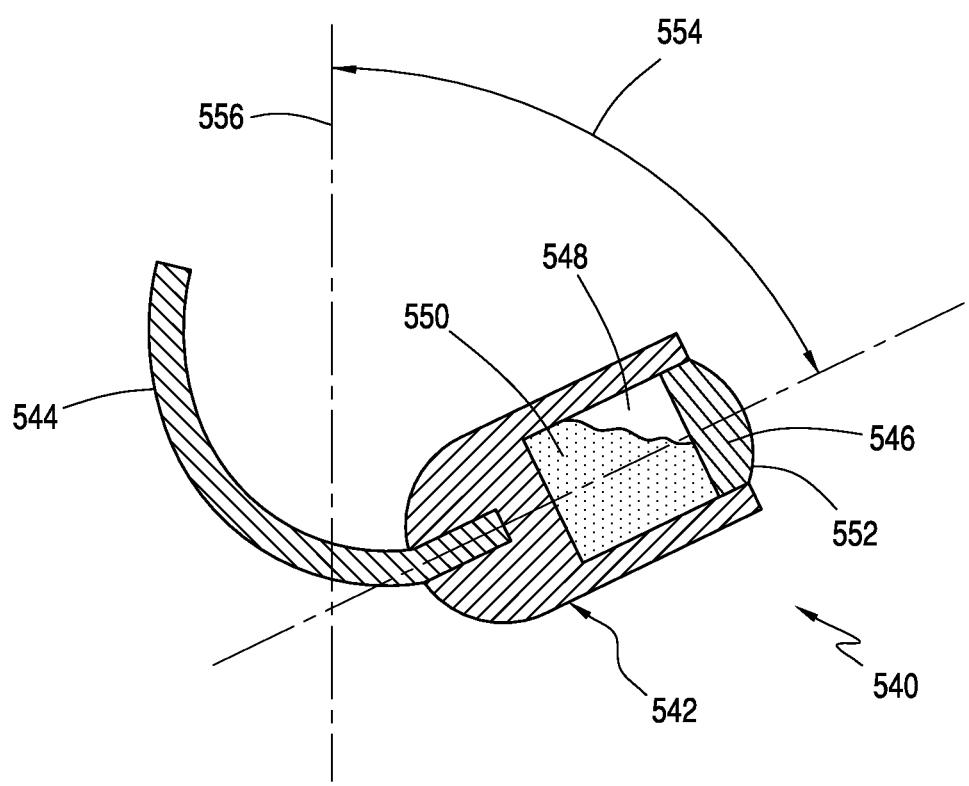
FIG. 47 is a view of a passive transdermal delivery device in accordance with an exemplary embodiment of the present disclosure.

FIG. 47 is a view of a passive transdermal delivery device in accordance with an exemplary embodiment of the present disclosure, indicated generally at 540. Device 540 includes a reservoir 542 located at the end of a flexible arm 544. Reservoir 542 is configured to include an interior chamber 548, which is closed at one end by an absorbent material 546. A liquid drug 550 is positioned within interior chamber 546 prior to the installation of absorbent material 546. Absorbent material 546 is protected by a drug impermeable and removable layer 552 that is separated from device 540 prior to use. In the exemplary embodiment of FIG. 47, device 540 is configured to be used on a patient or subject sitting or standing upright. To be configured for such an orientation, device 540 is positioned at an angle 554 to a vertical axis 556. In an exemplary embodiment, angle 554 is in the range 20 degrees to 75 degrees, which permits liquid drug 550 to contact absorbent material 546 for transport to the skin of ABTT terminus 10.

Figure 48:
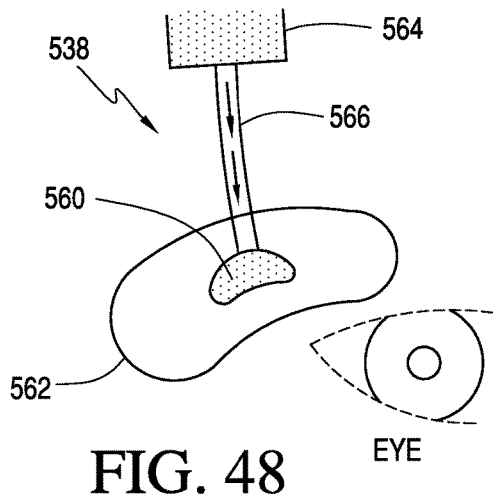
FIG. 48 is a view of a transdermal delivery device in accordance with an exemplary embodiment of the present disclosure.

FIG. 48 is a schematic view of a transdermal delivery device in accordance with an exemplary embodiment of the present disclosure, indicated generally at 558. Device 558 includes an absorbent material 560 positioned on a pad 562 and connected by a fluid passage to a separate reservoir 564.

Device 558 is configured to position absorbent material 560 on, over, or adjacent to the skin of ABTT terminus 10 when pad 562 is positioned on a subject or patient's face. Device 558 is configured to provide a drug located in reservoir 564 to ABTT terminus 10 for an extended period rather than being limited to the amount of drug that can be locally stored on a pad 562. Though not shown in FIG. 48, device 558 can be configured to include one or more elements to be considered an active device, such as a thermoelectric device.

Figure 49:
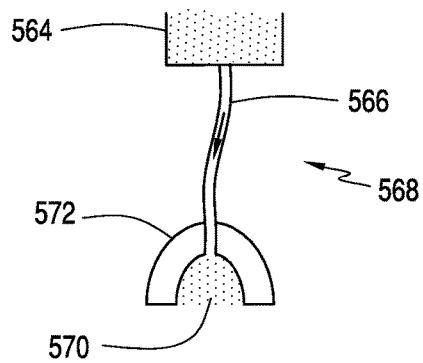
FIG. 49 is a view of a transdermal delivery device in accordance with an exemplary embodiment of the present disclosure.

FIG. 49 is a schematic view of a transdermal delivery device in accordance with an exemplary embodiment of the present disclosure, indicated generally at 568. Device 568 includes an absorbent material 570 located in a holder 572 and configured to be positioned on an ABTT terminus 10. Absorbent material 570 is connected by fluid passage 566 to separate reservoir 564 and, similar to the embodiment of FIG. 48, reservoir 564 provides additional time for drugs to be delivered via absorbent material 570 to ABTT terminus 10. Though not shown in FIG. 49, device 568 can be configured to include one or more elements to be considered an active device, such as a thermoelectric device.

Figure 50:
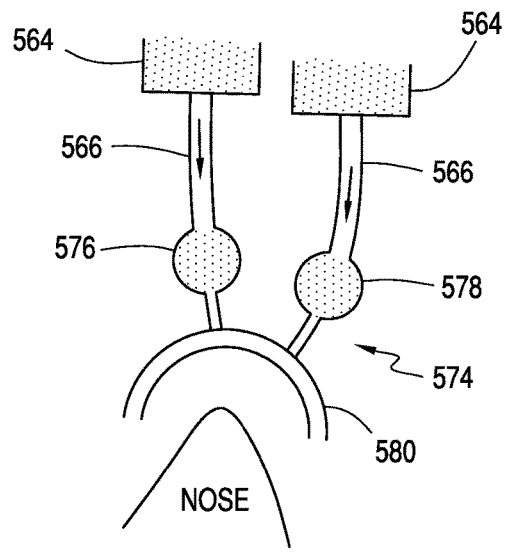
FIG. 50 is a view of a transdermal delivery device in accordance with an exemplary embodiment of the present disclosure.

FIG. 50 is a schematic view of a transdermal delivery device in accordance with an exemplary embodiment of the present disclosure, indicated generally at 574. Device 574 includes a first pad 576, shown schematically, and a second pad 578, also shown schematically, supported on a nose clip 580. Each of first pad 576 and second pad 578 are connected by fluid passage 566 to reservoir 564. The embodiment of FIG. 50 may include one or two reservoirs 564 to permit the delivery of drugs for a longer period or for the delivery of two different drugs. Though not shown in FIG. 50, device 574 can be configured to include one or more elements to be considered an active device, such as a thermoelectric device.

Figure 51:
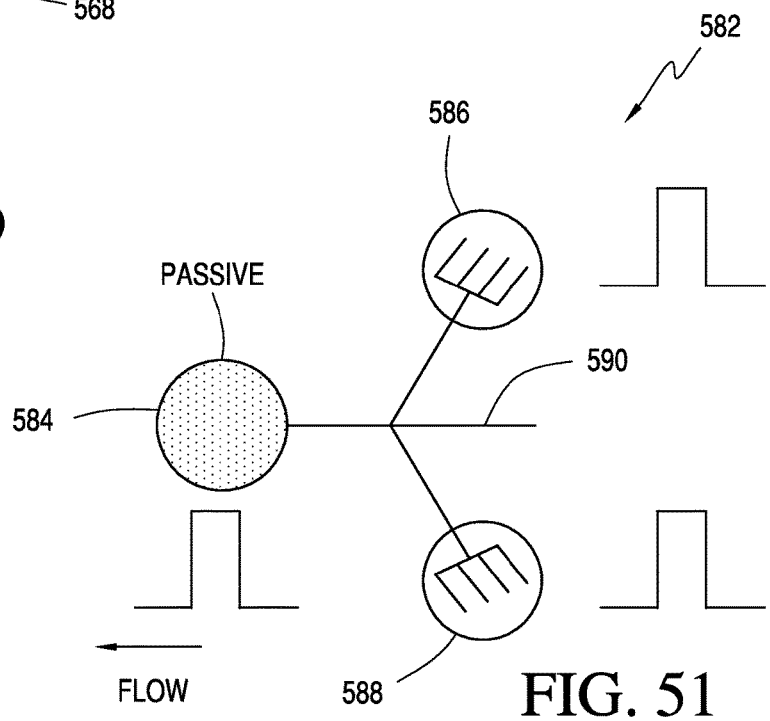
FIG. 51 is a view of a transdermal delivery device in accordance with an exemplary embodiment of the present disclosure.

FIG. 51 is a schematic view of a transdermal delivery device in accordance with an exemplary embodiment of the present disclosure, indicated generally at 582. Device 582 includes a first pad 584 configured to be positioned on ABTT terminus 10, a second pad 586 configured to be positioned on a vein, such as frontal vein 14, and a third pad 588 configured to be positioned on another vein, such as angular vein 20. Each of first pad 584, second pad, 586, and third pad 588 are connected to each other and supported by a frame 590. Though not shown in FIG. 51, device 582 can be configured to include one or more elements to be considered an active device, such as a thermoelectric device.

Figure 52:
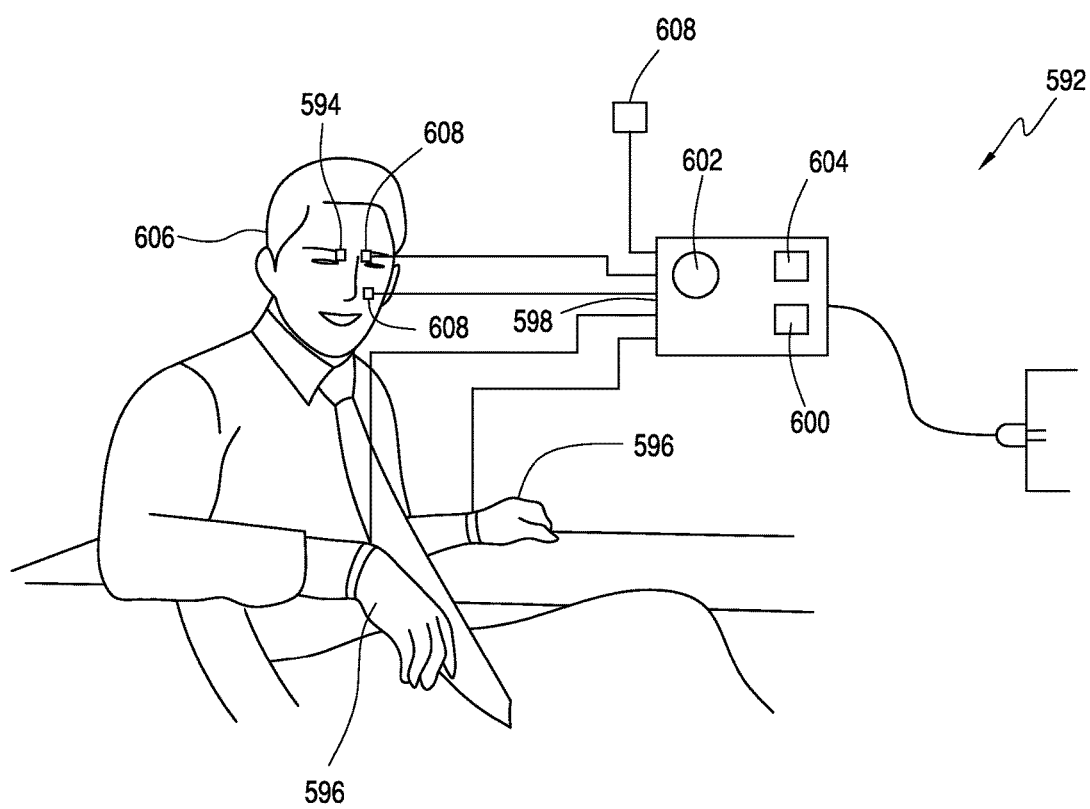
FIG. 52 is a view of a transdermal delivery system in accordance with an exemplary embodiment of the present disclosure.

FIG. 52 is a transdermal delivery system in accordance with an exemplary embodiment, indicated generally at 592. System 592 includes at least one passive or active transdermal delivery device 594 that may be any of the passive transdermal delivery devices described herein, and a pair of warming and cooling gloves 596. Gloves 596 are connected to a controller 598, which can be configured to include an ON/OFF switch 600, a temperature controller 602, and a temperature display 604. System 592 provides an enhanced delivery of drugs to a subject or patient 606 by tricking the brain into functioning in a certain way. More specifically, system 592 operates by making the brain think that the ambient temperature is about to become hot by activating thermal receptors in the subject's hands by applying heat to gloves 596. The brain, sensing the heat in the hands, prepares for the apparent increase in temperature by causing cool blood to flow from one or more veins 14, 16, 18, or 20 into ABTT 12. This blood flow will cause drugs flowing through ABTT terminus 10 and any drugs flowing through veins 14, 16, 18, or 20 to flow into ABTT 12 at a faster rate than might normally occur in typical ambient and body temperatures. Indeed, the brain may be causing warm blood to flow outwardly through ABTT 12, which would render the application of drugs less effective. Gloves 596 are also capable of cooling the hands. If the face contains warm blood, the brain can still cause inward blood flow, accomplishing the same effect. In order to know how the brain is functioning with respect to facial blood flow, system 592 may be configured to include a plurality of temperature sensors positioned to measure ambient temperature, facial skin temperature, and temperature at an ABTT 10, which can be presented on temperature display 604, as well as devices that measure blood flow.

Figure 53:
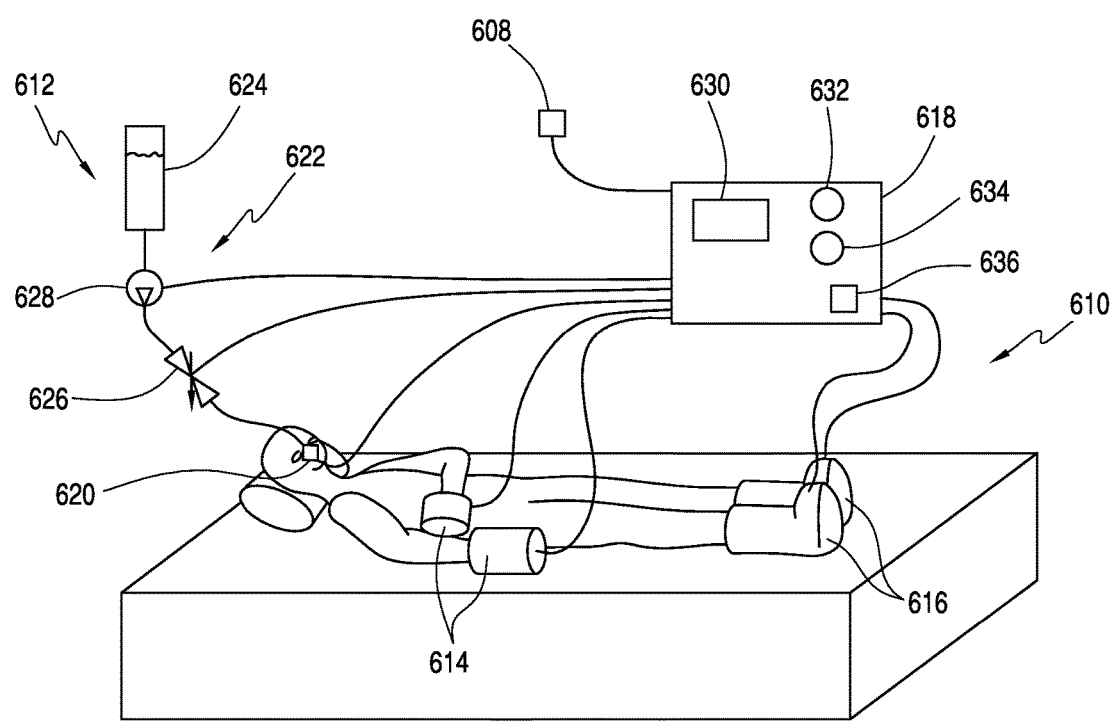
FIG. 53 is a view of an active transdermal delivery system in accordance with an exemplary embodiment of the present disclosure.

FIG. 53 is a view of an active transdermal delivery system in accordance with an exemplary embodiment of the present disclosure, indicated generally at 610. System 610 includes an active transdermal delivery device 612, one or more electric gloves 614, one or more electric boots 616, and a controller 618. Generally, device 612 is controllable to provide flow of a drug to a patient or subject while gloves 614 and boots 616 are heated or cooled to fool the brain into controlling blood flow from the face into ABTT 12. System 610 further includes a plurality of temperature sensors, such as temperature sensor 608 for measuring ambient temperature, and temperature sensors integral to gloves 614 and boots 616. Additional temperature sensor can be positioned to measure face and ABTT terminus temperature (not shown).

Device 612 includes a drug delivery interface 620 configured to deliver a drug to ABTT terminus 10. Drug delivery interface 620 is connected by a fluid delivery system 622 to a reservoir 624. Fluid delivery system 622 includes a variable or adjustable valve 626 and can include a pump 628. When commanded by controller 618, variable valve 626 can be opened to permit a drug to flow from reservoir 624 through fluid delivery system 622 to drug delivery interface 620. If needed to augment drug flow, controller 618 may also command a pump to move the drug through fluid delivery system 622 to drug delivery interface 620. Controller 618 can be configured to include a display 630 to provide a readout of temperature and other information, a temperature controller 632, a flow control 634, and an ON/OFF switch 636, along with other controls. As noted with the embodiment of FIG. 52, the brain may be tricked by heating or cooling thermal receptors in the hands or feet by heating of cooling gloves 614 and boots 616. The brain then causes blood flow, or increased blood flow, from the veins of the face into ABTT 12 in response to the thermal stimulation of the hands and feet, improving and controlling the delivery of drugs to the brain. It should be noted that excessive drug flow can also be controlled by reducing the blood flow to the brain by appropriate adjustment of glove 614 and boot 616 temperature.

Figure 54:
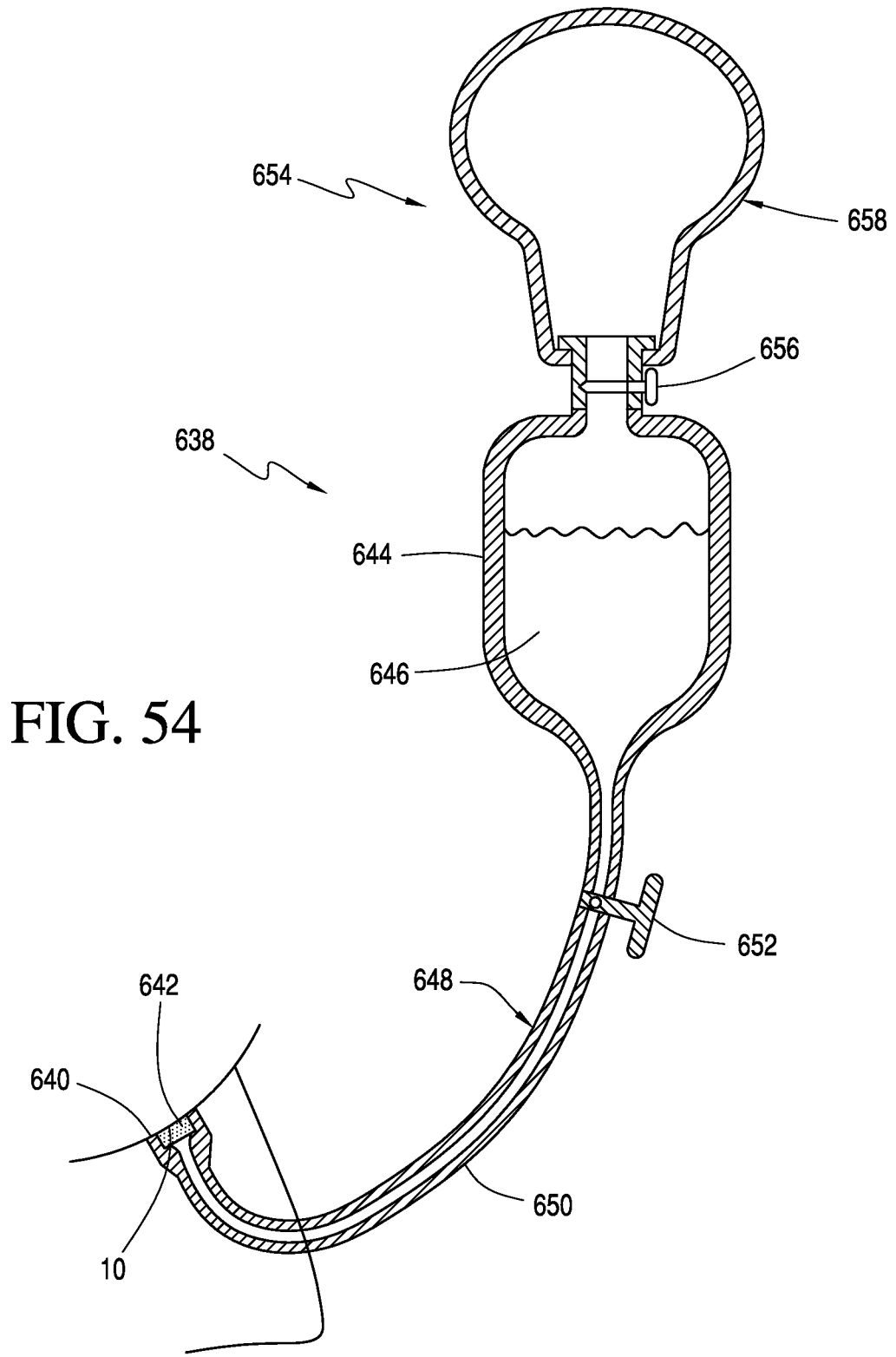
FIG. 54 is a view of another active transdermal delivery system in accordance with an exemplary embodiment of the present disclosure.

FIG. 54 is a view of another active transdermal delivery system in accordance with an exemplary embodiment of the present disclosure, indicated generally at 638. System 638 includes a drug delivery interface 640 configured to include a permeable material 642. Drug delivery interface 640 is connected to a fluid reservoir 644 containing a drug 646. Interface 640 is connected to reservoir 644 by a fluid delivery system that can include one or more fluid passages 650 and a variable valve 652. Reservoir 644 is configured to be pressurized by an air delivery system 654 that can include an air supply valve 656 positioned between an air source 658 and fluid delivery system 648. When a drug needs to be delivered to drug delivery interface 640, variable valve 652 can be opened to start the flow of drug 646 from reservoir 644 into fluid delivery system 648, and then to drug delivery interface 640. If the flow of drug 646 to drug delivery interface 640 is inadequate, air supply valve 656 is opened to connect air source 658 to reservoir 644, forcing additional flow of drug 646 into fluid delivery system 648 to drug delivery interface 640. Air source 658 can be any of a plurality of sources of pressurized air, including nitrogen systems, filtered air pumps, and bottled air. In the embodiment of FIG. 54, air source 658 is configured as a balloon, which often is sufficient to provide enough pressure to provide sufficient supply of drug 646 to drug delivery interface 640.

Figure 55:
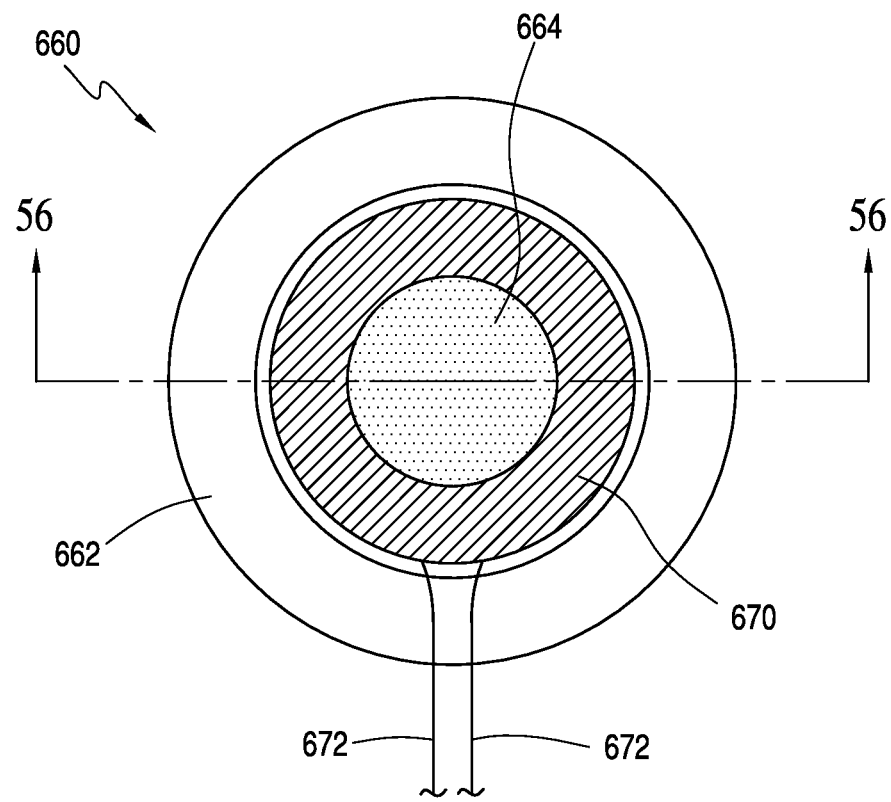
FIG. 55 is a view of yet another active transdermal delivery device in accordance with an exemplary embodiment of the present disclosure.
Figure 56:
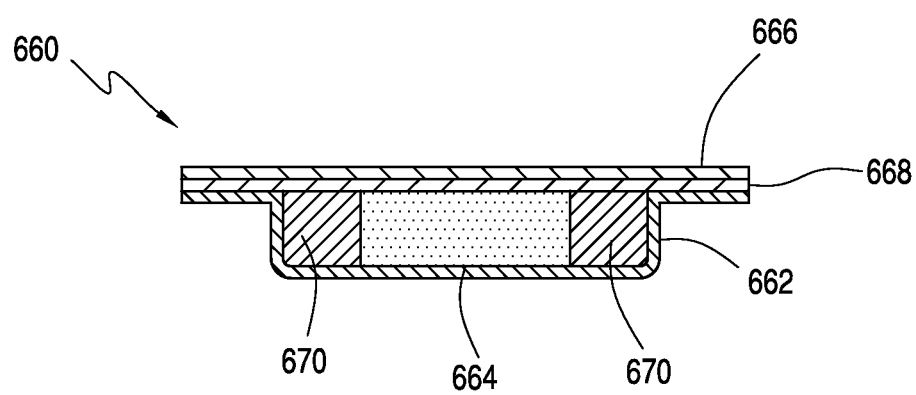
FIG. 56 is a cross-sectional view of the active transdermal delivery device of FIG. 55 along the lines 56-56.

FIGS. 55 and 56 are views of an active transdermal delivery device in accordance with an exemplary embodiment of the present disclosure, indicated generally at 660. Device 660 includes a support 662 configured to include a drug container or reservoir 664. Device 660 further includes a removable or peelable layer 666 configured to protect drug container 664 and an adhesive layer 668 positioned between removable layer 666 and device support 662. Device 660 also includes a thermoelectric device 670 positioned transversely between drug container 664 and device support 662. When removable layer 666 is removed from device 660, as shown in FIG. 55 (FIG. 56 shows removable layer 666 in place), drug container 664 is exposed and ready for placement on ABTT terminus 10, secured by adhesive layer 668. Power is applied to thermoelectric device 670 through wires 672 to heat drug container 664 and the skin around ABTT terminus 10. By heating drug container 664, the drug contained therein becomes more energetic and more likely to permeate skin. Furthermore, the skin of ABTT terminus 10 also increases in permeability due to the heat, and drug flow through ABTT terminus 10 is thereby enhanced.

Figure 57:
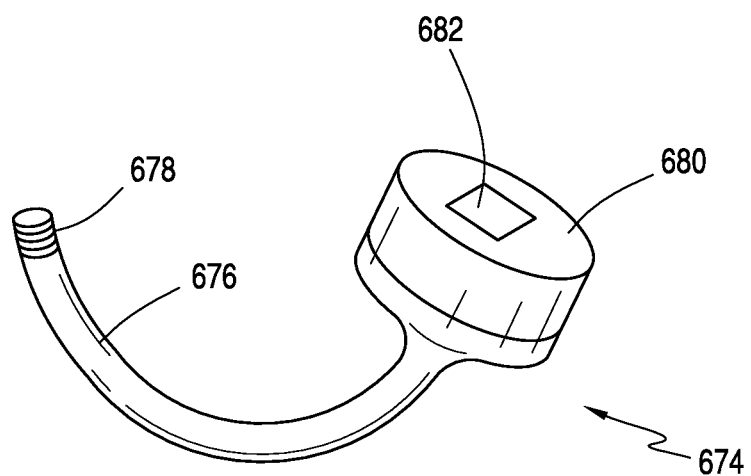
FIG. 57 is a view of a passive transdermal delivery module in accordance with an exemplary embodiment of the present disclosure.

FIG. 57 is a view of a passive transdermal delivery module in accordance with an exemplary embodiment of the present disclosure, indicated generally at 674. Module 674 is configured to be attached to a plurality of devices, such as glass frames, a head support, headband, hat, a standalone equipment support, etc. Module 674 includes a flexible arm 676 that includes an attachment arrangement 678, which can be, for example, a screw thread. A drug container or reservoir 680 is positioned on flexible arm 676 and is configured to contain a drug 682. Drug 682 can be protected by a removable layer (not shown), until module 674 is ready for use, at which time the removable layer is separated from module 674. Module 674 is beneficial for the flexibility that module 674 provides given that it can be attached to a plurality of devices and is infinitely adjustable to interface with ABTT terminus 10, and may not require an adhesive surface to maintain contact with a patient or subject ABTT terminus 10.

Figure 58:
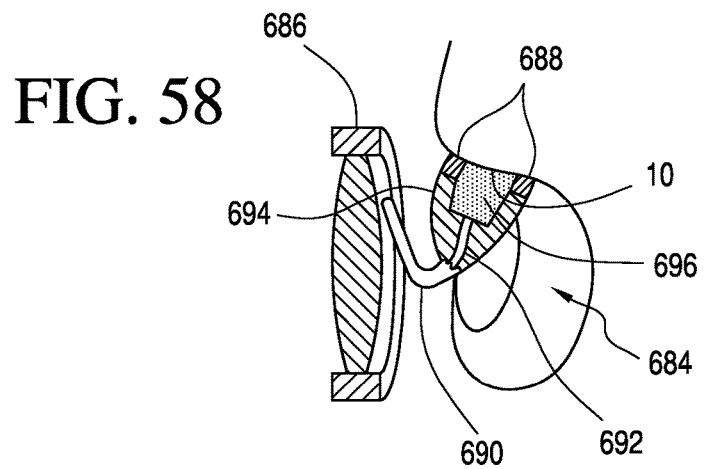
FIG. 58 is a view of an active transdermal delivery module in accordance with an exemplary embodiment of the present disclosure.

FIG. 58 is a view of an active transdermal delivery module in accordance with an exemplary embodiment of the present disclosure, indicated generally at 684. Module 684 is shown attached to a glasses frame 686, which includes a power supply configured to provide power to a thermoelectric device 688 positioned on module 684. Module 684 includes a flexible arm 690 that provides a route for wires 692 that provide power to thermoelectric device 688. Module 684 further includes a drug container or reservoir 694 that stores a drug 696 and provides a location to support thermoelectric device 688.

Figure 59:
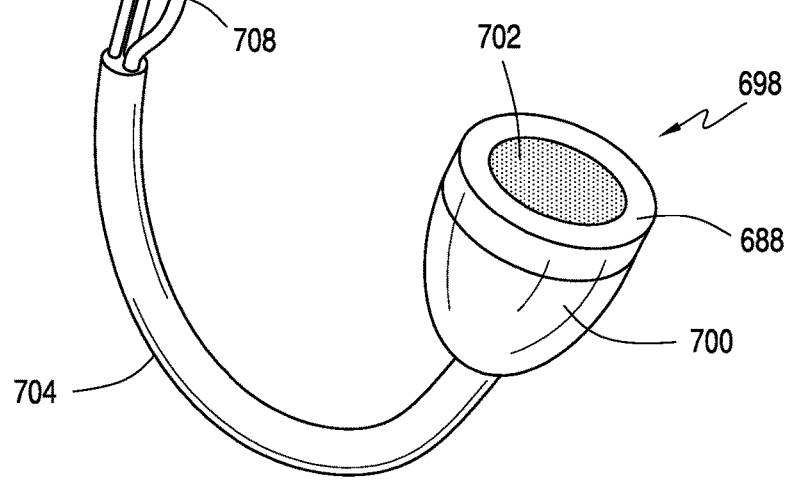
FIG. 59 is a view of another active transdermal delivery module in accordance with an exemplary embodiment of the present disclosure.

FIG. 59 is a view of another active transdermal delivery module in accordance with an exemplary embodiment of the present disclosure, indicated generally at 698. Module 698 includes a drug reservoir or container 700 configured to include a liquid drug and an absorbent material 702 to interface with ABTT terminus 10, and configured to support thermoelectric device 688. Module 698 further includes a flexible arm 704 configured to support drug reservoir 700. Flexible arm 704 is configured to include an attachment feature (not shown) to connect module 698 to one of a plurality of support devices. Flexible arm 704 is configured to provide support for wires 706 that provide power to thermoelectric device 688 and a fluid passage 708 that connects a separate drug reservoir to drug reservoir 700. As with other embodiments incorporating a thermoelectric device, the device can affect the flow of drugs into ABTT terminus 10.

Figure 60:
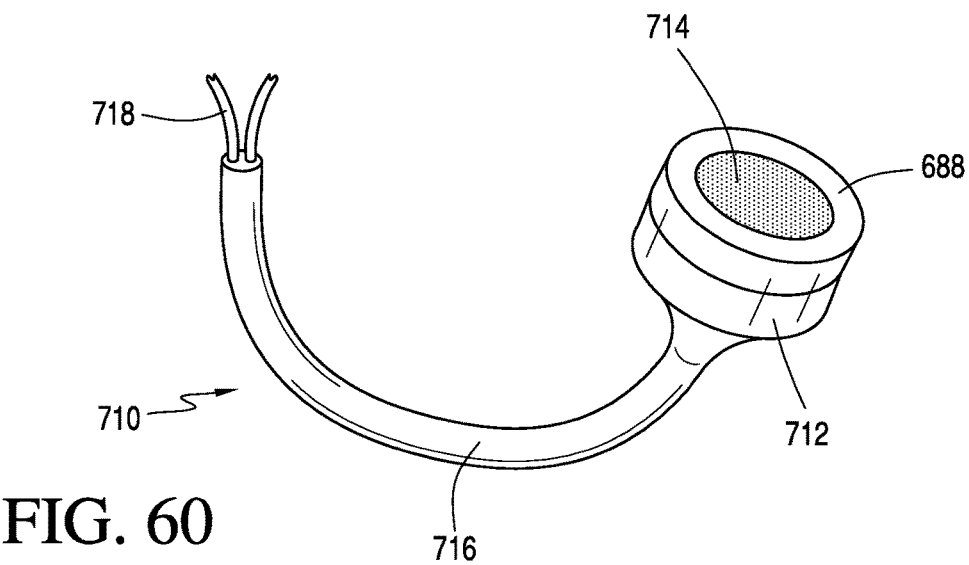
FIG. 60 is a view of yet another active transdermal delivery module in accordance with an exemplary embodiment of the present disclosure.

FIG. 60 is a view of yet another active transdermal delivery module in accordance with an exemplary embodiment of the present disclosure, indicated generally at 710. Device 710 includes a support 712 that provides a location for thermoelectric device 688 and drug delivery interface 714. Drug delivery interface 714 provides a limited source of drugs since drug delivery interface 714 is not connected to a reservoir. Support 712 is connected to a flexible arm 716 that provides a location for wires 718 that deliver power to thermoelectric device 688. Module 710 is useful for short term supply of a drug. Drug delivery interface 714 is configured to be readily replaceable to replenish the supply of drugs to a patient or subject.

Figure 61:
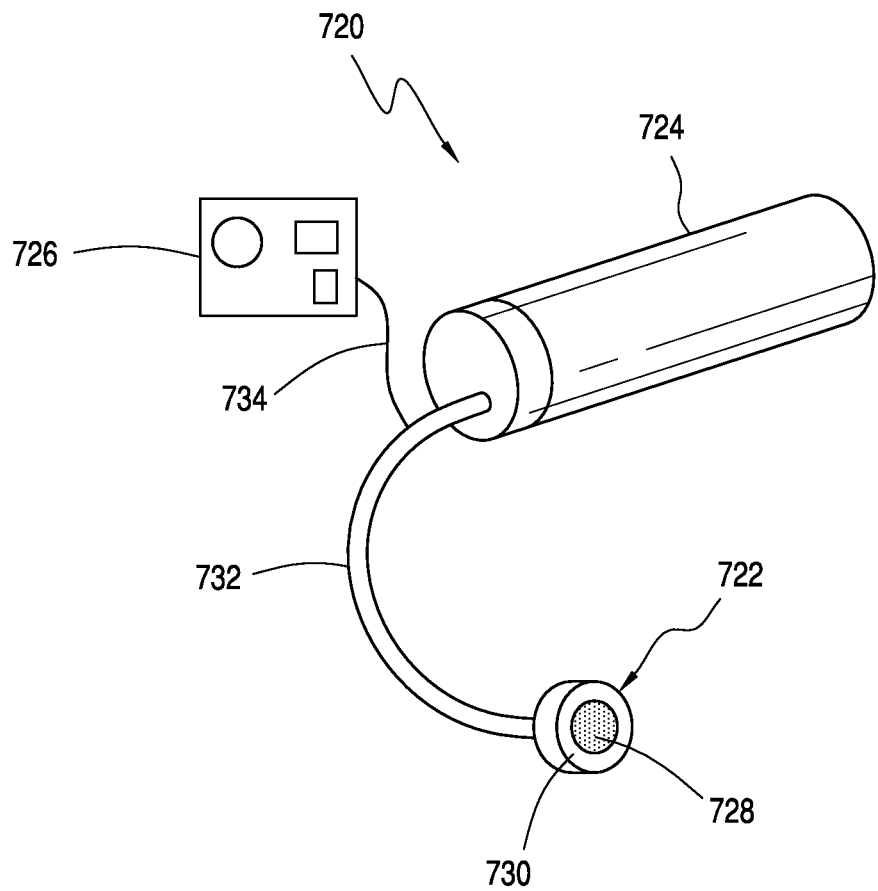
FIG. 61 is a view of a basic active transdermal delivery system in accordance with an exemplary embodiment of the present disclosure.

FIG. 61 is a view of a basic active transdermal delivery system in accordance with an exemplary embodiment of the present disclosure, indicated generally at 720. System 720 includes a drug delivery interface 722, a drug reservoir 724, and a controller 726. Drug delivery interface 722 includes an absorbent material 728 positioned in an annular thermoelectric device 730. Drug delivery device 722 is connected to reservoir 724 by a flexible arm or support 732, which is configured to support a fluid passage extending between reservoir 724 and absorbent material 728. Controller 726 is connected to thermoelectric device 730 by a wire or cable 734. Controller 726 is configured to connect and disconnect power to thermoelectric device 730, and to vary the amount of power to control temperature delivered to a subject or patient. In an exemplary embodiment, controller 726 can also be configured to control the flow of a drug from reservoir 724 to drug delivery interface 722. Controller 726 can further include a display to present the temperature of various locations, including ambient, facial skin, extremity (hands and feet), rectal, oral, axillary, ABTT terminus 10, and the like.

Figure 62:
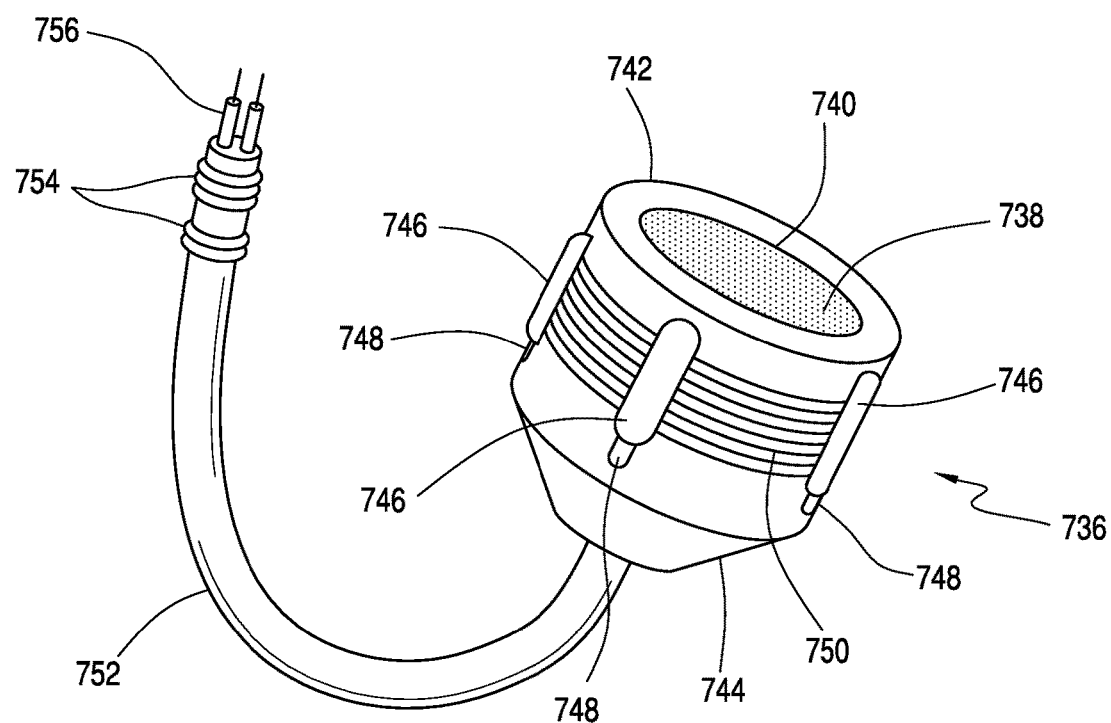
FIG. 62 is a view of a drug delivery interface including a spring, in accordance with an exemplary embodiment of the present disclosure.

The goal of the flexible arm or support 732 is to permit adjusting the position of drug delivery interface 722 to match the location of ABTT terminus 10 as well as possible, and to maintain contact between absorbent material 728, or other drug delivery media, and ABTT terminus 10. FIG. 62 is a view of a drug delivery interface incorporating a spring to assist in accordance with an exemplary embodiment of the present disclosure, indicated generally at 736. Drug delivery interface includes a drug container or reservoir 738 positioned in an annular opening 740 of a thermoelectric device 742. Thermoelectric device 742 and drug container are secured to a support base 744 by a plurality of connectors 746 that slidingly interface with a plurality of slots 748. In the exemplary embodiment of FIG. 62, slots 748 are located on support base 744, and connectors 746 are fixedly attached at a peripheral location of thermoelectric device 742. A spring 750 is positioned between thermoelectric device 742 and support base 744. The function of spring 750 is to permit drug delivery interface 736 to be moved into contact with ABTT terminus 10, which then compresses spring 750, which is configured to maintain contact with ABTT terminus 10 in the event of limited movement of drug delivery interface 736. Drug delivery interface 736 further includes a flexible arm or support 752, which further includes an attachment arrangement 754 to permit secure attachment of drug delivery interface 736 to another device or apparatus, such as a separate support. Flexible arm 752 further support wires 756 that route power from a power supply or controller to thermoelectric device 742.

Figure 63:
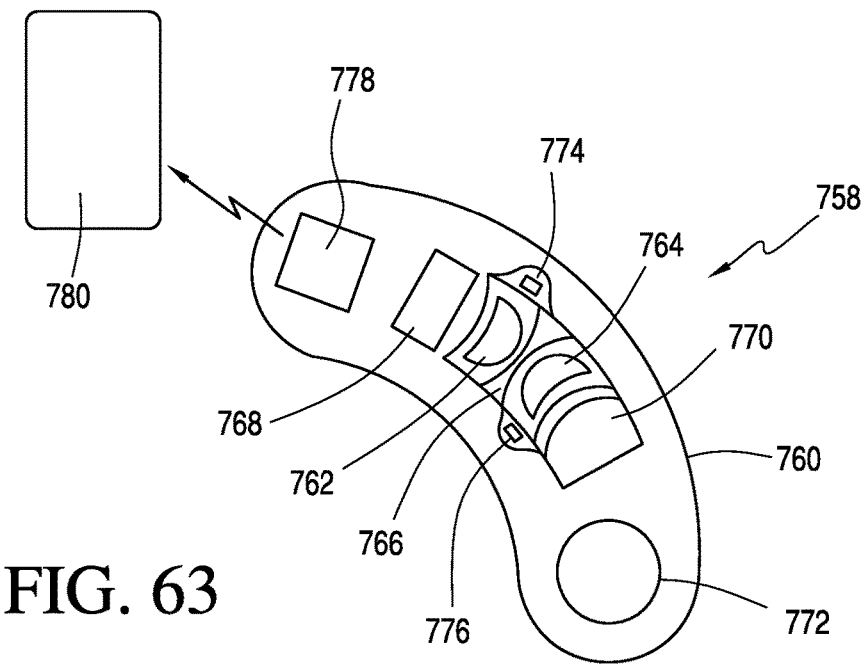
FIG. 63 is a view of an active transdermal delivery device configured to deliver two drugs, in accordance with an exemplary embodiment of the present disclosure.

FIG. 63 is a view of an active transdermal delivery device configured to deliver two drugs, in accordance with an exemplary embodiment of the present disclosure, indicated generally at 758. It should be understood that FIG. 63 is configured as a block diagram, and certain features, such as drug containers, are positioned such that when device 758 is properly placed on the skin, the appropriate features are positioned in contact with the skin. The thermoelectric devices described in conjunction with device 758 need not be positioned in direct contact with the skin, but need to be positioned in a location that provides thermal communication with the skin.

Device 758 is configured to take advantage of change in skin permeability with temperature, and, in some cases, the increased transport of drugs with temperature. For most drugs, as shown in studies by Applicant, skin permeability increases with an increase in temperature, and decreases with a decrease in temperature. Accordingly, the flow of drugs through the skin may be halted by modifying skin permeability with temperature. In addition, for drugs where skin permeability increases with temperature, the mobility of the drug increases with temperature, further improving the flow of drugs through the skin of ABTT terminus 10 to reach ABTT 12.

Device 758 includes a support 760, on which are positioned or located a first drug container or reservoir 762 and a second drug container or reservoir 764, separated by a thermal insulator 766. Device 758 further includes a first thermoelectric device 768 positioned on an opposite side of first drug container 762 from second drug container 764, and a second thermoelectric device 770 positioned on an opposite side of second drug container 764 from first drug container 762. In the exemplary embodiment of FIG. 63, a power supply 772 is also positioned on support 760 and connected to various elements of device 758 to provide power for operation. A first temperature sensor 774 and a second temperature sensor 776 are positioned in proximity to first drug container 762 and second drug container 764, respectively. First temperature sensor 774 and second temperature sensor 776 enable refined control of the temperature of first drug container 762 and second drug container 764, and, consequently, control of the delivery of drugs through the skin. For example, by decreasing the temperature of first thermoelectric device 768 by an amount equal to at least one degree Celsius below the initial or nominal skin temperature, permeability of the skin to most drugs drops to approximately zero, effectively stopping or shutting off the flow of drugs through the skin. Conversely, increasing the temperature of the skin a degree above the initial or nominal skin temperature increases skin permeability by about 30% for most of the drugs tested, and described herein. Thus, controlling the temperature of a thermoelectric device positioned adjacent to a drug container in contact with the skin controls drug flow through the skin. Thus, it is an object of the disclosure to provide a device that controls flow of drugs through the skin using a combination of warming and cooling.

Device 758 can further include a transmitter, receiver, or transceiver 778 configured for communication with a separate electronic device 780, such as a cell phone, laptop, tablet, watch, etc. Such communication with separate electronic device 780 permits control of device 758 and, when device 758 is provided with sensors, monitoring of device 758.

Figure 64:
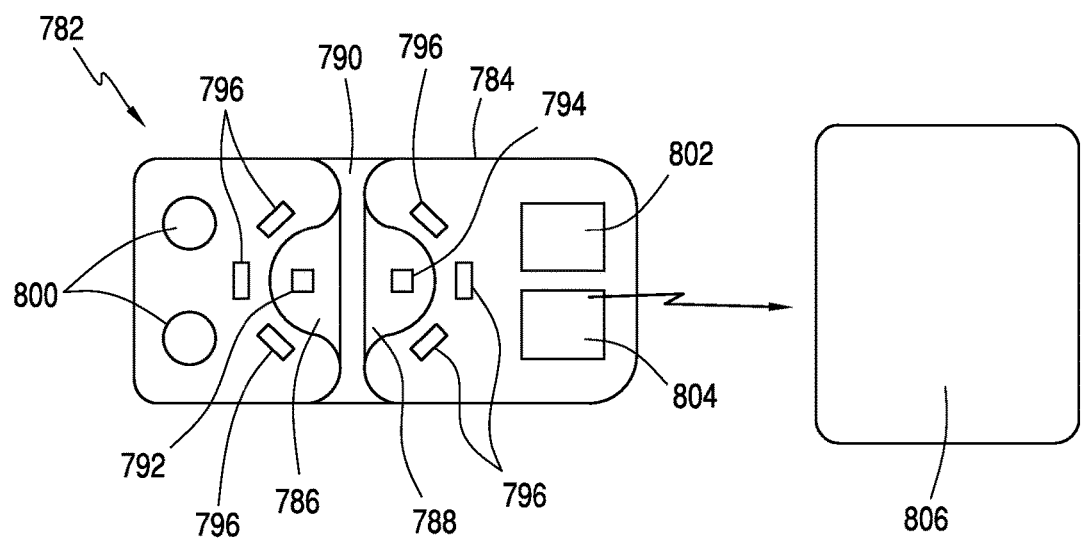
FIG. 64 is a view of another active transdermal delivery device configured to deliver two drugs, in accordance with an exemplary embodiment of the present disclosure.

FIG. 64 is a view of another active transdermal delivery device configured to deliver two drugs, in accordance with an exemplary embodiment of the present disclosure and indicated generally at 782. Device 782 includes a support 784 on which is positioned a first drug container or reservoir 786 and a second drug container or reservoir 788, separate by a thermal insulator 790. A first temperature sensor 792 may be positioned proximate or over first drug container 786 and a second temperature sensor 794 may be positioned proximate or over second drug container 788 to measure, indirectly, the temperature of the skin over which first drug container 786 and second drug container 788 are positioned. Device 782 further includes at least one first thermoelectric device 796, and may include a plurality of first thermoelectric devices 796 positioned about a periphery of first drug container 786, and at least one second thermoelectric device 798, and may include a plurality of second thermoelectric devices 798 positioned about a periphery of second drug container 788. First thermoelectric device(s) 796 and second thermoelectric device(s) 798 are positioned on a periphery that is away from the portion of the periphery that is along thermal insulator 790. Device 782 is further configured to include a power supply 800 for providing power to the various elements positioned on device support 784. Device 782 further includes a controller 802 configured to operate various elements of device 782, and a transceiver, transmitter, or receiver 804 configured to communicate with a separate electronic device 806, which may be a cell phone, tablet, laptop, watch, etc.

Figure 65:
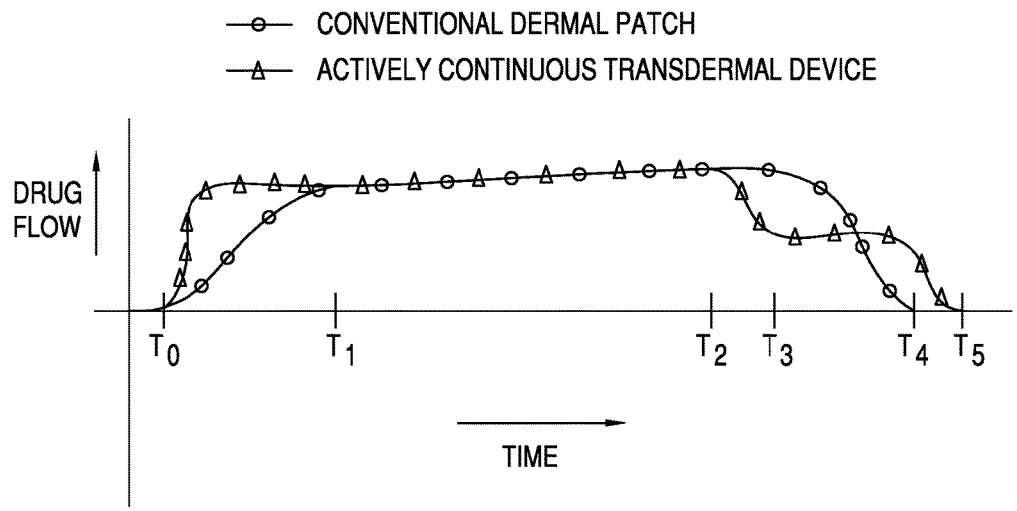
FIG. 65 is a first graph demonstrating controlled drug flow in accordance with an exemplary embodiment of the present disclosure.

FIG. 65 is a first graph demonstrating controlled drug flow in accordance with an exemplary embodiment of the present disclosure. As described herein, by controlling the temperature of the skin adjacent to an absorbent material, drug container, or drug reservoir, the flow of a drug through the skin can be controlled. FIG. 65 shows a stylized graph of drug flow from a conventional transdermal patch attached to the skin in comparison to one of the infinite patterns possible with an actively controlled transdermal device disclosed herein. A conventional device begins to deliver a drug to the skin at T0, building to a peak flow rate at T1. The drug then flows until drug depletion nears, at time T3, eventually falling to zero at time T4. In contrast, an actively controlled transdermal device generates transdermal drug delivery faster than a conventional device, shown by the steep slope at the beginning of the curve just after T0, which represents controlled fluid flow through the skin by increasing temperature with the thermal devices of the disclosure. At time T2, the temperature of the skin is reduced to decrease drug flow until a new steady state is reached at time T3. The delivery rate is sustained from time T3 to time T4, at which time drug delivery is reduced to zero, again by temperature control.

Figure 66:
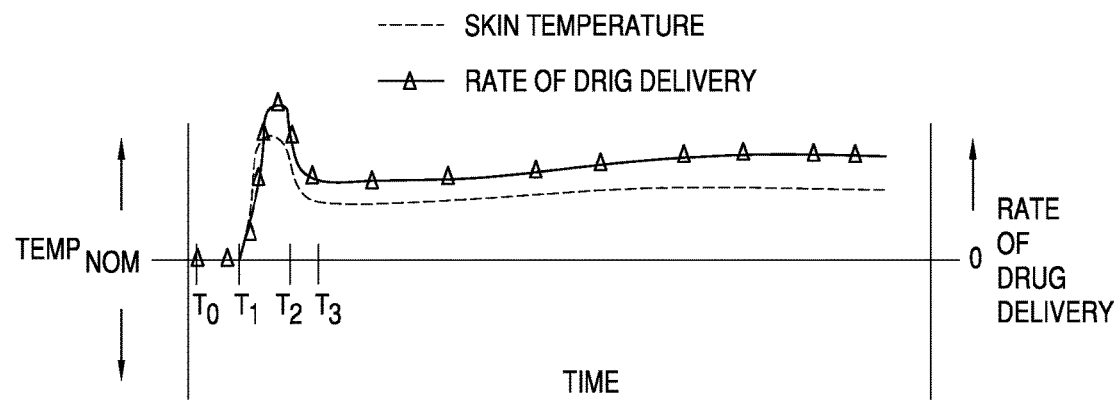
FIG. 66 is a second graph demonstrating controlled drug flow in accordance with an exemplary embodiment of the present disclosure.

FIG. 66 is a second graph demonstrating controlled drug flow in accordance with an exemplary embodiment of the present disclosure. From time T0 to T1, skin temperature is held below nominal, and a drug delivery rate is minimal or zero. At time T1, skin temperature is increased to raise the drug delivery rate rapidly to a peak at T2 to provide an initial flood of drugs, followed by a decrease in skin temperature from time T2 to time T3, which reduces the flow of drugs through the skin. From time T3 onward, the flow rate of drugs through the skin is maintained at a steady state, sometimes supported by a reservoir, which may be integral or separate.

Figure 67:
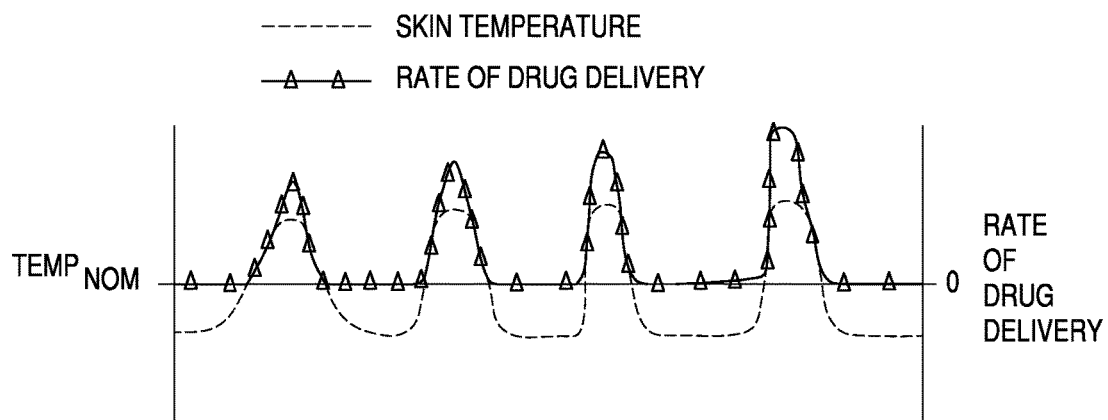
FIG. 67 is a third graph demonstrating controlled drug flow in accordance with an exemplary embodiment of the present disclosure.

FIG. 67 is a third graph demonstrating controlled drug flow in accordance with an exemplary embodiment of the present disclosure. In FIG. 67, the temperature is varied to turn drug flow off and on, increasing the rate of drug flow during each subsequent activation of drug flow.

Figure 68:
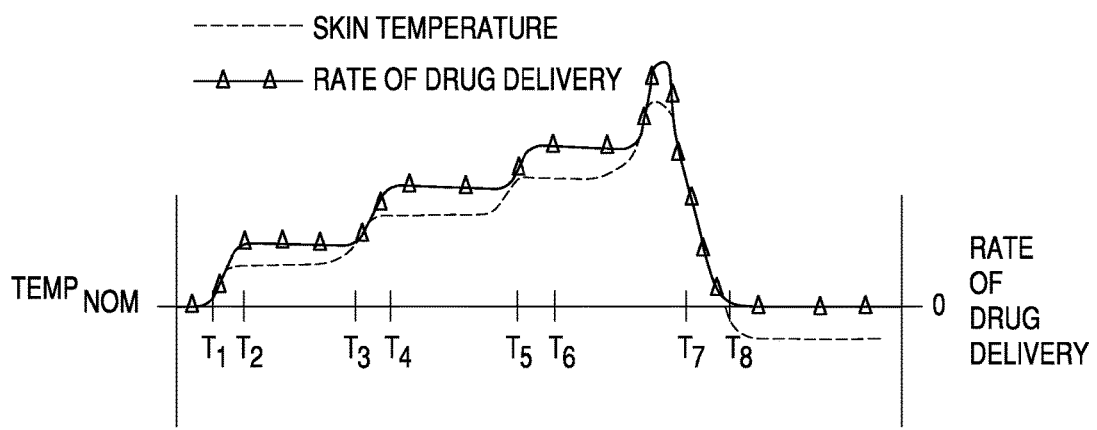
FIG. 68 is a fourth graph demonstrating controlled drug flow in accordance with an exemplary embodiment of the present disclosure.

FIG. 68 is a fourth graph demonstrating controlled drug flow in accordance with an exemplary embodiment of the present disclosure. In FIG. 68, the rate of drug flow is stepped up over time, until drug flow is turned off at time T8 by reducing skin temperature below nominal or normal.

Figure 69:
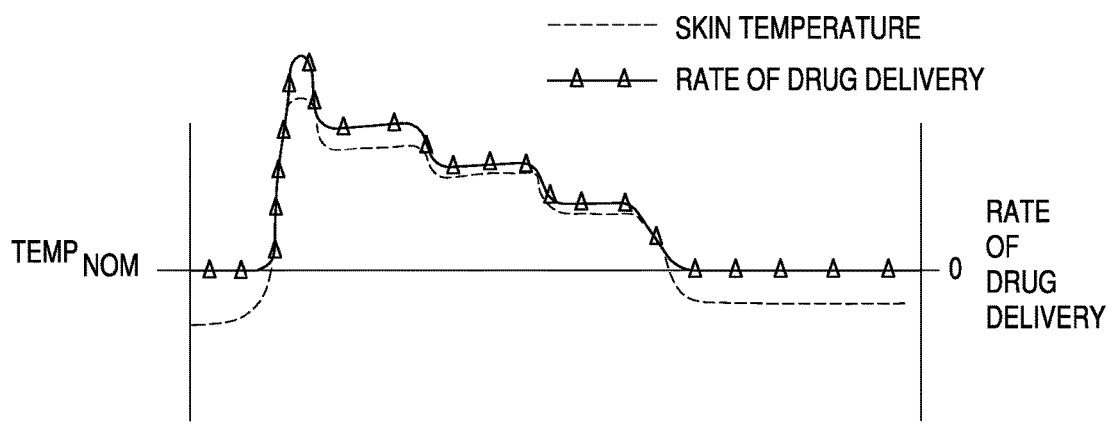
FIG. 69 is a fifth graph demonstrating controlled drug flow in accordance with an exemplary embodiment of the present disclosure.

FIG. 69 is a fifth graph demonstrating controlled drug flow in accordance with an exemplary embodiment of the present disclosure. The rate of drug flow is opposite that shown in FIG. 68, beginning at a relatively high level and decreasing in steps over time until the drug flow is eventually reduced to zero by controlling the temperature of the skin.

Figure 70:
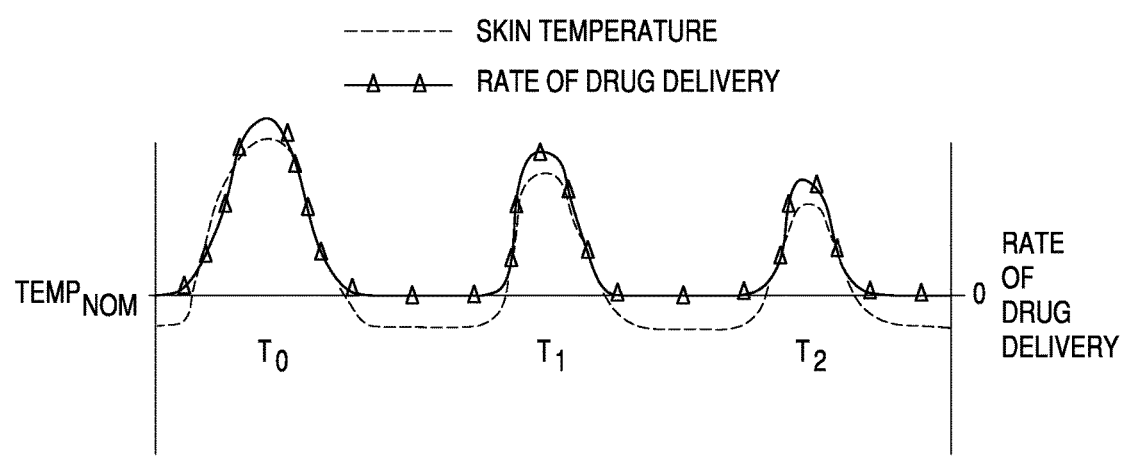
FIG. 70 is a sixth graph demonstrating controlled drug flow in accordance with an exemplary embodiment of the present disclosure.

FIG. 70 is a sixth graph demonstrating controlled drug flow in accordance with an exemplary embodiment of the present disclosure. In FIG. 70, drug flow is turned on and off with time, with the maximum flow rate decreased each time.

Figure 72:
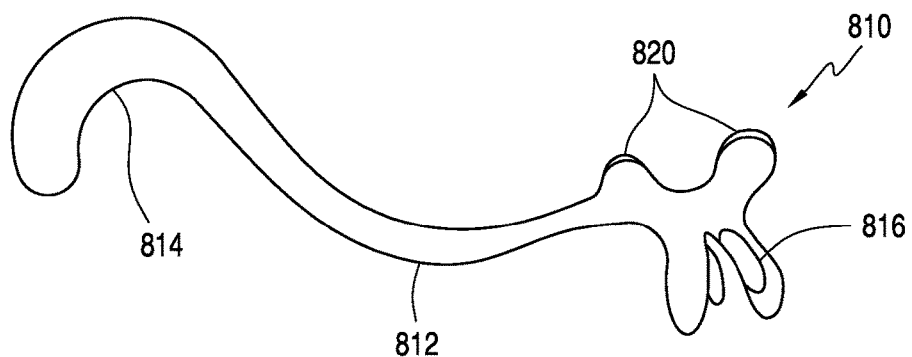
FIG. 72 is an exterior view of an active transdermal delivery device in accordance with an exemplary embodiment of the present disclosure.
Figure 73:
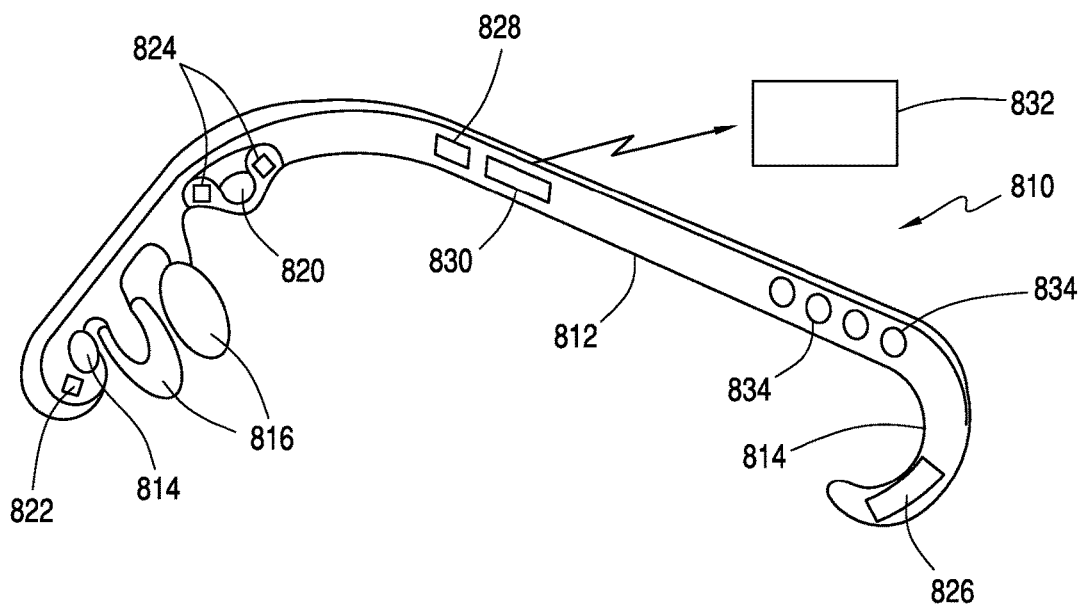
FIG. 73 is an interior view of the active transdermal delivery device of FIG. 72.

FIGS. 72 and 73 are views of an active transdermal delivery device in accordance with an exemplary embodiment of the present disclosure, indicated generally at 810. Device 810 includes a frame 812 configured to be supported on a person's ear and nose by an ear engagement portion 814 and nose pads 816. Device 810 further includes a first drug container 818 and a second drug container 820 configured to be positioned on a patient or subject's ABTT terminuses 10 when device 810 is positioned on an ear and a nose of a patient or subject's face. Device 810 further includes at least one first thermoelectric device 822 and at least one second thermoelectric device 824 positioned to contact the skin at or near ABTT terminus 10 when device 810 is positioned on a subject or patient's face. In the exemplary embodiment of FIG. 72, device 810 is configured to include a drug container or reservoir 826 positioned on ear engagement portion in a location configured to contact retroauricular blood vessels located behind the ear. Device 810 is further configured to include a controller 828, a transceiver, transmitter, or receiver 830 configured to communicate with an external electronic device 832, and a power supply or supplies 834 configured to provide power to the electronic elements of device 810.

Figure 74:
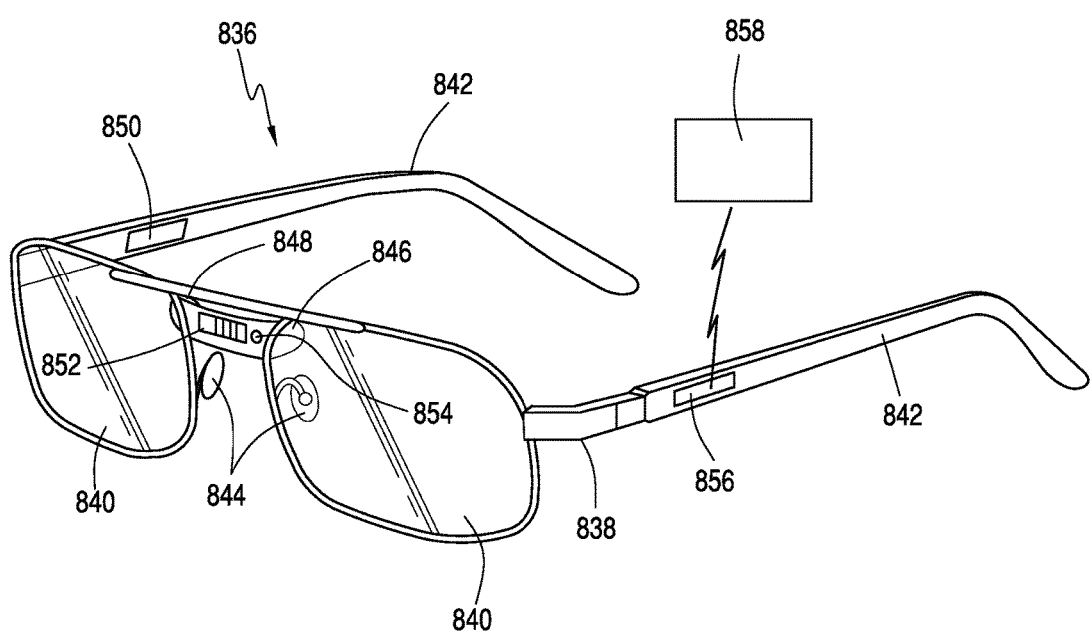
FIG. 74 is a perspective view of an active transdermal delivery device in accordance with an exemplary embodiment of the present disclosure.

FIG. 74 is a perspective view of an active transdermal delivery device in accordance with an exemplary embodiment of the present disclosure, indicated generally at 836. Device 836 is configured to include an eyeglass frame 838 including lenses 840, temple pieces, 842, and nose pads 844. Device 836 is configured to include a first drug container or reservoir 846 and a second drug container or reservoir 848 configured to be positionable such that first drug container 846 and second drug container 848 will contact ABTT terminuses 10 of a patient or subject when device 836 is positioned on the face of the patient or subject. Device 836 is further configured to include a plurality of electronic elements, such as a power supply 850, a controller 852, one or more temperature sensors 854, and a transceiver, transmitter, or receiver 856 configured to communicate with a separate electronic device 858. Device 836 is configured to provide the benefits of conventional eyeglasses with the benefits of the present disclosure to provide a multipurpose or multifunction device for vision correction and transdermal drug delivery.

Figure 75:
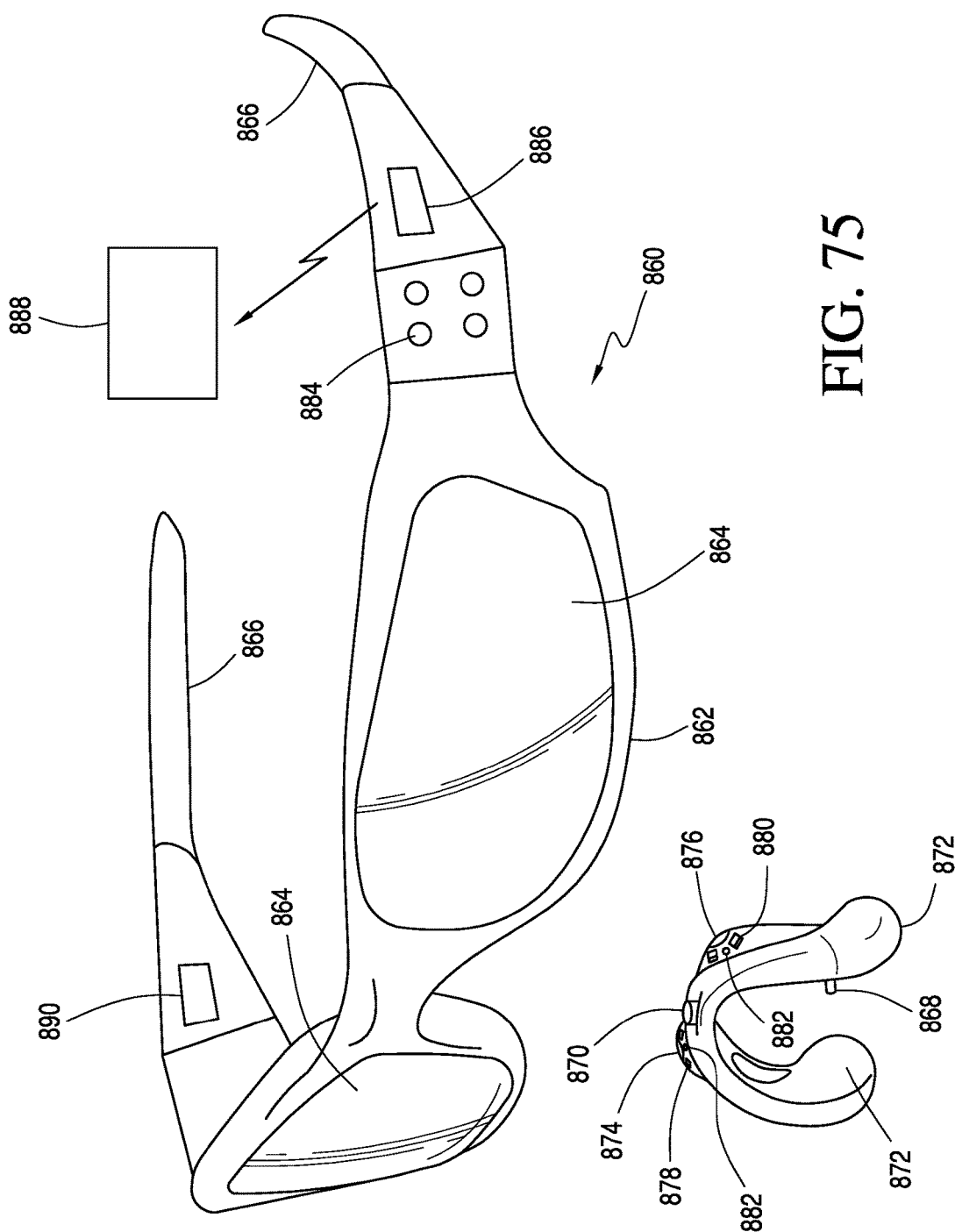
FIG. 75 is a perspective view of another active transdermal delivery device in accordance with an exemplary embodiment of the present disclosure.

FIG. 75 is a perspective view of an active transdermal delivery device in accordance with an exemplary embodiment of the present disclosure, indicated generally at 860. Device 860 is configured as a pair of eyeglasses, including a frame 862, lenses 864, and temple pieces 866. Device 860 further includes a separable nose piece 868 configured to attach to frame 862, and to communicate with electronic elements positioned on frame 862 by way of a connector 870. Nose piece 868 is configured to include a pair of nose pads 872, a first drug container or reservoir 874, and a second drug container or reservoir 876. First drug reservoir 874 and second drug reservoir 876 are configured to contact a patient or subject's ABTT terminuses 10 when device 860 is positioned on a patient or subject's head, supported by the patient or subject's ears and nose. Nose piece is further configured to include at least one first thermoelectric device 878 positioned adjacent or alongside first drug reservoir 874 and at least one second thermoelectric device 880 positioned adjacent or alongside second drug reservoir 876 to heat the skin of ABTT terminuses 10 and to heat the drugs in first drug reservoir 874 and second drug reservoir 876. Nose piece 868 can further include at least one temperature sensor 882 to measure the temperature of nose piece 868 in the area where first thermoelectric device 878 and second thermoelectric device 880 are positioned. Device 860 may be configured to include a plurality of electronic elements, including a power supply 884, a transceiver, transmitter, or receiver 886 for communication with a separate electronic device 888, and a controller 890.

Figure 76:
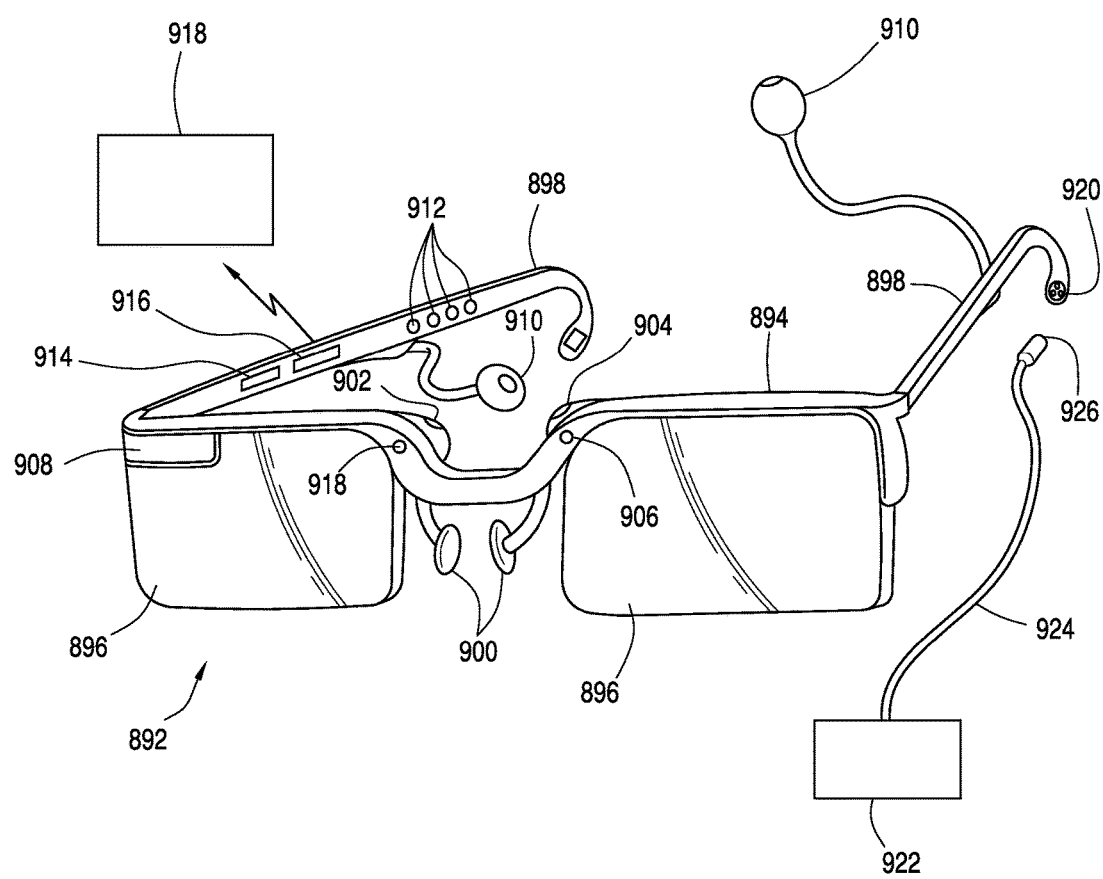
FIG. 76 is a perspective view of yet another active transdermal delivery device in accordance with an exemplary embodiment of the present disclosure.

FIG. 76 is a perspective view of another active transdermal delivery device in accordance with an exemplary embodiment of the present disclosure, indicated generally at 892. Device 892 is configured as a pair of eyeglasses, including a frame 894, lenses 896, and temple pieces 898. Device 892 further includes a pair of nose pads 900, a first drug container or reservoir 902, and a second drug container or reservoir 904. First drug reservoir 902 and second drug reservoir 904 are configured to contact a patient or subject's ABTT terminuses 10 when device 892 is positioned on a patient or subject's head, supported by the patient or subject's ears and nose. Device 892 may be configured to include thermoelectric devices (not shown) adjacent to first drug reservoir 902 and second drug reservoir 904, similar to, for example, the configuration shown in FIGS. 73 and 75. Device 892 is further configured to include one or more temperature sensors 906 positioned to measure ambient temperature and temperature of frame 894. Device 892 contains other electronic elements, such as a display screen 908; ear buds 910 configured to transmit information regarding drug delivery and other information to a subject or user; a power supply 912 configured to provide power to electronic elements of device 892; a controller 914; a transceiver, transmitter, or receiver 916 configured to communicate with a separate electronic device 918; and a connector 920 configured to permit attachment of another separate electronic device 922, such as a laptop, cell phone, tablet, watch, etc. by way of a cable 924 and connector 926.

Figure 77:
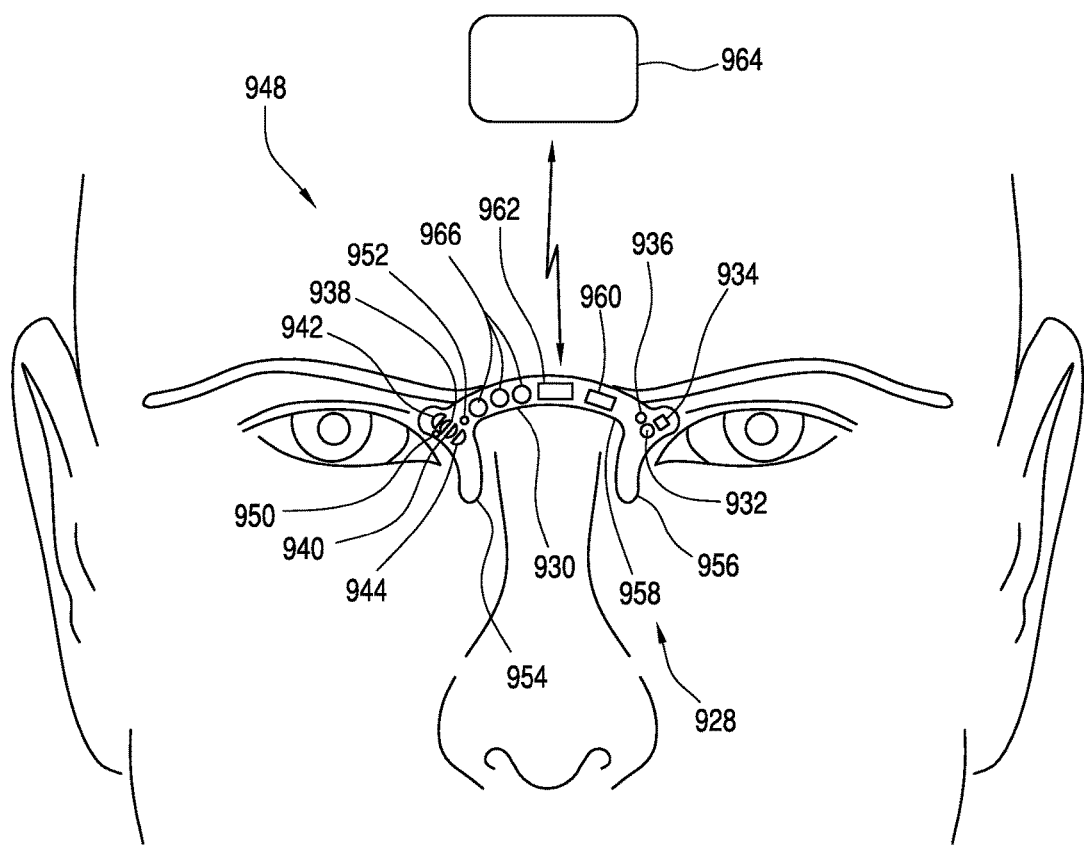
FIG. 77 is a view of an active transdermal delivery device in the form of a nose clip, in accordance with an exemplary embodiment of the present disclosure.

FIG. 77 is a view of an active transdermal delivery device in the form of a nose clip, in accordance with an exemplary embodiment of the present disclosure, indicated generally at 928. Device 928 includes a support 930 on which is positioned a first drug container or reservoir 932. To control drug delivery through ABTT terminus 10, a first thermoelectric device 934 is positioned adjacent to first drug container 932, and to monitor the temperature of device 928, a first temperature sensor 936 is positioned near first drug container 932, but a spaced distance from first thermoelectric device 934. First drug container 932 is configured to deliver a single drug to an associated first ABTT terminus 10. Device 928 is configured to include a second drug container 938 and a third drug container 940 positioned side-by-side over an associated second ABTT terminus 10. Device 928 further includes a second thermoelectric device 942 positioned alongside, adjacent to, or next to second drug container 938, and a third thermoelectric device 944 positioned alongside, adjacent to, or next to third drug container 940. Second thermoelectric device 942 is positioned to control the flow of drugs from second drug container 938 into second ABTT terminus 10, and third thermoelectric device 944 is positioned to control the flow of drugs from third drug container 940 into second ABTT terminus 10. Thus, a single active transdermal delivery device, such as device 928, can be configured to deliver a plurality of different drugs to a patient or subject 948. Device 928 can further include a second temperature sensor 950 and a third temperature sensor 952 positioned adjacent to second drug container 938 and third drug container 940, respectively, to monitor the temperature of each drug container.

Device support 930 further includes a first clip 954 and a second clip 956 connected to each other by a bridge 958. Bridge 958 can be configured to include a plurality of electronic elements, such as a controller 960; a transceiver, transmitter, or receiver 962 configured to communicate with a separate electronic device 964, such as a laptop, tablet, cell phone, watch, etc.; and a power supply 966.

Figure 78:
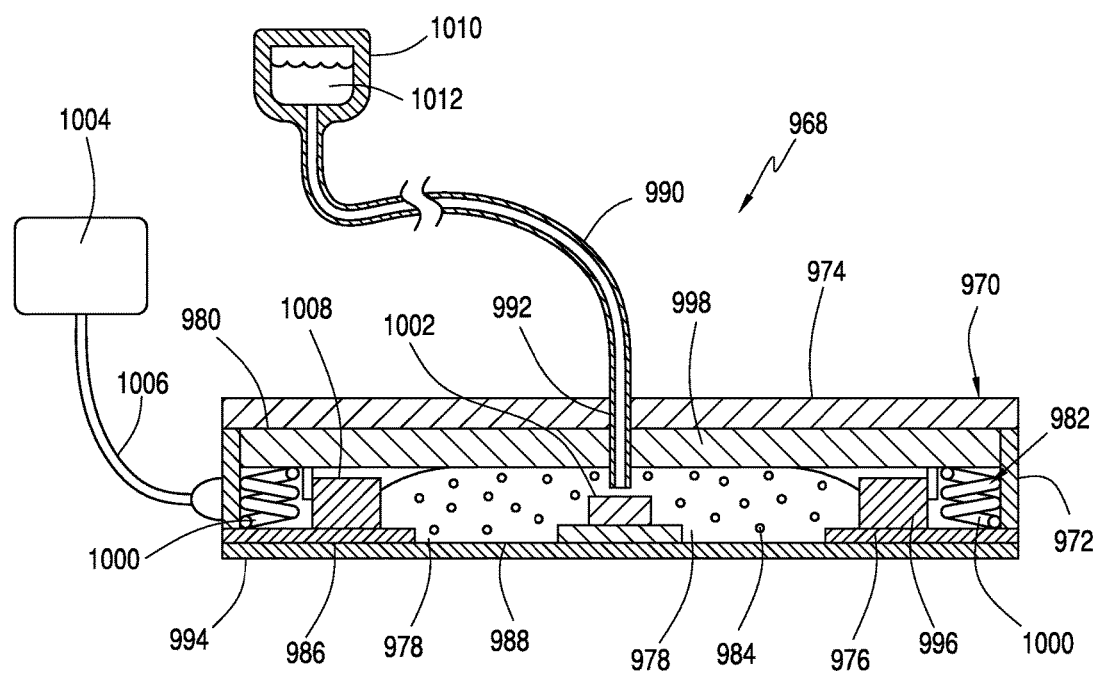
FIG. 78 is a cross-sectional view of an active transdermal delivery device connected to a separate reservoir, in accordance with an exemplary embodiment of the present disclosure.

FIG. 78 is a cross-sectional view of an active transdermal delivery device in accordance with an exemplary embodiment of the present disclosure, indicated generally at 968. Device 968 includes a housing assembly 970. Housing assembly 970 includes a side wall 972, which can be configured as an annulus, an upper cover 974, and a lower housing member 976. Lower housing member 976 includes a plurality of openings 978 formed therein. Housing assembly 970 forms an internal cavity, volume, or chamber 980, in which are positioned an actuation device 982 and an absorbent material 984. Absorbent material 984 is configured to extend into plurality of openings 978 such that a bottom surface 988 of absorbent material 984 is approximately parallel to a bottom surface 986 of lower housing member 976.

A removable or peelable layer 994 covers at least a portion of bottom surface 986 of lower housing member 976 and bottom surface 988 of absorbent material 984. Separation of removable layer 994 exposes bottom surface 988 so that bottom surface 988 can be accessible for contact with ABTT terminus 10.

Device 968 includes a movable fluid passage 990 that extends through an opening 992 formed in upper cover 974. As will be seen, fluid passage 990 is secured to an element of actuation device 982 and is movable by the operation of actuation device 982. A seal 1002 is positioned on lower housing member 976 so that when actuation device 982 operates, movable fluid passage 990 contacts seal 1002 and prevents the movement of fluid from movable fluid passage 990 into absorbent material 984. When actuation device 982 is released, fluid, e.g., a drug, is able to flow from movable fluid passage 990 into absorbent material 984.

Actuation device 982 includes a coil 996 and a movable plate 998 biased toward a top of internal cavity 980 by one or more bias springs 1000. When actuation device 982 is operated, such as by an external controller 1004 by way of a wireless connection or a wire or cable 1006, movable plate 998 is pulled toward a top surface 1008 of induction coil 996, which pulls fluid passage 990 downward toward seal 1002. Fluid passage 990 makes contact with seal 1002 just before movable plate 998 makes contact with induction coil 996, preventing a flow of fluid 1012, e.g., a drug, from a reservoir 1010 connected to movable fluid passage 990, blocking a flow of fluid 1012 to absorbent material 984. When actuation device 982 is released, movable plate 998 is released, moving an end of fluid passage 990 away from seal 1002, permitting fluid 1012 to flow from reservoir 1010 through fluid passage 990 into absorbent material. Thus, actuation device 982 controls the flow of fluid 1012 into absorbent material 984, and then into an associated ABTT terminus 10 and/or associated veins 14, 16, 18, 20, and 22.

Figure 79:
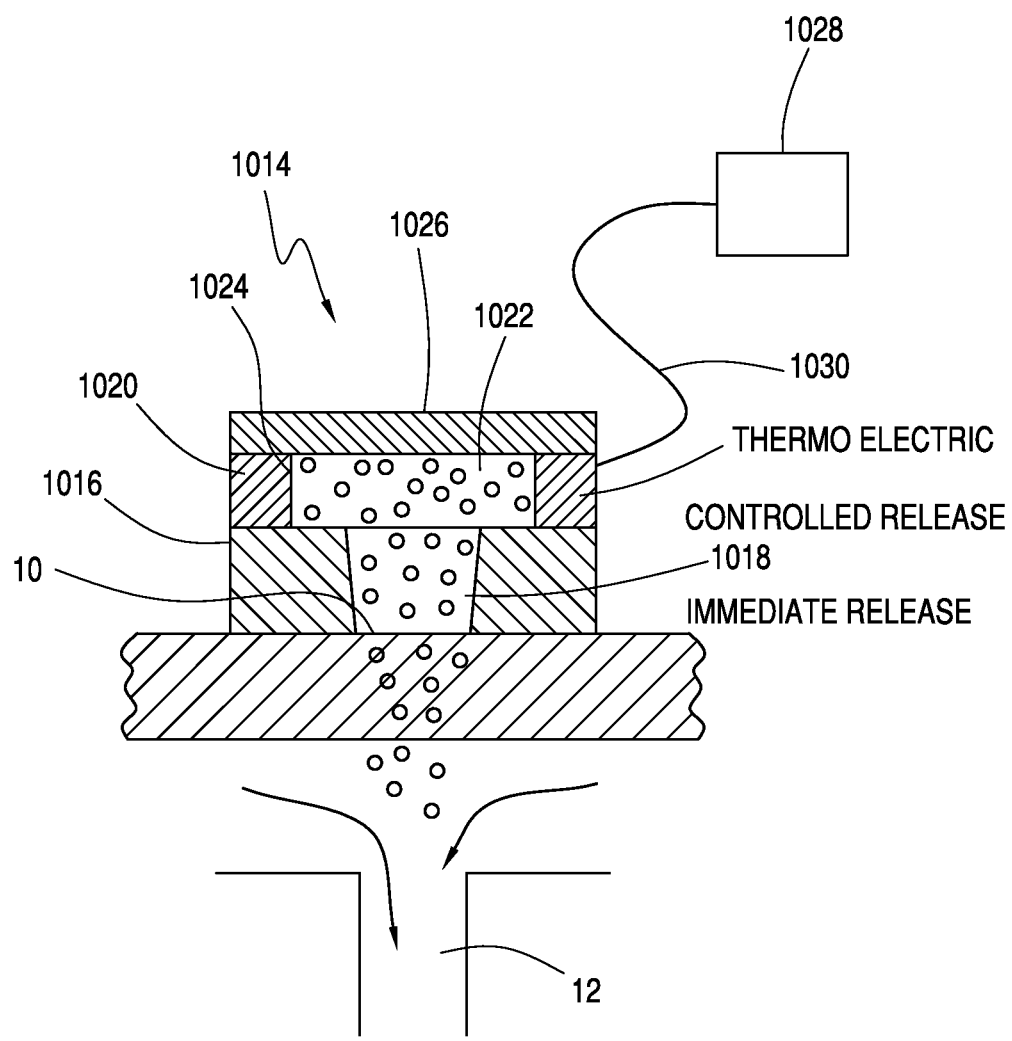
FIG. 79 is a cross-sectional view of an active transdermal delivery device configured to provide two types of drug release, in accordance with an exemplary embodiment of the present disclosure.

FIG. 79 is a view of an active transdermal delivery device in accordance with an exemplary embodiment of the present disclosure, indicated generally at 1014. Device 1014 includes a support 1016 in which is positioned a first drug container 1018, and an annular thermoelectric device 1020 positioned on device support 1016. A second drug container 1022 is positioned in a volume 1024 formed within a central portion of annular thermoelectric device 1020. To protect first drug container 1018 and second drug container 1022, device 1014 includes a removable or peelable layer (not shown) configured to cover at least first drug container 1018 and a cover layer 1026 configured to cover at least second drug container 1022.

When the removable layer is separated from device 1014, exposing first drug container 1018, and device 1014 is place on ABTT terminus 10, the drugs in first drug container 1018, which are configured with a higher skin permeability than the drugs in second drug container 1022, provide an immediate release of drugs to ABTT terminus 10. The drugs in second drug container 1022 are activated by heat from thermoelectric device 1020, powered by a controller 1028 connected to thermoelectric device 1020 by, for example, wires, or a cable 1030. Controller 1028 may be co-located with device 1014 or may be separately positioned.

Device 1014 is configured to provide a first release of drugs from first drug container 1018, typically at a first flow rate, and then to provide a second release of drugs from second drug container 1022, often at a lower flow rate that may be sustained for a period that is longer than the period for delivery of drugs from first drug container 1018. However, second drug container 1022 can be configured to deliver drugs at varying flow rates with the presence of thermoelectric device 1020, and can also be configured to deliver a second drug that is different from a first drug positioned in first drug container 1018. It should be understood that first drug container 1018 can contain a skin permeation enhancer that increases skin permeability, and second drug container 1022 contains a drug.

FIGS. 80-82 are views of a portion of a transdermal delivery device, which may be passive or active, incorporating a replaceable drug reservoir, in accordance with an exemplary embodiment of the present disclosure, indicated generally at 1032. Device 1032 includes a support frame 1034, which can be, for example, an eyeglass frame. Support frame 1034 includes nose pads 1036 to provide at least partial support for support frame 1034 on a subject or user's face. Support frame 1034 also includes a longitudinally extending cavity or recess 1036 configured to receive a separate reservoir 1038. Support frame 1034 further includes a transdermal drug delivery module 1040 positioned in a location such that when support frame 1034 is located on the subject or user's head, transdermal drug delivery module 1040 is configurable to be positioned on the subject or user's ABTT terminus 10. Though not shown, it should be understood that device 1032 is likely to include a second drug delivery module 1040 for the subject's other ABTT terminus 10.

Transdermal drug delivery module 1040 includes a reservoir cavity 1042 configured to contain a drug 1044, with reservoir cavity 1042 covered or enclosed by an absorbent material 1046 that permits drug 1044 flow therethrough when in contact with an ABTT terminus 10 for transdermal delivery of drug 1044 to the subject or patient. It should be understood that absorbent material 1046 can fill reservoir cavity 1042 in its entirety. Thus, liquid separate from absorbent material 1046 may not be present in reservoir cavity 1042, and in this alternative embodiment (not shown) the liquid is contained and stopped at the level of fluid passage 1052, thereby allowing better control of the delivery of drug 1044 to absorbent material 1046. Transdermal drug delivery module 1040 is connected or attached to support frame 1034 by a flexible arm 1048. Reservoir cavity 1042 is connected to separate reservoir 1038 by a first fluid passage 1050 formed in support frame 1034, which is fluidly connected to a second fluid passage 1052 that extends through flexible arm 1048 to connect with reservoir cavity 1042. Thus, when separate reservoir 1038 is positioned in support frame 1034, device 1032 is configured to provide an extended period of drug 1044 delivery to a patient or subject.

Separate reservoir 1038 may be fabricated from any suitable material that is inert with respect to drug 1044, which can include some types of glass and plastic. Reservoir 1038 is covered at one end by a membrane 1054 that seals drug 1044 in reservoir 1038 until reservoir 1038 is installed in support frame 1034. When reservoir 1038 is inserted into longitudinally extending cavity 1036, a penetration or piercing device, apparatus, or mechanism 1056 punctures membrane 1054, permitting drug 1044 to flow into first fluid passage 1050. Membrane 1054 extending about an end surface of separate reservoir 1038 serves as a seal to prevent leakage when separate reservoir 1038 is positioned in support frame 1034. Alternatively, membrane 1054 can be removed or punctured prior to installation in support frame 1034.

Figure 83:
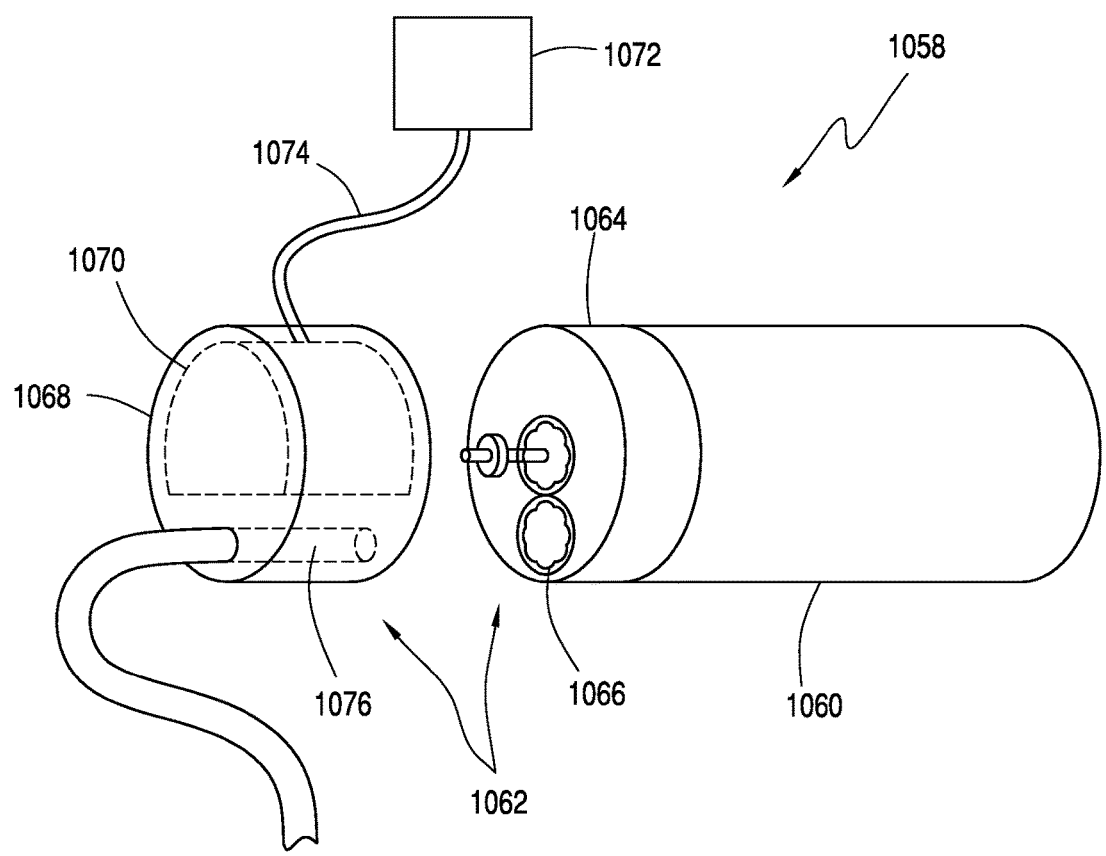
FIG. 83 is a perspective view of a separate drug reservoir in accordance with an exemplary embodiment of the present disclosure.

FIG. 83 is a perspective view of a separate drug reservoir in accordance with an exemplary embodiment of the present disclosure, indicated generally at 1058. While separate reservoir 1038 shown in FIGS. 80 and 81 is beneficial in many gravity fed systems, providing an active pump in association with a separate reservoir can be beneficial in some transdermal delivery device configurations. Separate drug reservoir 1058 includes a reservoir body 1060 that includes a cavity or volume for storage of a drug. An end cap or cover 1062 encloses the cavity or volume of reservoir 1058. In the exemplary embodiment of FIG. 83, end cap or cover 1062 includes a pump cap 1064 containing a small fluid pump 1066 that may be formed, for example, by a MEMS process. A driver cap 1068 configured to include a pump drive 1070 is configured to be positioned on pump cap 1064. Pump drive 1070 is configured to be power by an external power supply 1072 connected by wires or a cable 1074 driver cap 1068 and then to pump drive 1070. Driver cap 1068 further includes a fluid passage 1076 that connects fluid pump 1066 to, for example, a transdermal drug delivery module.

Figure 84:
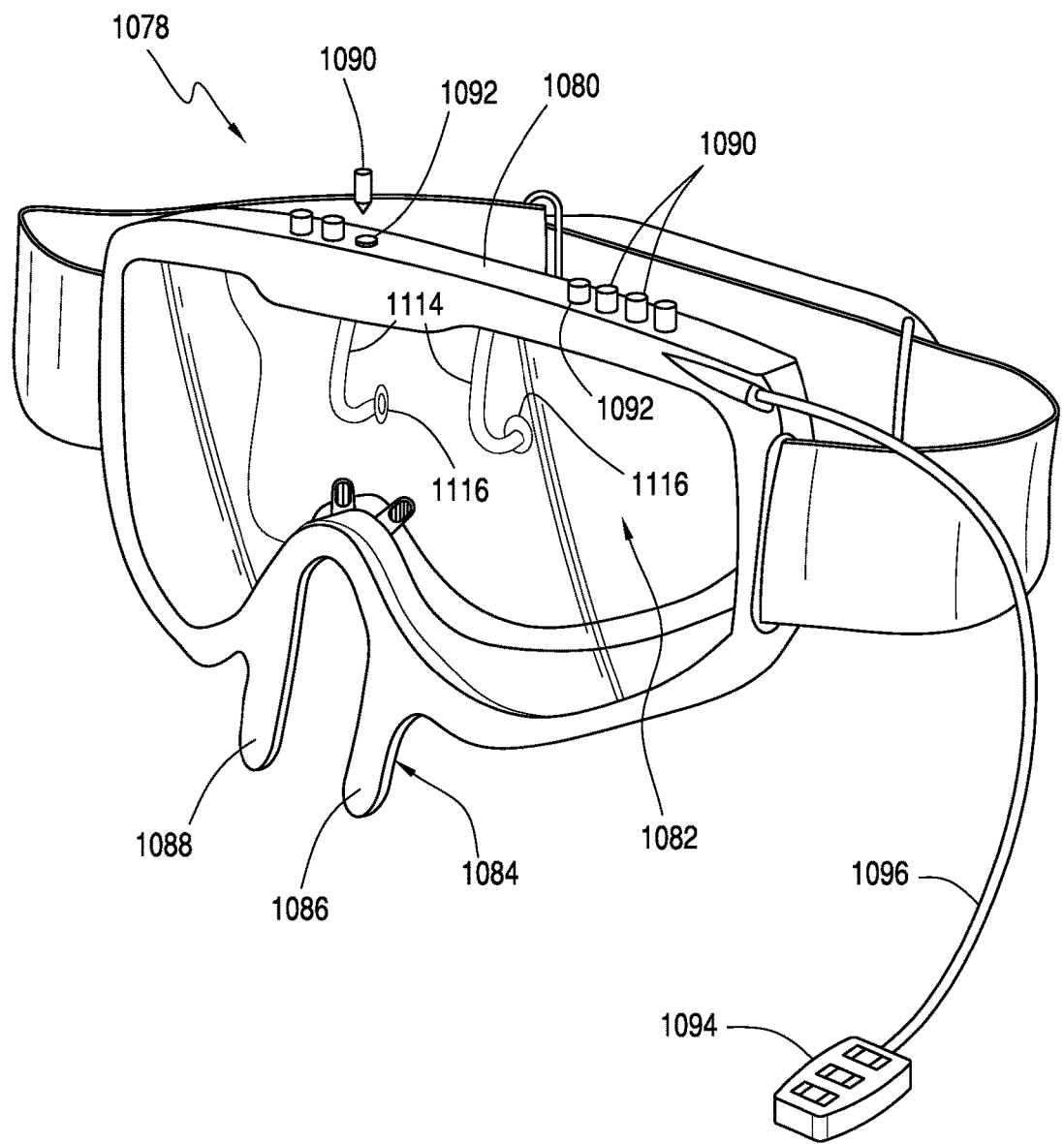
FIG. 84 is a perspective view of a mask incorporating an active transdermal delivery system in accordance with an exemplary embodiment of the present disclosure.

FIG. 84 is a perspective view of a mask incorporating an active transdermal delivery system in accordance with an exemplary embodiment of the present disclosure, indicated generally at 1078. Mask 1078 includes a mask body 1080 configured to include an active transdermal drug delivery system 1082, and a passive transdermal drug delivery device 1084.

Passive transdermal drug delivery device 1084 includes a first drug container, which may be similar to drug container 466 shown in FIG. 40, positioned on a first angular extension 1086, and a second drug container, which may be similar to drug container 468 shown in FIG. 40, positioned on a second angular extension 1088. The first drug container and the second drug container in this embodiment are configured to contact at least a portion of angular veins 20, and may extend to contact at least a portion of facial veins 22. First angular extension 1086 and second angular extension 1088 are preferably made with a flexible or conformable material for close apposition to the skin surface overlying the veins. It should be understood that an adhesive surface may be included in first angular extension 1086 and second angular extension 1088 or on the skin surface of the first drug container and the second drug container.

Active transdermal delivery device 1082 includes a plurality of drug reservoirs 1090 configured to mate with appropriately configured receptacles 1092 in mask body 1080. Drugs from any one drug reservoir 1090 may be released upon command, such as through a control device 1094 connected to mask 1078 wirelessly or by wires or a cable 1096.

Figure 71:
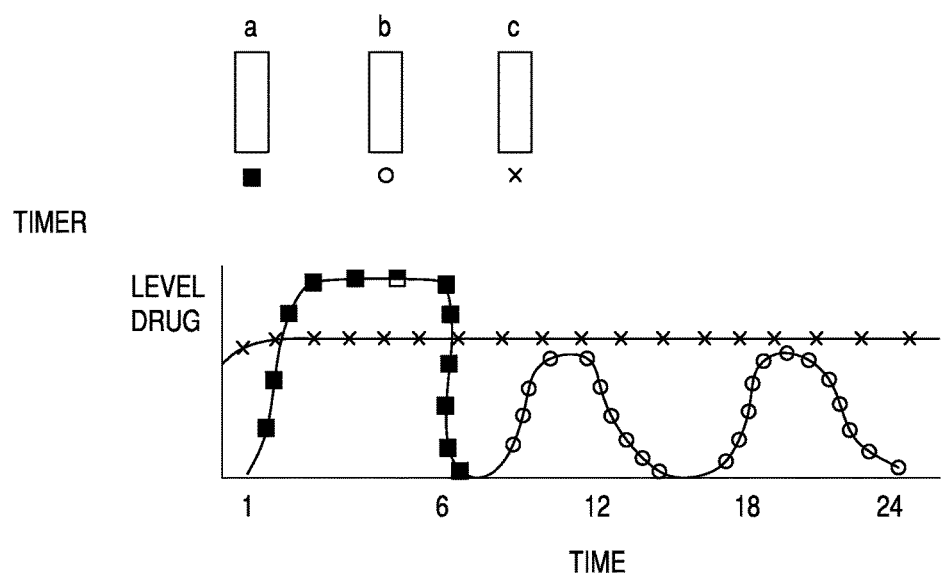
FIG. 71 is a seventh graph demonstrating controlled drug flow in accordance with an exemplary embodiment of the present disclosure.

FIG. 71 is a seventh graph demonstrating controlled drug flow in device 1082 in accordance with an exemplary embodiment of the present disclosure. Because device 1082 can be configured to include a plurality of different drugs, and delivery of each drug to ABTT terminus 10 can be controlled, an infinite number of delivery times and quantities are possible. For example, FIG. 71 plots the flow of three drugs A, B, and C during a twenty-four hour period. Drug A is provided during the first six hours, drug B is provided as shown in two intervals that do not overlap with the interval of drug A, and drug C is provided throughout the twenty-four hour interval.

Figure 85:
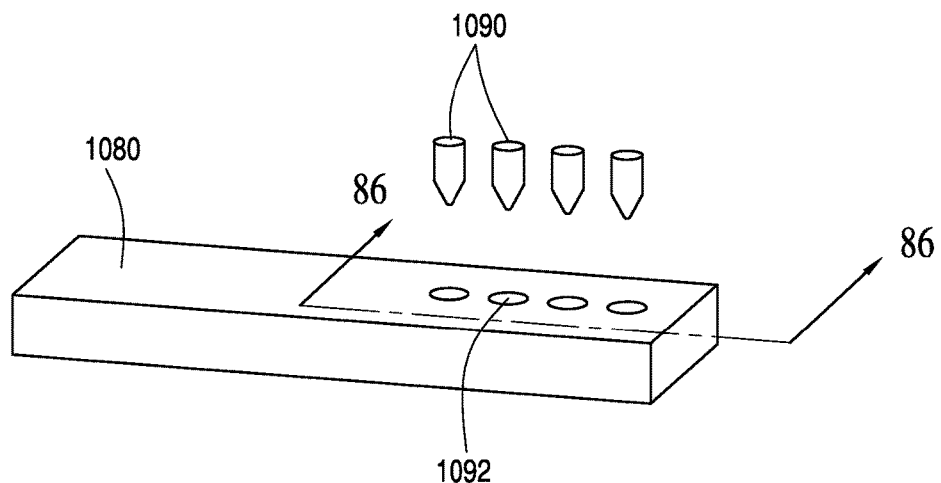
FIG. 85 is a perspective view of a portion of the active transdermal delivery system of FIG. 84.
Figure 86:
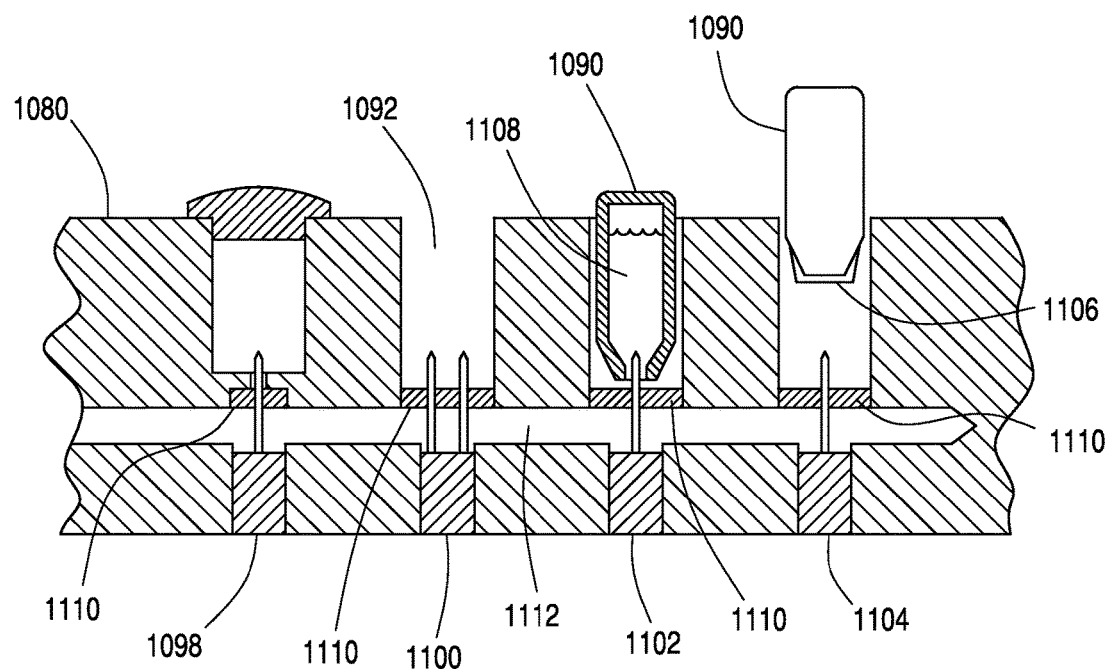
FIG. 86 is a cross-sectional view of the portion of FIG. 85 along the lines 86-86.

FIG. 85 is a perspective view of a portion of the active transdermal delivery system of FIG. 84, showing drug reservoirs 1090 removed from mask body 1080. FIG. 86 is a cross-sectional view of the portion of FIG. 85 along the lines 86-86. As shown in FIG. 86, mask 1078 further includes a plurality of penetrating, puncturing, or piercing devices, apparatuses, or mechanisms 1098-1104, which are configured to pierce or penetrate a membrane 1106 configured as a part of each drug reservoir 1090 to seal a drug 1108 in reservoir 1090. Mask 1078 further includes a plurality of flow control valves 1110 configured to control the flow of drugs from drug reservoirs 1090 into a fluid passage 1112 formed in mask body 1080. Once in fluid passage 1112, drugs flow into a flexible arm 1114 configured to extend from mask body 1080 and terminating in a drug delivery interface 1116. In the exemplary embodiment of FIGS. 84 and 86, flow control valves 1110 are electrically operated by way of control device 1094. In other embodiments, flow control valves 1110 may be operated mechanically, electrically under the control of a timer, by an external program stored, for example, in a cell phone, and in other ways.

FIG. 87 is a perspective view of a puncture, piercing, or penetrating device compatible with the configuration of FIG. 86, in accordance with an exemplary embodiment of the present disclosure and indicated generally at 1118. Device 1118 is configured with a penetrating, piercing, or puncturing first end 1120 configured to enter and extend through membrane 1106 when a reservoir, such as reservoir 1090, is inserted into a corresponding receptacle 1092. Device 1118 includes a first opening 1122 and a second opening 1124 fluidly connected to first opening 1122. In operation, a drug flows into first opening 1122, through a passage (not shown) internal to device 1118, and out from second opening 1124, entering flow control valve 1110.

FIG. 88 is a perspective view of a puncture, piercing, or penetrating device compatible with the configuration of FIG. 86, in accordance with an exemplary embodiment of the present disclosure and indicated generally at 1126. Device 1126 is configured with a penetrating, piercing, or puncturing first end 1128 configured to enter and extend through membrane 1106 when a reservoir, such as reservoir 1090, is inserted into a corresponding receptacle 1092. Device 1126 includes a longitudinally extending groove 1130. In operation, a drug flows into longitudinally extending groove 1130 at first end 1128, and along groove 1130 into flow control valve 1110.

FIG. 89 is a view of an active transdermal delivery system in accordance with an exemplary embodiment of the present disclosure, indicated generally at 1132. System 1132 is configured to include a capability to provide a drug when authorized by an authorized practitioner, such as a doctor. System 1132 includes a transdermal drug delivery module 1134 fluidly connected to a drug reservoir 1136. An electrically actuated valve 1138 is positioned along a fluid passage 1140 extending between drug delivery module 1134 and drug reservoir 1136. Valve 1138 is configured to be opened and closed in response to a command from a controller 1142 configured as a part of system 1132. In the embodiment of FIG. 89, controller 1142 can be operated from a control panel 1144, which may be configured as a part of controller 1142, or wirelessly by a separate electronic device 1146, such as a tablet, cell phone, laptop, and the like. System 1132 further includes a monitoring device 1148 configured to read signals from ABTT terminus 10. Monitoring device 1148 can be, for example, an infrared sensor or a temperature sensor configured to read the output from ABTT terminus 10. Output signals corresponding to the signals output from ABTT terminus 10 are provided to controller 1142. Control panel 1144 further includes an indicator light 1150. As will be seen, system 1132 provides benefits in remote and voluntary treatment of patients.

Figure 90:
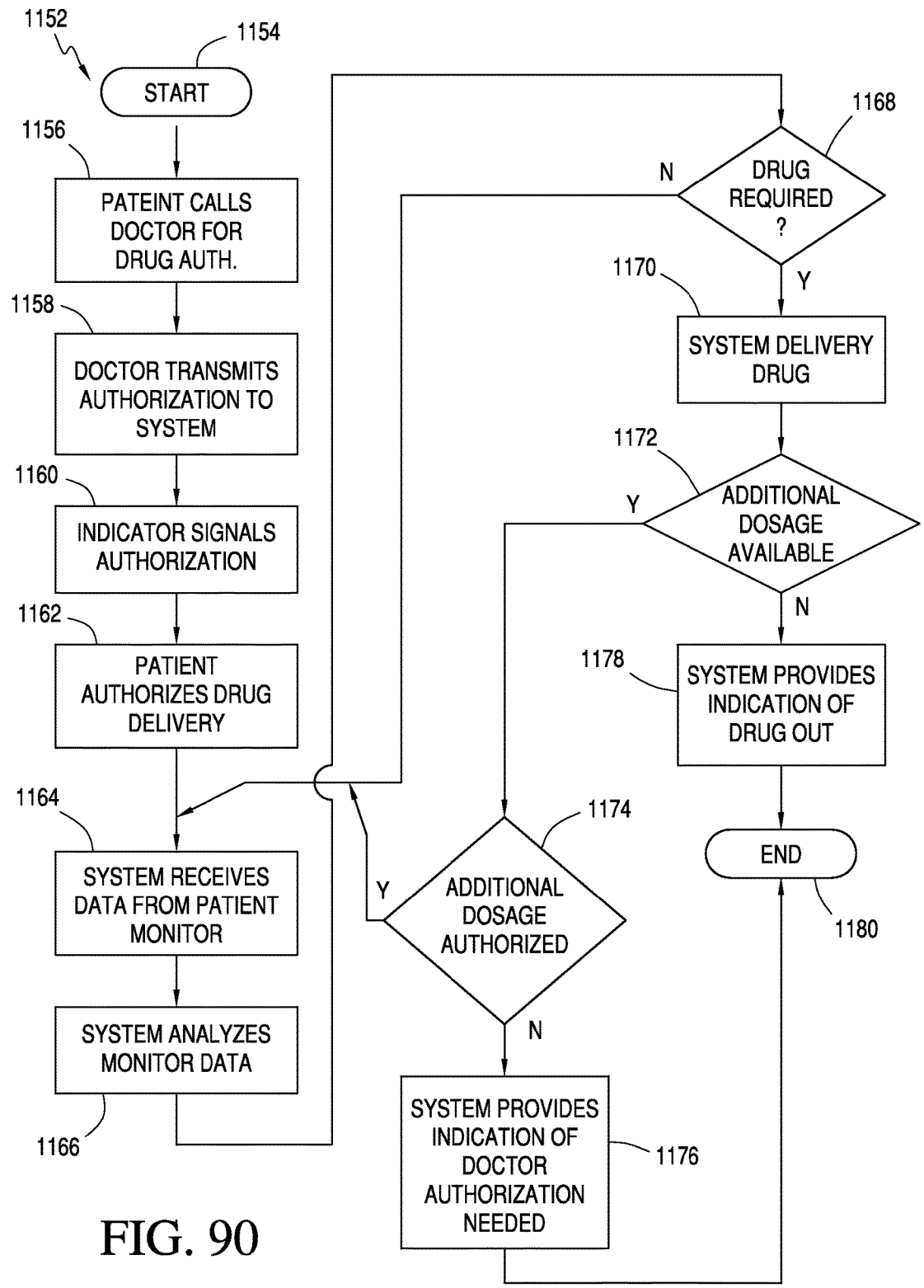
FIG. 90 is a process flow of the system of FIG. 89 in accordance with an exemplary embodiment of the present disclosure.

FIG. 90 is a drug delivery process flow of the system of FIG. 89 in accordance with an exemplary embodiment of the present disclosure, indicated generally at 1152. Process 1152 begins with a start process 1154. In start process 1154, system 1132 is powered, drug reservoir 1136 is filled with a drug and installed in system 1132, transdermal delivery module 1134 is positioned on a patient or subject's first ABTT terminus 10, and monitoring device 1148 is positioned on a patient or subject's second ABTT terminus 10. Once start process 1154 is complete, control passes from start process 1154 to a request authorization process 1156.

In request authorization process 1156, a patient, subject, or designated person requests authorization for the drug in reservoir 1136 to be provided to the patient or subject. Such request may be by phone, internet, in person, etc. Once the request is submitted, control passes from request authorization process 1156 to a practitioner authorization process 1158.

In practitioner authorization process 1158, a doctor, nurse, physician's assistant, or other legally authorized person transmits authorization for a particular patient to system 1132. Such transmission may be wireless, such as by separate electronic device 1146, by entry directly into control panel 1144, or by other apparatus. Once a legally authorized person has approved the drug use, control passes from practitioner authorization process 1158 to an indicator process 1160, where an indicator, such as indicator 1150 on control panel 1144, indicates that drug authorization has been received. Control then passes from indicator process 1160 to a patient authorization process 1162.

In patient authorization process 1162, a patient determines the need for the drug, and activates delivery by way of control panel 1144, wirelessly, or through other apparatus. Control then passes from patient authorization process 1162 to a patient monitoring process 1164.

In patient monitoring process 1164, system 1132 receives data from a monitoring device, such as a blood pressure monitor, a heart rate monitor, an oximeter, an electrocardiogram (EKG), an electroencephalogram (EEG), and the like. In the exemplary embodiment of FIG. 89, the monitoring device is ABTT monitoring device 1148. Control then passes from patient monitoring process 1164 to a monitor data analysis process 1166. In monitor data analysis process 1166, system 1152 determines, in view of signals from a monitor, such as ABTT monitoring device 1148, whether the patient is the correct patient by analysis of the thermal signature of the patient, and whether the patient requires the drug. Control then passes from monitor data analysis process 1166 to a drug required decision process 1168.

In drug required decision process 1168, system 1132 determines whether the authorized drug is required, in view of the analysis conducted in monitor data analysis process 1166. If the drug is not required, control passes from drug required decision process 1168 to patient monitoring process 1164, and process 1152 continues as previously described. If the drug is required, control passes from drug required decision process 1168 to a drug delivery process 1170.

In drug delivery process 1170, valve 1138 is opened and the drug in reservoir 1136 is delivered to ABTT terminus 10 by transdermal delivery module 1134. Control then passes to an additional drug available process 1172.

In additional drug available process 1172, system 1132 determines whether an additional dosage of the drug is available, which can be accomplished by determining the amount originally provided in reservoir 1136, less delivered amounts, by visual sensors, and the like. If an additional dose of drug is available, control passes from additional drug available process 1172 to a dose authorized process 1174.

In dose authorized process 1174, process 1152 determines whether an additional dose has been authorized. If an additional dose has been authorized, control passes from dose authorized process 1174 to patient monitoring process 1164, and process 1152 continues as previously described. If an additional dose has not been authorized, control passes to a practitioner authorization required process 1176, where an indicator, such as indicator 1150 on control panel 1144, indicates the need for a legally authorized practitioner, such as a doctor, physician's assistant, nurse, and the like, as permitted by law, to authorize another dose of the drug in reservoir 1136. Control then passes from practitioner authorization required process 1176 to an end process 1180, which terminates process 1152.

Returning to additional drug available process 1172, if an additional dosage is not available, control passes from process 1172 to a drug depleted process 1178, in which an indicator, such as indicator 1150 on control panel 1144, indicates the need to replenish the drug in reservoir 1136. Control then passes to end process 1180, which terminates process 1152.

It should be apparent that process 1152 is beneficial in that it allows a patient to have ready access to drugs when authorized by a practitioner, without the need to return to a pharmacy constantly. Furthermore, by monitoring a patient through ABTT terminus 10, a practitioner is able to verify a patient's condition prior to authorizing delivery of the drug in reservoir 1136, increasing the efficiency of medical care, and reducing costs. It should be understood that other medical monitoring devices, such as blood pressure monitoring, heart rate monitoring, oximetry, Electrocardiogram (EKG), electroencephalogram (EEG), and the like, can provide a feedback loop to system 1132. In this feedback loop embodiment, the signal from other medical devices may control automatically, by increasing drug flow or decreasing drug flow, the drugs being administered transdermally by system 1132.

Figure 91:
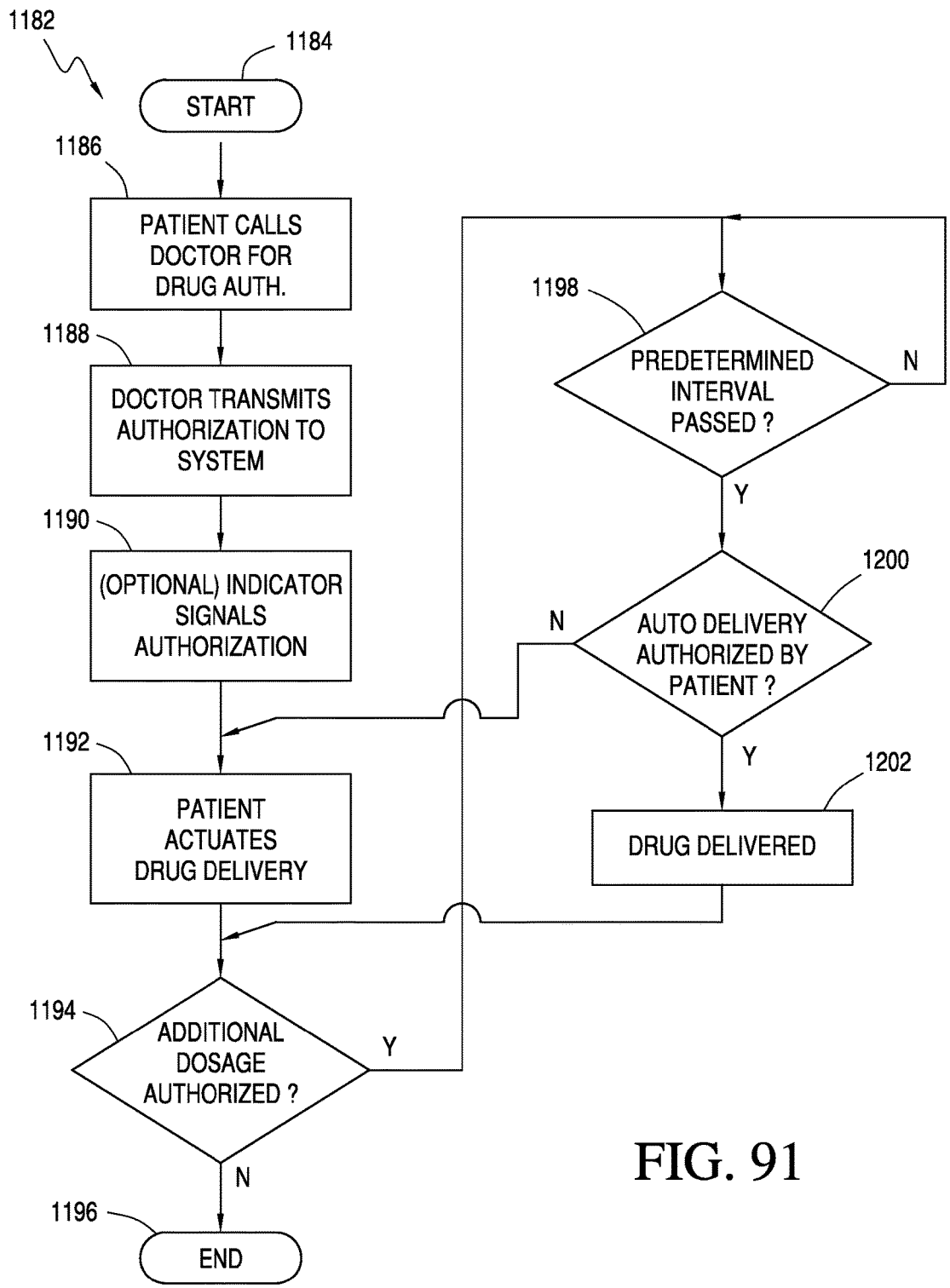
FIG. 91 is another process flow of the system of FIG. 89 in accordance with an exemplary embodiment of the present disclosure.

FIG. 91 is another drug delivery process flow of the system of FIG. 89 in accordance with an exemplary embodiment of the present disclosure, indicated generally at 1182. Process 1182 begins with a start process 1184. In start process 1184, system 1132 is powered, drug reservoir 1136 is filled with a drug and installed in system 1132, transdermal delivery module 1134 is positioned on a patient or subject's first ABTT terminus 10, and monitoring device 1148 is positioned on a patient or subject's second ABTT terminus 10. Once start process 1184 is complete, control passes from start process 1184 to a request authorization process 1186.

In request authorization process 1186, a patient, subject, or designated person requests authorization for the drug in reservoir 1136 to be provided to the patient or subject. Such request may be by phone, internet, in person, etc. Once the request is submitted, control passes from request authorization process 1186 to a practitioner authorization process 1188.

In practitioner authorization process 1188, a doctor, nurse, physician's assistant, or other legally authorized person transmits authorization for a particular patient to system 1132. Such transmission may be wireless, such as by a separate electronic device 1146, such as, for example, a cell phone, by entry directly into control panel 1144, or by other apparatus. Once a legally authorized person has approved the drug use, control passes from practitioner authorization process 1188 to an indicator process 1190, where an indicator, such as indicator 1150 on control panel 1144, indicates that drug authorization has been received. Control then passes from indicator process 1190 to a patient authorization process 1192.

In patient authorization process 1192, a patient determines the need for the drug, and activates delivery by way of control panel 1144, wirelessly, or through other apparatus. Control then passes from patient authorization process 1192 to an additional dosage authorized process 1194, where process 1182 determines whether the practitioner has authorized an additional dosage. If an additional dosage has been authorized, control passes from additional dosage authorized process 1194 to a predetermined interval process 1198. If an additional dosage is not authorized, control passes from additional dosage authorized process 1194 to an end process 1196, which terminates process 1182.

In predetermined interval process 1198, system 1132 measures a predetermined passage of time such as, for example, four, six, eight, twelve, or twenty-four hours. If the predetermined interval has yet to be reached, process 1198 continues in a loop until the predetermined time interval is reached, after which control passes from predetermined interval process 1198 to an automatic drug delivery authorization process 1200.

In automatic drug delivery authorization process 1200, process 1182 determines whether the patient has authorized automatic delivery of the drug in reservoir 1136. If automatic delivery has been authorized, control passes to a drug delivery process 1202, where the drug is delivered. Control then passes from drug delivery process 1202 to additional dosage process 1194, and process 1182 continues as previously described. If automatic delivery has not been authorized, control passes from automatic drug delivery authorization process 1200 to patient authorization process 1192, and process 1182 continues as previously described herein.

A benefit to process 1182 is that automatic delivery of drugs to ABTT terminus 10 can occur without a need for a patient to remember that it is time for another dosage. Further, delivery can, as with process 1152, be remotely authorized by a legally authorized practitioner, providing a safe, fast, efficient, process for authorizing and delivering drugs to a patient.

Figure 92:
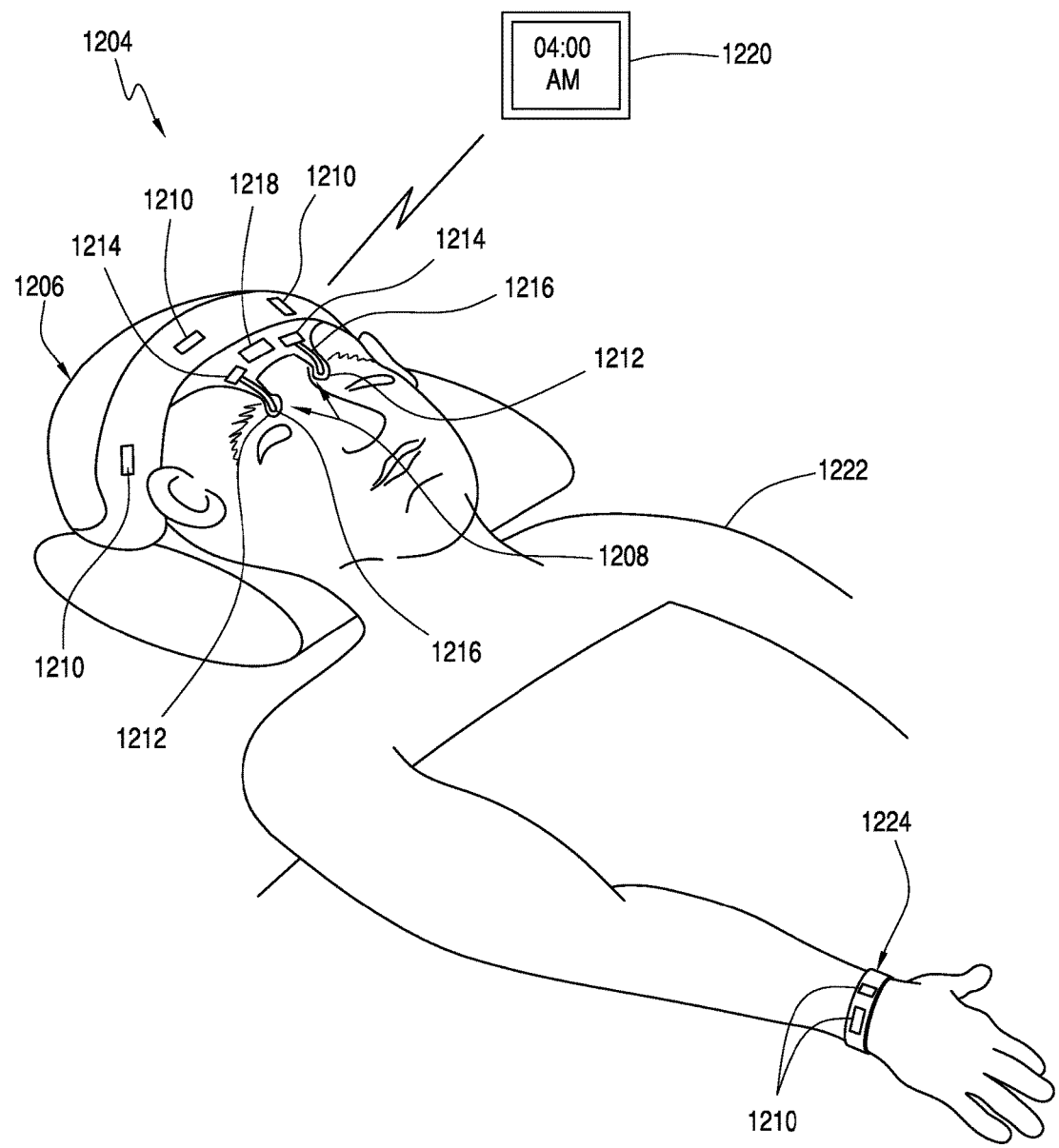
FIG. 92 is another transdermal delivery system in accordance with an exemplary embodiment of the present disclosure.

FIG. 92 is another transdermal delivery system in accordance with an exemplary embodiment of the present disclosure, indicated generally at 1204. System 1204 includes a support device 1206 on which is positioned a transdermal drug delivery module 1208 and a plurality of accelerometers or other motion detection devices 1210. Transdermal drug delivery module 1208 includes one or more drug containers 1212 configured to deliver a drug to a respective ABTT terminus 10. Drug containers 1212 are connected to a reservoir and flow control apparatus 1214 configured to supply a drug to drug containers 1212 by way of fluid passages 1216, when commanded by a controller 1218 positioned on support device 1206. Controller 1218 may include a transceiver, transmitter, or receiver (not shown), or such may be provided separately on support device 1206, which is configured to communicate with a separate electronic device 1220 for monitoring of a patient 1222 and control of system 1204. Controller 1218 further includes an integral timer or clock that can be configured to include a timer or timing function, including wake alarms. Timer-related alarms in controller 1218 can be set by way of, for example, separate electronic device 1220 when separate electronic device 1220 is configured with the appropriate interface software. System 1204 may also include a wrist band 1224 that includes one or more motion detection devices 1210. Wrist band 1224 may communicate with controller 1218 by a cable or wire (not shown) or wirelessly.

System 1204 is configured to provide one or more drugs to patient 1222 when needed for a condition that generates certain characteristic motions that can be detected by motion detection devices 1210. Such characteristic motions can include semi-wakefulness for sleep disorders and seizures. Wrist band 1222 can be beneficial for some conditions because hand movements are sometimes an indication of an imminent condition.

Figure 93:
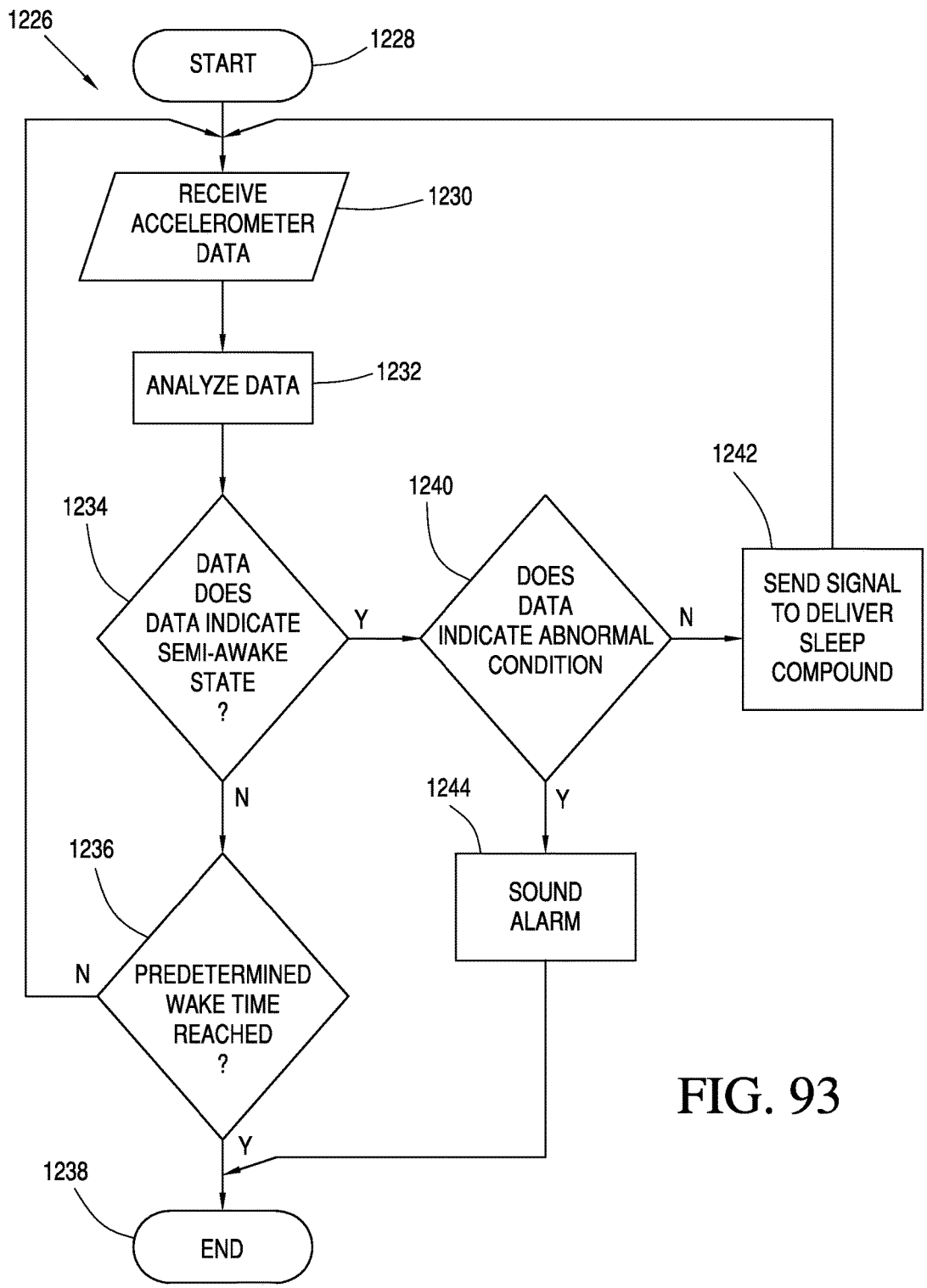
FIG. 93 is a process flow of the system of FIG. 92.

FIG. 93 is a sleep treatment process of the system of FIG. 92, indicated generally at 1226. Process 1226 begins with a start process 1228, where power may be provided to system 1204, which can be properly positioned on patient 1222, drugs can be provided to reservoir and flow control apparatus 1214, and other actions necessary to prepare system 1204 and process 1226 for operation. Once start process 1228 is complete, control passes from start process 1228 to a receive motion sensor data process 1230.

In receive motion sensor data process 1230, controller 1218 receives signals from motion detection devices 1210. Control then passes from receive motion sensor data process 1230 to an analyze data process 1232. After analysis of motion sensor data, control passes to a semi-awake state decision process 1234, where process 1226 determines whether the signals provided by motion detection devices 1210 is indicative of a semi-awake state that is likely to lead to an awakened state. If a semi-awake state is not indicated, control passes from semi-awake state decision process 1234 to a predetermined wake time decision process 1236.

In predetermined wake time decision process 1236, system 1204 determines whether a predetermined wake time has been reached. The predetermined wake time can be set, for example, by way of separate electronic device 1220, using a timer or clock internal to controller 1218. In order to decrease the effect of a drug after awakening, the predetermined wake time can be a time after which no drugs are provided, even if a semi-awake state is reached. Thus, if a patient or subject plans to awaken at, for example, 6 AM, the predetermined "wake time" can be set for 4 AM, and no drugs will be administered after that time. Thus, the predetermined "wake time" can be consider a time at which the administration of drugs is stopped. If such a time has been reached, then control passes from predetermined wake time decision process 1236 to an end process 1238, where process 1226 terminates and patient 1222 is permitted to awaken. If the predetermined wake time has not been reached, control passes from predetermined wake time decision process 1236 to receive motion sensor data process 1230, and process 1226 continues as previously described herein.

Returning to semi-awake state decision process 1234, if a semi-awake condition is detected that is likely to lead to awakening, control passes from semi-awake state decision process 1234 to a condition decision process 1240, where the condition of patient 1222 is determined from at least motion detection sensors 1210. If an abnormal condition is indicated, control passes from condition decision process 1240 to an alarm process 1244, where one or more alarms are actuated, which can include an alarm to separate electronic device 1220. Control then moves from alarm process 1244 to end process 1238, where process 1226 terminates.

Returning to condition decision process 1240, if an abnormal condition is not detected, control passes from condition decision process 1240 to a sleep compound delivery process 1242, where a drug is delivered by reservoir and flow control apparatus 1214 to drug containers 1212 by way of fluid passages 1216, which should return patient 1222 to a condition of sleep. Control then passes from sleep compound delivery process 1242 to receive motion sensor data process 1230, where process 1226 continues as previously described herein.

Figure 94:
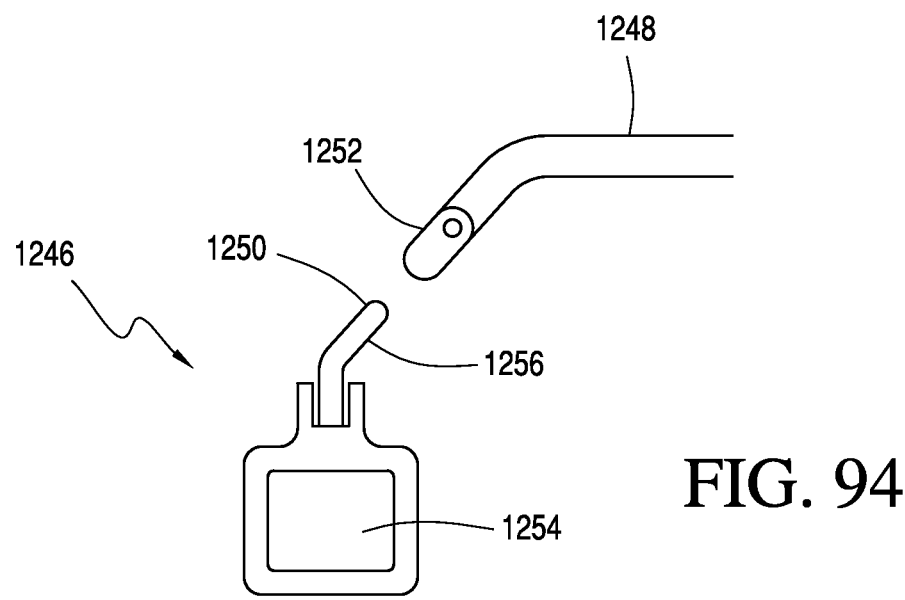
FIG. 94 is a view of a retroauricular drug delivery device in accordance with an exemplary embodiment of the present disclosure.

FIG. 94 is a view of a retroauricular drug delivery device in accordance with an exemplary embodiment of the present disclosure, indicated generally at 1246. Device 1246 is configured to connect or attach to a temple frame 1248, which may be a portion of, for example, a pair of eyeglasses. Device 1246 includes a fastening arrangement 1250 configured to mate with a complementary fastening arrangement 1252 on temple frame 1248. Device 1246 further includes a drug container 1254 positioned on a flexible arm 1256, which permits adjustment of the position of drug container 1254 to match the position of a retroauricular vein positioned behind a patient or subject's ear for transdermal drug delivery to the retroauricular vein. Delivery of drugs to the retroauricular vein is beneficial for certain conditions, such as motion sickness. An advantage of this embodiment includes a lack of adhesive surface, or if an adhesive surface is present it can contain a weak adhesive, by virtue of the end of the temples pressing the surface containing drug against the skin. This embodiment is clinically useful since the retroauricular skin is sensitive and can be easily damaged by an adhesive or even more severely by a strong adhesive.

Figure 95:
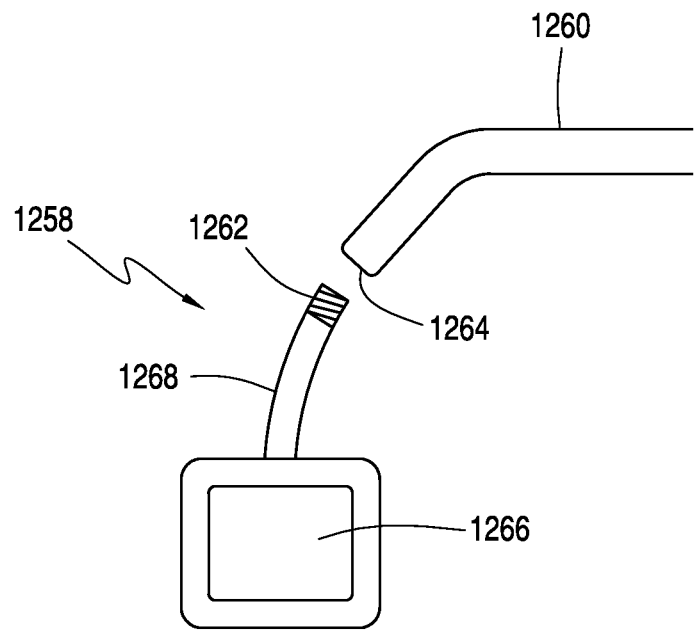
FIG. 95 is a view of another retroauricular drug delivery device in accordance with an exemplary embodiment of the present disclosure.

FIG. 95 is a view of another retroauricular drug delivery device in accordance with an exemplary embodiment of the present disclosure, indicated generally at 1258. Device 1258 is configured to connect or attach to a temple frame 1260, which may be a portion of, for example, a pair of eyeglasses. Device 1258 includes a fastening arrangement 1262, configured as screw threads, to mate with a complementary fastening arrangement 1264 on temple frame 1260. Device 1258 further includes a drug container 1266 positioned on a flexible arm 1268, which permits adjustment of the position of drug container 1266 to match the position of a retroauricular vein positioned behind a patient or subject's ear for transdermal drug delivery to the posterior auricular vein, also referred to in the present disclosure as the retroauricular vein. It should be understood that a sliding mechanism, telescopic mechanism, and the like can be included as part of arm 1268 in order to allow precise positioning of drug containing surface on the posterior auricular vein and/or stylomastoid vein.

Figure 96:
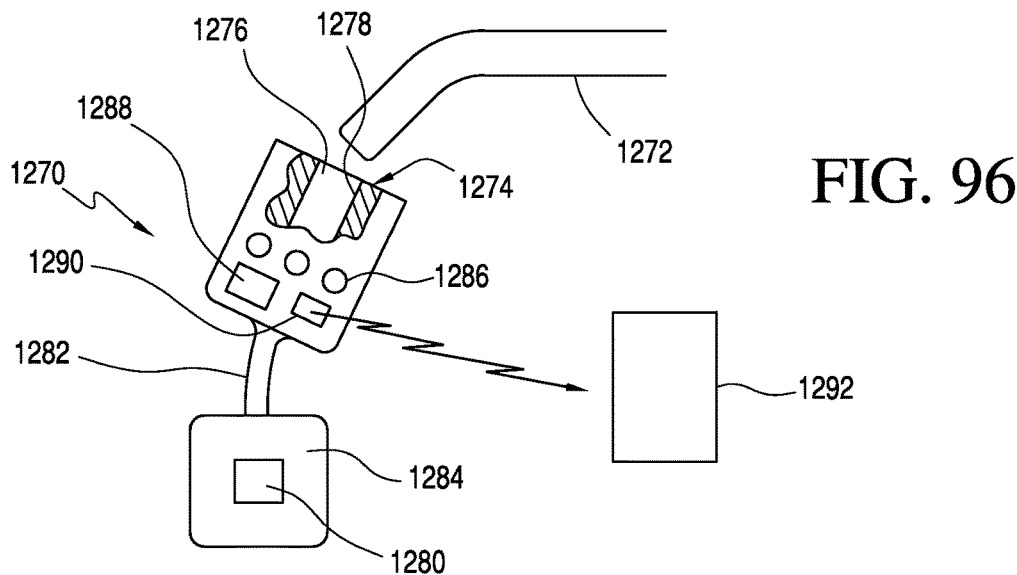
FIG. 96 is a view of yet another retroauricular drug delivery device in accordance with an exemplary embodiment of the present disclosure.

FIG. 96 is a view of yet another retroauricular drug delivery device in accordance with an exemplary embodiment of the present disclosure, indicated generally at 1270. A portion of device 1270 is cut away to reveal certain features of device 1270. Device 1270 is configured to connect or attach to a temple frame 1272, which may be a portion of, for example, a pair of eyeglasses. Device 1270 includes a fastening arrangement 1274, configured as a cavity 1276 that is configured to include a compressible material 1278. When device 1270 is pushed onto temple frame 1272, compressible material 1278 grips temple frame 1272, securing device 1270 to temple frame 1272. Device 1270 further includes a drug container 1280 positioned on a flexible arm 1282, which permits adjustment of the position of drug container 1280 to match the position of a posterior auricular vein positioned behind a patient or subject's ear for transdermal drug delivery to blood vessels located behind the ear. Device 1270 further includes a thermoelectric device 1284 positioned to heat drug container 1280 and the skin over the retroauricular vein. Device 1270 is also configured to include a power supply 1286, and may include a controller 1288 and a transceiver, transmitter, or receiver 1290 for communication with a separate electronic device 1292.

Figure 97:
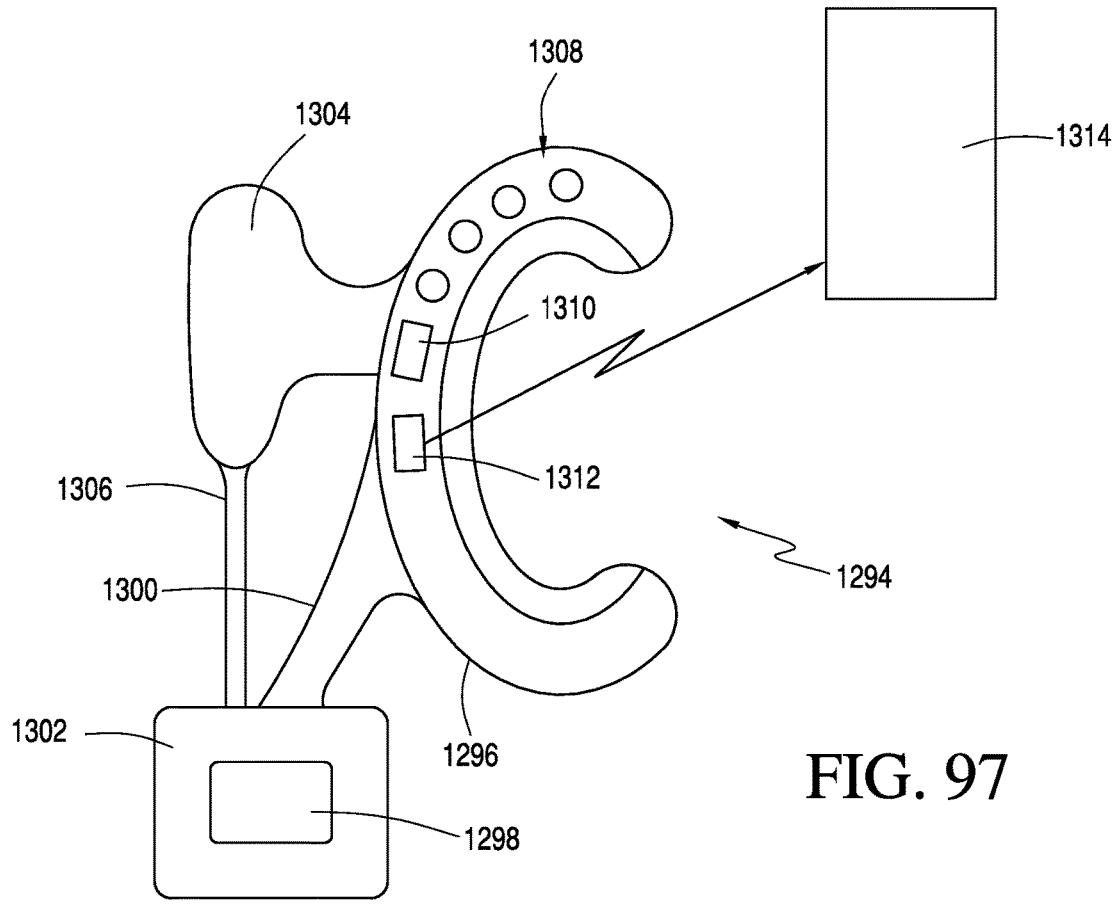
FIG. 97 is a view of a further retroauricular drug delivery device in accordance with an exemplary embodiment of the present disclosure.

FIG. 97 is a view of a further retroauricular drug delivery device in accordance with an exemplary embodiment of the present disclosure, indicated generally at 1294. Device 1294 is configured to be positioned on a subject or patient's ear. Device 1294 includes a support 1296; a drug container 1298 positioned on a flexible arm 1300, which permits adjustment of the position of drug container 1298 to match the position of a vein positioned behind a patient or subject's ear for transdermal drug delivery to a vein positioned behind a patient or subject's ear; a thermoelectric device 1302 positioned adjacent to drug container 1298; a reservoir 1304 and a flexible fluid passage 1306 connecting reservoir 1304 to drug container 1298; and a plurality of electronic elements. The plurality of electronic elements can include a power supply 1308, controller 1310, and a transceiver, transmitter, or receiver 1312 for communication with a separate electronic device 1314. It should be understood that device 1294 may not include a separate reservoir 1304 and flexible fluid passage 1306, and in this embodiment device 1294 includes an ear supported device having a support 1296 and a drug container 1298, said drug container being passive or active, the latter including a thermoelectric device. In this embodiment, drug container 1298 can be an extension of support 1296, with no connecting arm 1300 to said drug container 1298 being necessary.

Figure 98:
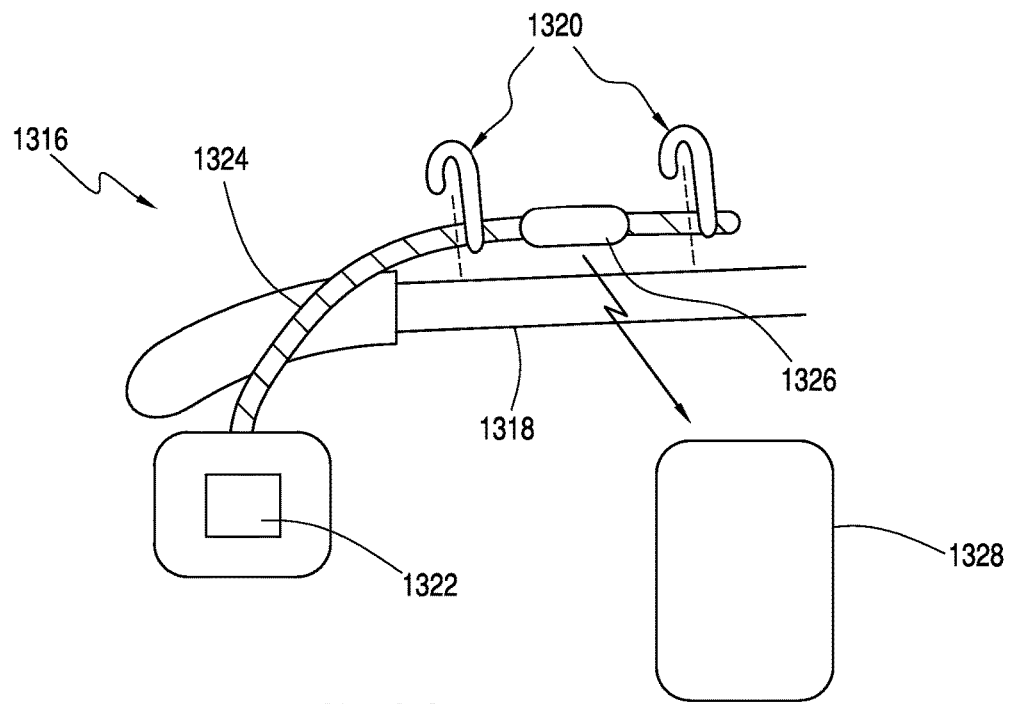
FIG. 98 is a view of a yet further retroauricular drug delivery device in accordance with an exemplary embodiment of the present disclosure.

FIG. 98 is a view of a yet further retroauricular drug delivery device in accordance with an exemplary embodiment of the present disclosure, indicated generally at 1316. Device 1316 is configured to connect or attach to a temple frame 1318, which may be a portion of, for example, a pair of eyeglasses. Device 1316 includes a fastening arrangement 1320, configured as hooks, clips and the like, to mate with temple frame 1318. Device 1258 is further configured to include a drug container 1322 positioned on a flexible arm 1324, which permits adjustment of the position of drug container 1322 to match the position of a posterior auricular vein positioned behind a patient or subject's ear for transdermal drug delivery to the posterior auricular vein. Device 1258 is yet further configured to include a powered transceiver, transmitter, or receiver 1326 configured to communicate with a separate electronic device 1328.

Figure 99:
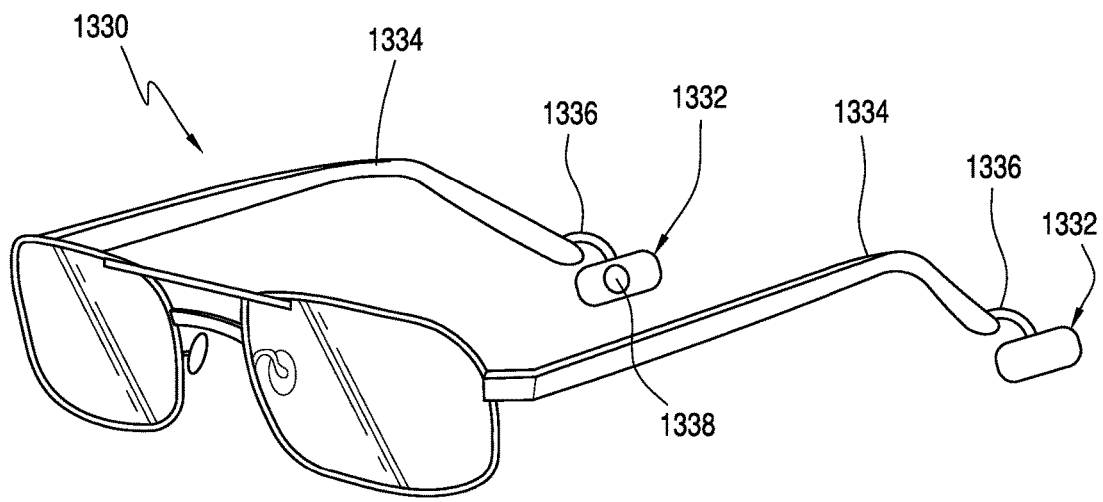
FIG. 99 is a view of still another retroauricular drug delivery device in accordance with an exemplary embodiment of the present disclosure.

FIG. 99 is a view of a pair of eyeglasses, indicated generally at 1330, configured to include a retroauricular drug delivery device in accordance with an exemplary embodiment of the present disclosure, indicated at 1332. Device 1332 is attached to a temple frame 1334 of eyeglasses 1330 by a flexible arm 1336, which permits adjustment of the position of device 1332 to match the position of a retroauricular vein positioned behind a patient or subject's ear for transdermal drug delivery to the retroauricular vein. Device 1332 further includes a drug container 1338.

Figure 100:
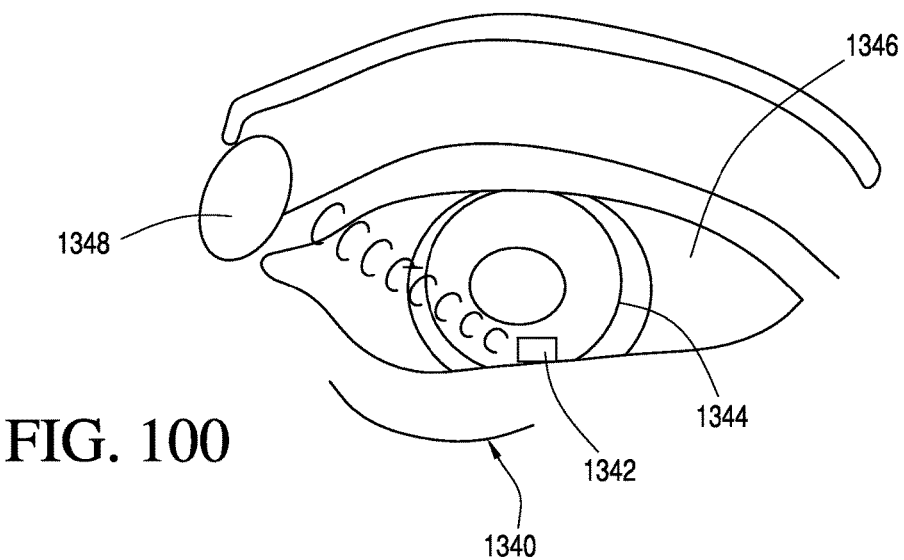
FIG. 100 is a view of a tear diagnostic system in accordance with an exemplary embodiment of the present disclosure.

FIG. 100 is a view of a tear diagnostic system in accordance with an exemplary embodiment of the present disclosure, indicated generally at 1340. Certain drugs administered through ABTT terminus 10 and the retroauricular vein can be detected through tears in the eye. Thus, closed loop feedback system 1340 can be configured with a detector 1342 positioned, for example, on a contact lens 1344 that is then positioned on an eye 1346. Detector 1342 detects a level of a chemical or drug in eye 1346, and transmits that information wirelessly to an active transdermal drug delivery device or module 1348, which then adjusts the rate of drug flow through ABTT terminus 10 accordingly.

Figure 101:
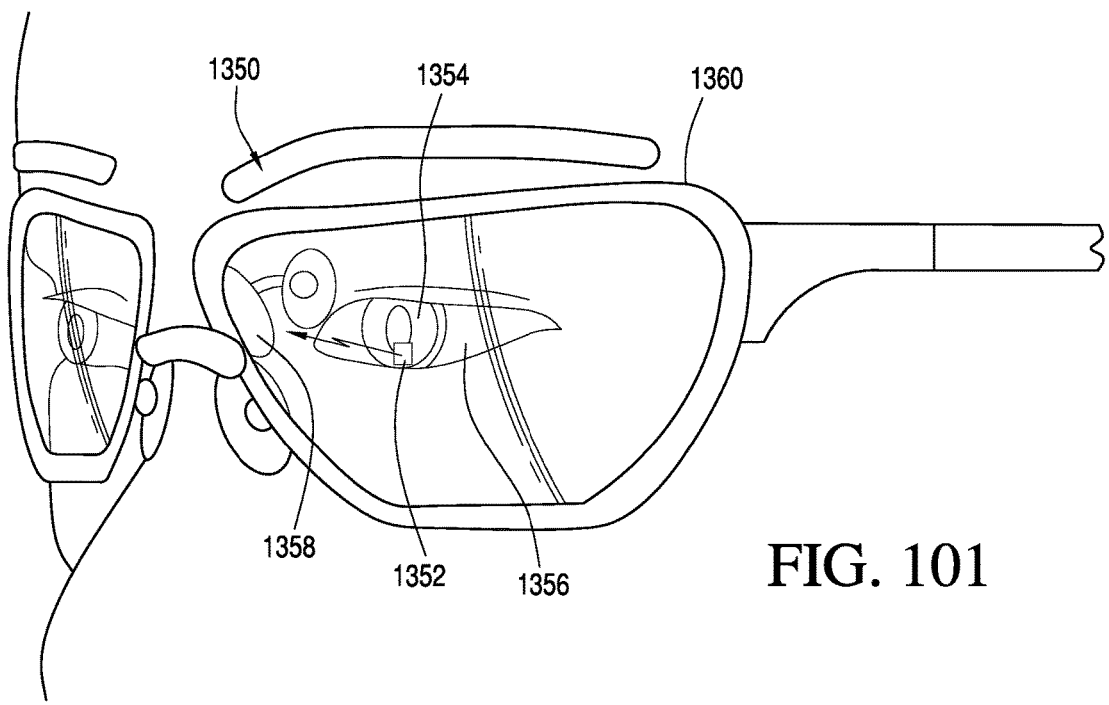
FIG. 101 is a view of another tear diagnostic system in accordance with an exemplary embodiment of the present disclosure.

FIG. 101 is a view of another tear diagnostic system in accordance with an exemplary embodiment of the present disclosure, indicated generally at 1350. System 1348 includes a detector 1352 positioned, for example, on a contact lens 1354 that is then positioned on an eye 1356. Detector 1352 detects a level of a chemical or drug in eye 1356, and transmits that information wirelessly to an active transdermal drug delivery device or module 1358 positioned on an eyeglass frame 1360, which then adjusts the rate of drug flow through ABTT terminus 10 accordingly. It should be understood that module 1358 can be positioned in any other support located in other parts of the body, and in other devices, such as the various embodiments described herein as clips, patches, masks, head gear, and the like.

Figure 102:
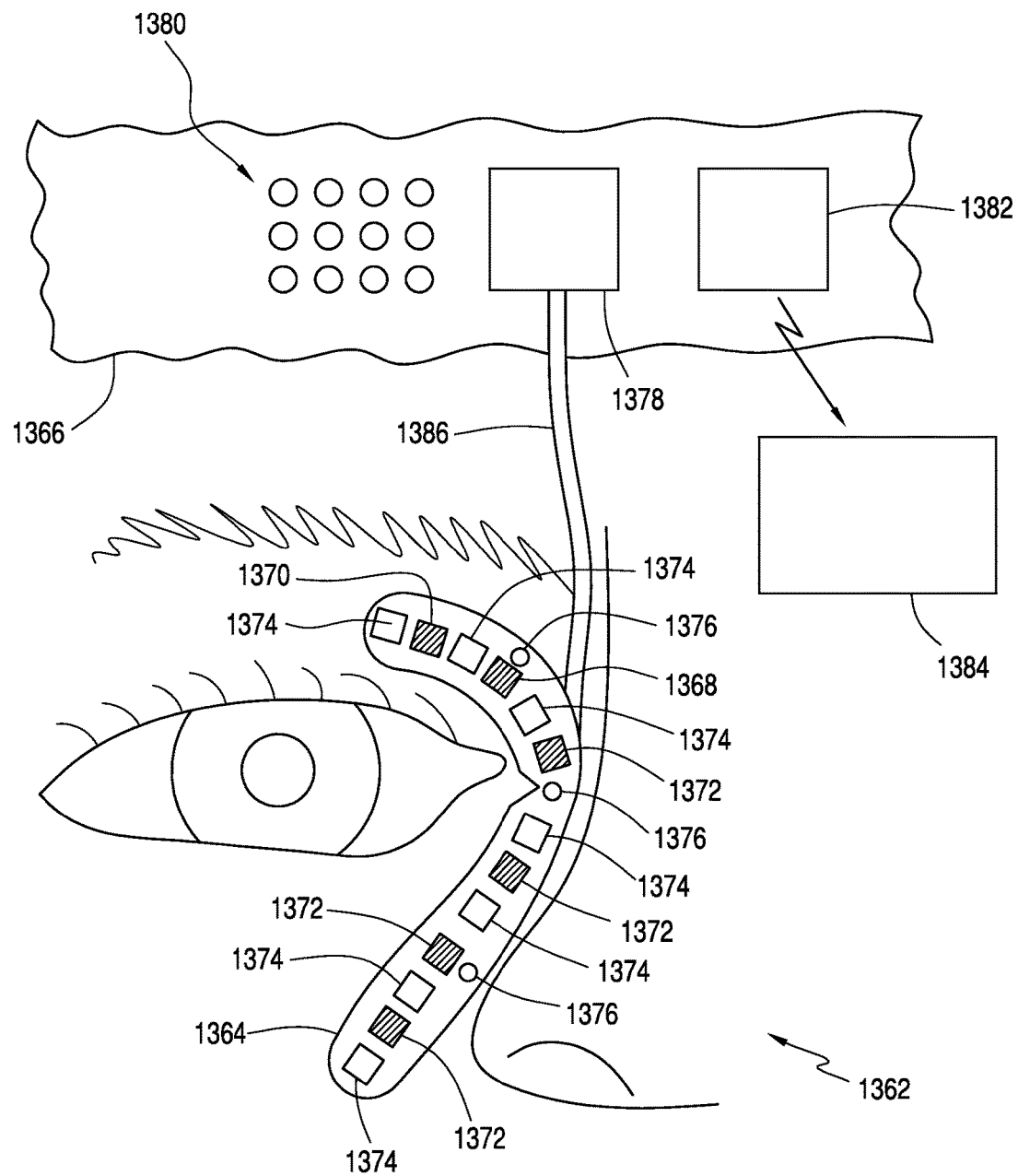
FIG. 102 is a view of yet another active transdermal delivery device in accordance with an exemplary embodiment of the present disclosure.

FIG. 102 is a view of another active transdermal delivery device in accordance with an exemplary embodiment of the present disclosure, indicated generally at 1362. Device 1362 is configured to include a support structure 1364, and a head support apparatus 1366.

Support structure 1364 includes a drug container 1368 positioned on, over, or adjacent the skin of ABTT terminus 10, at least one drug container 1370 positioned on, over, or adjacent the skin over superior palpebral vein 16, and at least one drug container 1372 positioned on, over, or adjacent the skin over frontal vein 20 and, in an alternative embodiment, over facial vein 22. It should be understood that drug containers 1368, 1370, and 1372 can be configured to include a same drug or a plurality of drugs. Support structure 1364 further includes a plurality of thermoelectric devices 1374 positioned in along support structure 1364. As described herein, by heating or cooling the skin, drug flow into associated veins is moderated or modified because the permeability of skin is related to temperature, and thermoelectric devices 1374 can both heat and cool. However, it should be understood that other temperature modification devices can be used in place of thermoelectric devices 1374, such as resistive heaters. Support structure 1364 can also be configured to include at least one temperature sensor 1376 to measure the temperature of support structure 1364, the temperature of one or more drug containers, or the temperature of the skin.

Head support apparatus 1366 is configured to include a controller 1378 and a power supply 1380 configured to provide power to the electronic elements of device 1362. Head support apparatus 1366 can also include a control panel or operator input device, or can also include a transceiver, transmitter, or receiver 1382 configured to communicate with a separate electronic device 1384, wherein separate electronic device 1384 is configured to operate device 1362. Controller 1378 can communicate with the electronic elements positioned on support structure 1364 wirelessly, or through a wire or cable 1386.

Figure 103:
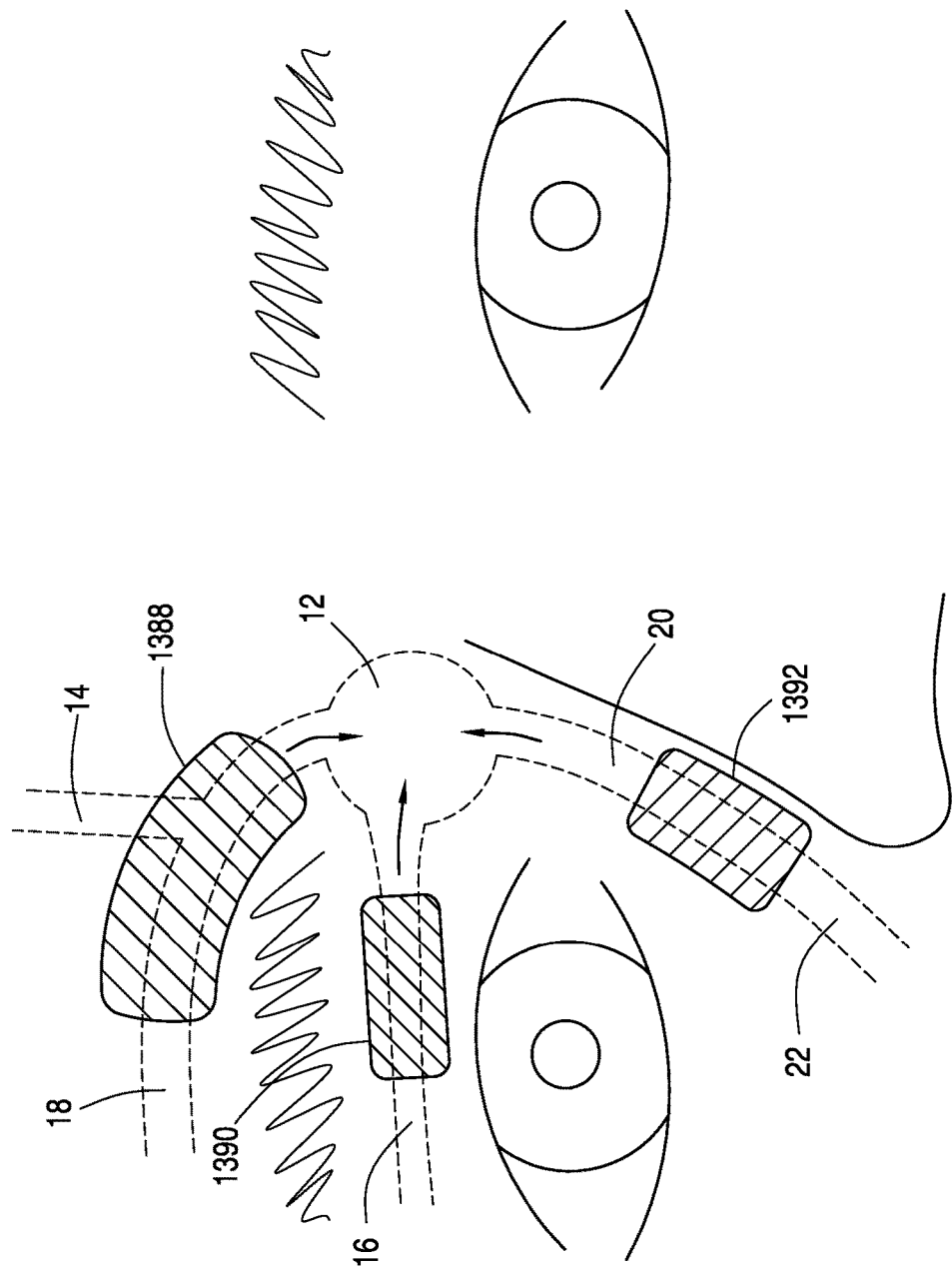
FIG. 103 is a view of a face showing locations for application of passive or active transdermal delivery devices, in accordance with an exemplary embodiment of the present disclosure.

FIG. 103 is a view of a face showing locations for application of passive or active transdermal delivery devices, in accordance with an exemplary embodiment of the present disclosure. As described herein, passive and active devices can be positioned in a nearly infinite number of locations and combination of locations. However, it should be understood that the present disclosure also includes placement of passive and active transdermal devices on one or more veins or locations that feed, provide, direct, or guide blood to ABTT 12. For example, and as shown in FIG. 103, a passive or active transdermal delivery device 1388 can be positioned along either frontal vein 14, supraorbital vein 18, or both, a passive or active transdermal delivery device 1388 can be positioned along superior palpebral vein 16, and a passive or active transdermal delivery device can be positioned along angular vein 20 or frontal vein 22, without placement of a transdermal delivery device over ABTT terminus 10. The benefit to such placement is naturally modifying the rate of drug delivery to the brain rather than doing so with permeability modification apparatus or chemicals.

Figure 104:
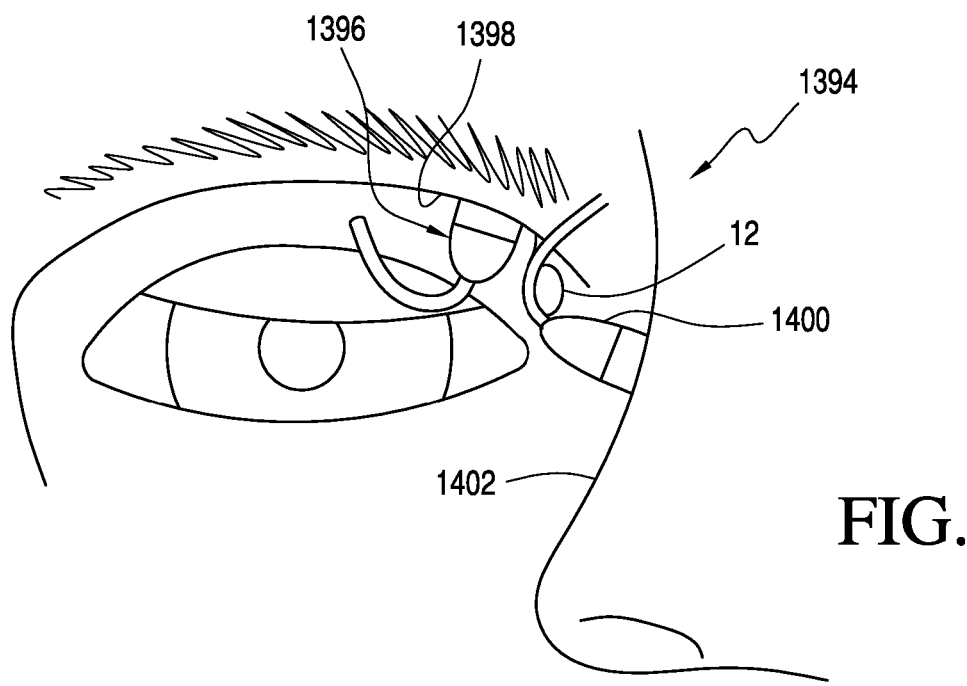
FIG. 104 is a view of a face showing additional locations available for placement of an active or a passive transdermal delivery device, in accordance with an exemplary embodiment of the present disclosure.

FIG. 104 is a view of a face showing additional locations available for placement of an active or a passive transdermal delivery device, in accordance with an exemplary embodiment of the present disclosure. A face 1394 shows placement of a passive or active transdermal delivery device 1396 on a roof of an orbit 1398, which may also be described as being under the eyebrow, or under the ridge of the brow. Face 1394 also shows placement of a passive or active transdermal delivery device 1400 on a side of nose 1402.

Figure 105:
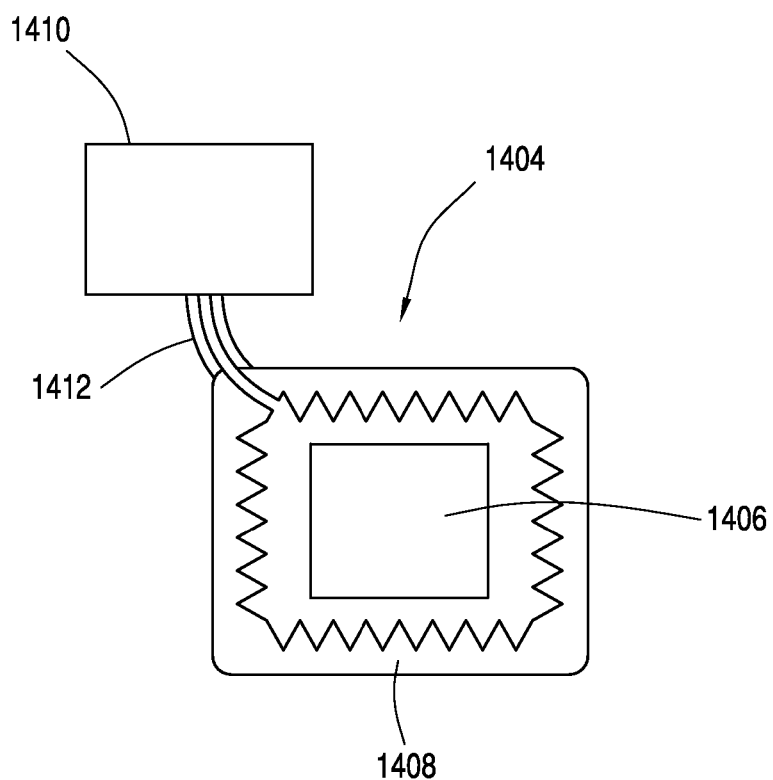
FIG. 105 is a schematic view of an active transdermal delivery device in accordance with an exemplary embodiment of the present disclosure.

Active embodiments of the present disclosure describe heating or cooling of portions of faces for transdermal delivery. These embodiments include thermoelectric devices, chemical heating and cooling, and resistive heating. FIG. 105 shows a schematic view of an active transdermal delivery device in accordance with an exemplary embodiment of the present disclosure, indicated generally at 1404. Device 1404 includes a drug container 1406 surrounded by a resistive heater 1408. Resistive heater 1408 is connected to a controller or power supply 1410 by a wire or cable 1412. Generally, thermoelectric devices provide the most capability given that they can heat or cool and are relatively accurate. Resistive devices are capable of heating only, and controlling such devices as precisely as thermoelectric devices typically requires more complex electronics than is necessary for thermoelectric devices. However, any heating or heating and cooling device can be used with the active devices disclosed herein as long as such devices can provide localized heating and cooling needed to control drug permeation through the skin.

Figure 106:
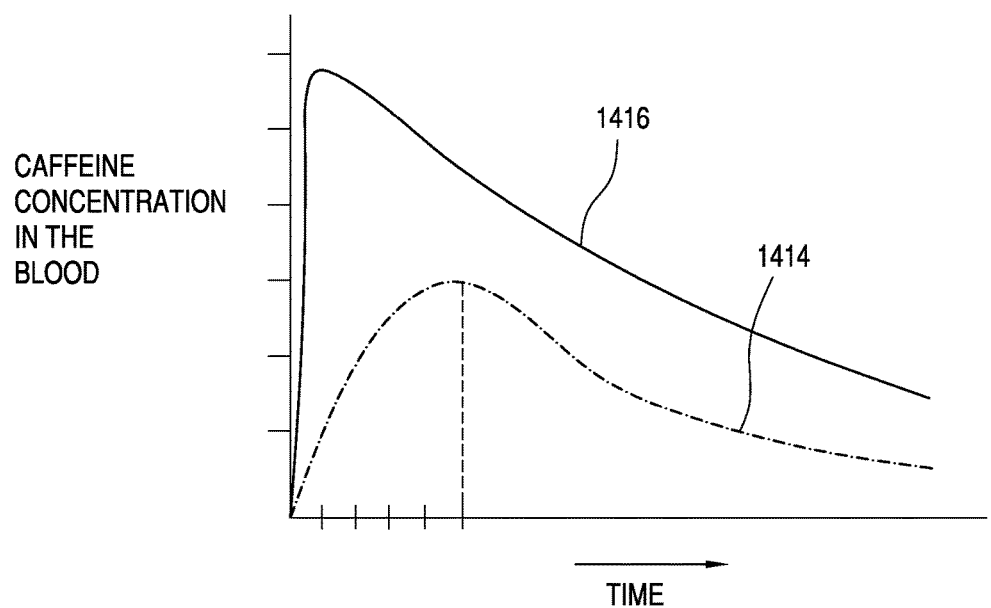
FIG. 106 is a graph showing a comparison of a chemical absorption through an arm patch and a patch on the ABTT terminus

One experimental technique used by Applicant to verify the efficacy of the systems, apparatuses, devices, processes, and methods disclosed herein was to compare absorption of a chemical into the blood stream. The chosen chemical was caffeine, and a comparison was made between distribution of caffeine in the body from a 15 mm by 15 mm patch placed on ABTT terminus 10 and a 15 mm by 15 mm patch placed on an upper arm. Caffeine concentration was measured in the same location on the body. As shown in FIG. 106, curve 1414 shows caffeine concentration with time for a caffeine patch positioned on the upper arm, and curve 1416 shows caffeine concentration with time for a caffeine patch positioned on ABTT terminus 10. As is evident from FIG. 106, the peak concentration of caffeine from the patch placed on the arm occurred five hours after placement of the patch, which peak concentration from the patch placed on ABTT terminus 10 was about 30 minutes after placement of the patch. Furthermore, peak concentration from placement of the patch on ABTT terminus 10 was more than twice as high as peak concentration from placement of the patch on the upper arm. Other compounds tested show similar results. Thus, the systems, apparatuses, devices, processes, and methods of the present disclosure, in addition to being novel, are significantly more effective than conventional application of transdermal patches. In addition, it should be noted that use of a known patch would be disadvantageous if applied to ABTT terminus 10, because a lesser quantity of a drug is required to achieve the same results. In fact, a conventional patch could prove to be dangerous if applied to ABTT terminus 10 due to the presence of a much higher quantity of drug than is required in combination with the high permeability of ABTT terminus 10, and the direct connection between ABTT terminus 10 and the brain. In order to achieve the same effect at ABTT terminus 10 as application of a conventional patch in a conventional application, only about ⅔ the quantity of a drug is required for the same effect at ABTT terminus 10.

Figure 107:
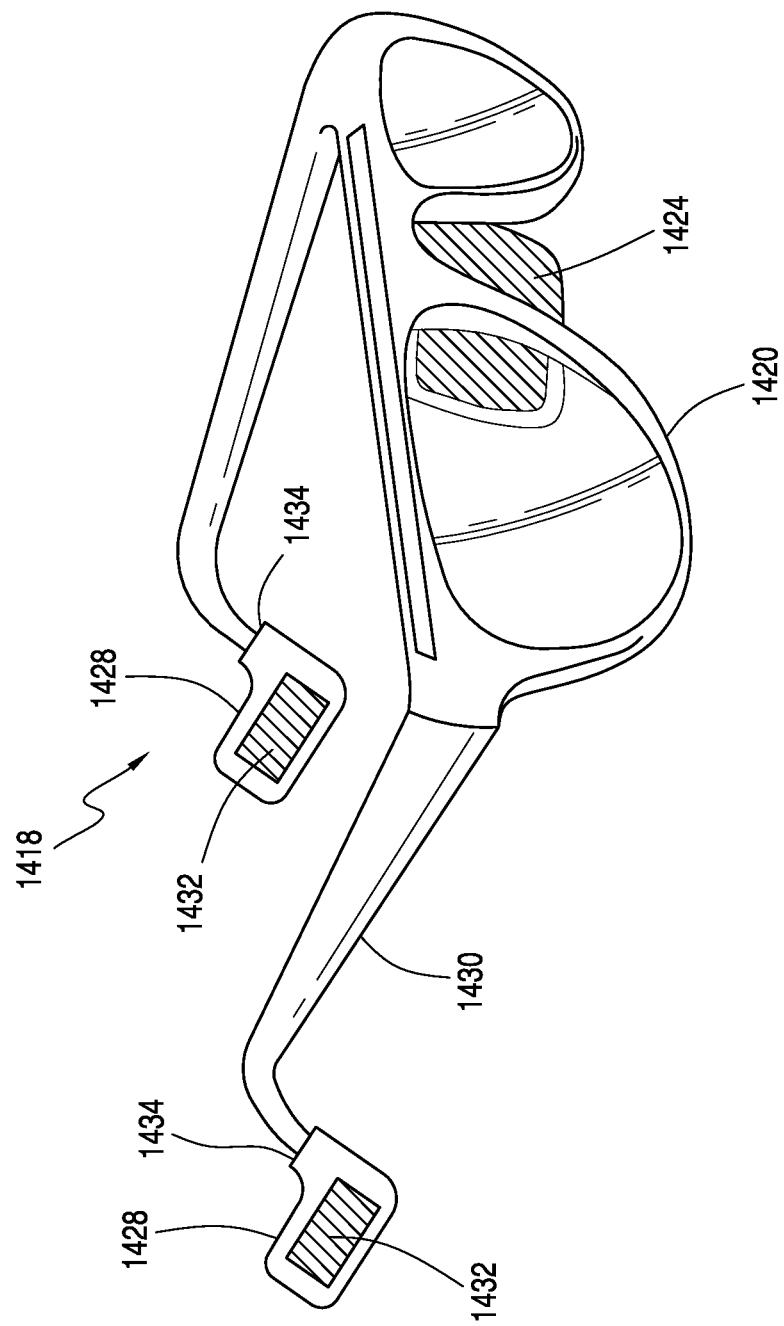
FIG. 107 is a perspective view of another transdermal delivery device in accordance with an exemplary embodiment of the present disclosure.

FIG. 107 is a perspective view of another transdermal delivery device in accordance with an exemplary embodiment of the present disclosure, indicated generally at 1418. Device 1418 is configured as an eyeglass frame 1420. Frame 1420 includes nose pads 1422, each of which is configured to include a drug container 1424 for placement on a portion of a nose and adjacent face, and a posterior auricular extension 1428 attach to or positioned on a temple frame 1430. Each posterior auricular extension 1428 includes a drug container 1432 configured to be positioned in contact with a posterior auricular vein when eyeglass frame 1420 is worn on a face. Each posterior auricular extension 1428 is configured to be slidable or adjustable on a respective temple frame 1430 by an adjustment arrangement or configuration 1434 to provide adjustment of each posterior auricular extension 1428 to match the position of drug container 1432 to a respective auricular vein.

Figure 108:
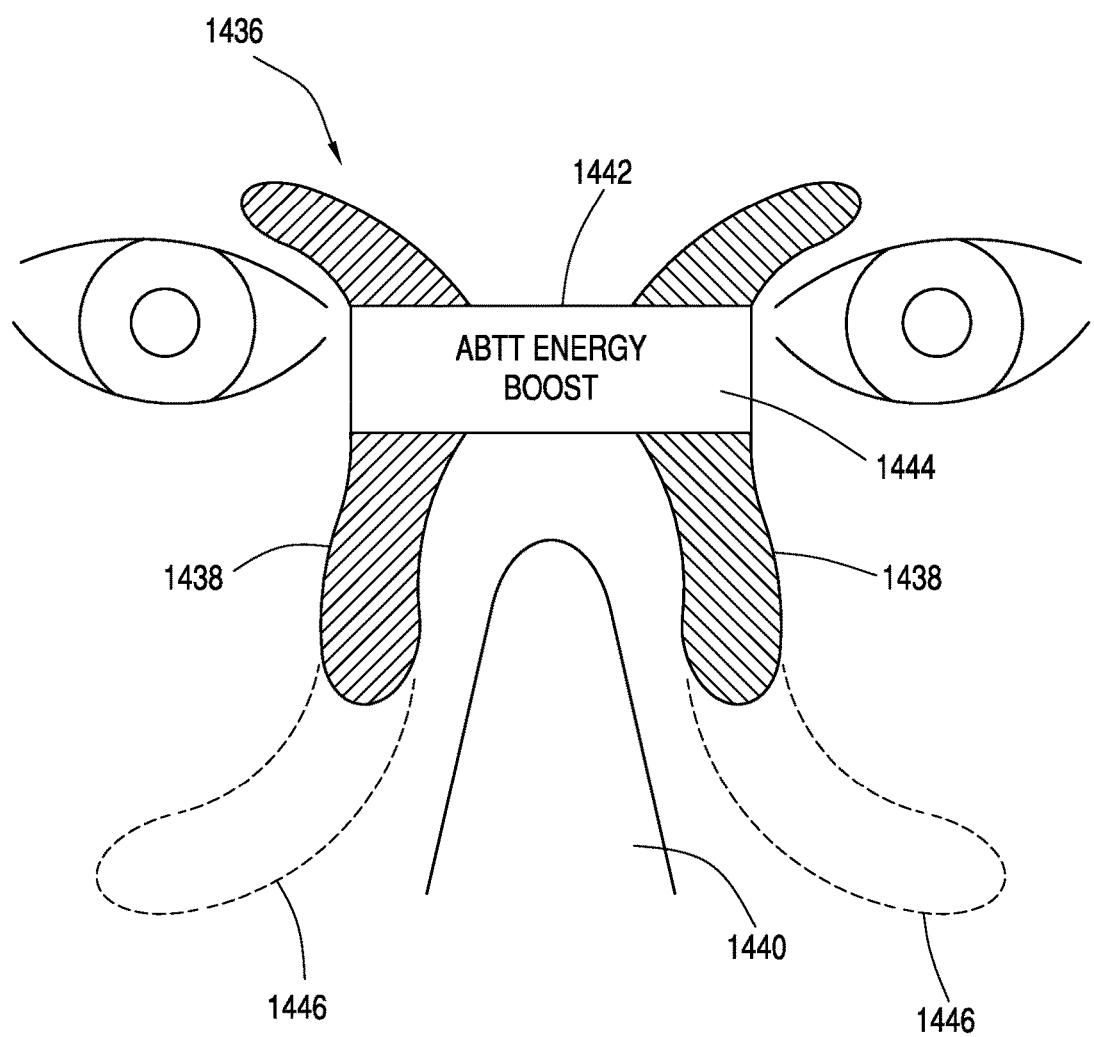
FIG. 108 is a view of a transdermal delivery device in accordance with an exemplary embodiment of the present disclosure.

FIG. 108 is a view of a transdermal delivery device in accordance with an exemplary embodiment of the present disclosure, indicated generally at 1436. Device 1436 includes adhesive and drug contained wings 1438 positioned on either side of a nose 1440. Wings 1438 can be configured to extend along angular vein 20 and frontal vein 22 by providing wings 1438 with added area 1446, shown with dashed lines. Wings 1438 are connected by a transversely extending bridge 1442, including a cover 1444. Cover 1444 is configured to be an area for printing, and indeed, the entire outer portion of device 1436, can be configured to provide a surface for writing or printing. By providing an area for writing, the drug or drugs included in device 1436 can be written or printed thereon, making such readily visible to an observer of device 1436. Alternatively, cover 1444 can include pre-printed information, such as the types and dosage of included drugs, along with permeation enhancers, if any. Furthermore, cover 1444 can include an advertisement for a product, for device 1436, artistic expression, etc. Thus, cover 1444 is a highly functional feature of device 1436.

Figure 109:
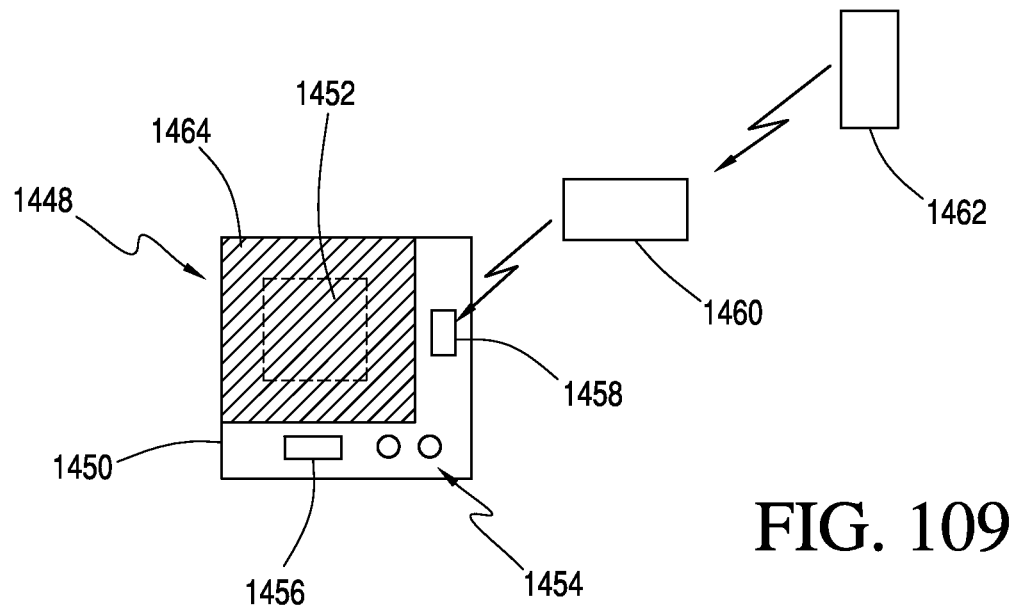
FIG. 109 is a view of a transdermal delivery device in accordance with an exemplary embodiment of the present disclosure.

FIG. 109 is a view of a transdermal delivery device in accordance with an exemplary embodiment of the present disclosure, indicated generally at 1448. Device 1448 is configured to include a support 1450, which is configured to include a removable and replaceable drug container or patch 1452 and a plurality of electronics. The plurality of electronics can include a power supply 1454, a controller 1456, and a transceiver, transmitter, or receiver 1458, configured to communicate with a separate electronic device 1460, such as a cell phone, laptop, tablet, etc., which can also be configured to communicate with yet another separate electronic device 1462, such as a cell phone, table, laptop, etc. Support 1450 can also be configured with a permeability modification device or apparatus, such as a thermoelectric device 1464.

Figure 110:
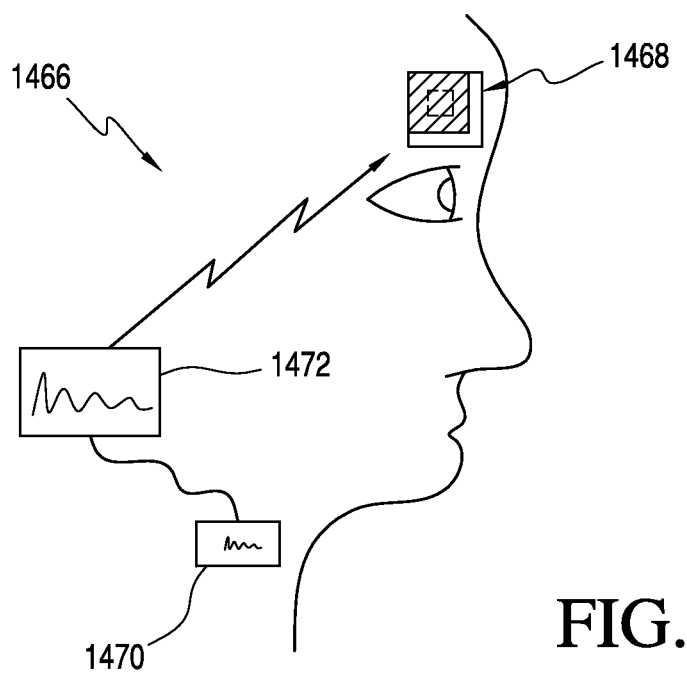
FIG. 110 is a view of a transdermal delivery system in accordance with an exemplary embodiment of the present disclosure.

FIG. 110 is a view of a transdermal delivery system in accordance with an exemplary embodiment of the present disclosure, indicated generally at 1466. System 1466 includes a transdermal delivery device 1468, which can be configured similar to device 1448 shown in FIG. 109, a sensor 1470, which can be any one of a plurality of sensors to measure various attributes of a body, such as oximetry, heart rate, blood pressure, glucose, and the like, and a sensor display or sensor controller 1472. Sensor controller 1472 can be configured to communicate with device 1468 to provide feedback to device 1468, which can then use that feedback to increase or decrease the rate of drug flow in a drug container to the patient or subject.

Figure 111:
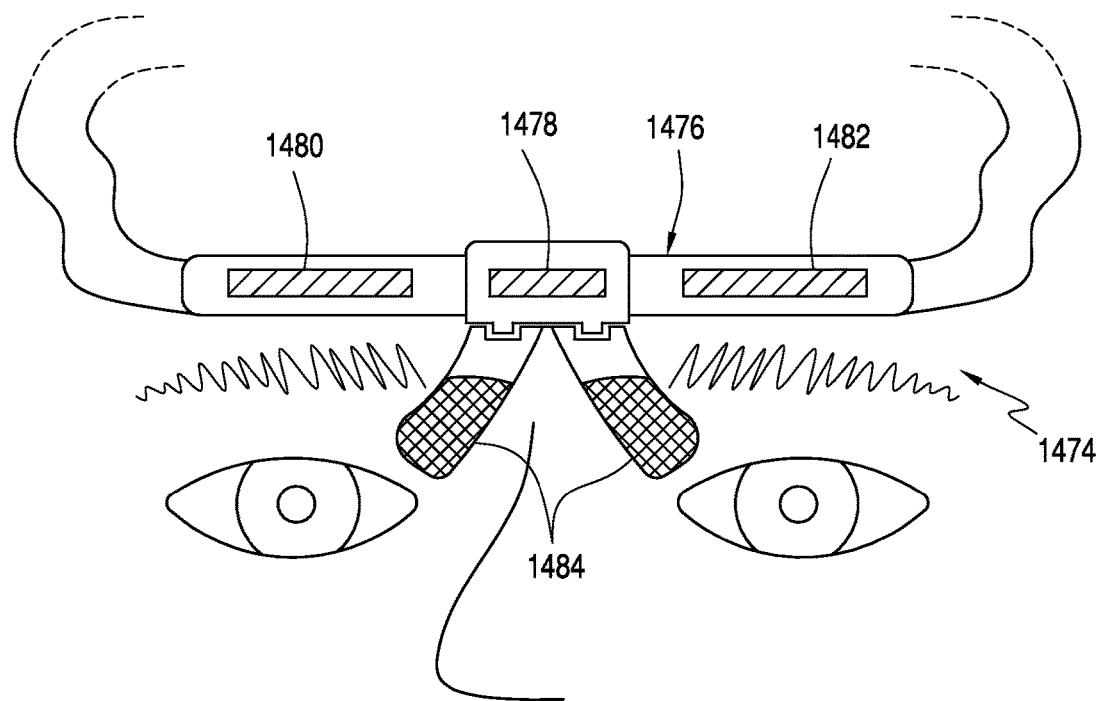
FIG. 111 is a view of a transdermal delivery system in accordance with an exemplary embodiment of the present disclosure.

FIG. 111 is a view of a transdermal delivery system in accordance with an exemplary embodiment of the present disclosure, indicated generally at 1474. System 1474 includes a support 1476 configured as a headband, on which are positioned at least one passive or active transdermal delivery device 1478, 1480, 1482, and 1484. Transdermal delivery devices 1478, 1489, 1482, and 1484 are configured to be replaceable.

Figure 112:
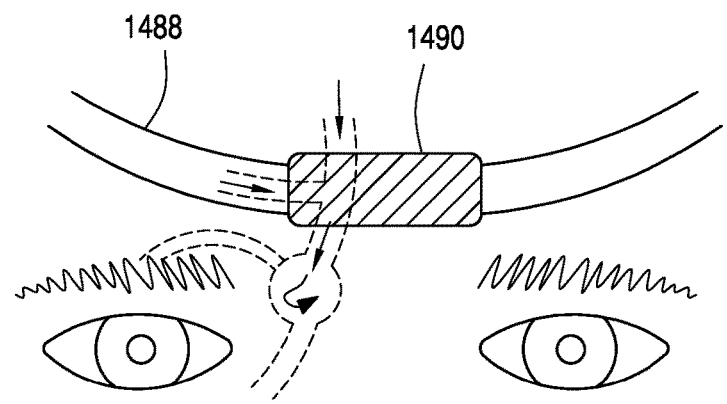
FIG. 112 is a view of a transdermal delivery system in accordance with an exemplary embodiment of the present disclosure.

FIG. 112 is a view of a transdermal delivery system in accordance with an exemplary embodiment of the present disclosure, indicated at 1486. System 1486 includes a support 1488 configured as a headband, including at least one passive or active transdermal delivery device 1488 positioned thereon.

Figure 113:
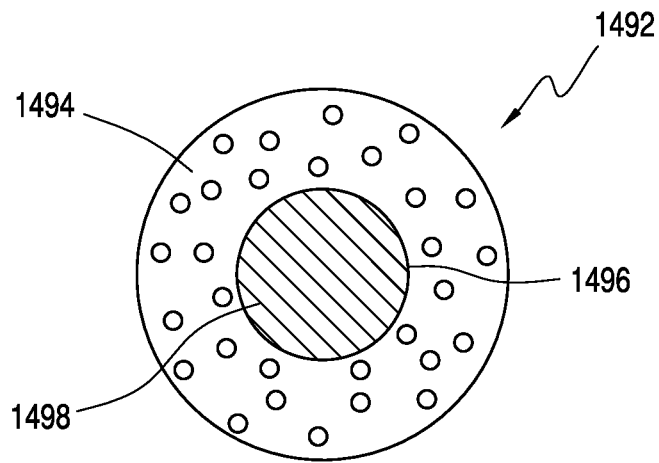
FIG. 113 is a view of another transdermal delivery device in accordance with an exemplary embodiment of the present disclosure.
Figure 114:
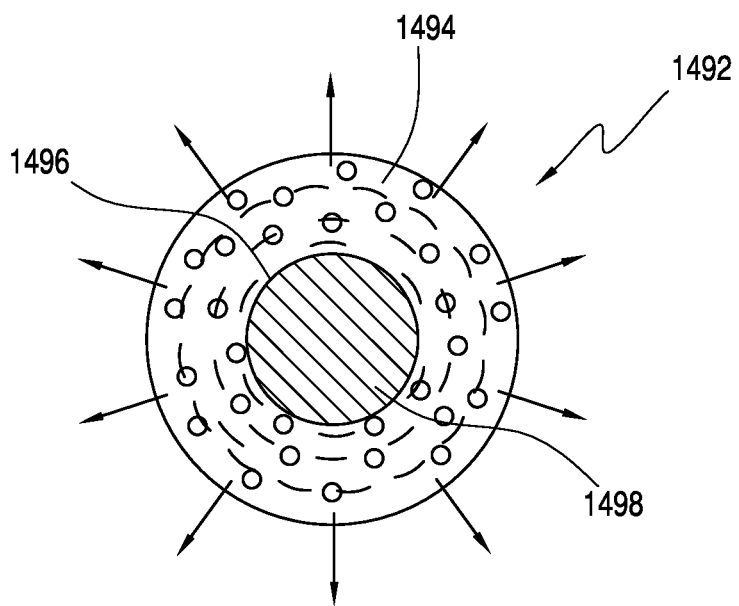
FIG. 114 is a view of the transdermal delivery device of FIG. 113, illustrating the operation of the device.

FIG. 113 is a view of a transdermal delivery device in accordance with an exemplary embodiment of the present disclosure, indicated generally at 1492. Similar to the device of FIG. 46, device 1492 includes an annular drug container or ABTT interface 1494 with a central opening 1496 in which is positioned a circular thermoelectric device 1498. As shown in FIG. 114, this configuration is advantageous because heat is distributed uniformly throughout drug container 1494, and drugs from drug container 1494 flow over a larger area than in designs of a similar size where the thermoelectric device is annular and the drug container is positioned in a central opening of the thermoelectric device.

Figure 115:
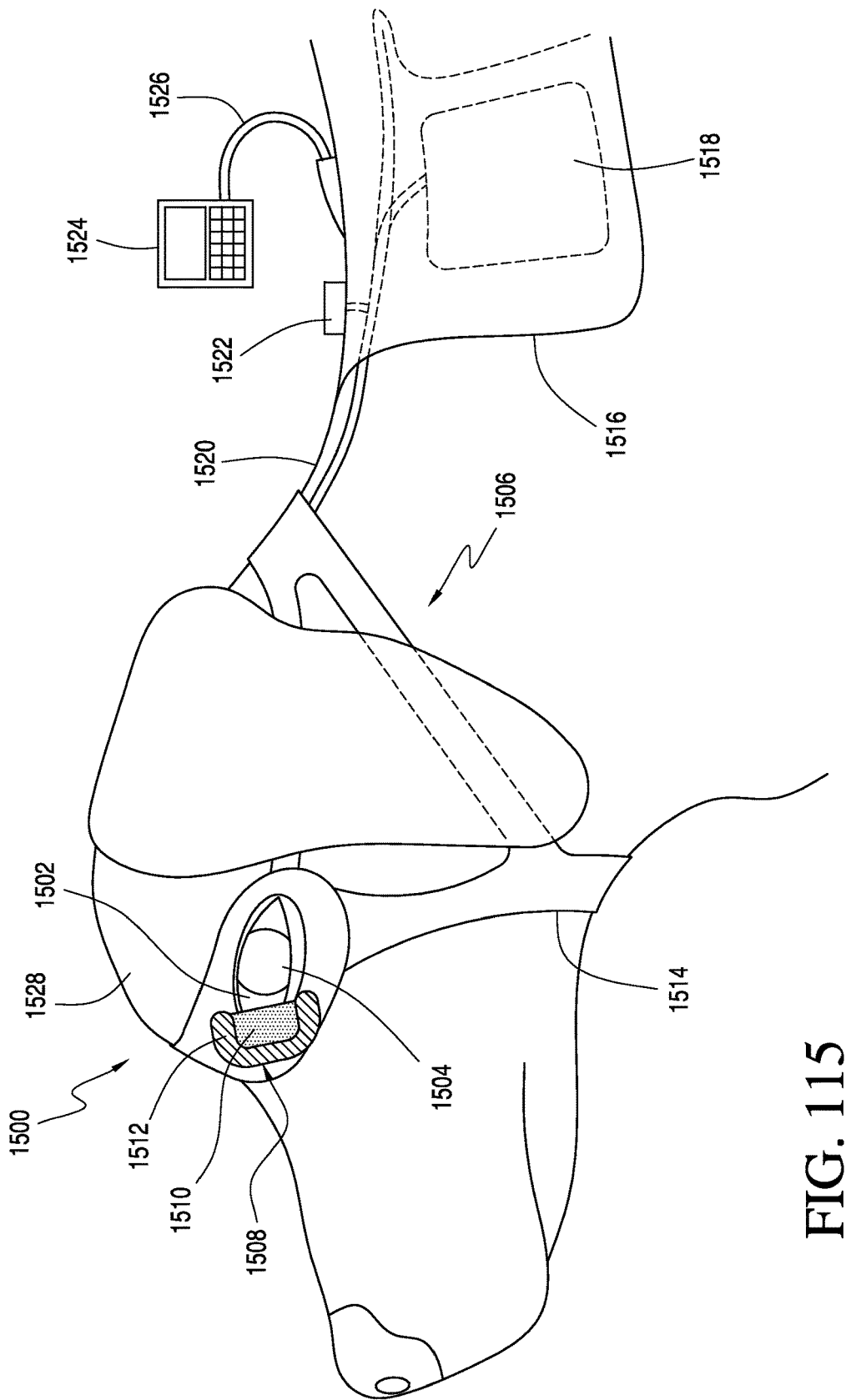
FIG. 115 is a view of an animal wearing a transdermal delivery system in accordance with an exemplary embodiment of the present disclosure

While the present disclosure has been focused on humans to this point, animals have a similar, though less effective, passage between the brain and the surface that is described as an intracranial thermal path (ITP). For example, FIG. 115 shows an animal, such as a dog 1500. Dog 1500 includes an ITP (not shown) that extends from the dog's brain to an ITP terminus 1502 positioned adjacent to an eye 1504 of dog 1500. As the disclosed embodiments presented herein benefit humans, modifications of the devices presented herein can be modified to interface with ITP terminus 1502 for benefit to animals. For example, FIG. 115 shows a transdermal drug delivery system in accordance with an exemplary embodiment of the present disclosure and indicated generally at 1506.

Animals may have fur and fat insulation that reduces thermal conductivity, shifting the position of the equivalent of ABTT terminus 10 in animals to ITP terminus 1502, which is represented by an area of transition skin-mucosa located in the corner of the eye, frequently adjacent to the tear duct and caruncle or conjunctival surface and referred to herein as the transition area. In some species, such as canines, felines and other predators, the transition area or ITP terminus 1502 is located in the anterior or medial portion of the corner of the eye; in swine, ITP terminus 1502 tends to be located in the posterior or lateral corner of the eye; in ovine, bovine and equines, ITP terminus 1502 tends to be located in the anterior corner of the eye; and in primates such as chimpanzees, ITP terminus 1502 tends to be located in both the medial corner and the lateral corner of the eye.

In the exemplary embodiment of FIG. 115, transdermal delivery system 1506 includes an ITP interface 1508 configured to include a drug container 1510, which is configured to interface with ITP 1502, and a thermoelectric device 1512 configured to heat or cool the drug in drug container 1510 and/or ITP 1502 to control the permeability of the drug. Typically, because animals frequently object to the presence of objects near their eyes, transdermal drug delivery system 1506 includes a harness 1514 for attachment of drug delivery system 1506 to head 1528 of animal 1500. Harness 1514 is configured to position transdermal drug delivery system 1506 over ITP terminus 1502. In the exemplary embodiment of FIG. 115, thermoelectric device 1512 is configured to be connected to a pack 1516 configured to be positioned, attached, secured, or mounted on animal 1500 to provide a location for one or more batteries 1518. Batteries 1518 are then connected to thermoelectric device 1512 by, for example, wires or a cable 1520 extending between batteries 1518 and ITP interface 1508. Transdermal drug delivery system 1506 may include a controller 1522 configured to operate transdermal drug delivery system 1506, and controller 1522 is configured to be programmed, adjusted, or set by a separate electronics device 1524, which can be wirelessly or through wires or a cable 1526. Separate electronics device 1524 can be a device specifically configured to program, adjust, or set transdermal drug delivery, or it can be, for example, a cell phone, laptop, tablet, watch, or the like.

Figure 116:
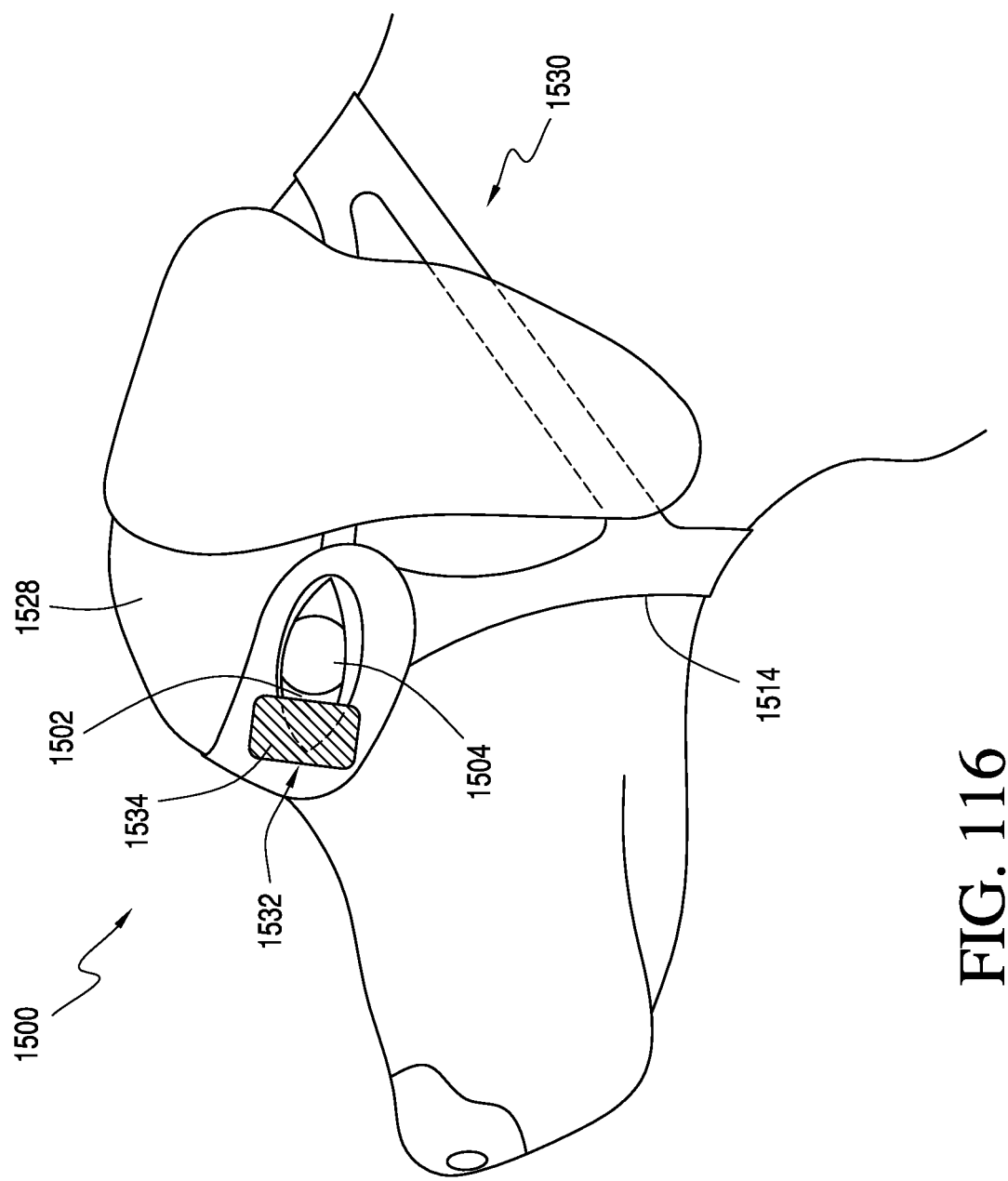
FIG. 116 is a view of an animal wearing another transdermal delivery system in accordance with an exemplary embodiment of the present disclosure.

FIG. 116 is a view of an animal wearing another transdermal delivery system in accordance with an exemplary embodiment of the present disclosure, indicated generally at 1530. System 1530 includes an ITP interface 1532 positioned on harness 1514. ITP interface 1532 includes a drug container 1534 configured to be positioned on ITP terminus 1502 when animal 1500 wears harness 1514.

Figure 117:
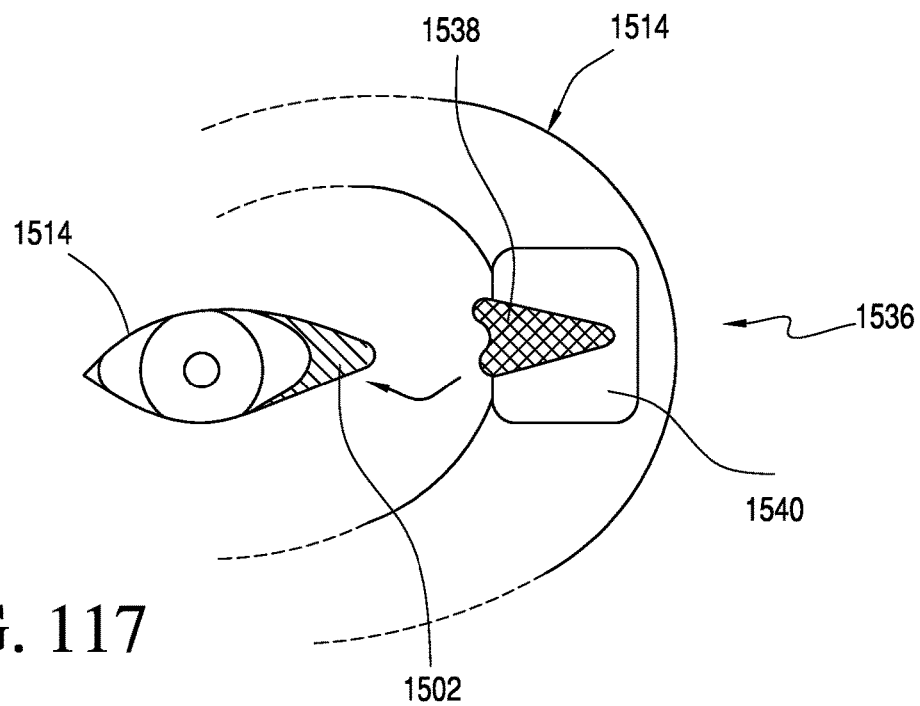
FIG. 117 is a view of an intracranial thermal path interface in accordance with an exemplary embodiment of the present disclosure.

FIG. 117 is a view of an ITP interface in accordance with an exemplary embodiment of the present disclosure, indicated generally at 1536. Interface 1536 includes a drug container 1538 configured to interface with ITP 1502 when harness 1514 is positioned, attached, mounted, or located on animal 1500. Interface 1536 may be configured to include a drug container support 1540 that connects, attaches, supports, or mounts drug container 1534 to harness 1514.

Figure 118:
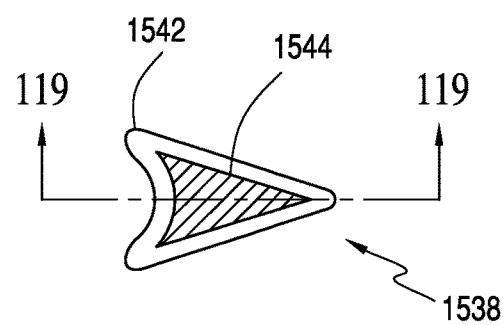
FIG. 118 is a view of a drug container of the interface of FIG. 117.
Figure 119:
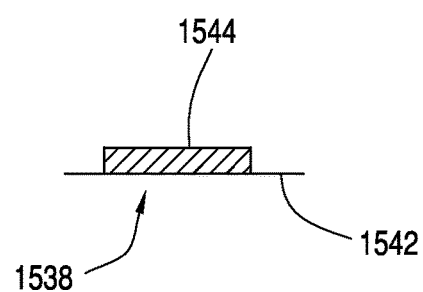
FIG. 119 is a cross-sectional view of the drug container of FIG. 118 along the lines 119-119.

FIG. 118 is a view of a drug container 1538 of ITP interface 1532. Drug container 1538 is configured to be supported in drug container support 1540, and includes a backing layer 1542 and a drug 1544, which may be located in an absorbent material. FIG. 119 is a cross-sectional view of the drug container of FIG. 118 along the lines 119-119.

Figure 120:
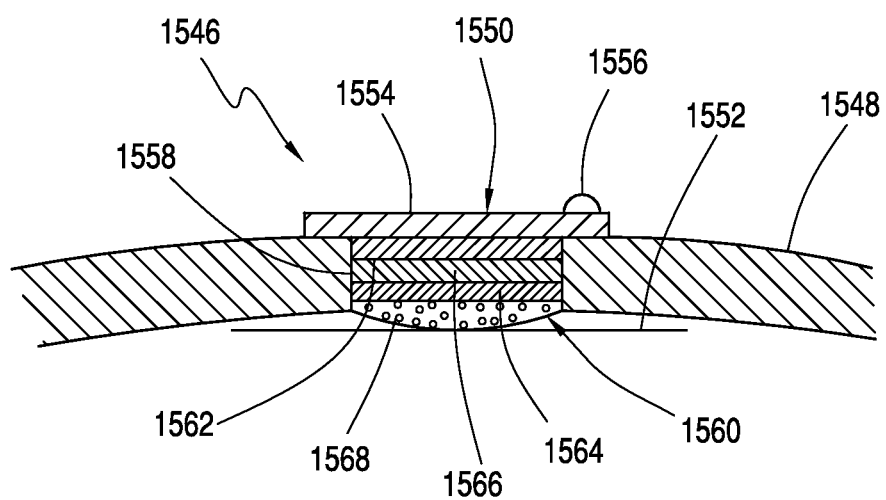
FIG. 120 is a cross-sectional view of another intracranial thermal path interface in accordance with an exemplary embodiment of the present disclosure.

FIG. 120 is a cross-sectional view of another intracranial thermal path interface in accordance with an exemplary embodiment of the present disclosure, indicated generally at 1546. ITP interface 1546 is configured to provide an easily removable module for the replenishment or replacement of a drug. ITP interface 1546 is configured to be positioned and supported in a harness 1548, and captured between a retention mechanism, device, or apparatus 1550 configured as a part of harness 1548 and an ITP terminus 1552 of an animal. Retention mechanism 1550 includes a retention plate 1554 configured to swing or rotation on a pivot pin 1556. Harness 1548 further includes a receptacle, opening, cavity, or the like 1558 configured to support a drug module 1560 of ITP interface 1546.

Drug module 1560 includes a base plate 1562, a drug container support 1564 connected to base plate 1562 by a bias spring 1566, and a drug container or absorbent material 1568 positioned or supported on drug container support 1564. When drug module 1560 is positioned and retained in receptacle 1558, bias spring 1566 presses drug container or absorbent material 1568 against ITP terminus 1552, permitting drug to flow from drug container or absorbent material 1568 into ITP terminus 1552 and then into the brain of the animal.

Figure 121:
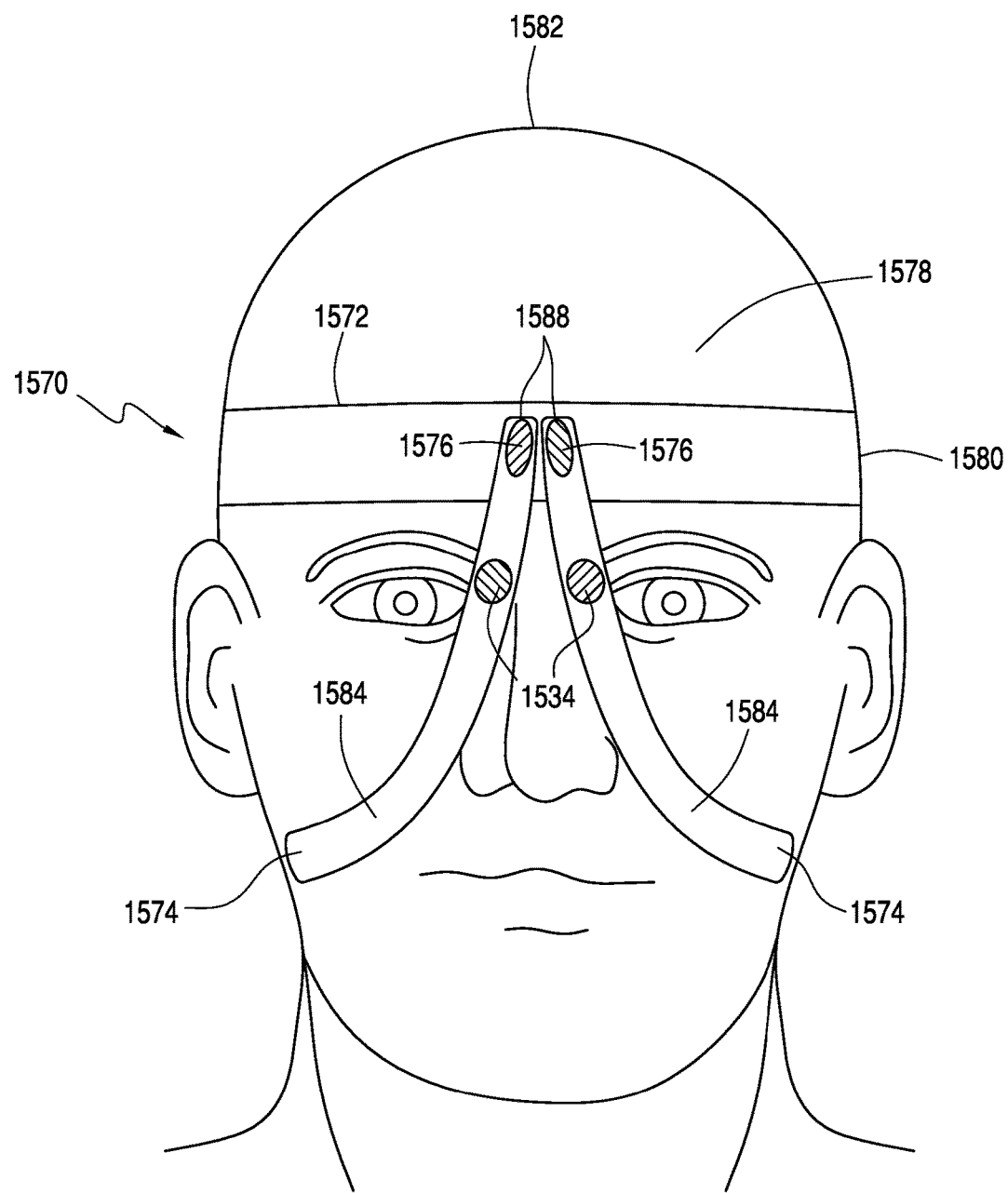

FIG. 121 is a view of a transdermal delivery device positioned on a head of a subject or patient in accordance with an exemplary embodiment of the present disclosure, indicated generally at 1570. Device 1570 includes a headband support 1572, and one or more face extensions 1574. Headband support 1572 is configured to contain a drug 1576 positioned along a forehead area 1578 that, when headband support 1572 is attached to forehead 1578, is in contact with portions of frontal vein 14 and supraorbital vein 18, and, depending on the size and configuration of headband support 1572, possibly superior palpebral vein 16. Headband support 1572 includes a strap 1580 configured to encircle a head 1582, thus securing headband support 1572 to head 1582. Face extensions 1574 are configured to contain a drug in zones, regions, or portions 1584 that extend down the sides of the nose and onto the cheek area, thus covering a portion of angular vein 20 and extending into the region of facial vein 22. Face extensions 1574 comprise preferably convex or comma, boomerang or banana shape configuration with nodes or ABTT interfaces 1586 that will allow nodes 1586 to conform closely to the special topography of ABTT target area 10 and associated veins. Face extensions 1574 contain one or more drugs and are configured to fit precisely in the medial canthal area adjacent to the medial corner of the eye in the superomedial orbit, where ABTT target area 10 and the convergence of four veins 14, 16, 18, and 20 is located. In an exemplary embodiment, each face extension 1574 can include a strap (not shown) that extends beyond the facial/angular vein area to wrap around the head below the ears to fit each facial extension 1574 securely to the face. For both headband support 1572 and face extensions 1574 of device 1570, the opposite ends of strap 1580 and straps attached to face extensions 1574 are configured to be fastened to one another to form a secure fit. In an exemplary embodiment, strap 1580 may be fastened using a hook and loop arrangement, but may also use snaps, buttons, ties, hooks, adhesive, or other fastening mechanism, device, or apparatus. Headband support 1572 includes a strip of a fastening arrangement (not shown), which in an exemplary embodiment is a hook and loop arrangement, located in a region at the center of the headband support 1572. When worn by a user, the fastening arrangement will be located on the forehead directly between the eyebrows. Face extensions 1574 include a mating fastening arrangement (not shown) located on an upper end 1588 that, when positioned on the face of a user, is located above the bridge of the nose. The fastening arrangement of each face extension 1574 is configured to mate and attach to the fastening arrangement of headband support 1572. Once face extensions 1574 are attached to headband support 524, the assembly forms transdermal delivery device 1570, which is one mask-like structure to cover vital areas related to ABTT 12. The fastening arrangement of each face extension 1574 is smaller than the fastening arrangement of headband support 1572. This size differential allows each face extension 1574 to be adjusted by moving face extensions 1574 left or right, or up and down the face. This adjustable configuration allows transdermal drug delivery device 1570 to adapt to fit many different face types and shapes. For example, some people have longer faces or broader noses. With an adjustable fastening arrangement such as hook and loop, and two separate portions, i.e., headband support 1572 and face extensions 1574, transdermal drug delivery device 1570 may be suitable for any number of wearers that have innumerable anatomical differences. It should be understood that device 1570 may include thermoelectric devices configured to heat the drug or drugs in positioned in device 1570.

Figure 122:
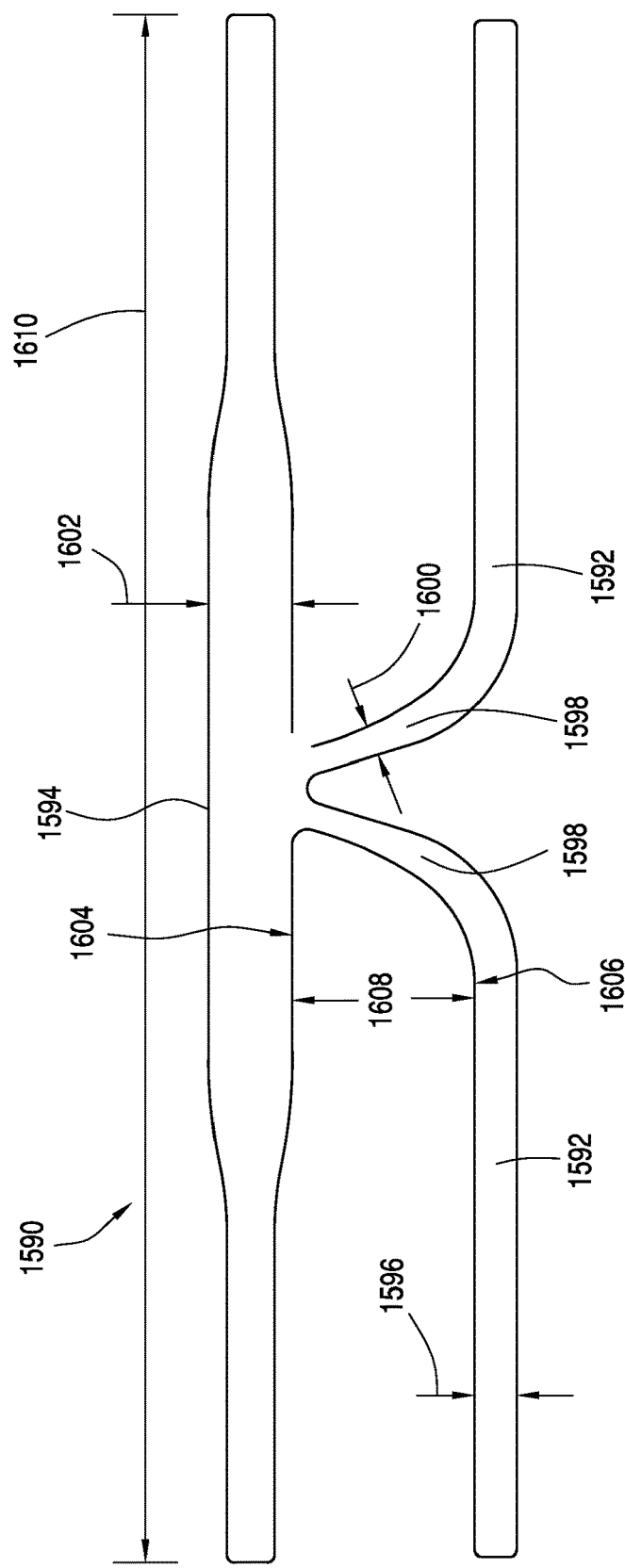

FIG. 122 is a view of another transdermal delivery device in accordance with an exemplary embodiment of the present disclosure, indicated generally at 1590. Transdermal delivery device 1590 is formed of one piece, rather than having separate headband and face portions. Device 1590 is not as easily adjustable for size as some embodiments, but transdermal drug transfer is still readily available, as device 1590 covers at least one of the key venous areas; i.e., ABTT terminus 11 and the areas of the skin over veins 14, 16, 18, 20, and 22. In this embodiment, three to four different sizes are used to cover a whole range of different head sizes.

Device 1590 includes a face portion 1592 and a forehead portion 1594. Dimensions, such as width of the bands covering the veins are important, otherwise drug transfer into the vein area is inefficient. In an exemplary embodiment, specialized preferred dimension of face portion 1592, shown by arrows 1596, is 4.5 cm or less, preferably is 3.5 cm or less, and more preferably is 2.5 cm or less, and most preferably is 1.5 cm or less, and yet most preferably is 1 cm or less. Specialized preferred dimension of a nose portion 1598, shown by arrows 1600, is 3.7 cm or less, and preferably 2.7 cm or less, and most preferably 1.7 cm or less, and yet most preferably 1.2 cm or less, and even most preferably 1 cm or less. A specialized preferred dimension of forehead portion 1594, shown by arrows 1602, is 5.5 cm or less, is preferably 4.5 cm or less, is more preferably 3.5 cm or less, is even more preferably 2.5 cm or less, and is most preferably 2.0 cm or less. A specialized preferred distance between a lower edge 1604 of forehead portion 1594 and an upper edge 1606 of facial portion 1592, shown by arrows 1608, is 10.5 cm or less, is preferably 9.5 cm or less, is more preferably 8.5 cm or less, is even more preferably 7.5 cm or less, and is most preferably 6.0 cm or less. A specialized preferred length of forehead portion 1594, shown by arrows 1610, is 17 cm or less, is preferably 14 cm or less, is more preferably 12 cm or less, is even more preferably 10.5 cm or less, and is most preferably 9.5 cm or less.

Figure 123:
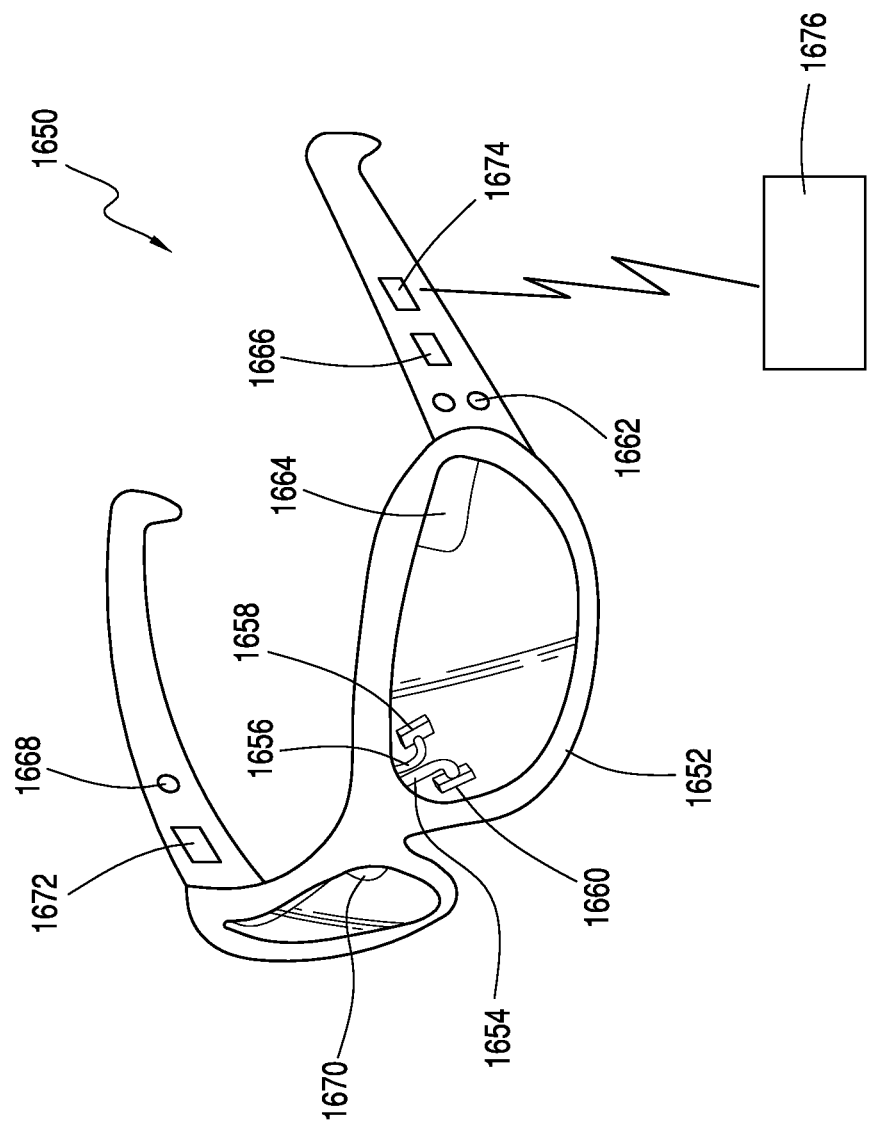
Figure 124:
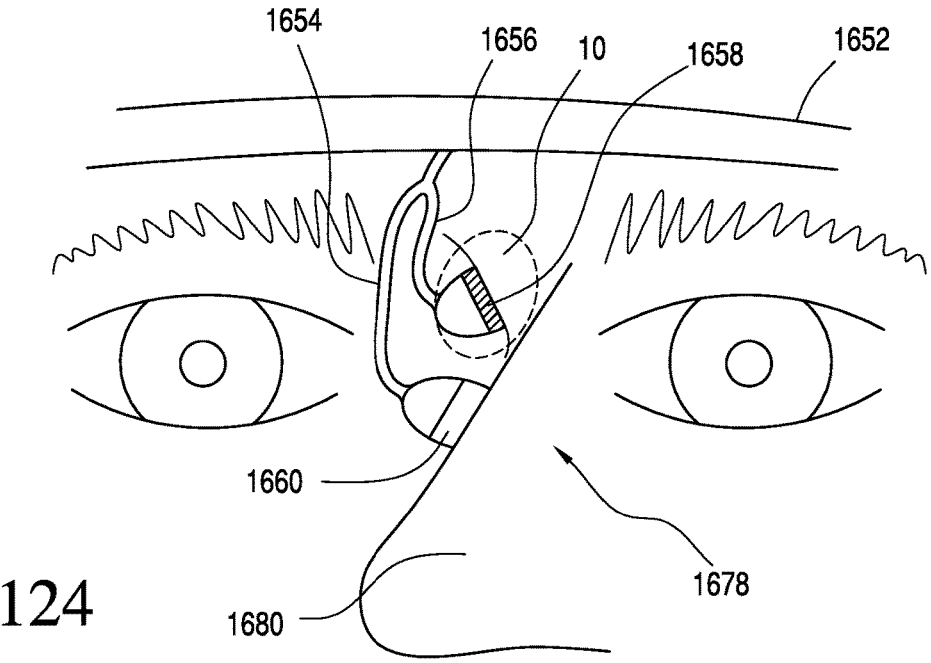
Figure 125:
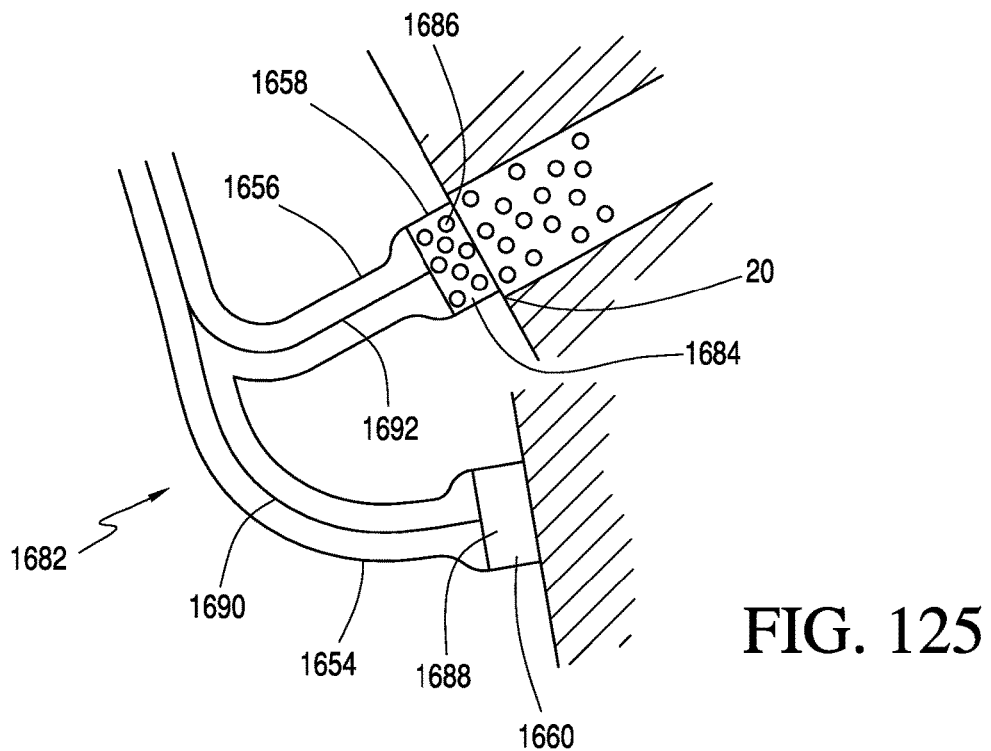
Figure 126:
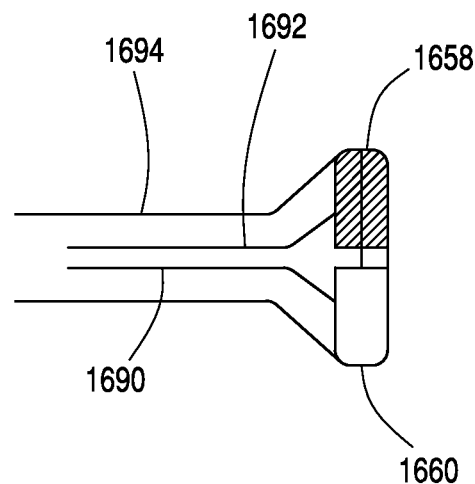

FIGS. 123 to 126 show exemplary ABTT eyewear iontophoretic system with two structures, one structure having one arm as shown in FIG. 126, and another structure having two arms, as shown in FIG. 123. FIG. 123 shows an ABTT iontophoretic eyewear in accordance with an exemplary embodiment of the present disclosure, indicated generally at 1650. ABTT iontophoretic eyewear 1650 includes a frame 1652, with frame 1652 configured to include two arms 1654 and 1656, each arm configured to include a set of electrodes 1658 and 1660 represented by a working electrode in one arm and a passive electrode in the other arm, disposed as an anode and a cathode, electrodes 1658 and 1660 configured to be located at an end of each arm 1656 and 1654, respectively, which are viewed in a magnified fashion in FIGS. 124 and 125. Frame 1652 is also configured to include a power source 1662, such as batteries, which generate a low level electrical current that increases permeation of a drug located in the working electrode. Frame 1652 also houses a screen 1664, electronics 1666, including a controller and a timer, a speaker 1668, an LED 1670, a dosing button 1672, and a transmitter, receiver, or transceiver 1674 wirelessly connected to a separate electronic device 1676 such as a cell phone, a watch, and the like. Electrodes 1658 and 1660 may comprise a pad, a hydrogel, and the like, in which the working electrode contains the drug, and the passive electrode may contain a salt solution. For example, in anaphoresis, an anode is the working electrode, which is the electrode containing the drug to be administered, and the second electrode (passive or return electrode) is the cathode used to complete the electrical circuit and to initiate current flow. When frame 1652 is positioned on a face 1678, working electrode 1658 held by arm 1656 is positioned on the skin at ABTT terminus 10, shown in dashed lines, and passive electrode 1660 is positioned against the skin of a nose 1680, below ABTT terminus 10, as shown in FIG. 124.

FIG. 125 is a close-up view of a two arm structure 1682 in accordance with an exemplary embodiment of the present disclosure, in which arm 1656 with working electrode 1658 is configured to include a pad 1684 containing a drug 1686. When a frame supporting arm 1656 is positioned on a subject or user's head, pad 1684 rests on ABTT terminus 10, with drug 1686 being delivered to ABTT terminus 10 when activated, and arm 1654 with passive electrode 1660 configured to include a pad 1688 with salt solution and configured to be positioned away from ABTT terminus 10. Two arm structure 1682 is configured to include a wire 1690 extending through arm 1654 and a wire 1692 extending through arm 1656, which connect electrodes 1658 and 1660 to a power source and electronics housed in the frame, such as those shown in FIG. 123.

Figure 127:
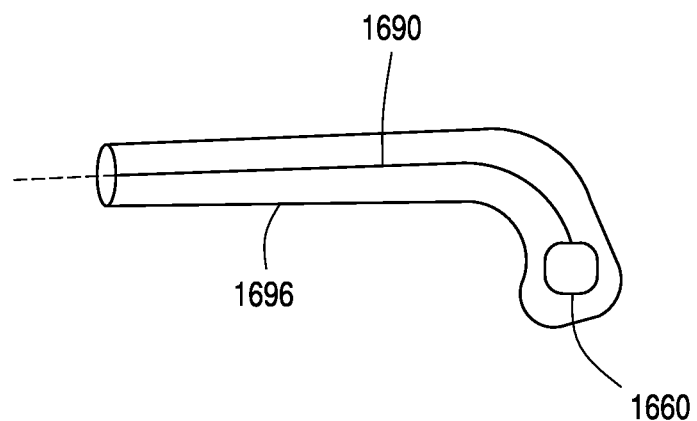

It should be understood that frame 1652 can be configured to include only one arm 1694, as shown in FIG. 126, with arm 1694 housing both active electrode 1658 containing the drug and passive electrode 1660 containing an inert solution, which are electrically connected by wire 1692 and 1690 with power and electronics of frame 1652 (not shown). It should be understood that passive electrode 1660 can be located anywhere in the frame 1652, as long as there is good contact with the skin, and by way of example, as shown in FIG. 127 passive electrode 1660 is positioned at the end of a temple 1696 in apposition against auricular skin (not shown).

Figure 128:
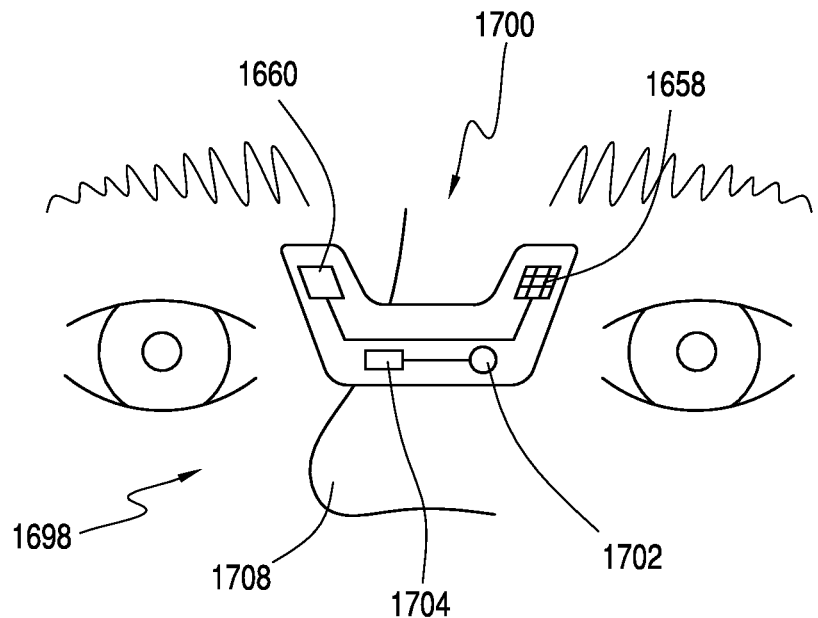
Figure 129:
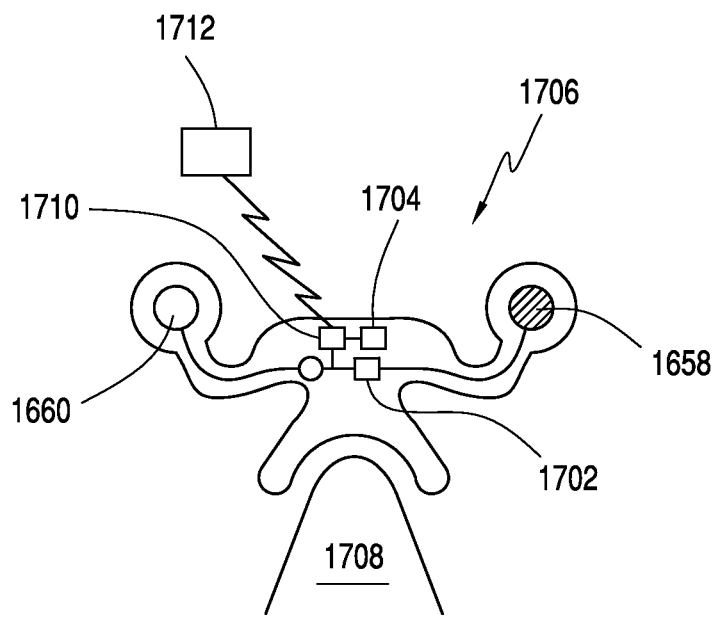

It should also be understood that an ABTT iontophoretic system can be integrated in a patch 1700, as shown in FIG. 128, with patch 1700 being positioned on a face 1698 and housing active electrode 1658 and passive electrode 1660, a power source 1702 and electronics 1704. It should further be understood that the ABTT iontophoretic system can be integrated in a nose clip 1706, as shown in FIG. 129, with nose clip 1706 being positioned on a nose 1708 and housing active electrode 1658 and passive electrode 1660, power source 1702, electronics 1704, and a wireless device 1710 communicating with an external electronic device 1712.

Although only the aspects discussed above have been described in detail, it should be understood that active means of transdermal delivery as discussed in detail above may also be adapted to be included in any of the support systems presented in the figures. In addition, it should be understood that, when sensing and regulatory means are employed, active or passive transdermal delivery methods may be used to deliver the drug to the patient. For example, in the apparatus of FIGS. 71 and 72, one side may comprise electronics and sensors needed to collect data and store or transmit data, while the opposite side may be configured to deliver a drug transdermally using a passive method. As such, the transdermal delivery is not necessarily regulated or controlled, but data regarding drug levels in the patient's body may be collected and monitored.

It should be understood that the embodiments may include a variety of reservoirs or structures containing drugs, including single-layer, multi-layer, reservoir, matrix, and vapor. The structure may also comprise a support layer or backing and a single layer that contains both the adhesive material and the drug to be released. The single layer patch embodiment is preferred for immediate release of a drug. Multi-layer patches have multiple layers including a layer of the drug and adhesive and may be used for extended release of a drug. Some embodiments may include a porous layer. It should be understood that the embodiments can include a liner designed to extend delivery of a drug over a specified time period. Multiple-layer passive patches of the disclosure are designed preferably for a timed release of the drug and to provide a constant delivery of a drug. A reservoir with liquid compartment may be incorporated into a patch, clip, drug delivery modules, eyeglasses frame, and any other embodiment of the present disclosure, with the liquid kept in a liquid compartment before release. It should be understood that patches and other embodiments of the present disclosure may include a matrix, which may contain semisolid matrix solution with a drug, suspension with drugs, and the like. All of the embodiments can include a release liner, comprised preferably of a thin sheet of plastic to protect the adhesive and drug layer.

Although permeation through ABTT terminus 10 is increased, and the apparatus of the present disclosure augments permeation of a drug, the drug has a short and direct path to a blood vessel, and thus in general does not require permeation enhancers, it should be understood that any permeation enhancer can be used with any of the embodiments of present disclosure, and may include compounds that optimize the properties of the drug, and by way of example, but not limitation, includes the use of prodrugs, liposomes, transferosomes, ethosomes, niosomes, nanoparticles, saturated and supersaturated solutions, eutectic systems, encapsulation in vesicles, cyclodextrin, and the like, or any compound that alters the physical properties of the drug to increase fat solubility or that optimize transport in the stratum corneum. It should be understood that any known alteration of a drug that will increase its permeability can be used in any of the embodiments of the present disclosure. Direct treatment of the skin can also be used and is within the scope of the invention, and may include hydration, lipid fluidization through chemical penetration, keratin treatment, increased solubility in the stratum corneum, use of ointments such as paraffins, oils, waxes, water-in-oil emulsions that donate water to the skin. Any substance that disrupt or alter the stratum corneum may be used in the embodiments of the present disclosure and include lauryl lactate, oleic acid, turpentine, decylmethylsulphoxide, and the like. Any solvent can also be use with the embodiments disclosed herein and include by way of illustration, ethanol, propylene glycol, methyl pyrrolidone, and the like.

It should also be understood that a variety of active device that increase permeation can be used with the embodiments of the present disclosure. Active types of transdermal delivery that use some form of energy to enhance permeation are, for example, iontophoresis, driving high concentrations of charged molecules using a small direct current, as shown in FIGS. 123 to 129, sonophoresis, electroporation, and the like. It should be understood that a frame of eyewear, goggles, and masks of the present disclosure can include a sonophoresis device that generate micro-vibrations in the skin of the ABTT terminus 10 and adjacent areas and veins 14, 16, 18, 20, and 22 using ultrasound waves to increase lipid fluidity and create cavities, with subsequent administration of medications, in accordance with the principles of the present disclosure. Other active apparatus can be integrated in the embodiments described herein, including electroporation with application of short electrical pulses to introduce a voltage gradient and create pores in ABTT terminus 10 and adjacent areas and veins 14, 16, 18, 20, and 22. Photomechanical devices generating waves including laser-generated stress waves to open pores at the ABTT terminus 10 and adjacent areas and veins 14, 16, 18, 20, and 22 can also be incorporated in the frames and embodiments of the present disclosure, and are within the scope of the disclosure. The support structure, shown in other embodiments housing electrodes, can be adapted to contain microneedles or microprojection devices comprising solid or hollow needles, measuring 100 µm or less in length that are adapted to penetrate just through the stratum corneum into the upper epidermis of the skin of ABTT terminus 10 and adjacent areas and veins 14, 16, 18, 20, and 22 skin). Embodiments and frames of the present disclosure can also include jet-propelled particles that are applied against ABTT terminus 10 and adjacent areas and veins 14, 16, 18, 20, and 22 consisting of high-velocity micro jet of compressed gas carrying drug particles.

It should be further understood that an ABTT iontophoretic system and thermoelectric systems as described herein can be integrated in variety of embodiments of the present invention including masks, goggles, hats, head mounted gear, and the like. It should also be understood that a combination of embodiments or a combination of components of each embodiment are within the scope of the invention.

Although only the aspects discussed herein have been described in detail, it should be understood that active means of transdermal delivery as discussed in detail herein may also be adapted to be included in any of the support systems presented in the figures. In addition, it should be understood that when sensing and regulatory means are employed, active or passive transdermal delivery methods may be used to deliver the drug to the patient.

While various embodiments of the disclosure have been shown and described, it is understood that these embodiments are not limited thereto. The embodiments may be changed, modified, and further applied by those skilled in the art. Therefore, these embodiments are not limited to the detail shown and described previously, but also include all such changes and modifications.

I claim:

1. A device configured to deliver a drug transdermally to the skin of a face feeding an Abreu brain thermal tunnel (ABTT), the device comprising:
   a curvilinear device support;
   a first drug container having a first, drug delivery side, a second side on an opposite side of the first drug container from the first, drug delivery side, and at least one connecting side extending between the first, drug delivery side and the second side; and
   a first thermoelectric device positioned directly in contact alongside the at least one connecting side of the first drug container;
   the first drug container and the first thermoelectric device being commonly supported in the curvilinear device support for transdermal delivery of a drug from the first drug container, the curvilinear device support being shaped and configured to deliver the drug transdermally to the skin by permeating the skin and flowing into at least one of a frontal vein, an angular vein, a supraorbital vein, and a superior vein,
   the curvilinear device support having a first end configured to be positioned in a region between a patient's eye and a patient's eyebrow, and a second end configured to be positioned in a region between the patients eye and a patient's nose,
   the first end including a first transverse width positioned a first longitudinal length from the first end along a centerline of the curvilinear device support, the first transverse width is 15 mm+/−8 mm, and the first longitudinal length is 7.5 mm+/−5 mm,
   the second end including a second transverse width positioned a second longitudinal length from the second end along the centerline of the curvilinear device support, the second transverse width is greater than or equal to the first transverse width and the second longitudinal length is approximately equal to the first longitudinal length.

2. The device of claim 1, further including a second drug container and a second thermoelectric device positioned adjacent the second drug container.

3. The device of claim 2, wherein when the device is positioned on the skin of the face, the temperature of the first thermoelectric device and the temperature of the second thermoelectric device is adjusted to control delivery of a first drug from the first drug container and a second drug from a second drug container through the skin of the face.

4. The device of claim 1, wherein the drug delivered transdermally to the skin permeates the skin of an ABTT terminus and flows into the ABTT.

5. A device configured to deliver a drug transdermally to the skin of a face feeding an Abreu brain thermal tunnel (ABTT), the device comprising:
   a curvilinear device support for placement between the eye and the eyebrow, and measuring in its largest dimension 22 mm;
   a first drug container positioned on the curvilinear device support, the first drug container having a first, drug delivery side, a second side on an opposite side of the first drug container from the first, drug delivery side, and at least one connecting side extending between the first, drug delivery side and the second side;
   a first thermoelectric device positioned directly in contact alongside the at least one connecting side of the first drug container;
   the curvilinear device support commonly supporting the first drug container and the first thermoelectric device for transdermal delivery of a drug from the first drug container, the curvilinear device support being shaped and configured to deliver the drug transdermally to the skin by permeating the skin and flowing into at least one of a frontal vein, an angular vein, a supraorbital vein, and a superior vein,
   the curvilinear device support having a first end configured to be positioned in a region between a patient's eye and a patient's eyebrow, and a second end configured to be positioned in a region between the patients eye and a patient's nose,
   the first end including a first transverse width positioned a first longitudinal length from the first end along a centerline of the curvilinear device support, the first transverse width is 15 mm+/−8 mm, and the first longitudinal length is 7.5 mm+/−5 mm,
   the second end including a second transverse width positioned a second longitudinal distance from the second end along the centerline of the curvilinear device support, the second transverse width is approximately equal to the first transverse width and the second longitudinal distance is approximately equal to the first longitudinal distance.

6. The device of claim 5, including a second drug container, the first drug container positioned closer to the first end than the second end and the second drug container positioned closer to the second end than the first end.

7. The device of claim 6, including a third drug container positioned between the first drug container and the second drug container.

8. The device of claim 6, wherein the first drug container includes a first drug, the second drug container includes a second drug, and the first drug is different from the second drug.

* * * * *